US011119104B2

(12) United States Patent
Barasch et al.

(10) Patent No.: US 11,119,104 B2
(45) Date of Patent: Sep. 14, 2021

(54) METHODS OF TREATING VOLUME DEPLETION AND KIDNEY INJURY

(71) Applicant: THE TRUSTEES OF COLUMBIA UNIVERSITY IN THE CITY OF NEW YORK, New York, NY (US)

(72) Inventors: Jonathan Barasch, New York, NY (US); Katherine Xu, New York, NY (US); Paul Rosenstiel, New York, NY (US); Paolo Guarnieri, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 214 days.

(21) Appl. No.: 15/752,230

(22) PCT Filed: Aug. 12, 2016

(86) PCT No.: PCT/US2016/046920
§ 371 (c)(1),
(2) Date: Feb. 12, 2018

(87) PCT Pub. No.: WO2017/027858
PCT Pub. Date: Feb. 16, 2017

(65) Prior Publication Data
US 2019/0064166 A1 Feb. 28, 2019

Related U.S. Application Data

(60) Provisional application No. 62/354,494, filed on Jun. 24, 2016, provisional application No. 62/204,205, filed on Aug. 12, 2015.

(51) Int. Cl.
*G01N 33/573* (2006.01)
*G01N 33/68* (2006.01)
*G01N 33/70* (2006.01)

(52) U.S. Cl.
CPC ........... *G01N 33/573* (2013.01); *G01N 33/68* (2013.01); *G01N 33/6893* (2013.01); *G01N 33/70* (2013.01); *G01N 2333/96486* (2013.01); *G01N 2800/347* (2013.01)

(58) Field of Classification Search
CPC .......... G01N 2800/347; G01N 33/6893; A61P 13/12
See application file for complete search history.

(56) References Cited

U.S. PATENT DOCUMENTS

| | | | |
|---|---|---|---|
| 8,263,072 B2 | 9/2012 | Grigoryev et al. | |
| 2005/0084909 A1 | 4/2005 | Uchiyama et al. | |
| 2009/0123946 A1 | 5/2009 | Birkenmeyer et al. | |
| 2009/0170143 A1 | 7/2009 | Uttenthal et al. | |
| 2009/0258002 A1 | 10/2009 | Barrett et al. | |
| 2009/0305963 A1 | 12/2009 | Sukhatme et al. | |
| 2011/0091912 A1 | 4/2011 | Barasch et al. | |
| 2013/0295589 A1 | 11/2013 | Devarajan et al. | |
| 2013/0323751 A1 | 12/2013 | Singbartl et al. | |
| 2014/0038203 A1 | 2/2014 | Arthur et al. | |
| 2014/0141456 A1 | 5/2014 | Kumar et al. | |
| 2014/0187652 A1 | 7/2014 | Heudig et al. | |
| 2014/0329334 A1 | 11/2014 | Irarrazbal Muñoz et al. | |

FOREIGN PATENT DOCUMENTS

| WO | WO 2010/057184 | 5/2010 |
|---|---|---|
| WO | WO 2012/068545 | 5/2012 |
| WO | WO-2013009572 A1 | 1/2013 |

OTHER PUBLICATIONS

Anthony et al. "Fluid management in pre-eclampsia", Obstetric Medicine 6(3) 100-104 (2013), DOI 10.1177/1753495X13486896 (Year: 2013).*
International Search Report dated Dec. 30, 2016 of International Application No. PCT/US2016/046920, filed Aug. 12, 2016 (3 pages).
Written Opinion of the International Searching Authority dated Dec. 30, 2016 for International Application No. PCT/US2016/046920 filed Aug. 12, 2016. (10 pages).
Parikh et al., "Does NGAL reduce costs? A cost analysis of urine NGAL (UNGAL) and serum creatinine (SCR) for acute kidney injury (AKI) diagnosis," Crit. Care Med., 38 (2010), 2 pages.
The UniProt Consortium, "Activities at the Universal Protein Resource (UniProt)," Nucleic Acids Research., 42 (Database issue), pp. D191-198 (Jan. 2014).
Arany et al., "CREB mediates ERK-induced survival of mouse renal tubular cells after oxidant stress," Kidney Int., 68(4), pp. 1573-1582 (2005).

(Continued)

*Primary Examiner* — Christine Foster
(74) *Attorney, Agent, or Firm* — Wilmer Cutler Pickering Hale and Dorr LLP

(57) ABSTRACT

The present invention provides methods for treatment of volume-dependent Acute Kidney Injury (vAKI) and ischemic Acute Kidney Injury (iAKI), as well as methods for diagnosing vAKI and iAKI. The methods are based on determining the levels of PAPPA2, NGAL, KRT20, or TACSTD2 protein in a sample from a patient, such as a urine sample. The present invention also provides a device and a diagnostics kit for determining whether a sample from a subject contains PAPPA2, NGAL, KRT20, or TACSTD2 protein.

11 Claims, 69 Drawing Sheets
(64 of 69 Drawing Sheet(s) Filed in Color)
Specification includes a Sequence Listing.

(56) References Cited

OTHER PUBLICATIONS

Aregger et al., "Identification of IGFBP-7 by urinary proteomics as a novel prognostic marker in early acute kidney injury," Kidney Int., 85(4), pp. 909-919 (2014).
Bagshaw et al., "Septic acute kidney injury in critically ill patients: clinical characteristics and outcomes," Clin. J. Am. Soc. Nephrol., 2(3), pp. 431-439 (2007).
Banay-Schwartz et al., "The pH dependence of breakdown of various purified brain proteins by cathepsin D preparations," Neurochem. Int., 7(4), pp. 607-614 (1985).
Basu et al., "Combining functional and tubular damage biomarkers improves diagnostic precision for acute kidney injury after cardiac surgery," J. Am. Coll. Cardiol., 64(25), pp. 2753-2762 (2014).
Basu et al., "Incorporation of biomarkers with the renal angina index for prediction of severe AKI in critically ill children," Clin. J. Am. Soc. Nephrol., 9(4), pp. 654-662 (2014).
Neuhofer and Beck, "Response of renal medullary cells to osmotic stress," Contrib. Nephrol., 148, pp. 21-34 (2005).
Belcher et al., "Kidney biomarkers and differential diagnosis of patients with cirrhosis and acute kidney injury," Hepatology, 60(2), pp. 622-632 (2014).
Bengatta et al., "MMP9 and SCF protect from apoptosis in acute kidney injury," J. Am. Soc. Nephrol., 20(4), pp. 787-797 (2009).
Benjamini and Hochberg, "Controlling the False Discovery Rate: A Practical and Powerful Approach to Multiple Testing," J. R. Statist. Soc. B, 57(1), pp. 289-300 (1995).
Bergler-Klein et al., "The long-term effect of simultaneous heart and kidney transplantation on native renal function," Transplantation, 71(11), pp. 1597-1600 (2001).
Bonventre, "Dedifferentiation and Proliferation of Surviving Epithelial Cells in Acute Renal Failure," J. Am. Soc. Nephrol., 14(Suppl. 1), pp. S55-S61 (2003).
Brenner and Berliner, "Relationship between extracellular volume and fluid reabsorption by the rat nephron," Am. J. Physiol., 217(1), pp. 6-12 (1969).
Brière et al., "Heterogeneous distribution of alkaline phosphatase and gamma-glutamyl transpeptidase in the mouse nephron," Acta Histochem., 74(1), pp. 103-108 (1984).
Chen et al., "SPD-a web-based secreted protein database," Nucleic Acids Research, 33(Database issue), pp. D169-173 (2005).
Chertow et al., "Acute kidney injury, mortality, length of stay, and costs in hospitalized patients," J. Am. Soc. Nephrol., 16, pp. 3365-3370 (2005).
Chin et al., "Microfluidics-based diagnostics of infectious diseases in the developing world," Nat. Med., 17, pp. 1015-1019 (2011).
Chin et al., "Mobile Device for Disease Diagnosis and Data Tracking in Resource-Limited Settings," Clin. Chem., 59, pp. 629-40 (2013).
Christians et al., "*Pappa2* deletion alters IGFBPs but has little effect on glucose disposal or adiposity," Growth Horm. IGF Res., 25(5), pp. 232-239 (2015).
Cockcroft and Gault, "Prediction of creatinine clearance from serum creatinine," Nephron, 16(1), pp. 31-41 (1976).
Cowley, Jr. et al., "Pappa2 is linked to salt-sensitive hypertension in Dahl S rats," Physiol. Genomics, 48(1), pp. 62-72 (2016).
Croft et al., "The Reactome pathway knowledgebase," Nucleic Acids Research, 42(Database issue) pp. D472-477 (2014).
Dennen et al., "Urine interleukin-6 is an early biomarker of acute kidney injury in children undergoing cardiac surgery," Crit. Care., 14:R181, 13 pages (2010).
di Mari et al., "MAPK activation determines renal epithelial cell survival during oxidative injury," Am. J. Physiol., 277(2 Pt 2), pp. F195-F203 (1999).
Dworniczak et al., "Inducible Cre/loxP Recombination in the Mouse Proximal Tubule," Nephron Exp. Nephrol., 106(1), e11-e20 (2007).
Feinstein et al., "Severe hyperuricemia in patients with volume depletion," Am. J. Nephrol., 4(2), pp. 77-80 (1984).
Flicek et al., "Ensembl 2014," Nucleic Acids Research, 42(Database issue), pp. D749-755 (2014).

Garner et al., "Detection of patients with acute kidney injury by the clinical laboratory using rises in serum creatinine: comparison of proposed definitions and a laboratory delta check," Ann. Clin. Biochem., 49(Pt 1), pp. 59-62 (2012).
Gauer et al., "IL-18 is expressed in the intercalated cell of human kidney," Kidney Int., 72(9), pp. 1081-1087 (2007).
Gault and Cockcroft, "Letter: Creatinine clearance and age," Lancet, 2(7935), pp. 612-613 (1975).
Gay et al., "Mouse TU tagging: a chemical/genetic intersectional method for purifying cell type-specific nascent RNA," Genes Dev., 27(1), pp. 98-115 (2013).
Gobé et al., "Cell survival or death in renal tubular epithelium after ischemia-reperfusion injury," Kidney Int., 56(4), pp. 1299-1304 (1999).
Goetz et al., "The Neutrophil Lipocalin NGAL Is a Bacteriostatic Agent that Interferes with Siderophore-Mediated Iron Acquisition," Molecular Cell, 10(5), pp. 1033-1043 (2002).
Goldfarb et al, "Contrast-Induced Acute Kidney Injury: Specialty-Specific Protocols for Interventional Radiology, Diagnostic Computed Tomography Radiology, and Interventional Cardiology," Mayo Clin. Proc., 84(2), pp. 170-179 (2009).
Goldfarb et al., "Compensated heart failure predisposes to outer medullary tubular injury: studies in rats," Kidney Int., 60(2), pp. 607-613 (2001).
Haase et al., "Subclinical AKI—an emerging syndrome with important consequences," Nat. Rev. Nephrol., 8(12), pp. 735-739 (2012).
Haase-Fielitz et al., "Neutrophil gelatinase-associated lipocalin as a biomarker of acute kidney injury: a critical evaluation of current status," Ann. Clin. Biochem., 51(Pt 3), pp. 335-351 (2014).
Heyman et al., "Cellular adaptive changes in AKI: mitigating renal hypoxic injury," Nephrol. Dial. Transplant., 27(5), pp. 1721-1728 (2012).
Hood et al., "Renal hemodynamics and limitations of creatinine clearance in determining filtration rate in glomerular disease," Scand. J. Urol. Nephrol., 5(2), pp. 154-161 (1971).
Hsu et al., "Community-based incidence of acute renal failure," Kidney Int., 72, pp. 208-12 (2007).
Humphreys et al., "Intrinsic epithelial cells repair the kidney after injury," Cell Stem Cell, 2(3), pp. 284-291 (2008).
Igarashi, "Kidney-specific gene targeting," J. Am. Soc. Nephrol., 15(8), pp. 2237-2239 (2004).
Inker et al., "Estimating glomerular filtration rate from serum creatinine and cystatin C," N. Engl. J. Med., 367(1), pp. 20-29 (2012).
International Society of Nephrology, "KDIGO Clinical Practice Guideline for Acute Kidney Injury," Kidney International Supplements, 2(Supplement 1), 141 pages (2012).
Jaffe, "Ueber den Niederschlag welchen Pikrinsäure in normalen Harn erzeugt and über eine neue reaction des Kreatinins," Z Physiol. Chem., 10, pp. 391-400 (1886).
Kanehisa et al., "KEGG: kyoto encyclopedia of genes and genomes," Nucleic Acids Research, 28(1), pp. 27-30 (2000).
Kimmel et al., "Nutrition, ageing and GFR: is age-associated decline inevitable?" Nephrol. Dial. Transplant., 11(Suppl 9) pp. 85-88 (1996).
Labban et al., "The role of kidney biopsy in heart transplant candidates with kidney disease," Transplantation, 89(7), pp. 887-893 (2010).
Laksanasopin et al., "A smartphone dongle for diagnosis of infectious diseases at the point of care," Sci. Transl. Med., 7, 273re1 pp. 1-9 (2015).
Laverty and Skadhauge, "Adaptive strategies for post-renal handling of urine in birds," Comp. Biochem. Physiology, Part A., 149(3), pp. 246-54 (2008).
Lee et al., "Distinct macrophage phenotypes contribute to kidney injury and repair," Journal of the American Society of Nephrology: JASN, 22(2), pp. 317-326 (2011).
Lee et al., "Effects of furosemide on renal calcium handling," Am. J. Physiol. Renal. Physiol., 293(4), pp. F1231-F1237 (2007).
Lin et al., "False-Positive Rate of AKI Using Consensus Creatinine-Based Criteria," Clin. J. Am. Soc. Nephroi., 10(10), pp. 1723-1731 (2015).

(56) References Cited

OTHER PUBLICATIONS

Macedo et al., "Fluid accumulation, recognition and staging of acute kidney injury in critically-ill patients," Crit. Care, 14:R82, 7 pages (2010).
Mandelbaum et al., "Outcome of critically ill patients with acute kidney injury using the AKIN criteria," Author Manuscript published in final edited form as: Crit. Care Med., 39(12), pp. 2659-2664, 16 pages (2011).
Mar et al., "Heterogeneity of epigenetic changes at ischemia/reperfusion- and endotoxin-induced acute kidney injury genes," Kidney Int., 88(4), pp. 734-744 (2015).
Mather and Pollock, "Glucose handling by the kidney," Kidney Int. Suppl., 79(120), p. S1-6 (2011).
Mehta et al., "Acute Kidney Injury Network: report of an initiative to improve outcomes in acute kidney injury," Critical Care, 11(2):R31, 8 pages (2007).
Mishra et al., "Identification of neutrophil gelatinase-associated lipocalin as a novel early urinary biomarker for ischemic renal injury," J. Am. Soc. Nephrol., 14, pp. 2534-2543 (2003).
Mishra et al., "Neutrophil gelatinase-associated lipocalin: A novel early urinary biomarker for cisplatin nephrotoxicity," Am. J. Nephrol., 24, pp. 307-315 (2004).
Moretti et al., "Androgens and body composition in the aging male," J. Endocrinol. Invest., 28(3 Suppl), pp. 56-64 (2005).
Mortazavi et al., "Mapping and quantifying mammalian transcriptomes by RNA-Seq," Nat. Methods, 5(7), pp. 621-628 (2008).
Murray et al., "Potential use of biomarkers in acute kidney injury: report and summary of recommendations from the 10th Acute Dialysis Quality Initiative consensus conference," Kidney Int., 85(3), pp. 513-521 (2014).
Musso et al., "Creatinine reabsorption by the aged kidney," Int Urol. Nephrol., 41(3), pp. 727-731 (2009).
Nejat et al., "Some biomarkers of acute kidney injury are increased in pre-renal acute injury," Kidney Int., 81(12), pp. 1254-1262 (2012).
Nickolas et al., "Diagnostic and Prognostic Stratification in the Emergency Department Using Urinary Biomarkers of Nephron Damage: A Multicenter Prospective Cohort Study," J. Am. Coll. Cardiol., 59(3), pp. 246-255 (2012).
Nickolas et al., "Sensitivity and Specificity of a Single Emergency Department Measurement of Urinary Neutrophil Gelatinase-Associated Lipocalin for Diagnosing Acute Kidney Injury," Annals of Internal Medicine, 148(11), pp. 810-819 (2008).
Paragas et al., "The Ngal reporter mouse detects the response of the kidney to injury in real time," Author Manuscript published in final edited form as: Nat. Med., 17(2), pp. 216-222, 18 pages (2011).
Paragas et al.,"α-Intercalated cells defend the urinary system from bacterial infection," The Journal of Clinical Investigation, 124(7), pp. 2963-2976 (2014).
Parikh and Coca, "Acute kidney injury: defining prerenal azotemia in clinical practice and research," Nat. Rev. Nephrol., 6(11), pp. 641-642 (2010).
Parravicini et al., "Urinary Neutrophil Gelatinase-Associated Lipocalin Is a Promising Biomarker for Late Onset Culture-Positive Sepsis in Very Low Birth Weight Infants," Pediatr. Res., 67(6), pp. 636-640 (2010).
Perazella, "Onco-Nephrology: Renal Toxicities of Chemotherapeutic Agents," Clin. J. Am. Soc. Nephrol., 7(10), pp. 1713-1721 (2012).
Ramcharan and Matas, "Long-term (20-37 years) follow-up of living kidney donors," Am. J. Transplant., 2(10), pp. 959-964 (2002).
Rewa and Bagshaw, "Acute kidney injury-epidemiology, outcomes and economics," Nat. Rev. Nephrol., 10, pp. 193-207 (2014).
Robinson et al., "SplicerAV: a tool for mining microarray expression data for changes in RNA processing," BMC Bioinformatics, 11(108), 16 pages (2010).
Schaeffner et al., "Two novel equations to estimate kidney function in persons aged 70 years or older," Ann, Intern. Med., 157(7), pp. 471-481 (2012).
Schrier, "Diagnostic value of urinary sodium, chloride, urea, and flow," J. Am. Soc. Nephrol., 22, pp. 1610-1613 (2011).
Shahrbaf and Assadi, "Drug-induced renal disorders," J. Ren. Inj. Prey., 4(3), pp. 57-60 (2015).
Sharma et al., "Renal functional reserve and renal recovery after acute kidney injury," Nephron. Clin. Pract., 14;127(1-4) pp. 94-100 (2014).
Siew et al., "Predictors of Recurrent AKI," J. Am. Soc. Nephrol., 27, pp. 1190-1200 (2015).
Singer et al., "Urinary neutrophil gelatinase-associated lipocalin distinguishes pre-renal from intrinsic renal failure and predicts outcomes," Kidney international, 80, pp. 405-414 (2011).
Sise et al., "Urine neutrophil gelatinase-associated lipocalin identifies unilateral and bilateral urinary tract obstruction," Nephrol. Dial. Transplant., 26(12), pp. 4132-4135 (2011).
Sjöström et al., "Extensive tubular secretion and reabsorption of creatinine in humans," Scand. J. Urol. Nephrol., 22(2), pp. 129-131 (1988).
Skorecki and Brenner, "Body fluid homeostasis in man: A contemporary overview," Am. J. Med., 70(1), pp. 77-88 (1981).
Smith, "The fate of sodium and water in the renal tubules," Bull NY Acad. Med., 35(5), pp. 293-316 (1959).
Subramanian et al., "Gene set enrichment analysis: a knowledge-based approach for interpreting genome-wide expression profiles," Proc. Natl. Acad. Sci. USA, 102(43), pp. 15545-15550 (2005).
Sutherland et al., "AKI in hospitalized children: comparing the pRIFLE, AKIN, and KDIGO definitions," Clin. J. Am. Soc. Nephrol., 10(4), pp. 554-561 (2015).
Svara et al., "Distribution and amount of cathepsin B in gentamicin-induced acute kidney injury in rats," Pol. J. Vet. Sci., 13(1), pp. 75-82 (2010).
Tarca et al., "A novel signaling pathway impact analysis," Bioinformatics, 25(1), pp. 75-82 (2009).
Trapnell et al., "TopHat: discovering splice junctions with RNA-Seq," Bioinformatics, 25(9), pp. 1105-1111 (2009).
Trapnell et al., "Transcript assembly and quantification by RNA-Seq reveals unannotated transcripts and isoform switching during cell differentiation," Nat. Biotechnol., 28(5), pp. 511-515 (2009).
U.S. Department of Health & Human Services, Centers for Disease Control and Prevention, National Center for Health Statistics: Emergency Department Visits, <http://www.cdc.gov/nchs/fastats/emergency-department.htm>, 3 pages, Page last updated: May 3, 2017.
Uchino et al., "Transient azotaemia is associated with a high risk of death in hospitalized patients," Nephrol. Dial. Transplant., 25(6), pp. 1833-1839 (2010).
Van Sant et al., "A phylogenetic approach to total evaporative water loss in mammals," Physiol. Biochem. Zool., 85(5), pp. 526-532 (2012).
Vanmassenhove et al., "Urinary and serum biomarkers for the diagnosis of acute kidney injury: an in-depth review of the literature," Nephrol. Dial. Transplant., 28(2), pp. 254-273 (2013).
Vicente-Vicente et al., "Increased urinary excretion of albumin, hemopexin, transferrin and VDBP correlates with chronic sensitization to gentamicin nephrotoxicity in rats," Toxicology, 304, pp. 8391 (2013).
Yan et al., "Involvement of pregnancy-associated plasma protein-A2 in insulin-like growth factor (IGF) binding protein-5 proteolysis during pregnancy: a potential mechanism for increasing IGF bioavailability," J. Clin. Endocrinol. Metab., 95(3), pp. 1412-1420 (2010).
Yuen et al., "Ischemic and nephrotoxic acute renal failure are distinguished by their broad transcriptomic responses," Author Manuscript published in final edited form as: Physiol. Genomics., 25(3), pp. 375-386, 30 pages (2006).
Zager, "Alterations of intravascular volume: influence on renal susceptibility to ischemic injury," J. Lab Clin. Med., 108(1), pp. 60-69 (1986).
FDA, "FDA allows marketing of the first test to assess risk of developing acute kidney injury," Press Announcements, 4 pages (Sep. 5, 2014) <https://www.ptcommunity.com/news/20140907/fda-allows-marketing-first-test-assess-risk-developing-acute-kidney-injury>.

(56) References Cited

OTHER PUBLICATIONS

National Institute of Diabetes and Digestive and Kidney Diseases (NIDDK), "Kidney Disease Statistics for the United States" 11 pages (Dec. 2016) <https://www.niddk.nih.gov/health-information/health-statistics/kidney-disease>.

Philip R. Lee Institute for Health Policy Studies, "ICU Outcomes," 83 pages (retrieved online (2018) <https://healthpolicy.ucsf.edu/icu-outcomes>.

Au et al., "Urinary Neutrophil Gelatinase-Associated Lipocalin (NGAL) Distinguishes Sustained from Transient Acute Kidney Injury After General Surgery," Kidney International Reports, 1, pp. 3-9 (2016).

Gámez-Valero et al., "Urinary extracellular vesicles as source of biomarkers in kidney diseases," Frontiers in Immunology, 6(6), pp. 1-10 (Jan. 2015).

Kløverpris et al., "A robust immunoassay for pregnancy-associated plasma protein-A2 based on analysis of circulating antigen: establishment of normal ranges in pregnancy", Molecular Human Reproduction, 19(11), pp. 756-763 (2013).

Nishizawa et al., "Increased levels of pregnancy-associated plasma protein-A2 in the serum of pre-eclamptic patients," Molecular Human Reproduction, 14(10), pp. 595-602 (2008).

Supplementary European Search Report for European Patent Application No. 16836016 dated Dec. 14, 2018 (10 pages).

Xu et al., "Unique Transcriptional Programs Identify Subtypes of AKI," Journal of the American Society of Nephrology, 28(6) pp. 1729-1740 (2016).

Aregger, F et al., "Urinary proteomics before and after extracorporeal circulation in patients with and without acute kidney injury", Journal of Thoracic and Cardiovascular Surgery, 139(3):692-700, Mar. 2010 (9 pages).

Baron, D., et al., "A common gene signature across multiple studies relate biomarkers and functional regulation in tolerance to renal allograft", Kidney International, 87:984-995, published online Jan. 28, 2015 (12 pages).

De Loor, J., et al., "How has urinary proteomics contributed to the discovery of early biomarkers of acute kidney injury?", Expert Review of Proteomics, 11 (4):415-424, published online Jun. 25, 2014 (11 pages).

Grigoryev, D.N., et al., "The Local and Systemic Inflammatory Transcriptome after Acute Kidney Injury", J Am Soc Nephrol, 19:547-558, doi:10.1681/ASN.2007040469, 2008 (12 pages).

Haase, M., et al., "Accuracy of Neutrophil Gelatinase-Associated Lipocalin (NGAL) in Diagnosis and Prognosis in Acute Kidney Injury: A Systematic Review and Meta-analysis", American Journal of Kidney Diseases, 54(6):1012-1024, Dec. 2009 (13 pages).

Ho, J et al., "Mass Spectrometry-Based Proteomic Analysis of Urine in Acute Kidney Injury Following Cardiopulmonary Bypass: A Nested Case-Control Study", American Journal of Kidney Diseases, 53(4):584-595, Apr. 2009 (12 pages).

Ho, J., et al., "Urinary Hepcidin-25 and Risk of Acute Kidney Injury Following Cardiopulmonary Bypass", Clin J. Am Soc Nephrol, 6:2340-2346, doi: 10.2215/CJN.01000211, Oct. 2011 (7 pages).

Jiang, S., et al., "Chapter 15: The Application of Urinary Proteomics for the Detection of Biomarkers of Kidney Diseases", in *Urine Proteomics in Kidney Disease Biomarker Discovery, Advances in Experimental Medicine and Biology*, Gao, Editor, Book 845, Springer, New York, pp. 151-165, 2015 (15 pages).

Kashani, K., et al., "Discovery and validation of cell cycle arrest biomarkers in human acute kidney injury", <URL:http://ccforum.com/content/17/1/R25, Critical Care, 17:R25, 2013 (12 pages).

Konvalinka, A., et al., "Searching for New Biomarkers of Renal Diseases through Proteomics", Clinical Chemistry, 58(2):353-365, DOI: 10.1373/clinchem.2011.165969, 2012 (13 pages).

Kwon, S.-H., et al., "Intercellular Transfer of GPRC5B via Exosomes Drives HGF-Mediated Outward Growth", <URL: http://dx.doi.Org/10.1016/j.cub.2013.12.010>, Current Biology, 24(2): 199-204, Jan. 20, 2014 (6 pages).

Masson, S., et al., "Circulating presepsin (soluble CD14 subtype) as a marker of host response in patients with severe sepsis or septic shock: data from the multicenter, randomized ALBIOS trial", Intensive Care Med, 41:12-20, Doi 10.1007/S00134-014-3514-2, published online Oct. 16, 2014 (9 pages).

Mittwede, P.N., et al., "A novel experimental model of orthopedic trauma with acute kidney injury in obese Zucker rats", Physiological Reports, 1(5):e00097, doi:10.1002/phy2.97, 2013 (9 pages).

Oh, Y., et al., "Synthesis and Characterization of Insulin-like Growth Factor-binding Protein (IGFBP)-7", The Journal of Biological Chemistry, 271(48):30322-30325, doi:10.1074/jbc.271.48.30322, Nov. 29, 1996 (5 pages).

Palmer, M.B., et al., "Quantification and localization of M2 macrophages in human kidneys with acute tubular injury", International Journal of Nephrology and Renovascular Disease, 7:415-419, 2014 (5 pages).

Pan, J. S.-C., et al., "Stanniocalcin-1 Inhibits Renal Ischemia/Reperfusion Injury via an AMP-Activated Protein Kinase-Dependent Pathway", <URL:http://www.ncbi.nlm.nih.gov/pmc/articles/PMC4310644/?report=printable> [accessed Apr. 22, 2021], J Am Soc Nephrol, 26(2):364-378, doi: 10.1681/ASN.2013070703: published online Jul. 10, 2014 (31 pages).

Parikh, C.R., et al., "Urine IL-18 Is an Early Diagnostic Marker for Acute Kidney Injury and Predicts Mortality in the Intensive Care Unit", Journal American Society of Nephrology, 16:3046-3052, DOI: 10.1681/ASN.2005030236, Nov. 2005 (8 pages).

Ranganathan, P., et al., "Semaphorin 3A inactivation suppresses ischemia-reperfusion-induced inflammation and acute kidney injury", Am J Physiol Renal Physiol, 307:F183-F194, doi:10.1152/ajprenal.00177.2014, May 14, 2014 (12 pages).

Schiffl, H. and Lang, S.M., "Update on Biomarkers of Acute Kidney Injury: Moving Closer to Clinical Impact?", Mol. Diagn Ther., 16(4): 199-207, 2012 (9 pages).

Srisawat, N., et al., "Urinary Biomarkers and Renal Recovery in Critically Ill Patients with Renal Support", Clin. J. Am. Soc. Nephrol., 6:1815-1823, doi: 10.2215/CJN.11261210, Aug. 2011 (9 pages).

Vuaden, F.C., et al., "Endotoxin-induced effects on nucleotide catabolism in mouse kidney", European Journal of Pharmacology, 674:422-429, published online Nov. 12, 2011 (8 pages).

Waikar, S.S., et al., "Normalization of urinary biomarkers to creatinine during changes in glomerular filtration rate", Kidney International, 78:486-494. doi:10.1038/ki.2010.165, published online Jun. 16, 2010 (9 pages).

Wang, Z and Li, M., "Chapter 10: Evolution of the Urinary Proteome During Human Renal Development and Maturation", in *Urine Proteomics in Kidney Disease Biomarker Discovery, Advances in Experimental Medicine and Biology*, Gao, Editor, Book 845, Springer, New York, pp. 95-101, 2015 (7 pages).

Witzgall, R., et al., "Localization of Proliferating Cell Nuclear Antigen, Vimentin, c-Fos, and Clusterin in the Postischemic Kidney", <URL:http://www.jci.org; http://dx.doi.Org/10.1172/JC1117214> [accessed Feb. 26, 2015], J. Clin. Invest., 93:2175-2188, May 1994 (14 pages).

Yu, B., et al., "The Changes of filamin distribution in renal tubular epithelial cells during kidney ischemia/reperfusion injury in neonatal rats", Sichuan Da Xue Xue Bao Yi Xue Ban, 34(3):445-448, Jul. 2003 (1 page)—English Abstract Only.

Zhang, G., and Eddy, A., "Urokinase and its Receptors in Chronic Kidney Disease", Author Manuscript published in final edited form as Front Biosci., 13:5462-5478, Feb. 2008 (29 pages).

Zhao, Z-G., et al., "Normal mesenteric lymph ameliorates acute kidney injury following lipopolysaccharide challenge in mice", Renal Failure, 36(8):1304-1309, DOI: 10.3109/0886022X.2014.938585, published online Jul. 14, 2014 (7 pages).

Zhu, D, et al., "Acute kidney injury in Chinese patients with lupus nephritis: a large cohort study from a single center", Lupus, 20:1557-1565, doi: 10.1177/0961203311417035,2011 (9 pages).

* cited by examiner

* p<0.01 vs. Control
‡ p<0.05 vs. Control
† p<0.01 vs. Ischemia

FIG. 9A
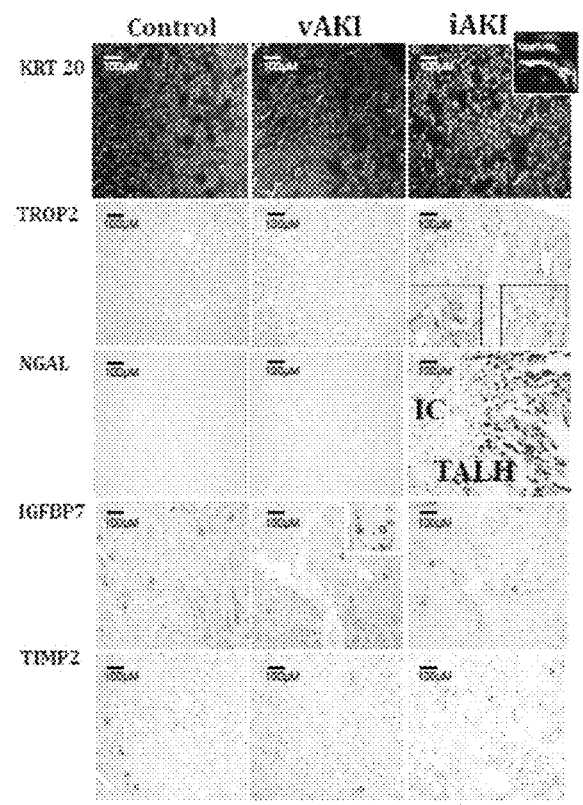
FIG. 9B
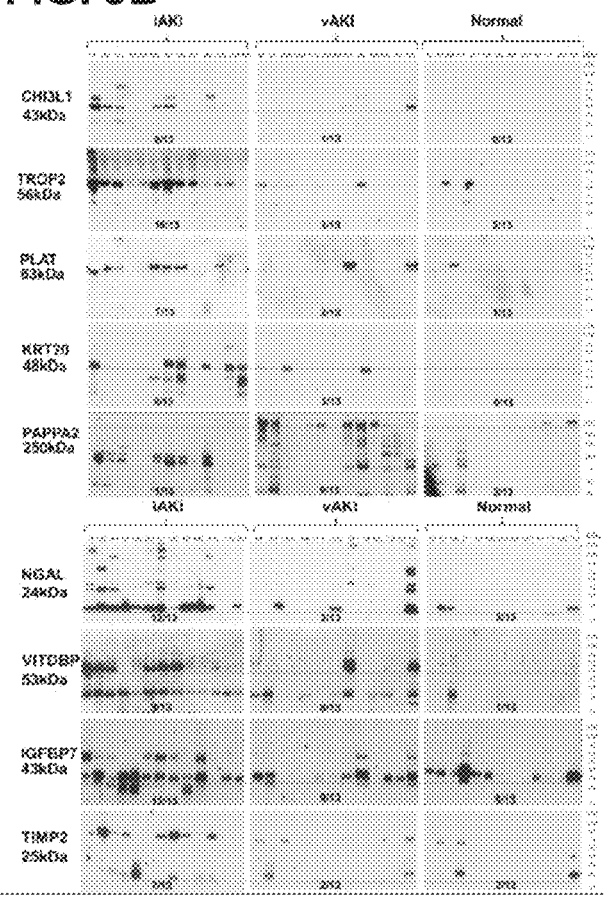
FIG. 9C

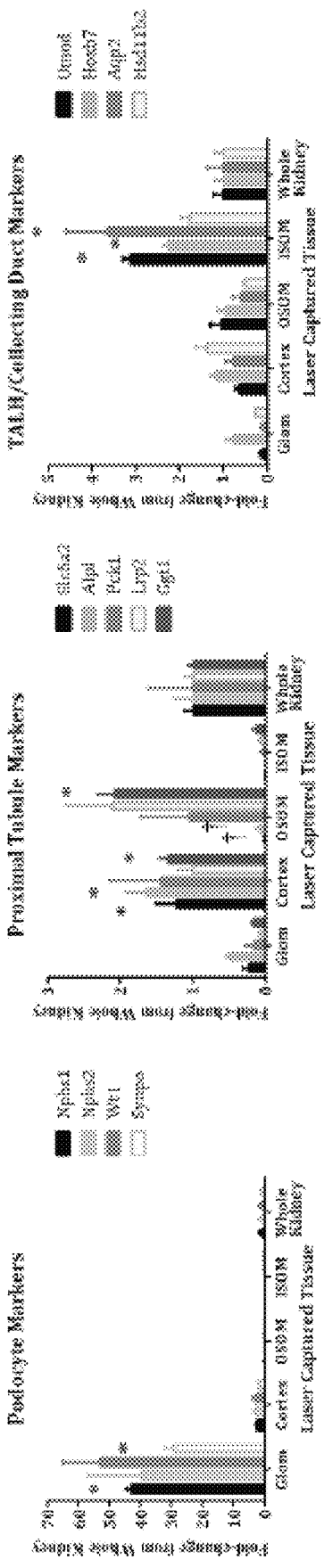
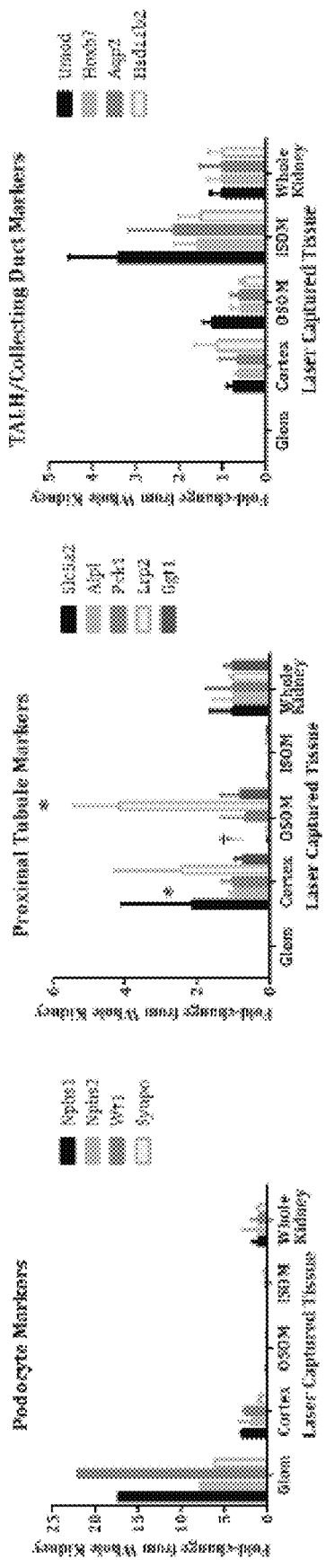
FIG. 11A
FIG. 11B

|  | Control | iAKI: Bilateral Ischemia (24Hr) | pAKI: Volume Depletion (72Hr) |
|---|---|---|---|
| Body weight loss | 0% | 10.9% (NS) | 21.1% |
| Crea (mg/dL) | 0.20 ± 0 | 0.30 ± 0.07 * | 0.38 ± 0.12 * |
| BUN (mg/dL) | 17.3 ± 6.5 | 24.7 ± 10.5 | 44.9 ± 13.7 *† |
| Na (mmol/L) | 146.3 ± 0.6 | 147 ± 6.4 | 159.6 ± 3.5 *† |
| Hct (%PCV) | 37.7 ± 2.1 | 34.7 ± 4.1 | 46 ± 4.3 *† |
| Hgb (g/dL) | 12.8 ± 0.7 | 11.8 ± 1.4 | 15.6 ± 1.5 *† |

FPKM (RNA-seq)

Real-time qPCR

| | | | | | |
|---|---|---|---|---|---|
| Spp2 | | NS | ISOM | 7.77 | 2.83E-05 |
| Arhgef37 | | NS | ISOM | 2.87 | 2.91E-05 |
| Nxph4 | | NS | Glom | 61.30 | 2.95E-05 |
| Slc22a8 | | NS | ISOM | 6.23 | 2.97E-05 |
| Gas7 | | NS | Cortex | 2.05 | 3.05E-05 |
| Gm1332 | | NS | ISOM | 8.44 | 3.08E-05 |
| Ucp1 | | NS | Cortex | 31.77 | 3.27E-05 |
| H6st1h2bb | | NS | ISOM | 5.47 | 3.48E-05 |
| Ebox2 | | NS | ISOM | 2.03 | 3.58E-05 |
| Abca1 | | NS | Cortex | 2.18 | 5.01E-05 |
| Mamu3 | | NS | Cortex | 2.04 | 5.08E-05 |
| Tmem27 | | NS | ISOM | 2.37 | 5.38E-05 |
| Cyp2d26 | | NS | ISOM | 5.02 | 5.44E-05 |
| Igfbp5 | | NS | ISOM | 2.34 | 5.94E-05 |
| Nrap | | NS | ISOM | 3.68 | 5.95E-05 |
| Acmsd | | NS | ISOM | 7.75 | 8.84E-05 |
| Gpr5b | | NS | ISOM | 2.38 | 9.88E-05 |

FIG. 28 CONTINUED

| GENE | sAKI - ISCHEMIA REPERFUSION | | | pAKI - VOLUME DEPLETION | | | EXPRESSION PATTERN (FPKM) | | | | | | | | | | | |
|---|---|---|---|---|---|---|---|---|---|---|---|---|---|---|---|---|---|---|
| | Region with Most Significant Fold Change | Fold Change | P-value | Region with Most Significant Fold Change | Fold Change | P-value | Control | | | | Ischemia | | | | Volume Depletion | | | |
| | | | | | | | Gl | Co | OM | IM | Gl | Co | OM | IM | Gl | Co | OM | IM |
| Plat | OSOM | 28.47 | 1.75E-36 | | | NS | | | | | | | | | | | | |
| Cd68 | OSOM | 17.29 | 1.92E-33 | | | NS | | | | | | | | | | | | |
| Il34 | OSOM | 9.51 | 5.61E-31 | | | NS | | | | | | | | | | | | |
| Rdh11 | OSOM | 6.30 | 4.58E-30 | | | NS | | | | | | | | | | | | |
| Anxa3 | OSOM | 10.57 | 2.88E-29 | | | NS | | | | | | | | | | | | |
| Steap1 | OSOM | 48.10 | 5.67E-29 | | | NS | | | | | | | | | | | | |
| Pvr | OSOM | 9.16 | 6.64E-29 | | | NS | | | | | | | | | | | | |
| Spp1 | OSOM | 49.50 | 3.44E-27 | | | NS | | | | | | | | | | | | |
| Lgals3 | OSOM | 14.52 | 1.58E-26 | | | NS | | | | | | | | | | | | |
| Cxcl1 | OSOM | 219.95 | 6.09E-26 | | | NS | | | | | | | | | | | | |
| Gale | OSOM | 6.79 | 1.63E-25 | | | NS | | | | | | | | | | | | |
| Nop56 | OSOM | 3.59 | 2.95E-25 | | | NS | | | | | | | | | | | | |
| Cbx3 | Cortex | 11.12 | 3.17E-25 | | | NS | | | | | | | | | | | | |
| Tubb5 | OSOM | 5.11 | 1.29E-24 | | | NS | | | | | | | | | | | | |
| Rrad | OSOM | 12.88 | 1.07E-23 | | | NS | | | | | | | | | | | | |
| Anxa2 | OSOM | 9.54 | 1.42E-23 | | | NS | | | | | | | | | | | | |
| Plaur | OSOM | 18.74 | 1.65E-23 | | | NS | | | | | | | | | | | | |
| Cd14 | OSOM | 15.97 | 8.42E-23 | | | NS | | | | | | | | | | | | |
| Srxn1 | OSOM | 7.83 | 9.02E-23 | | | NS | | | | | | | | | | | | |
| Fzr1 | OSOM | 5.58 | 3.02E-22 | | | NS | | | | | | | | | | | | |
| Ppa1 | ISOM | 2.71 | 3.78E-22 | | | NS | | | | | | | | | | | | |
| Tmem43 | OSOM | 3.12 | 5.03E-22 | | | NS | | | | | | | | | | | | |
| Lcn2 | OSOM | 214.29 | 6.10E-22 | | | NS | | | | | | | | | | | | |
| Sptlc2 | OSOM | 3.43 | 7.97E-22 | | | NS | | | | | | | | | | | | |
| Chrnb1 | OSOM | 5.44 | 8.55E-22 | | | NS | | | | | | | | | | | | |
| Tuba1b | OSOM | 3.75 | 1.84E-21 | | | NS | | | | | | | | | | | | |
| Nans | OSOM | 3.28 | 4.22E-21 | | | NS | | | | | | | | | | | | |
| Arnt2 | OSOM | 4.80 | 8.39E-21 | | | NS | | | | | | | | | | | | |
| Slc25a24 | OSOM | 9.98 | 1.03E-20 | | | NS | | | | | | | | | | | | |
| Ngf | OSOM | 6.81 | 1.26E-20 | | | NS | | | | | | | | | | | | |
| Ywhah | OSOM | 3.58 | 2.83E-20 | | | NS | | | | | | | | | | | | |
| Nup93 | OSOM | 4.39 | 3.04E-20 | | | NS | | | | | | | | | | | | |
| Sfn | OSOM | 16.45 | 4.21E-20 | | | NS | | | | | | | | | | | | |
| Lrg1 | OSOM | 68.88 | 4.54E-20 | | | NS | | | | | | | | | | | | |
| Cxadr | OSOM | 3.45 | 6.40E-20 | | | NS | | | | | | | | | | | | |
| Tmd2 | OSOM | 44.47 | 1.03E-19 | | | NS | | | | | | | | | | | | |
| Gdf15 | OSOM | 25.80 | 3.15E-19 | | | NS | | | | | | | | | | | | |
| Sdc4 | OSOM | 3.81 | 5.16E-19 | | | NS | | | | | | | | | | | | |
| Slc3a2 | OSOM | 3.80 | 8.33E-19 | | | NS | | | | | | | | | | | | |
| Car13 | OSOM | 17.74 | 8.09E-19 | | | NS | | | | | | | | | | | | |
| Tuba1c | OSOM | 4.12 | 1.54E-18 | | | NS | | | | | | | | | | | | |
| Gprc5a | OSOM | 13.31 | 1.73E-18 | | | NS | | | | | | | | | | | | |
| Gch1 | OSOM | 12.74 | 3.22E-18 | | | NS | | | | | | | | | | | | |
| Prr15 | ISOM | 6.81 | 3.48E-18 | | | NS | | | | | | | | | | | | |
| Aldh18a1 | OSOM | 8.50 | 3.64E-18 | | | NS | | | | | | | | | | | | |
| Vasp | OSOM | 3.24 | 5.89E-18 | | | NS | | | | | | | | | | | | |
| Rgs19 | OSOM | 3.82 | 8.37E-18 | | | NS | | | | | | | | | | | | |
| Slc2a1 | OSOM | 3.41 | 1.13E-17 | | | NS | | | | | | | | | | | | |
| Tes | OSOM | 3.85 | 1.15E-17 | | | NS | | | | | | | | | | | | |
| Lhfpl2 | OSOM | 6.33 | 1.49E-17 | | | NS | | | | | | | | | | | | |
| Litaf | OSOM | 4.97 | 2.34E-17 | | | NS | | | | | | | | | | | | |
| Slc7a1 | OSOM | 3.54 | 2.97E-17 | | | NS | | | | | | | | | | | | |
| Myof | OSOM | 5.31 | 3.24E-17 | | | NS | | | | | | | | | | | | |
| Nop58 | OSOM | 3.06 | 6.52E-17 | | | NS | | | | | | | | | | | | |
| Smad2 | OSOM | 2.32 | 6.54E-17 | | | NS | | | | | | | | | | | | |
| Rcc1 | OSOM | 2.87 | 1.75E-16 | | | NS | | | | | | | | | | | | |
| Acsl5 | ISOM | 2.40 | 1.84E-16 | | | NS | | | | | | | | | | | | |
| Bag2 | OSOM | 4.49 | 1.92E-16 | | | NS | | | | | | | | | | | | |
| Pold4 | OSOM | 3.37 | 2.21E-16 | | | NS | | | | | | | | | | | | |
| Defb1 | OSOM | 5.79 | 2.51E-16 | | | NS | | | | | | | | | | | | |
| Pea15a | OSOM | 4.45 | 2.60E-16 | | | NS | | | | | | | | | | | | |
| Rin1 | OSOM | 10.68 | 2.66E-16 | | | NS | | | | | | | | | | | | |
| Smox | OSOM | 8.72 | 3.06E-16 | | | NS | | | | | | | | | | | | |
| Vcan1 | OSOM | 20.54 | 3.07E-16 | | | NS | | | | | | | | | | | | |
| Spcs3 | OSOM | 2.99 | 3.39E-16 | | | NS | | | | | | | | | | | | |
| Cks1b | OSOM | 6.37 | 4.00E-16 | | | NS | | | | | | | | | | | | |
| Arpc1b | OSOM | 3.86 | 5.35E-16 | | | NS | | | | | | | | | | | | |
| Ankrd1 | OSOM | 19.44 | 5.83E-16 | | | NS | | | | | | | | | | | | |
| Plp2 | OSOM | 4.25 | 6.89E-16 | | | NS | | | | | | | | | | | | |
| Tex10 | OSOM | 2.34 | 7.08E-16 | | | NS | | | | | | | | | | | | |
| Kif6 | OSOM | 5.90 | 7.75E-16 | | | NS | | | | | | | | | | | | |
| Rras2 | OSOM | 4.56 | 8.49E-16 | | | NS | | | | | | | | | | | | |

| | | | | | |
|---|---|---|---|---|---|
| Tnbim1 | OSOM | 2.31 | 1.3E-12 | NS | |
| Nup62 | OSOM | 2.09 | 1.31E-12 | NS | |
| Reit1 | OSOM | 3.75 | 1.41E-12 | NS | |
| Alcam | OSOM | 2.74 | 1.77E-12 | NS | |
| Lig1 | OSOM | 4.37 | 1.88E-12 | NS | |
| Gadd45a | OSOM | 5.90 | 1.92E-12 | NS | |
| Fgg | OSOM | 108.21 | 1.95E-12 | NS | |
| Cpne8 | OSOM | 3.52 | 2E-12 | NS | |
| Smpd3b | OSOM | 13.27 | 2.25E-12 | NS | |
| Golm1 | OSOM | 4.81 | 2.31E-12 | NS | |
| Rrp8 | OSOM | 2.11 | 2.35E-12 | NS | |
| Kctd1 | OSOM | 6.25 | 2.47E-12 | NS | |
| Mettl21a | OSOM | 2.58 | 2.5E-12 | NS | |
| Tmem173 | OSOM | 7.74 | 2.5E-12 | NS | |
| Maff | OSOM | 7.51 | 2.5E-12 | NS | |
| Plscr1 | OSOM | 3.08 | 2.58E-12 | NS | |
| Tmem171 | OSOM | 3.87 | 2.65E-12 | NS | |
| C3 | OSOM | 13.62 | 2.68E-12 | NS | |
| Pcna | OSOM | 2.82 | 2.88E-12 | NS | |
| Fen1 | OSOM | 3.58 | 2.89E-12 | NS | |
| A130040M12Rik | OSOM | 28.06 | 2.89E-12 | NS | |
| Rad18 | OSOM | 6.48 | 3.04E-12 | NS | |
| Eif6 | OSOM | 3.25 | 3.34E-12 | NS | |
| Ptpn12 | OSOM | 2.53 | 3.43E-12 | NS | |
| Kcnh1 | ISOM | 16.14 | 3.48E-12 | NS | |
| Hsd3b7 | OSOM | 2.31 | 3.63E-12 | NS | |
| Npl | OSOM | 4.81 | 3.68E-12 | NS | |
| Gmds | ISOM | 2.40 | 3.8E-12 | NS | |
| Serpina3n | Cortex | 24.04 | 3.81E-12 | NS | |
| Msn | OSOM | 3.83 | 4.54E-12 | NS | |
| Btg1 | OSOM | 2.72 | 4.58E-12 | NS | |
| Mboat1 | OSOM | 6.21 | 5.17E-12 | NS | |
| Ifngr2 | OSOM | 2.75 | 5.58E-12 | NS | |
| Nupr1 | OSOM | 6.53 | 5.63E-12 | NS | |
| Dnmt1 | OSOM | 3.50 | 6.2E-12 | NS | |
| Krt8 | OSOM | 4.08 | 6.21E-12 | NS | |
| Pgm1 | OSOM | 3.46 | 6.69E-12 | NS | |
| Tnfaip2 | OSOM | 2.82 | 7.82E-12 | NS | |
| Wdr72 | OSOM | 4.46 | 8.03E-12 | NS | |
| Gnl3 | OSOM | 2.51 | 8.13E-12 | NS | |
| Cish | OSOM | 10.74 | 8.38E-12 | NS | |
| Rbc2 | OSOM | 2.70 | 8.86E-12 | NS | |
| Itgam | OSOM | 6.80 | 9.05E-12 | NS | |
| Lsr | OSOM | 2.25 | 9.24E-12 | NS | |
| Dusp5 | OSOM | 53.86 | 9.66E-12 | NS | |
| B4galt6 | OSOM | 2.81 | 9.98E-12 | NS | |
| Vopp1 | OSOM | 3.02 | 1.07E-11 | NS | |
| G6pdx | Cortex | 2.58 | 1.14E-11 | NS | |
| B4galnt1 | OSOM | 3.85 | 1.18E-11 | NS | |
| Mcm2 | OSOM | 4.56 | 1.22E-11 | NS | |
| Gm6682 | OSOM | 5.55 | 1.22E-11 | NS | |
| Clu | OSOM | 32.67 | 1.24E-11 | NS | |
| Xdh | OSOM | 4.79 | 1.25E-11 | NS | |
| Nrg1 | OSOM | 10.45 | 1.3E-11 | NS | |
| Sntb2 | OSOM | 3.29 | 1.38E-11 | NS | |
| Gpm6b | OSOM | 3.09 | 1.45E-11 | NS | |
| 5830416P10Rik | OSOM | 45.80 | 1.52E-11 | NS | |
| Slc7a5 | OSOM | 9.54 | 1.57E-11 | NS | |
| Tubb6 | OSOM | 4.72 | 1.6E-11 | NS | |
| Cxcl2 | Cortex | 428.35 | 1.69E-11 | NS | |
| Dnajc2 | OSOM | 2.15 | 1.7E-11 | NS | |
| Mettl1 | ISOM | 3.89 | 1.72E-11 | NS | |
| Wars | OSOM | 2.53 | 1.76E-11 | NS | |
| Akap2 | OSOM | 3.35 | 1.82E-11 | NS | |
| Adm2 | ISOM | 38.36 | 1.85E-11 | NS | |
| Emp3 | OSOM | 4.89 | 2.01E-11 | NS | |
| Mall | OSOM | 14.90 | 2.13E-11 | NS | |
| Il11 | OSOM | 258.12 | 2.22E-11 | NS | |
| Tgfb1 | OSOM | 3.31 | 2.3E-11 | NS | |
| Myc | OSOM | 14.19 | 2.3E-11 | NS | |
| Eno1 | OSOM | 5.63 | 2.31E-11 | NS | |
| Saa1 | OSOM | 728.38 | 2.71E-11 | NS | |
| Sema3c | Cortex | 3.28 | 2.74E-11 | NS | |
| Ppm1j | OSOM | 16.42 | 2.86E-11 | NS | |
| Plin2 | Cortex | 7.24 | 3.03E-11 | NS | |

| | | | | | |
|---|---|---|---|---|---|
| Pwp2 | OSOM | 2.38 | 2.58E-09 | NS | |
| Pogk | OSOM | 2.19 | 2.59E-09 | NS | |
| Ywhag | OSOM | 2.35 | 2.59E-09 | NS | |
| Slc4a11 | OSOM | 3.41 | 2.68E-09 | NS | |
| Serpine1 | OSOM | 20.06 | 2.69E-09 | NS | |
| Dysf | OSOM | 2.86 | 2.69E-09 | NS | |
| Csdx | OSOM | 2.58 | 2.71E-09 | NS | |
| Etv4 | OSOM | 86.58 | 2.79E-09 | NS | |
| Rrp1b | OSOM | 2.73 | 2.83E-09 | NS | |
| Fgb | OSOM | 1396.00 | 2.85E-09 | NS | |
| Eroc1 | OSOM | 2.91 | 2.85E-09 | NS | |
| Gpr110 | OSOM | 248.94 | 3.11E-09 | NS | |
| Grwd1 | OSOM | 2.82 | 3.13E-09 | NS | |
| Dusp8 | OSOM | 5.89 | 3.24E-09 | NS | |
| Syt12 | OSOM | 3.67 | 3.31E-09 | NS | |
| Flot1 | Cortex | 2.86 | 3.39E-09 | NS | |
| Impdh1 | OSOM | 2.65 | 3.43E-09 | NS | |
| Mvp | OSOM | 3.26 | 3.73E-09 | NS | |
| Fam203a | OSOM | 2.51 | 3.87E-09 | NS | |
| Serpine2 | OSOM | 2.22 | 3.91E-09 | NS | |
| Chka | OSOM | 2.37 | 4.17E-09 | NS | |
| Dspp | OSOM | 173.09 | 4.22E-09 | NS | |
| Heatr1 | OSOM | 2.36 | 4.28E-09 | NS | |
| Wdr1 | OSOM | 2.28 | 4.49E-09 | NS | |
| Glipr2 | OSOM | 12.28 | 4.55E-09 | NS | |
| Btg2 | OSOM | 8.13 | 4.6E-09 | NS | |
| Pcsk9 | OSOM | 8.39 | 4.6E-09 | NS | |
| Abpb | OSOM | 16.48 | 4.71E-09 | NS | |
| Orc2 | OSOM | 2.01 | 4.72E-09 | NS | |
| Bks1 | OSOM | 2.54 | 4.82E-09 | NS | |
| Sdc1 | ISOM | 4.41 | 4.97E-09 | NS | |
| Nfkbiz | OSOM | 5.13 | 5.1E-09 | NS | |
| Upp1 | OSOM | 2.45 | 5.12E-09 | NS | |
| Emp1 | OSOM | 3.04 | 5.19E-09 | NS | |
| Cept70 | OSOM | 2.88 | 5.4E-09 | NS | |
| Ccdc164 | Glom | 228.72 | 5.43E-09 | NS | |
| Tnfrsf1a | Cortex | 2.33 | 5.48E-09 | NS | |
| Pa2g4 | OSOM | 2.08 | 5.6E-09 | NS | |
| Tmod3 | OSOM | 2.10 | 5.74E-09 | NS | |
| Tmem184b | OSOM | 2.05 | 5.79E-09 | NS | |
| Mid1 | OSOM | 3.79 | 5.79E-09 | NS | |
| Pdlim7 | OSOM | 4.64 | 5.92E-09 | NS | |
| Isg20 | OSOM | 3.94 | 6.1E-09 | NS | |
| Foxs1 | OSOM | 7.76 | 6.24E-09 | NS | |
| Cdh3 | OSOM | 4.58 | 6.28E-09 | NS | |
| Cdk6 | OSOM | 4.60 | 6.37E-09 | NS | |
| Rps6ka3 | OSOM | 3.04 | 6.51E-09 | NS | |
| Zfand2a | OSOM | 2.37 | 6.53E-09 | NS | |
| Arid5a | OSOM | 6.67 | 6.57E-09 | NS | |
| S100a6 | OSOM | 7.11 | 6.76E-09 | NS | |
| Rnps1 | OSOM | 2.19 | 6.82E-09 | NS | |
| 2200002D01Rik | ISOM | 4.74 | 6.83E-09 | NS | |
| Tnfaip3 | OSOM | 2.45 | 6.94E-09 | NS | |
| 9610040J01Rik | Glom | 2.88 | 7.02E-09 | NS | |
| Tf812 | OSOM | 2.32 | 7.03E-09 | NS | |
| Cyb561 | ISOM | 2.23 | 7.1E-09 | NS | |
| C5ar1 | OSOM | 6.00 | 7.37E-09 | NS | |
| Pkmyt1 | OSOM | 5.82 | 7.44E-09 | NS | |
| Zfp36l1 | OSOM | 4.23 | 7.46E-09 | NS | |
| Naa25 | Cortex | 2.40 | 7.46E-09 | NS | |
| Parp3 | ISOM | 2.29 | 7.5E-09 | NS | |
| Sh2d4b | OSOM | 5.85 | 7.53E-09 | NS | |
| Dusp10 | OSOM | 6.19 | 7.69E-09 | NS | |
| Ece2 | OSOM | 3.17 | 7.82E-09 | NS | |
| 1110008P14Rik | ISOM | 2.84 | 7.88E-09 | NS | |
| Samd5 | OSOM | 16.52 | 7.97E-09 | NS | |
| Rgs2 | OSOM | 5.14 | 8.19E-09 | NS | |
| Nol10 | OSOM | 2.14 | 8.41E-09 | NS | |
| Rmi1 | OSOM | 2.61 | 8.53E-09 | NS | |
| Kpnb1 | OSOM | 2.14 | 8.67E-09 | NS | |
| Cdk2 | OSOM | 2.17 | 8.7E-09 | NS | |
| Gjb3 | OSOM | 40.88 | 8.38E-09 | NS | |
| Hyou1 | ISOM | 2.33 | 9.47E-09 | NS | |
| Junb | OSOM | 18.02 | 9.63E-09 | NS | |
| Bcl3 | OSOM | 6.93 | 9.81E-09 | NS | |

FIG. 29 CONTINUED

| | | | | | |
|---|---|---|---|---|---|
| Sertad4 | OSOM | 3.30 | 9.84E-09 | NS | |
| Csf3r | OSOM | 23.95 | 1.14E-08 | NS | |
| Alg8 | OSOM | 2.41 | 1.15E-08 | NS | |
| Tacc2 | OSOM | 3.41 | 1.16E-08 | NS | |
| 1300014l06Rik | OSOM | 3.01 | 1.16E-08 | NS | |
| Anxa5 | OSOM | 2.25 | 1.16E-08 | NS | |
| Large | OSOM | 2.18 | 1.17E-08 | NS | |
| Rnd3 | OSOM | 2.57 | 1.18E-08 | NS | |
| Dap | OSOM | 2.43 | 1.21E-08 | NS | |
| Tfpi2 | OSOM | 4.74 | 1.23E-08 | NS | |
| Uck2 | OSOM | 2.52 | 1.35E-08 | NS | |
| Sh3bp2 | ISOM | 4.74 | 1.39E-08 | NS | |
| Zdhhc18 | OSOM | 2.19 | 1.44E-08 | NS | |
| Lgi1 | OSOM | 2.00 | 1.51E-08 | NS | |
| D430020J02Rik | OSOM | 9.40 | 1.51E-08 | NS | |
| Ak5 | OSOM | 3.30 | 1.52E-08 | NS | |
| Adora1 | OSOM | 3.97 | 1.57E-08 | NS | |
| Slfn4 | OSOM | 24.35 | 1.57E-08 | NS | |
| Tfa | Cortex | 3.27 | 1.58E-08 | NS | |
| Ckap4 | OSOM | 2.95 | 1.59E-08 | NS | |
| Atf3 | OSOM | 29.77 | 1.65E-08 | NS | |
| Arrdc4 | OSOM | 3.37 | 1.65E-08 | NS | |
| Panx1 | OSOM | 4.58 | 1.75E-08 | NS | |
| Fchsd1 | OSOM | 3.43 | 1.78E-08 | NS | |
| Igf2bp2 | OSOM | 5.83 | 1.8E-08 | NS | |
| Zmynd19 | OSOM | 2.19 | 1.81E-08 | NS | |
| Nop2 | OSOM | 2.11 | 1.81E-08 | NS | |
| Nudcd1 | OSOM | 2.34 | 1.85E-08 | NS | |
| Mal2 | OSOM | 2.88 | 1.87E-08 | NS | |
| Bdt3 | OSOM | 2.96 | 1.89E-08 | NS | |
| Itk | OSOM | 2.13 | 1.91E-08 | NS | |
| Ezh2 | OSOM | 3.05 | 1.94E-08 | NS | |
| Lmk1 | OSOM | 2.81 | 1.96E-08 | NS | |
| Tirap | OSOM | 2.95 | 1.97E-08 | NS | |
| Spry2 | OSOM | 2.59 | 2E-08 | NS | |
| Bicap | OSOM | 2.05 | 2.02E-08 | NS | |
| Coro1c | OSOM | 2.19 | 2.04E-08 | NS | |
| Mchr1 | OSOM | 23.77 | 2.05E-08 | NS | |
| Sgtb | OSOM | 3.72 | 2.05E-08 | NS | |
| Chaf1b | OSOM | 6.41 | 2.05E-08 | NS | |
| Pabpc4 | OSOM | 2.32 | 2.08E-08 | NS | |
| Gmppb | ISOM | 2.16 | 2.1E-08 | NS | |
| Hspb6 | Cortex | 3.18 | 2.11E-08 | NS | |
| Pola1 | OSOM | 3.31 | 2.12E-08 | NS | |
| S100a10 | Cortex | 3.54 | 2.17E-08 | NS | |
| Srm | OSOM | 2.59 | 2.18E-08 | NS | |
| Ppp2r5b | OSOM | 2.06 | 2.19E-08 | NS | |
| Gja5 | OSOM | 2.79 | 2.2E-08 | NS | |
| Vars | OSOM | 2.38 | 2.27E-08 | NS | |
| Pdia6 | ISOM | 2.02 | 2.35E-08 | NS | |
| Gemin6 | OSOM | 2.41 | 2.39E-08 | NS | |
| S100a8 | OSOM | 108.44 | 2.41E-08 | NS | |
| 2010109K11Rik | OSOM | 3.20 | 2.59E-08 | NS | |
| Nek6 | Cortex | 3.72 | 2.76E-08 | NS | |
| Ccdc149 | OSOM | 2.57 | 2.85E-08 | NS | |
| Mab21l3 | OSOM | 6.07 | 2.86E-08 | NS | |
| Pak1 | OSOM | 2.24 | 2.86E-08 | NS | |
| Brca1 | OSOM | 3.79 | 2.88E-08 | NS | |
| Wisp1 | OSOM | 3.96 | 2.89E-08 | NS | |
| Crlf1 | OSOM | 54.98 | 2.92E-08 | NS | |
| Fignl1 | OSOM | 13.38 | 3.1E-08 | NS | |
| Ccne1 | OSOM | 8.77 | 3.14E-08 | NS | |
| 1700017B05Rik | OSOM | 2.23 | 3.15E-08 | NS | |
| Jun | OSOM | 4.38 | 3.16E-08 | NS | |
| 2610034B18Rik | OSOM | 2.10 | 3.22E-08 | NS | |
| Zdhhc13 | OSOM | 2.07 | 3.26E-08 | NS | |
| Dusp4 | OSOM | 4.18 | 3.29E-08 | NS | |
| Cars | OSOM | 2.34 | 3.33E-08 | NS | |
| Haus6 | OSOM | 2.78 | 3.37E-08 | NS | |
| Nras | OSOM | 2.29 | 3.4E-08 | NS | |
| Col18a1 | OSOM | 2.82 | 3.48E-08 | NS | |
| Actn1 | OSOM | 3.45 | 3.49E-08 | NS | |
| Tspan8 | OSOM | 2.67 | 3.56E-08 | NS | |
| Cttn | ISOM | 2.09 | 3.6E-08 | NS | |
| Gstd | Cortex | 2.75 | 3.71E-08 | NS | |

FIG. 29 CONTINUED

| Gene | Region | Value1 | p-value |
|---|---|---|---|
| Lrrc28 | OSOM | 3.24 | 3.72E-08 |
| 6330406I15Rik | OSOM | 12.28 | 4.04E-08 |
| Mphosph6 | OSOM | 2.13 | 4.04E-08 |
| D430041D05Rik | Cortex | 201.92 | 4.08E-08 |
| Iars | OSOM | 2.19 | 4.11E-08 |
| Rpp25 | OSOM | 8.85 | 4.15E-08 |
| Gjb4 | OSOM | 47.13 | 4.16E-08 |
| Pycr1 | ISOM | 7.33 | 4.18E-08 |
| Arhgef10 | OSOM | 2.09 | 4.31E-08 |
| Isyna1 | OSOM | 2.25 | 4.51E-08 |
| Hap1 | OSOM | 2.70 | 4.54E-08 |
| Fam83c | OSOM | 23.04 | 4.63E-08 |
| Ntf5 | Glom | 9.54 | 4.79E-08 |
| Mmp19 | OSOM | 8.46 | 4.97E-08 |
| Rhbd2 | OSOM | 6.41 | 5.1E-08 |
| Fst | OSOM | 6.25 | 5.21E-08 |
| Fam111a | OSOM | 3.18 | 5.23E-08 |
| Ch3l3 | ISOM | 205.92 | 5.29E-08 |
| Uchl3 | OSOM | 2.55 | 5.38E-08 |
| Frk | OSOM | 2.55 | 5.56E-08 |
| Net1 | ISOM | 4.11 | 5.58E-08 |
| 8630045M09Rik | OSOM | 3.78 | 5.71E-08 |
| Tcof1 | OSOM | 2.24 | 5.94E-08 |
| Ostc | OSOM | 2.24 | 5.97E-08 |
| Topbp1 | OSOM | 2.04 | 6.07E-08 |
| Spece1 | OSOM | 2.14 | 6.16E-08 |
| Ube2ckp | OSOM | 2.89 | 6.3E-08 |
| Nolc1 | OSOM | 2.10 | 6.37E-08 |
| Rab11fip3 | OSOM | 2.17 | 6.45E-08 |
| Arg2 | Cortex | 3.91 | 6.6E-08 |
| Ksr1 | OSOM | 3.07 | 6.67E-08 |
| Aldh1a2 | Cortex | 5.75 | 6.9E-08 |
| Ier5 | OSOM | 3.76 | 6.91E-08 |
| Il13ra1 | ISOM | 2.29 | 6.98E-08 |
| Ercc6l | OSOM | 18.12 | 7.08E-08 |
| Rgs16 | OSOM | 10.81 | 7.2E-08 |
| Strl1 | OSOM | 3.71 | 7.41E-08 |
| Slc26a1 | ISOM | 9.04 | 7.81E-08 |
| Zbtb42 | OSOM | 2.54 | 7.95E-08 |
| Ch25h | Cortex | 5.43 | 8.38E-08 |
| Bdkrb2 | OSOM | 96.29 | 8.58E-08 |
| Serpinb9 | OSOM | 2.40 | 8.61E-08 |
| Cep78 | OSOM | 2.72 | 8.81E-08 |
| Prkx | OSOM | 2.80 | 8.98E-08 |
| Cerkl | OSOM | 13.73 | 9E-08 |
| Unc13b | OSOM | 2.33 | 9.13E-08 |
| Camkk2 | ISOM | 2.08 | 9.7E-08 |
| Itga5 | OSOM | 3.23 | 1.02E-07 |
| Mcam | OSOM | 2.49 | 1.05E-07 |
| Hspd | OSOM | 2.51 | 1.07E-07 |
| Klrg2 | OSOM | 5.31 | 1.08E-07 |
| Gsta1 | Cortex | 42.19 | 1.09E-07 |
| Wdhd1 | OSOM | 5.08 | 1.12E-07 |
| Asf1b | OSOM | 7.70 | 1.13E-07 |
| Uprt | Cortex | 10.97 | 1.15E-07 |
| Hk2 | OSOM | 17.59 | 1.21E-07 |
| Steap2 | OSOM | 2.63 | 1.21E-07 |
| Fut1 | ISOM | 53.67 | 1.23E-07 |
| Gpr153 | OSOM | 2.87 | 1.3E-07 |
| St14 | OSOM | 2.13 | 1.31E-07 |
| Anp32b | OSOM | 2.01 | 1.32E-07 |
| Slc7a11 | OSOM | 12.59 | 1.34E-07 |
| BC052040 | OSOM | 2.72 | 1.4E-07 |
| Slc35e4 | OSOM | 2.41 | 1.47E-07 |
| Kif5 | OSOM | 7.43 | 1.49E-07 |
| Slc39a14 | ISOM | 2.33 | 1.51E-07 |
| Apobr | OSOM | 3.34 | 1.54E-07 |
| Ecsor | OSOM | 2.84 | 1.58E-07 |
| Rcn1 | OSOM | 2.77 | 1.6E-07 |
| Lpin3 | OSOM | 2.27 | 1.61E-07 |
| Fut2 | OSOM | 92.48 | 1.64E-07 |
| Emi2 | OSOM | 2.05 | 1.64E-07 |
| Sh3bgrl2 | OSOM | 2.18 | 1.65E-07 |
| Shq1 | OSOM | 2.26 | 1.67E-07 |
| Ppap2c | ISOM | 2.05 | 1.71E-07 |

FIG. 29 CONTINUED

| Gene | Region | Value | p-value | Sig |
|---|---|---|---|---|
| Egr2 | OSOM | 38.53 | 1.79E-07 | NS |
| Cadm1 | OSOM | 2.82 | 1.79E-07 | NS |
| Grp | ISOM | 3087.87 | 1.82E-07 | NS |
| Rnd1 | OSOM | 7.21 | 1.83E-07 | NS |
| Cyp4f16 | OSOM | 2.08 | 1.87E-07 | NS |
| Gc | OSOM | 8.26 | 1.87E-07 | NS |
| Fjx1 | OSOM | 3.71 | 1.88E-07 | NS |
| Adamts1 | Cortex | 4.70 | 1.9E-07 | NS |
| Rrm2 | OSOM | 8.22 | 1.93E-07 | NS |
| Mybpc2 | OSOM | 11.79 | 1.95E-07 | NS |
| Mettl2 | OSOM | 2.07 | 1.96E-07 | NS |
| Fam38a | Cortex | 2.59 | 1.97E-07 | NS |
| Efna5 | OSOM | 2.35 | 1.97E-07 | NS |
| Ptprj | OSOM | 2.22 | 1.97E-07 | NS |
| Map3k2 | OSOM | 2.00 | 2.01E-07 | NS |
| Marveld3 | Glom | 2.77 | 2.02E-07 | NS |
| Mapk7 | OSOM | 2.34 | 2.08E-07 | NS |
| Tgif1 | OSOM | 4.30 | 2.08E-07 | NS |
| Sema6b | Cortex | 3.03 | 2.12E-07 | NS |
| Smyd5 | OSOM | 2.84 | 2.13E-07 | NS |
| Sprr2f | Cortex | 2882.73 | 2.16E-07 | NS |
| D730005E14Rik | OSOM | 6.39 | 2.16E-07 | NS |
| Ipo7 | Cortex | 2.39 | 2.18E-07 | NS |
| Mapkapk2 | Cortex | 2.25 | 2.31E-07 | NS |
| Mospd2 | Cortex | 2.79 | 2.33E-07 | NS |
| Nxn1 | Glom | 106.33 | 2.4E-07 | NS |
| Baz1a | OSOM | 2.56 | 2.41E-07 | NS |
| Itpr3 | OSOM | 3.47 | 2.46E-07 | NS |
| Sox4 | Cortex | 5.42 | 2.53E-07 | NS |
| Mthfd1l | OSOM | 4.36 | 2.57E-07 | NS |
| Paqr5 | Glom | 2.36 | 2.66E-07 | NS |
| Tyro3 | ISOM | 2.50 | 2.66E-07 | NS |
| Uchl4 | OSOM | 2.42 | 2.71E-07 | NS |
| Fkbp11 | OSOM | 5.30 | 2.71E-07 | NS |
| Il6 | Cortex | 466.36 | 2.73E-07 | NS |
| Spsb1 | OSOM | 5.22 | 2.75E-07 | NS |
| Hkdc1 | OSOM | 9.89 | 2.84E-07 | NS |
| Dclk1 | OSOM | 8.51 | 2.9E-07 | NS |
| Trem1 | OSOM | 47.02 | 2.9E-07 | NS |
| Tbc37 | Cortex | 2.73 | 2.97E-07 | NS |
| Agt | Glom | 5.98 | 3.01E-07 | NS |
| Clic1 | OSOM | 2.33 | 3.03E-07 | NS |
| Rbpms | OSOM | 2.13 | 3.06E-07 | NS |
| Ugt1a9 | Cortex | 22.03 | 3.07E-07 | NS |
| Tjp2 | Cortex | 2.20 | 3.14E-07 | NS |
| Mki1 | OSOM | 2.19 | 3.24E-07 | NS |
| Mbnl3 | OSOM | 2.38 | 3.26E-07 | NS |
| Bapp1 | OSOM | 3.00 | 3.28E-07 | NS |
| Rab29 | Glom | 2.17 | 3.35E-07 | NS |
| Vcl | OSOM | 2.40 | 3.4E-07 | NS |
| Odc1 | ISOM | 2.50 | 3.49E-07 | NS |
| Wfdc2 | ISOM | 2.46 | 3.51E-07 | NS |
| Myd88 | OSOM | 2.24 | 3.54E-07 | NS |
| Mmp9 | OSOM | 18.54 | 3.56E-07 | NS |
| Fhdc1 | OSOM | 3.52 | 3.8E-07 | NS |
| Slc26a9 | OSOM | 388.73 | 3.63E-07 | NS |
| Rhbdf2 | OSOM | 2.51 | 3.65E-07 | NS |
| Ell2 | OSOM | 2.20 | 3.66E-07 | NS |
| Lzic | OSOM | 2.10 | 3.79E-07 | NS |
| 6330512M04Rik | OSOM | 18.61 | 3.8E-07 | NS |
| Slc6a9 | Cortex | 2.39 | 4.05E-07 | NS |
| Ppp1r15a | OSOM | 2.63 | 4.06E-07 | NS |
| Elf3 | Glom | 3.81 | 4.25E-07 | NS |
| Ugt1a10 | Glom | 397.37 | 4.28E-07 | NS |
| Gpt2 | OSOM | 2.53 | 4.32E-07 | NS |
| Nt5dc3 | OSOM | 2.80 | 4.35E-07 | NS |
| Slc15a3 | OSOM | 3.13 | 4.45E-07 | NS |
| 5433427O19Rik | Glom | 15.89 | 4.52E-07 | NS |
| G530911C06Rik | Glom | 12.16 | 4.6E-07 | NS |
| Prim1 | OSOM | 2.56 | 4.6E-07 | NS |
| Mapk4 | ISOM | 4.57 | 4.66E-07 | NS |
| Akap12 | OSOM | 3.89 | 4.68E-07 | NS |
| Nle1 | OSOM | 2.79 | 4.73E-07 | NS |
| Fkra | OSOM | 2.99 | 4.78E-07 | NS |
| Tmem56 | OSOM | 276.81 | 4.9E-07 | NS |

FIG. 29 CONTINUED

| Gene | Region | Value | P-value | | Sig |
|---|---|---|---|---|---|
| Ears2 | ISOM | 2.03 | 4.93E-07 | | NS |
| Myo3b | OSOM | 3.27 | 5.05E-07 | | NS |
| Orc1 | OSOM | 8.59 | 5.13E-07 | | NS |
| Ung | OSOM | 4.95 | 5.14E-07 | | NS |
| 3110082I17Rik | ISOM | 2.77 | 5.24E-07 | | NS |
| Gm3776 | OSOM | 452.45 | 5.25E-07 | | NS |
| Ccdc86 | OSOM | 2.33 | 5.32E-07 | | NS |
| Suv39h1 | OSOM | 2.14 | 5.5E-07 | | NS |
| Wrb | OSOM | 2.05 | 5.5E-07 | | NS |
| Nipal1 | OSOM | 4.14 | 5.53E-07 | | NS |
| Cldn14 | Glom | 789.82 | 5.57E-07 | | NS |
| Mapk8 | Cortex | 2.48 | 5.67E-07 | | NS |
| Gpatch4 | OSOM | 2.73 | 5.7E-07 | | NS |
| Nasp | OSOM | 3.11 | 5.79E-07 | | NS |
| Mdfi | OSOM | 8.36 | 5.97E-07 | | NS |
| Map3k1 | OSOM | 2.77 | 6.09E-07 | | NS |
| Gsip1 | Cortex | 2.18 | 6.1E-07 | | NS |
| Ccdc128 | OSOM | 2.48 | 6.22E-07 | | NS |
| Esyt1 | OSOM | 2.25 | 6.46E-07 | | NS |
| Sec24d | OSOM | 2.20 | 6.59E-07 | | NS |
| Fgr | ISOM | 5.88 | 6.81E-07 | | NS |
| Gla | OSOM | 2.25 | 7.02E-07 | | NS |
| Tub | OSOM | 18.72 | 7.06E-07 | | NS |
| Cre11 | OSOM | 416.52 | 7.11E-07 | | NS |
| Ric3 | OSOM | 2.82 | 7.22E-07 | | NS |
| Has1 | OSOM | 108.53 | 7.31E-07 | | NS |
| Ppan | OSOM | 2.73 | 7.39E-07 | | NS |
| Ncapg2 | OSOM | 3.83 | 7.68E-07 | | NS |
| Lrrc8e | OSOM | 2.98 | 7.74E-07 | | NS |
| Icam1 | Cortex | 2.54 | 7.78E-07 | | NS |
| Wasf1 | OSOM | 2.73 | 7.83E-07 | | NS |
| Stil | OSOM | 8.15 | 8.09E-07 | | NS |
| Nln | OSOM | 2.25 | 8.19E-07 | | NS |
| Serpinb1a | ISOM | 4.95 | 8.27E-07 | | NS |
| Itga6 | ISOM | 4.92 | 8.39E-07 | | NS |
| Aldh1a1 | Cortex | 3.10 | 8.4E-07 | | NS |
| Plekho1 | OSOM | 2.36 | 8.49E-07 | | NS |
| Gm10845 | Glom | 103.06 | 8.6E-07 | | NS |
| Trf | OSOM | 7.08 | 8.7E-07 | | NS |
| Pmepa1 | OSOM | 2.15 | 8.83E-07 | | NS |
| 9930005F22Rik | OSOM | 7.07 | 8.94E-07 | | NS |
| Bcl6 | OSOM | 3.11 | 9.47E-07 | | NS |
| Dph2 | OSOM | 2.10 | 9.7E-07 | | NS |
| Trp53 | OSOM | 2.32 | 9.85E-07 | | NS |
| Erap1 | Cortex | 2.05 | 9.9E-07 | | NS |
| Vps37b | OSOM | 2.15 | 9.91E-07 | | NS |
| Pus7l | OSOM | 2.98 | 9.92E-07 | | NS |
| Serp2 | OSOM | 6.93 | 9.99E-07 | | NS |
| Fgf21 | OSOM | 126.28 | 1.01E-06 | | NS |
| Itpkc | OSOM | 2.35 | 1.03E-06 | | NS |
| Myo9b | OSOM | 2.13 | 1.05E-06 | | NS |
| Fam84b | OSOM | 2.13 | 1.08E-06 | | NS |
| St6gal1 | OSOM | 2.14 | 1.09E-06 | | NS |
| Glrx | OSOM | 2.19 | 1.13E-06 | | NS |
| Me2 | ISOM | 2.01 | 1.14E-06 | | NS |
| Ascc3 | Cortex | 2.17 | 1.17E-06 | | NS |
| Prost | OSOM | 2.93 | 1.18E-06 | | NS |
| Fam185a | OSOM | 2.16 | 1.18E-06 | | NS |
| Ttl7 | OSOM | 3.06 | 1.19E-06 | | NS |
| Snhg5 | OSOM | 3.62 | 1.19E-06 | | NS |
| Cxcr2 | OSOM | 87.56 | 1.23E-06 | | NS |
| Samd4 | OSOM | 2.83 | 1.24E-06 | | NS |
| Gm5506 | Cortex | 2.53 | 1.25E-06 | | NS |
| Gbe1 | Cortex | 2.33 | 1.27E-06 | | NS |
| E030011O05Rik | OSOM | 9.11 | 1.29E-06 | | NS |
| Tipin | OSOM | 2.34 | 1.32E-06 | | NS |
| Adss | OSOM | 2.08 | 1.33E-06 | | NS |
| Mrps18b | Glom | 2.34 | 1.34E-06 | | NS |
| Gipt1 | ISOM | 2.04 | 1.35E-06 | | NS |
| A1414108 | OSOM | 3.58 | 1.35E-06 | | NS |
| Asb4 | OSOM | 6.75 | 1.36E-06 | | NS |
| 2010003K11Rik | Glom | 16.90 | 1.36E-06 | | NS |
| 1810029B16Rik | OSOM | 2.70 | 1.38E-06 | | NS |
| Sh3pxd2b | OSOM | 2.94 | 1.38E-06 | | NS |
| Ppp1r9b | OSOM | 2.82 | 1.39E-06 | | NS |

FIG. 29 CONTINUED

| | | | |
|---|---|---|---|
| Cd300lf | OSOM | 71.88 | 1.4E-08 |
| Grhl2 | Glom | 2.73 | 1.43E-08 |
| Gm13889 | OSOM | 2.65 | 1.44E-08 |
| Tgm2 | OSOM | 2.04 | 1.46E-08 |
| Ccl2 | OSOM | 11.42 | 1.48E-08 |
| Sdf2l1 | ISOM | 3.58 | 1.48E-08 |
| Fbxo2 | OSOM | 3.71 | 1.49E-08 |
| Mmp24 | OSOM | 225.94 | 1.53E-08 |
| Tbc1d9 | OSOM | 2.18 | 1.56E-08 |
| Gstm5 | Glom | 3.24 | 1.58E-08 |
| Hpgds | OSOM | 4.58 | 1.59E-08 |
| Ogg1 | OSOM | 2.11 | 1.62E-08 |
| Lmnb1 | OSOM | 2.98 | 1.66E-08 |
| 1300002K09Rik | Glom | 8.91 | 1.67E-08 |
| Cdca7 | OSOM | 6.93 | 1.67E-08 |
| 4930579G22Rik | Glom | 17.52 | 1.68E-08 |
| Sntg2 | Glom | 17.92 | 1.72E-08 |
| Fgfbp1 | Glom | 3.44 | 1.75E-08 |
| Spred3 | OSOM | 7.86 | 1.77E-08 |
| Akr1c13 | OSOM | 3.32 | 1.82E-08 |
| Lsm11 | OSOM | 2.28 | 1.83E-08 |
| Pof1b | Glom | 93.31 | 1.83E-08 |
| Muc4 | OSOM | 31.28 | 1.88E-08 |
| Oas1f | OSOM | 3.83 | 1.93E-08 |
| Thbs1 | OSOM | 2.55 | 1.93E-08 |
| Fbxw17 | OSOM | 2.77 | 1.96E-08 |
| Zwint | OSOM | 2.04 | 1.97E-08 |
| Psd4 | OSOM | 3.78 | 2.04E-08 |
| Brsk1 | OSOM | 3.27 | 2.04E-08 |
| Usp43 | OSOM | 2.30 | 2.05E-08 |
| Pfn1 | OSOM | 2.03 | 2.09E-08 |
| Zfp365 | OSOM | 17.26 | 2.1E-08 |
| Ddx10 | OSOM | 2.02 | 2.13E-08 |
| Ttc22 | OSOM | 2.58 | 2.13E-08 |
| Pik3 | OSOM | 6.23 | 2.14E-08 |
| Fblim1 | OSOM | 2.40 | 2.15E-08 |
| Emilin1 | OSOM | 2.16 | 2.15E-08 |
| Cdc6 | OSOM | 15.31 | 2.19E-08 |
| 4930506M07Rik | Cortex | 2.51 | 2.23E-08 |
| Sh3bp4 | OSOM | 2.09 | 2.24E-08 |
| Mmp14 | OSOM | 2.87 | 2.27E-08 |
| Dcbld1 | Glom | 2.02 | 2.28E-08 |
| Chek1 | OSOM | 6.83 | 2.33E-08 |
| Ap1s2 | OSOM | 2.13 | 2.34E-08 |
| Elf4 | OSOM | 2.31 | 2.34E-08 |
| Mex3a | OSOM | 3.76 | 2.38E-08 |
| Nrm | OSOM | 3.17 | 2.46E-08 |
| Cdc7 | OSOM | 4.20 | 2.5E-08 |
| Pmaip1 | OSOM | 4.47 | 2.55E-08 |
| Pafah1b3 | Glom | 2.80 | 2.58E-08 |
| Tpm2 | OSOM | 3.19 | 2.69E-08 |
| Snhg3 | OSOM | 2.09 | 2.7E-08 |
| B3gnt7 | ISOM | 2.22 | 2.72E-08 |
| Rrp15 | OSOM | 2.01 | 2.73E-08 |
| Adm | OSOM | 3.88 | 2.73E-08 |
| Ccdc21 | Cortex | 2.11 | 2.82E-08 |
| Manf | OSOM | 2.14 | 2.85E-08 |
| Anln | OSOM | 6.59 | 2.93E-08 |
| Flt3 | OSOM | 4.08 | 2.93E-08 |
| AU022252 | Glom | 2.02 | 2.94E-08 |
| Astn2 | ISOM | 5.16 | 2.98E-08 |
| Emx2 | Glom | 2.20 | 3E-08 |
| Vgf | ISOM | 805.18 | 3.04E-08 |
| Gpr56 | OSOM | 2.10 | 3.09E-08 |
| Atp8b1 | OSOM | 2.35 | 3.09E-08 |
| Ptpn23 | OSOM | 2.21 | 3.19E-08 |
| Fam83g | OSOM | 2.58 | 3.2E-08 |
| Rem2 | OSOM | 10.65 | 3.2E-08 |
| Nup43 | OSOM | 2.27 | 3.32E-08 |
| Gm1631 | ISOM | 15.28 | 3.33E-08 |
| Syt12 | Cortex | 2.49 | 3.35E-08 |
| Nhp2 | ISOM | 2.21 | 3.48E-08 |
| Ethe1 | ISOM | 2.19 | 3.5E-08 |
| Srd5a1 | ISOM | 3.85 | 3.5E-08 |
| Ier2 | OSOM | 4.17 | 3.52E-08 |

FIG. 29 CONTINUED

| Gene | Region | Value | P-value | | |
|---|---|---|---|---|---|
| Styxl1 | Glom | 112.27 | 3.53E-06 | NS | |
| Octd | OSOM | 3.87 | 3.58E-06 | NS | |
| Nt5c | OSOM | 2.92 | 3.61E-06 | NS | |
| Diap3 | OSOM | 10.68 | 3.61E-06 | NS | |
| Ocam2l2 | Glom | 157.81 | 3.62E-06 | NS | |
| Egfr | OSOM | 2.23 | 3.71E-06 | NS | |
| Sh3bgrl3 | OSOM | 3.70 | 3.73E-06 | NS | |
| Lgmn | OSOM | 2.10 | 3.78E-06 | NS | |
| BC048355 | ISOM | 2.64 | 3.84E-06 | NS | |
| Eps8l3 | OSOM | 8.42 | 3.86E-06 | NS | |
| E2f3 | OSOM | 2.42 | 3.9E-06 | NS | |
| Txnrd1 | Cortex | 2.25 | 3.91E-06 | NS | |
| Gins1 | OSOM | 4.02 | 3.91E-06 | NS | |
| Fkbp10 | OSOM | 2.77 | 4.03E-06 | NS | |
| Ftsjd1 | OSOM | 2.38 | 4.06E-06 | NS | |
| Rapgef4 | OSOM | 2.10 | 4.07E-06 | NS | |
| Plek | OSOM | 2.79 | 4.11E-06 | NS | |
| Pdlim3 | ISOM | 3.80 | 4.15E-06 | NS | |
| Creb3 | OSOM | 18.97 | 4.29E-06 | NS | |
| Ypel2 | OSOM | 3.28 | 4.31E-06 | NS | |
| Pla2g4c | OSOM | 9.30 | 4.52E-06 | NS | |
| S100a11 | ISOM | 2.35 | 4.57E-06 | NS | |
| Incenp | OSOM | 2.89 | 4.58E-06 | NS | |
| Btl | OSOM | 16.56 | 4.73E-06 | NS | |
| Btbd17 | OSOM | 252.53 | 4.84E-06 | NS | |
| Sorbs2 | OSOM | 2.25 | 4.87E-06 | NS | |
| A130049A11Rik | Glom | 10.77 | 4.9E-06 | NS | |
| Mms22l | OSOM | 4.03 | 4.96E-06 | NS | |
| Slc16a1 | OSOM | 5.12 | 4.96E-06 | NS | |
| Slpi | OSOM | 38.93 | 5.06E-06 | NS | |
| Wdr76 | OSOM | 2.32 | 5.12E-06 | NS | |
| Rrp12 | OSOM | 2.48 | 5.57E-06 | NS | |
| Reep4 | OSOM | 2.03 | 5.62E-06 | NS | |
| Actb | OSOM | 2.27 | 5.63E-06 | NS | |
| 2900008C10Rik | Glom | 6.91 | 5.67E-06 | NS | |
| Lgi2 | OSOM | 11.59 | 5.81E-06 | NS | |
| Cdx2l | OSOM | 2.74 | 5.9E-06 | NS | |
| Slc5a10 | Glom | 6.51 | 6.01E-06 | NS | |
| Cftr | OSOM | 5.05 | 6.02E-06 | NS | |
| Tnfsf18 | OSOM | 309.22 | 6.07E-06 | NS | |
| Sec1 | OSOM | 10.04 | 6.08E-06 | NS | |
| Snrpd1 | OSOM | 2.03 | 6.1E-06 | NS | |
| Hmga2-ps1 | OSOM | 6.07 | 6.17E-06 | NS | |
| Lrrc10b | OSOM | 6.09 | 6.26E-06 | NS | |
| Sox9 | OSOM | 19.22 | 6.37E-06 | NS | |
| Selp | OSOM | 28.55 | 6.46E-06 | NS | |
| Accn1 | OSOM | 10.48 | 6.47E-06 | NS | |
| Cxcl15 | OSOM | 2.04 | 6.53E-06 | NS | |
| Spsb4 | Glom | 2.13 | 6.61E-06 | NS | |
| Mrpl52 | OSOM | 2.05 | 6.65E-06 | NS | |
| Xlr3a | Glom | 30.87 | 6.71E-06 | NS | |
| Suv39h2 | OSOM | 2.81 | 6.82E-06 | NS | |
| Cyr61 | OSOM | 5.41 | 6.95E-06 | NS | |
| Acsbg1 | OSOM | 12.89 | 6.98E-06 | NS | |
| Syt2 | ISOM | 17.53 | 7.25E-06 | NS | |
| Wdr89 | Glom | 6.48 | 7.28E-06 | NS | |
| Map3k14 | Cortex | 2.46 | 7.35E-06 | NS | |
| Col5a3 | OSOM | 7.28 | 7.37E-06 | NS | |
| Trip13 | OSOM | 8.96 | 7.39E-06 | NS | |
| Slc24a1 | OSOM | 4.05 | 7.41E-06 | NS | |
| Tuba1a | OSOM | 2.60 | 7.48E-06 | NS | |
| 4930579G24Rik | OSOM | 3.34 | 7.57E-06 | NS | |
| 4930427A07Rik | OSOM | 5.21 | 7.66E-06 | NS | |
| Slc16a3 | OSOM | 4.22 | 7.67E-06 | NS | |
| Trib1 | OSOM | 4.35 | 7.72E-06 | NS | |
| Adam11 | OSOM | 4.22 | 7.88E-06 | NS | |
| Hpca4 | ISOM | 12.48 | 7.88E-06 | NS | |
| Shisa4 | ISOM | 3.40 | 7.97E-06 | NS | |
| Birc3 | Cortex | 2.28 | 8.1E-06 | NS | |
| Arl4c | OSOM | 3.37 | 8.27E-06 | NS | |
| Cp | Cortex | 3.55 | 8.45E-06 | NS | |
| Fth1 | ISOM | 2.28 | 8.51E-06 | NS | |
| Mgst1 | Cortex | 2.93 | 8.56E-06 | NS | |
| Sema7a | OSOM | 2.94 | 8.63E-06 | NS | |
| Rhob | OSOM | 2.28 | 8.65E-06 | NS | |

FIG. 29 CONTINUED

| | | | |
|---|---|---|---|
| Sbf4 | OSOM | 2.20 | 8.66E-06 |
| Kif4 | OSOM | 2.34 | 8.7E-06 |
| Spred1 | OSOM | 2.28 | 8.76E-06 |
| Mum1l1 | OSOM | 2.91 | 8.86E-06 |
| Mrs2 | ISOM | 2.12 | 8.87E-06 |
| Zswim4 | OSOM | 2.05 | 8.92E-06 |
| Bok | OSOM | 2.84 | 9.04E-06 |
| Ripk3 | OSOM | 3.29 | 9.28E-06 |
| Pask | OSOM | 3.60 | 9.34E-06 |
| Apex1 | ISOM | 3.00 | 9.36E-06 |
| Mt2 | OSOM | 11.39 | 9.42E-06 |
| Smc2 | OSOM | 2.36 | 9.53E-06 |
| Sect4l2 | OSOM | 2.65 | 9.59E-06 |
| Ncaph | OSOM | 5.28 | 1.01E-05 |
| E130012A19Rik | OSOM | 2.90 | 1.01E-05 |
| Slc9a3 | OSOM | 2.77 | 1.02E-05 |
| Hmga2 | OSOM | 25.70 | 1.04E-05 |
| Pth2r | OSOM | 106.10 | 1.05E-05 |
| Dpep2 | OSOM | 6.30 | 1.05E-05 |
| Prss22 | OSOM | 44.54 | 1.06E-05 |
| E030018A14Rik | OSOM | 3.31 | 1.06E-05 |
| 5430407P10Rik | OSOM | 3.93 | 1.08E-05 |
| Soat2 | OSOM | 20.24 | 1.12E-05 |
| Tbl1x | Cortex | 2.56 | 1.12E-05 |
| Emilin2 | OSOM | 6.30 | 1.13E-05 |
| Ctxn1 | OSOM | 3.59 | 1.13E-05 |
| Ccl12 | ISOM | 11.75 | 1.15E-05 |
| Chaf1a | OSOM | 3.74 | 1.18E-05 |
| Fez1 | Glom | 9.06 | 1.18E-05 |
| Slc16a14 | OSOM | 13.68 | 1.2E-05 |
| Fam129b | OSOM | 2.17 | 1.21E-05 |
| Mcph1 | OSOM | 2.19 | 1.24E-05 |
| Anxa13 | Glom | 9.10 | 1.25E-05 |
| Cdon | OSOM | 2.33 | 1.27E-05 |
| Abcb1b | OSOM | 3.13 | 1.29E-05 |
| 2310043J07Rik | OSOM | 11.34 | 1.3E-05 |
| Ptpn5 | OSOM | 3.94 | 1.31E-05 |
| A530055G03Rik | OSOM | 12.13 | 1.34E-05 |
| Abhd2 | Cortex | 2.95 | 1.34E-05 |
| Las1l | OSOM | 2.86 | 1.35E-05 |
| Cyb5r2 | ISOM | 15.99 | 1.36E-05 |
| Cyp4f18 | OSOM | 4.52 | 1.36E-05 |
| Abcc4 | OSOM | 2.41 | 1.37E-05 |
| Chsy3 | OSOM | 3.44 | 1.37E-05 |
| Cdh2 | OSOM | 3.14 | 1.4E-05 |
| Nupl1 | OSOM | 2.19 | 1.4E-05 |
| Acot5 | OSOM | 88.04 | 1.43E-05 |
| Mpp6 | Glom | 2.21 | 1.46E-05 |
| Gm14137 | OSOM | 4.23 | 1.46E-05 |
| Mob1a | Cortex | 2.94 | 1.48E-05 |
| Iti6 | Cortex | 411.20 | 1.52E-05 |
| F630110N24Rik | Cortex | 2.81 | 1.53E-05 |
| Vps13c | Cortex | 2.94 | 1.53E-05 |
| Lysmd3 | Cortex | 2.37 | 1.53E-05 |
| Hmox1 | OSOM | 6.81 | 1.53E-05 |
| Tmcc3 | OSOM | 2.16 | 1.54E-05 |
| Syne2 | Cortex | 2.34 | 1.57E-05 |
| Scin | Glom | 2.87 | 1.57E-05 |
| Snx10 | OSOM | 3.00 | 1.6E-05 |
| Tonsl | OSOM | 2.95 | 1.61E-05 |
| Plin4 | OSOM | 6.46 | 1.64E-05 |
| Rgs6 | OSOM | 3.06 | 1.65E-05 |
| Bst1 | OSOM | 2.33 | 1.66E-05 |
| Gpr39 | OSOM | 5.19 | 1.66E-05 |
| S100a3 | OSOM | 47.81 | 1.67E-05 |
| Itgb6 | Glom | 2.95 | 1.74E-05 |
| Pi16 | OSOM | 3.32 | 1.75E-05 |
| Sema3f | OSOM | 2.14 | 1.8E-05 |
| Ces2e | OSOM | 2.85 | 1.8E-05 |
| Efcab5 | ISOM | 3.46 | 1.81E-05 |
| Pkir | Glom | 6.08 | 1.81E-05 |
| Timeless | OSOM | 2.37 | 1.84E-05 |
| Sesn3 | OSOM | 2.80 | 1.85E-05 |
| Plekhg2 | OSOM | 2.18 | 1.87E-05 |
| Mad2l1 | OSOM | 2.52 | 1.88E-05 |

FIG. 29 CONTINUED

| | | | | | |
|---|---|---|---|---|---|
| Bhlhe15 | ISOM | 6.11 | 1.89E-05 | NS | |
| Gpbar1 | OSOM | 39.33 | 1.92E-05 | NS | |
| Zfp202 | OSOM | 2.38 | 2E-05 | NS | |
| D10Bwg1379e | ISOM | 4.04 | 2.01E-05 | NS | |
| Fos | OSOM | 29.29 | 2.1E-05 | NS | |
| Tnfsf9 | OSOM | 5.28 | 2.13E-05 | NS | |
| Catsper3 | Glom | 89.85 | 2.24E-05 | NS | |
| Ammecr1 | OSOM | 3.41 | 2.25E-05 | NS | |
| Tead4 | OSOM | 2.73 | 2.28E-05 | NS | |
| Fhod3 | Glom | 2.48 | 2.29E-05 | NS | |
| Sc4mol | OSOM | 2.35 | 2.3E-05 | NS | |
| Gm11974 | OSOM | 3.83 | 2.31E-05 | NS | |
| Nfe2 | OSOM | 23.02 | 2.33E-05 | NS | |
| Tpbg | OSOM | 2.86 | 2.35E-05 | NS | |
| Mmp7 | Cortex | 57.72 | 2.4E-05 | NS | |
| Itgb3 | OSOM | 3.99 | 2.52E-05 | NS | |
| Adora2b | Cortex | 4.18 | 2.53E-05 | NS | |
| Rad51ap1 | OSOM | 7.47 | 2.53E-05 | NS | |
| Gtse1 | OSOM | 6.82 | 2.57E-05 | NS | |
| Chi3l8 | OSOM | 5.03 | 2.6E-05 | NS | |
| Grhl1 | OSOM | 2.58 | 2.61E-05 | NS | |
| Gm20324 | Glom | 5.59 | 2.67E-05 | NS | |
| Lmna | OSOM | 2.03 | 2.68E-05 | NS | |
| Pglyrp1 | OSOM | 4.93 | 2.74E-05 | NS | |
| 2910002N04Rik | Glom | 2.75 | 2.74E-05 | NS | |
| Osbpl3 | Glom | 2.01 | 2.75E-05 | NS | |
| Chi3l1 | Glom | 5.93 | 2.76E-05 | NS | |
| Ptger4 | OSOM | 2.20 | 2.77E-05 | NS | |
| A330021E22Rik | OSOM | 2.62 | 2.8E-05 | NS | |
| Bicc1 | Cortex | 3.09 | 2.8E-05 | NS | |
| Ptprc | OSOM | 2.78 | 2.81E-05 | NS | |
| Prkar2a | Cortex | 2.13 | 2.82E-05 | NS | |
| Pik4 | OSOM | 2.36 | 2.83E-05 | NS | |
| Hes1 | OSOM | 2.13 | 2.85E-05 | NS | |
| Ccdc183 | Glom | 4.51 | 2.85E-05 | NS | |
| Snora3 | Glom | 77.44 | 2.9E-05 | NS | |
| Pnr9 | OSOM | 3.03 | 2.91E-05 | NS | |
| Arhgap28 | OSOM | 2.48 | 2.91E-05 | NS | |
| Itgb2 | OSOM | 2.47 | 2.91E-05 | NS | |
| Clec4d | OSOM | 32.54 | 2.94E-05 | NS | |
| Naif1 | Cortex | 2.74 | 2.94E-05 | NS | |
| Retnlg | OSOM | 112.35 | 2.95E-05 | NS | |
| Tagln2 | OSOM | 2.33 | 2.96E-05 | NS | |
| Pltra | OSOM | 8.47 | 2.99E-05 | NS | |
| Prss23 | Glom | 2.03 | 3.03E-05 | NS | |
| Sox | OSOM | 2.95 | 3.07E-05 | NS | |
| Gpr35 | OSOM | 4.30 | 3.08E-05 | NS | |
| Pex11c | Glom | 2.39 | 3.14E-05 | NS | |
| Sgol2 | OSOM | 5.18 | 3.17E-05 | NS | |
| Clec4e | OSOM | 164.31 | 3.19E-05 | NS | |
| 1810033B17Rik | ISOM | 37.98 | 3.2E-05 | NS | |
| Pir | Cortex | 2.96 | 3.24E-05 | NS | |
| B3gnt3 | OSOM | 2.28 | 3.24E-05 | NS | |
| Slc25a43 | ISOM | 4.75 | 3.27E-05 | NS | |
| Hs3st6 | OSOM | 4.02 | 3.31E-05 | NS | |
| 4833422C13Rik | OSOM | 5.59 | 3.34E-05 | NS | |
| Ctsd | OSOM | 2.23 | 3.35E-05 | NS | |
| Pgbd5 | Cortex | 6.31 | 3.4E-05 | NS | |
| Inhbb | Cortex | 4.07 | 3.45E-05 | NS | |
| Ms4a6d | OSOM | 5.73 | 3.47E-05 | NS | |
| BC055324 | OSOM | 3.32 | 3.48E-05 | NS | |
| Rad51 | OSOM | 7.02 | 3.58E-05 | NS | |
| Deptor | Cortex | 4.60 | 3.61E-05 | NS | |
| Ociad2 | OSOM | 2.33 | 3.61E-05 | NS | |
| Msr1 | OSOM | 4.72 | 3.73E-05 | NS | |
| Dyrk3 | ISOM | 3.74 | 3.74E-05 | NS | |
| AA467197 | OSOM | 12.06 | 3.76E-05 | NS | |
| 2310417H13Rik | OSOM | 9.42 | 3.81E-05 | NS | |
| Grrp1 | OSOM | 2.87 | 3.86E-05 | NS | |
| Hmga1 | OSOM | 39.45 | 3.88E-05 | NS | |
| Epn3 | OSOM | 2.01 | 3.91E-05 | NS | |
| Tb2 | Cortex | 2.81 | 3.94E-05 | NS | |
| Impdh2 | OSOM | 2.25 | 3.98E-05 | NS | |
| Ccdc109b | OSOM | 3.41 | 4.06E-05 | NS | |
| Slc48a1 | OSOM | 2.51 | 4.06E-05 | NS | |

FIG. 29 CONTINUED

| | | | |
|---|---|---|---|
| Pcsk2 | ISOM | 29.82 | 4.1E-05 |
| Sqstm1 | OSOM | 2.09 | 4.19E-05 |
| Unc13d | OSOM | 3.26 | 4.2E-05 |
| Nlgn2 | OSOM | 2.07 | 4.25E-05 |
| Pla2g2e | OSOM | 157.11 | 4.27E-05 |
| Nol12 | ISOM | 2.00 | 4.29E-05 |
| Slc44a3 | OSOM | 2.02 | 4.33E-05 |
| Gpr84 | OSOM | 77.41 | 4.35E-05 |
| O3far1 | Glom | 75.52 | 4.36E-05 |
| Slc41a2 | Glom | 2.62 | 4.37E-05 |
| Plec | OSOM | 2.66 | 4.37E-05 |
| Zfp575 | Glom | 89.66 | 4.38E-05 |
| Npm3 | OSOM | 2.11 | 4.43E-05 |
| Slc35a30 | Cortex | 2.57 | 4.63E-05 |
| Dmrt2 | OSOM | 2.17 | 4.7E-05 |
| 4833417C18Rik | Glom | 11.28 | 4.71E-05 |
| Stx2 | ISOM | 3.74 | 4.75E-05 |
| Exo1 | OSOM | 12.80 | 4.84E-05 |
| Sele | OSOM | 13.05 | 4.93E-05 |
| Bcl2a1a | Glom | 8.92 | 4.93E-05 |
| Slc22a15 | OSOM | 2.17 | 4.95E-05 |
| Mfi2 | Glom | 194.22 | 4.97E-05 |
| Guca2a | ISOM | 6.58 | 4.98E-05 |
| Eif2z2 | Cortex | 2.86 | 4.98E-05 |
| Chac1 | OSOM | 8.05 | 5.03E-05 |
| Tsr1 | OSOM | 2.03 | 5.04E-05 |
| Mical3 | OSOM | 3.06 | 5.11E-05 |
| Sh2d5 | OSOM | 12.19 | 5.15E-05 |
| Pus1l | OSOM | 2.07 | 5.18E-05 |
| Tcf15 | OSOM | 3.18 | 5.23E-05 |
| Cldn1 | OSOM | 3.21 | 5.25E-05 |
| Ptprn | OSOM | 18.57 | 5.27E-05 |
| Mpz2 | Glom | 2.10 | 5.29E-05 |
| Spata5l1 | OSOM | 2.39 | 5.32E-05 |
| Wnt7a | ISOM | 80.58 | 5.38E-05 |
| Rbm11 | ISOM | 2.11 | 5.45E-05 |
| Tmem88 | OSOM | 2.03 | 5.51E-05 |
| Fem1c | Cortex | 2.08 | 5.51E-05 |
| Tiam2 | OSOM | 2.10 | 5.51E-05 |
| Thbd | OSOM | 2.05 | 5.53E-05 |
| Gm5918 | Glom | 2.00 | 5.56E-05 |
| 1700034O15Rik | Glom | 74.15 | 5.57E-05 |
| Col5a1 | OSOM | 2.55 | 5.58E-05 |
| Gm711 | Glom | 18.38 | 5.59E-05 |
| Capn5 | OSOM | 2.05 | 5.67E-05 |
| Capg | Glom | 2.32 | 5.68E-05 |
| Serpina3m | OSOM | 238.54 | 5.72E-05 |
| Elfn1 | Glom | 6.88 | 5.73E-05 |
| Cd276 | OSOM | 5.02 | 5.78E-05 |
| Dsp | OSOM | 2.21 | 5.78E-05 |
| Rfc4 | OSOM | 2.56 | 5.88E-05 |
| Slc19a1 | Glom | 2.18 | 5.89E-05 |
| E2f7 | OSOM | 5.03 | 5.91E-05 |
| Serpina1a | Glom | 19.72 | 6.15E-05 |
| Gpr77 | OSOM | 6.70 | 6.24E-05 |
| Uba6 | Cortex | 2.49 | 6.3E-05 |
| Slc1a2 | Glom | 12.13 | 6.3E-05 |
| 6230409E13Rik | ISOM | 2.98 | 6.42E-05 |
| Dusp6 | OSOM | 2.31 | 6.52E-05 |
| Pole | OSOM | 3.96 | 6.54E-05 |
| 1520402A15Rik | Glom | 2.68 | 6.54E-05 |
| Pcdhga2 | Glom | 8.84 | 6.67E-05 |
| Fam54a | OSOM | 7.05 | 6.7E-05 |
| Ccdc112 | OSOM | 2.04 | 6.75E-05 |
| Pdgfa | OSOM | 2.18 | 6.8E-05 |
| Ift9 | OSOM | 113.15 | 6.91E-05 |
| Ubxn10 | Glom | 7.15 | 6.92E-05 |
| Krt12 | OSOM | 23.12 | 7.09E-05 |
| Ube2u | Glom | 5.22 | 7.1E-05 |
| Cyp4a12b | OSOM | 16.16 | 7.13E-05 |
| Phlda3 | OSOM | 2.26 | 7.13E-05 |
| Hcn3 | Glom | 8.44 | 7.16E-05 |
| Rassf8 | Cortex | 3.18 | 7.18E-05 |
| Cd109 | Glom | 3.49 | 7.31E-05 |
| Mmp3 | OSOM | 7.13 | 7.53E-05 |

FIG. 29 CONTINUED

| | | | | |
|---|---|---|---|---|
| Met | Glom | 2.25 | 7.53E-05 | NS |
| Slc5a1 | Glom | 2.38 | 7.54E-05 | NS |
| S1pr2 | OSOM | 2.09 | 7.67E-05 | NS |
| D030028A08Rik | ISOM | 3.52 | 7.85E-05 | NS |
| Tpte | Glom | 58.23 | 7.94E-05 | NS |
| Acsf2 | Cortex | 2.21 | 7.96E-05 | NS |
| Cdca8 | OSOM | 3.81 | 8.01E-05 | NS |
| Gprt76 | OSOM | 4.02 | 8.03E-05 | NS |
| Tlr9 | Glom | 68.68 | 8.12E-05 | NS |
| 2810459M11Rik | OSOM | 8.83 | 8.18E-05 | NS |
| Lpo | Glom | 34.61 | 8.36E-05 | NS |
| Foxd3 | Glom | 130.05 | 8.41E-05 | NS |
| Itga2 | OSOM | 7.81 | 8.81E-05 | NS |
| Zfp593 | OSOM | 2.32 | 8.9E-05 | NS |
| Mir3091 | OSOM | 12.80 | 8.94E-05 | NS |
| Lypd3 | OSOM | 6.08 | 8.97E-05 | NS |
| Cldn2 | Glom | 2.90 | 8.97E-05 | NS |
| Syce2 | Glom | 2.74 | 8.97E-05 | NS |
| Csf2rb2 | Glom | 4.39 | 9.06E-05 | NS |
| C630064H02Rik | OSOM | 2.34 | 9.12E-05 | NS |
| Usp9x | Cortex | 2.46 | 9.2E-05 | NS |
| Serpina1b | OSOM | 12.45 | 9.21E-05 | NS |
| Cyp4b1 | OSOM | 2.66 | 9.25E-05 | NS |
| Fer1s | OSOM | 5.04 | 9.35E-05 | NS |
| H2B | Glom | 54.39 | 9.35E-05 | NS |
| Bpysl3 | Cortex | 4.19 | 9.42E-05 | NS |
| Zcchc12 | Glom | 6.93 | 9.47E-05 | NS |
| 4632434I11Rik | OSOM | 3.58 | 9.56E-05 | NS |
| Cxcl17 | OSOM | 19.24 | 9.56E-05 | NS |
| Creb3l3 | Glom | 229.75 | 9.58E-05 | NS |
| Cacng1 | Glom | 90.78 | 9.59E-05 | NS |
| C1ql3 | Glom | 86.72 | 9.72E-05 | NS |
| Dbi | Glom | 2.58 | 9.78E-05 | NS |
| Xk | OSOM | 3.34 | 9.82E-05 | NS |
| 5430425J12Rik | Glom | 188.90 | 9.94E-05 | NS |
| Ascl4 | Glom | 59.33 | 9.95E-05 | NS |

FIG. 29 CONTINUED

| GENE | iAKI - ISCHEMIA REPERFUSION | | | pAKI - VOLUME DEPLETION | | | EXPRESSION PATTERN (FPKM) | | | | | | | | | | | |
|---|---|---|---|---|---|---|---|---|---|---|---|---|---|---|---|---|---|---|
| | Region with Most Significant Fold Change | Fold Change | P-value | Region with Most Significant Fold Change | Fold Change | P-value | Control | | | | Ischemia | | | | Volume Depletion | | | |
| | | | | | | | Gl | Co | OM | IM | Gl | Co | OM | IM | Gl | Co | OM | IM |
| Tuba4a | | | NS | ISOM | 3.45 | 1.02E-24 | | | | | | | | | | | | |
| Stc1 | | | NS | Cortex | 10.72 | 9.35E-18 | | | | | | | | | | | | |
| Impa1 | | | NS | ISOM | 2.19 | 1.03E-13 | | | | | | | | | | | | |
| Ip6k2 | | | NS | Cortex | 3.11 | 2.60E-13 | | | | | | | | | | | | |
| Ddit4l | | | NS | Cortex | 3.57 | 7.45E-13 | | | | | | | | | | | | |
| Sec14l1 | | | NS | OSOM | 2.60 | 2.61E-12 | | | | | | | | | | | | |
| Cdc42 | | | NS | ISOM | 7.23 | 1.76E-11 | | | | | | | | | | | | |
| Tfdp2 | | | NS | ISOM | 2.37 | 2.4E-10 | | | | | | | | | | | | |
| Rnf19b | | | NS | ISOM | 2.09 | 4.62E-10 | | | | | | | | | | | | |
| Srls | | | NS | ISOM | 2.19 | 8.03E-10 | | | | | | | | | | | | |
| Plkp | | | NS | ISOM | 3.14 | 1.54E-09 | | | | | | | | | | | | |
| Mtfr | | | NS | OSOM | 2.52 | 3.14E-09 | | | | | | | | | | | | |
| Fam84a | | | NS | OSOM | 2.34 | 4.23E-09 | | | | | | | | | | | | |
| Slc45a3 | | | NS | ISOM | 3.88 | 4.73E-09 | | | | | | | | | | | | |
| Msd7b | | | NS | ISOM | 2.25 | 4.98E-09 | | | | | | | | | | | | |
| Pappa2 | | | NS | Cortex | 6.35 | 1.04E-08 | | | | | | | | | | | | |
| Kctd10 | | | NS | Glom | 2.21 | 1.15E-08 | | | | | | | | | | | | |
| Arrdc3 | | | NS | OSOM | 3.79 | 4.9E-08 | | | | | | | | | | | | |
| Slc25a48 | | | NS | ISOM | 4.14 | 8.08E-08 | | | | | | | | | | | | |
| Cxcr4 | | | NS | Cortex | 2.91 | 5.87E-08 | | | | | | | | | | | | |
| Cdk18 | | | NS | ISOM | 2.19 | 6.14E-08 | | | | | | | | | | | | |
| Cidea | | | NS | Cortex | 28.52 | 7.07E-08 | | | | | | | | | | | | |
| Cxcl13 | | | NS | ISOM | 15.47 | 7.21E-08 | | | | | | | | | | | | |
| Suox | | | NS | ISOM | 2.20 | 7.28E-08 | | | | | | | | | | | | |
| Lpin2 | | | NS | ISOM | 2.41 | 8.05E-08 | | | | | | | | | | | | |
| Gem | | | NS | Cortex | 8.19 | 9.55E-08 | | | | | | | | | | | | |
| Camk1d | | | NS | ISOM | 2.71 | 1.28E-07 | | | | | | | | | | | | |
| Kiss1 | | | NS | Glom | 13.23 | 1.86E-07 | | | | | | | | | | | | |
| Rph3al | | | NS | Glom | 3.05 | 2.86E-07 | | | | | | | | | | | | |
| Atp4a | | | NS | OSOM | 3.80 | 3.1E-07 | | | | | | | | | | | | |
| Nr4a2 | | | NS | ISOM | 4.01 | 5.07E-07 | | | | | | | | | | | | |
| Rassf10 | | | NS | ISOM | 3.27 | 6.63E-07 | | | | | | | | | | | | |
| Ppp2r3a | | | NS | Cortex | 2.03 | 8.63E-07 | | | | | | | | | | | | |
| Sesn2 | | | NS | Glom | 3.19 | 8.75E-07 | | | | | | | | | | | | |
| Mogat1 | | | NS | ISOM | 8.68 | 9.84E-07 | | | | | | | | | | | | |
| A230056P14Rik | | | NS | Glom | 4.12 | 1.08E-06 | | | | | | | | | | | | |
| Gm6184 | | | NS | Glom | 3.56 | 1.12E-06 | | | | | | | | | | | | |
| Rfn29 | | | NS | OSOM | 3.69 | 1.23E-06 | | | | | | | | | | | | |
| Slc34a1 | | | NS | Cortex | 4.63 | 1.34E-06 | | | | | | | | | | | | |
| Luzp2 | | | NS | ISOM | 6.19 | 1.38E-06 | | | | | | | | | | | | |
| Pgap1 | | | NS | ISOM | 2.15 | 1.41E-06 | | | | | | | | | | | | |
| F13b | | | NS | ISOM | 6.33 | 1.62E-06 | | | | | | | | | | | | |
| Rasal1 | | | NS | OSOM | 3.87 | 2.05E-06 | | | | | | | | | | | | |
| Aqp2 | | | NS | Glom | 7.22 | 2.1E-06 | | | | | | | | | | | | |
| Zfp266 | | | NS | OSOM | 3.77 | 2.21E-06 | | | | | | | | | | | | |
| Zfp185 | | | NS | OSOM | 3.39 | 2.49E-06 | | | | | | | | | | | | |
| Nlgn1 | | | NS | Glom | 128.41 | 2.48E-06 | | | | | | | | | | | | |
| Slc4a7 | | | NS | ISOM | 2.99 | 2.57E-06 | | | | | | | | | | | | |
| Ppp4r4 | | | NS | OSOM | 2.87 | 2.58E-06 | | | | | | | | | | | | |
| Nup62cl | | | NS | Glom | 123.94 | 2.9E-06 | | | | | | | | | | | | |
| Enpp2 | | | NS | OSOM | 3.28 | 2.79E-06 | | | | | | | | | | | | |
| Cort4l | | | NS | Cortex | 2.91 | 3.18E-06 | | | | | | | | | | | | |
| Apod | | | NS | Cortex | 6.81 | 3.41E-06 | | | | | | | | | | | | |
| Rnf182 | | | NS | Glom | 127.73 | 4.26E-06 | | | | | | | | | | | | |
| Nostrin | | | NS | Cortex | 2.06 | 4.13E-06 | | | | | | | | | | | | |
| Nxph3 | | | NS | ISOM | 3.04 | 4.29E-06 | | | | | | | | | | | | |
| Nek11 | | | NS | Glom | 80.38 | 4.38E-06 | | | | | | | | | | | | |
| Unc13c | | | NS | Glom | 85.67 | 4.88E-06 | | | | | | | | | | | | |
| 9530026P05Rik | | | NS | Cortex | 3.25 | 5.06E-06 | | | | | | | | | | | | |
| Clcnka | | | NS | ISOM | 2.26 | 5.4E-06 | | | | | | | | | | | | |
| E030018J19Rik | | | NS | ISOM | 6.08 | 5.61E-06 | | | | | | | | | | | | |
| Csmd1 | | | NS | Glom | 8.48 | 7.2E-06 | | | | | | | | | | | | |
| Nt5c3 | | | NS | ISOM | 5.93 | 7.23E-06 | | | | | | | | | | | | |
| Ldoc1l | | | NS | OSOM | 3.82 | 7.25E-06 | | | | | | | | | | | | |
| Usp53 | | | NS | Cortex | 3.02 | 7.54E-06 | | | | | | | | | | | | |
| Shbg | | | NS | OSOM | 5.15 | 7.59E-06 | | | | | | | | | | | | |

FIG. 30

| | | | | | |
|---|---|---|---|---|---|
| Dab1 | NS | OSOM | 2.55 | 7.81E-06 | |
| Cited4 | NS | ISOM | 3.34 | 9.24E-06 | |
| Trim9 | NS | OSOM | 14.79 | 9.43E-06 | |
| Sema4c | NS | Cortex | 2.27 | 1E-05 | |
| Acsm2 | NS | ISOM | 7.44 | 1.02E-05 | |
| 6230312C03Rik | NS | ISOM | 14.53 | 1.09E-05 | |
| Gpr98 | NS | OSOM | 5.29 | 1.09E-05 | |
| 2010187G23Rik | NS | Glom | 2.73 | 1.11E-05 | |
| Ednrb | NS | Cortex | 2.37 | 1.14E-05 | |
| Hpd | NS | ISOM | 10.97 | 1.28E-05 | |
| Mapk10 | NS | OSOM | 3.78 | 1.31E-05 | |
| Rdh16-ps | NS | ISOM | 3.37 | 1.51E-05 | |
| Peg3 | NS | Cortex | 3.13 | 1.65E-05 | |
| Espnl | NS | OSOM | 3.49 | 1.71E-05 | |
| Cpne8 | NS | OSOM | 6.48 | 1.93E-05 | |
| Folh1 | NS | ISOM | 7.02 | 1.96E-05 | |
| 2210408F21Rik | NS | ISOM | 2.94 | 2.39E-05 | |
| Nptx1 | NS | ISOM | 9.48 | 2.39E-05 | |
| Plxxd1 | NS | OSOM | 2.58 | 2.46E-05 | |
| Arrdc2 | NS | ISOM | 2.04 | 2.5E-05 | |
| Spp2 | NS | ISOM | 7.77 | 2.83E-05 | |
| Arhgef37 | NS | ISOM | 2.87 | 2.91E-05 | |
| Naph4 | NS | Glom | 81.30 | 2.95E-05 | |
| Slc22a6 | NS | ISOM | 6.28 | 2.97E-05 | |
| Gas7 | NS | Cortex | 2.08 | 3.05E-05 | |
| Gm1332 | NS | ISOM | 2.44 | 3.08E-05 | |
| Ucp1 | NS | Cortex | 31.77 | 3.27E-05 | |
| Hist1h2bb | NS | ISOM | 5.47 | 3.48E-05 | |
| Ethk2 | NS | ISOM | 2.03 | 3.58E-05 | |
| Abca1 | NS | Cortex | 2.15 | 3.81E-05 | |
| Mamd3 | NS | Cortex | 2.04 | 5.08E-05 | |
| Tmem27 | NS | ISOM | 2.37 | 5.38E-05 | |
| Cyp2d26 | NS | ISOM | 5.02 | 5.44E-05 | |
| Igfbp3 | NS | ISOM | 2.34 | 5.94E-05 | |
| Nrap | NS | ISOM | 3.88 | 5.99E-05 | |
| Acmsd | NS | ISOM | 7.78 | 6.84E-05 | |
| Gpr55a | NS | ISOM | 2.28 | 6.85E-05 | |

| SECRETED pAKI - VOLUME DEPLETION DIFFERENTIALLY EXPRESSED GENES ≥ 2 FOLD CHANGE | | | | | | | | | EXPRESSION PATTERN (FPKM) | | | | | | | | | | | |
|---|---|---|---|---|---|---|---|---|---|---|---|---|---|---|---|---|---|---|---|---|
| | Glomerulus | | Cortex | | Outer Medulla | | Inner Medulla | | Control | | | | Ischemia | | | | Volume Depletion | | | |
| GENE | Fold Change | PValue | Fold Change | PValue | Fold Change | PValue | Fold Change | PValue | Gl | Co | OM | IM | Gl | Co | OM | IM | Gl | Co | OM | IM |
| Stc1 | | NS | 18.72 | 9.36E-15 | 5.90 | 1.92E-09 | | NS | | | | | | | | | | | | |
| Pappa2 | | NS | 6.35 | 1.89E-08 | | NS | | NS | | | | | | | | | | | | |
| Apod | | NS | 6.51 | 3.41E-06 | | NS | | NS | | | | | | | | | | | | |
| Grem1 | | NS | 98.99 | 4.17E-05 | | NS | | NS | | | | | | | | | | | | |
| Enpp2 | | NS | | NS | 3.28 | 2.75E-06 | 3.18 | 6.98E-06 | | | | | | | | | | | | |
| Folh1 | | NS | | NS | | NS | 7.69 | 1.96E-05 | | | | | | | | | | | | |
| Hpd | | NS | | NS | | NS | 10.97 | 1.25E-05 | | | | | | | | | | | | |
| Gprc5b | | NS | | NS | | NS | 2.26 | 9.85E-05 | | | | | | | | | | | | |
| Nptx1 | | NS | | NS | | NS | 9.40 | 2.38E-05 | | | | | | | | | | | | |
| Camk1d | | NS | | NS | | NS | 2.71 | 1.28E-07 | | | | | | | | | | | | |

FIG. 32

METHODS OF TREATING VOLUME DEPLETION AND KIDNEY INJURY

This application is the U.S. National Stage of International Application no. PCT/US2016/046920 filed Aug. 12, 2016, which claims priority to U.S. Ser. No. 62/204,205 filed Aug. 12, 2015, and U.S. Ser. No. 62/354,494 filed Jun. 24, 2016, the contents of which are hereby incorporated by reference in their entirety.

GOVERNMENT SUPPORT

This invention was made with government support under Grant No. DK073462 awarded by the National Institutes of Health. The government has certain rights in the invention.

All patents, patent applications and publications, and non-patent publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted in ASCII format via EFS-Web and is hereby incorporated by reference in its entirety. Said ASCII copy, created on Nov. 2, 2018, is named 0019240_01100US2_SL.txt and is 55,557 bytes in size.

BACKGROUND

Nephrology is the only field in Medicine that uses a single analyte—serum creatinine (sCr)—to suggest organ injury. Yet the rise of sCr trails the injury by 24 hrs, if not by days, and it is insensitive to <50% damage. Most vexing is the fact that common volume depletion (75%) and tubular injury ("ATN" 25%) both increase sCr, meaning that therapy is not based on a prospective physiological assay. The consequence of unguided decisions includes unacceptable morbidity, multiple testing, escalation of care—LOS and increased aggregate costs of $7500 ppt. Accordingly, there is a need for methods of diagnosis and treatment for volume depletion and kidney injury.

BRIEF DESCRIPTION OF THE FIGURES

The patent or application file contains at least one drawing executed in color. Copies of this patent or patent application publication with color drawing(s) will be provided by the United States Patent and Trademark Office upon request and payment of the necessary fee.

FIG. 9A. Immunofluorescence (Krt20) and in situ hybridization (Trop2, NGAL) demonstrate specificity for iAKI. Note that Krt20 (red) was expressed in proximal tubules (megalin=green) and in intercalated cells (inset: Krt20=red; Aqp2=white). Note that Trop2 was expressed in distal nephron segments. NGAL RNA was expressed by Thick Ascending Limbs of Henle (TALH) as well as Intercalated Cells (IC) of the Collecting Ducts in iAKI. Timp2 and Igfbp7 RNA are shown for comparison. Note the expression of these genes in scattered glomerular (G) and tubular cells.

FIG. 9B. Secreted proteins (CHI3L1, TROP2, Plat, Krt20) are elevated in most human iAKI urine but not in most vAKI urine. Conversely, secreted protein PAPPA2 is elevated in many vAKI urines, but it is degraded in iAKI patients. Orange bars denote canonical molecular weights of the analyte.

FIG. 9C. Secreted proteins (NGAL, VitDBP, TIMP2, IGFBP7) are shown for comparison and demonstrate different degrees of specificity of iAKI patients. Orange bars denote canonical molecular weights of the analyte.

FIGS. 11A-B. Segment-specific gene expression analysis using (FIG. 11A) RNA-seq and (FIG. 11B) RT-qPCR. RNA extracted and pooled from Laser Captured Tissues showed segment specific genes[16] demonstrating enrichment or de-enrichment in each anatomic compartment compared to whole kidney extracts (n=3 for cortex, OSOM, ISOM, Whole Kidney; n=2 for Glom; * p<0.05 compared to every other region, † p<0.05 compared to cortex).

FIG. 21A). FPKM analysis of RNA-Seq pools and FIG. 21B) Real-time quantitative PCR analysis of the RNA pools. Cellular and segment specific genes[14] demonstrate relative enrichment or de-enrichment in each anatomic compartment compared to whole kidney extracts (n=3 for cortex, OSOM, ISOM, Whole Kidney; n=2 for Glom; * p<0.05 compared to every other region, † p<0.05 compared to cortex.

FIG. 24. Published iAKI biomarkers are specific to the iAKI model[43]. They are not expressed in the vAKI model. The region with most significant fold change was reported for each condition. Only FPKM values with significant fold change (q<0.01) from control are reported. The expression pattern displays relative FPKM expression values, row normalized to the highest FPKM across regions and conditions. NS: non-significant.

FIG. 25. 1158 differentially expressed iAKI genes (≥2-fold change, $p<10^{-5}$) were not significantly expressed in vAKI. Table shows fold change from control; genes were ranked by q-value. Only FPKM values with significant fold change (q<0.01) from control are reported. NS: non-significant. Expression pattern displays relative FPKM expression values, row normalized to the highest FPKM across all regions and conditions.

FIG. 26. 103 differentially expressed vAKI genes (≥2-fold change, $p<10^{-5}$) were not significantly expressed in iAKI. Table shows fold change from control genes were ranked by q-value. Only FPKM values with significant fold change (q<0.01) from control are reported. NS: non-significant. Expression pattern displays relative FPKM expression values, row normalized to the highest FPKM across all regions and conditions.

Figure 27:
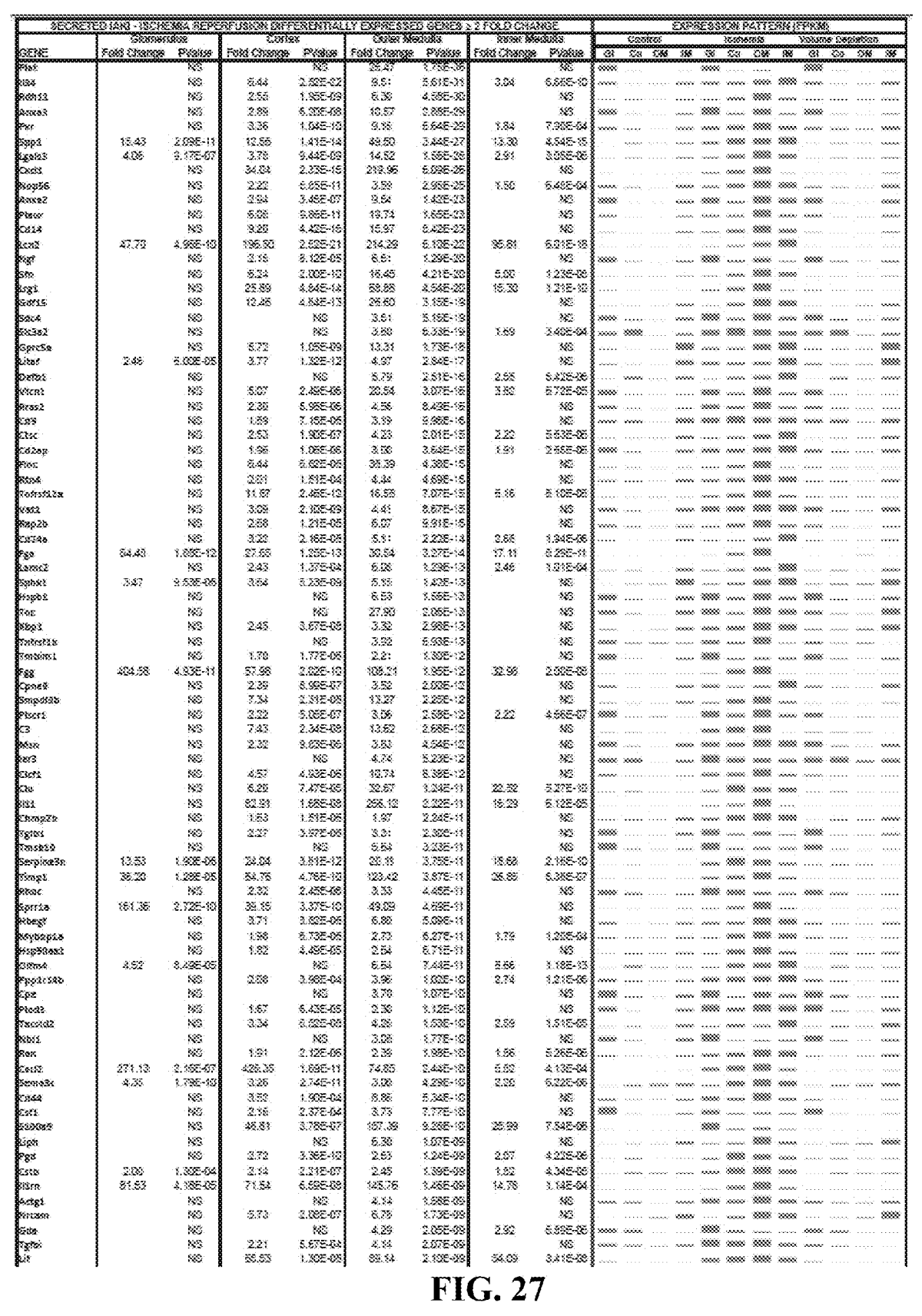
Figure 27:
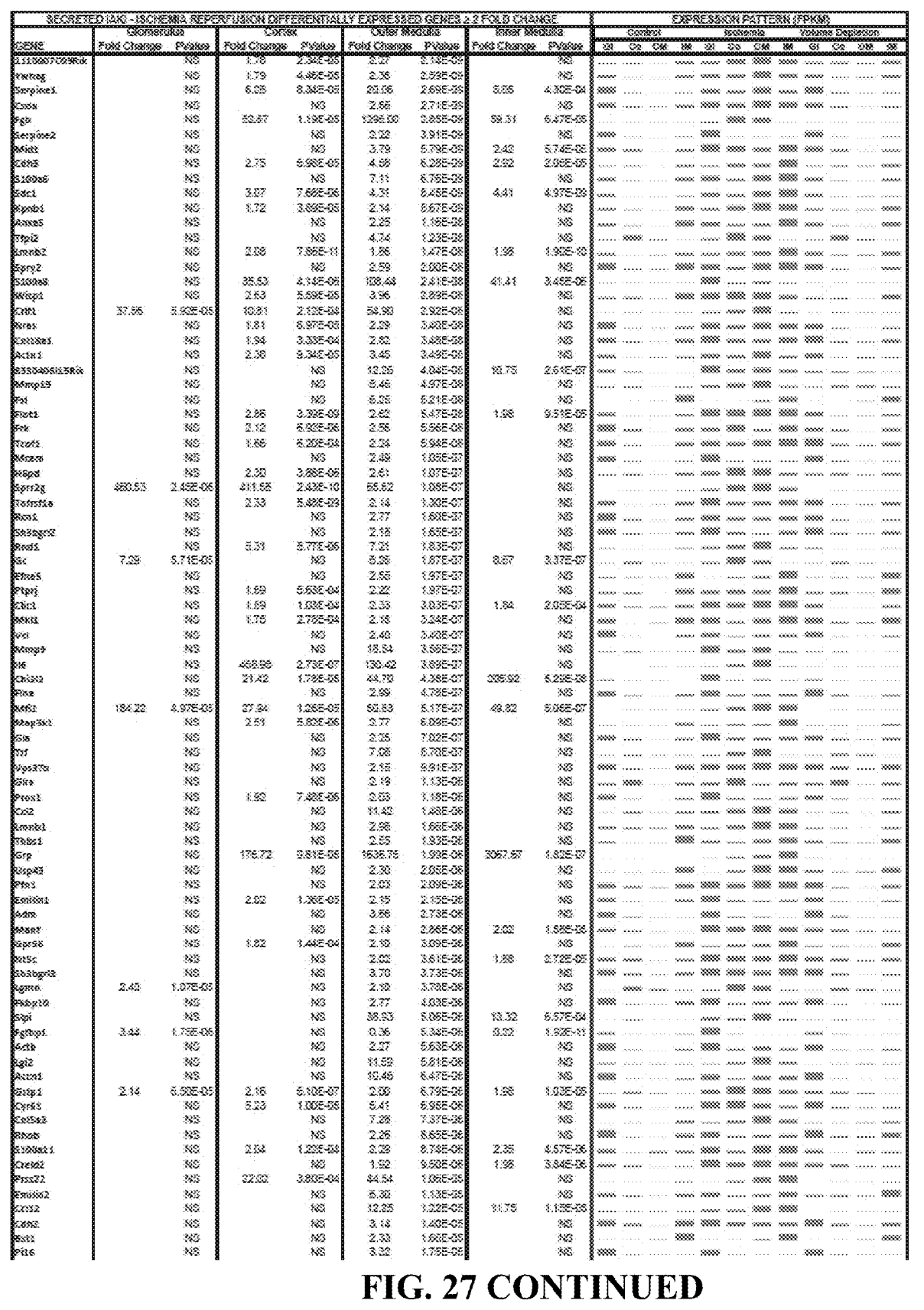
Figure 27:
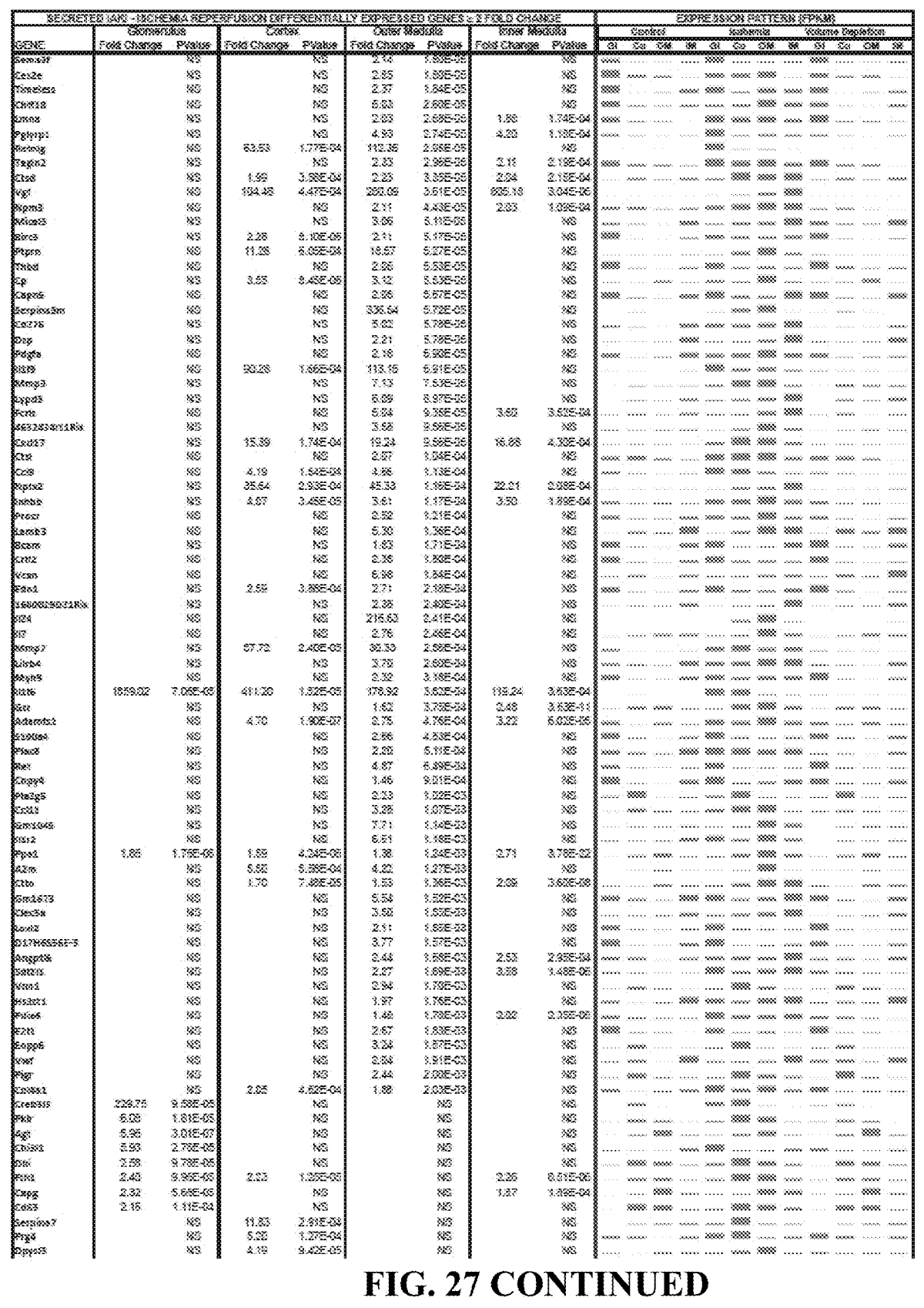
Figure 27:
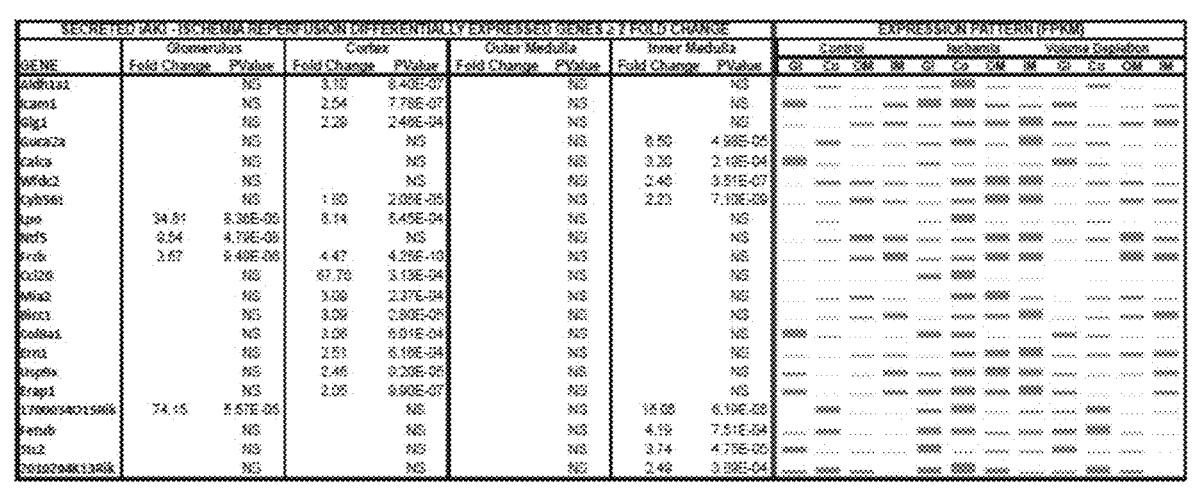

FIG. 27. 267 secreted proteins induced by iAKI (≥1-fold change, $p<10^{-5}$) annotated in the Max Planck Unified Proteome Database or the Secretonome database and expressed at FPKM levels >1. Table shows fold change from control. Genes were ranked by q-value. Only FPKM values with significant fold change (q<0.01) from control are reported. NS: non-significant. Expression pattern displays relative FPKM expression values, row normalized to the highest FPKM across all regions and conditions.

Figure 28:
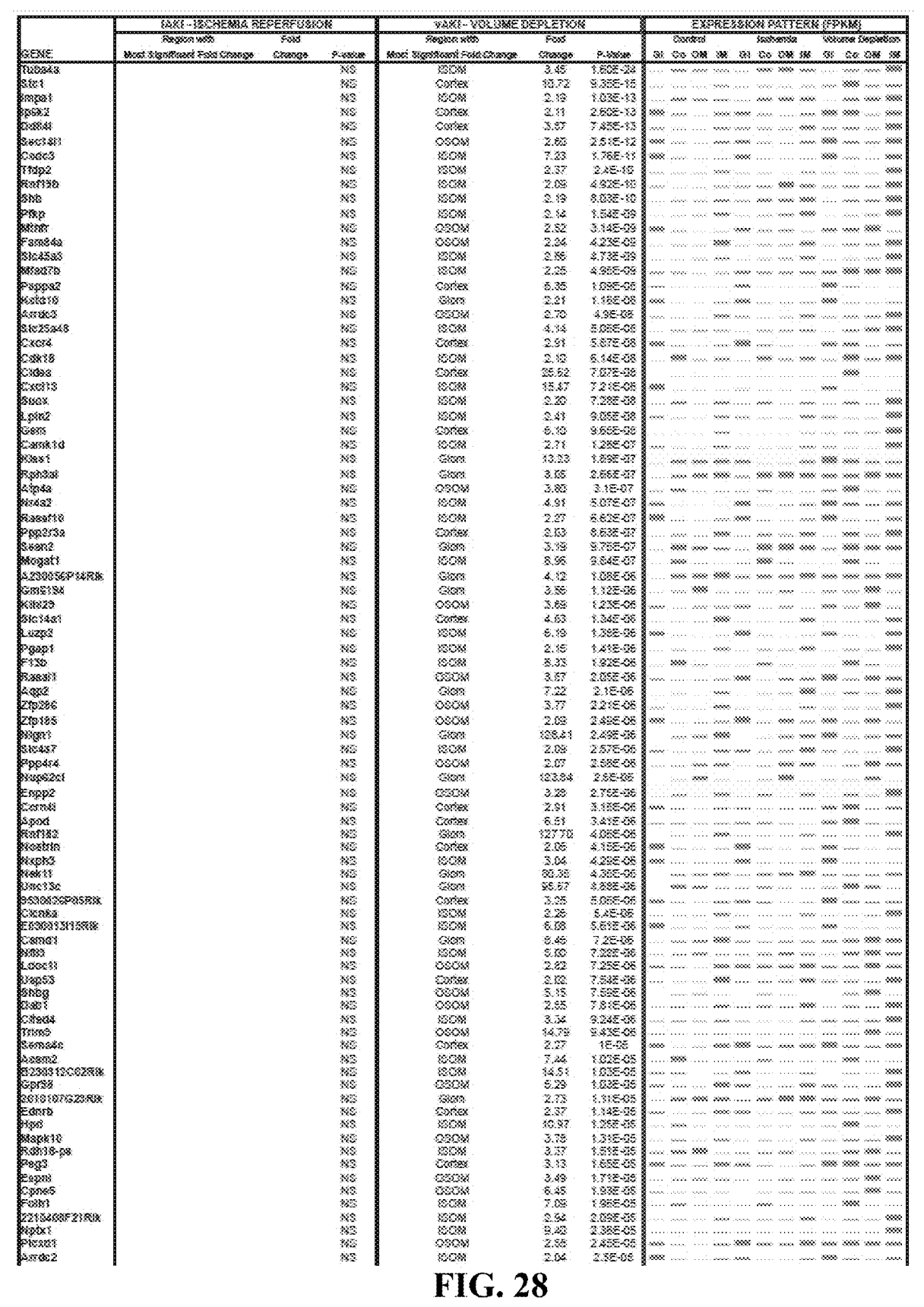

FIG. 28. 30 secreted proteins induced by vAKI (≥1-fold change, p<10-5) annotated in the Max Planck Unified Proteome Database or the Secretonome database and expressed at FPKM levels >1. Table shows fold change from control. Genes were ranked by q-value. Only FPKM values with significant fold change (q<0.01) from control are reported. NS: non-significant. Expression pattern displays relative FPKM expression values, row normalized to the highest FPKM across all regions and conditions.

FIG. 29 1158 differentially expressed iAKI genes (>2-fold change, $p<10^{-5}$) were not significantly expressed in pAKI. Table shows fold change from control; genes were ranked by q-value. Furthest right columns display relative FPKM expression values, row normalized to the highest FPKM across all regions and conditions. Only FPKM values with significant fold change (q<0.01) from control are reported. NS: non-significant.

FIG. 30. 103 differentially expressed pAKI genes (>2-fold change, $p<10^{-5}$) were not significantly expressed in iAKI. Table shows fold change from control, genes were ranked by q-value. Furthest right columns display relative FPKM expression values, row normalized to the highest FPKM across all regions and conditions. Only FPKM values with significant fold change (q<0.01) from control are reported. NS: non-significant.

FIG. 31. 108 secreted proteins induced by iAKI (>2-fold change, $p<10^{-5}$) annotated in the Max Planck Unified Proteome Database or the Secretonome database. Table shows fold change from control. Table shows fold change from control, genes were ranked by q-value. Furthest right columns display relative FPKM expression values, row normalized to the highest FPKM across all regions and conditions. Only FPKM values with significant fold change (q<0.01) from control are reported. NS: non-significant.

FIG. 32. 10 secreted proteins induced by pAKI (>2-fold change, $p<10^{-5}$) annotated in the Max Planck Unified Proteome Database or the Secretonome database. Table shows fold change from control. Table shows fold change from control, genes were ranked by q-value. Furthest right columns display relative FPKM expression values, row normalized to the highest FPKM across all regions and conditions. Only FPKM values with significant fold change (q<0.01) from control are reported. NS: non-significant.

SUMMARY OF THE INVENTION

Figure 1:
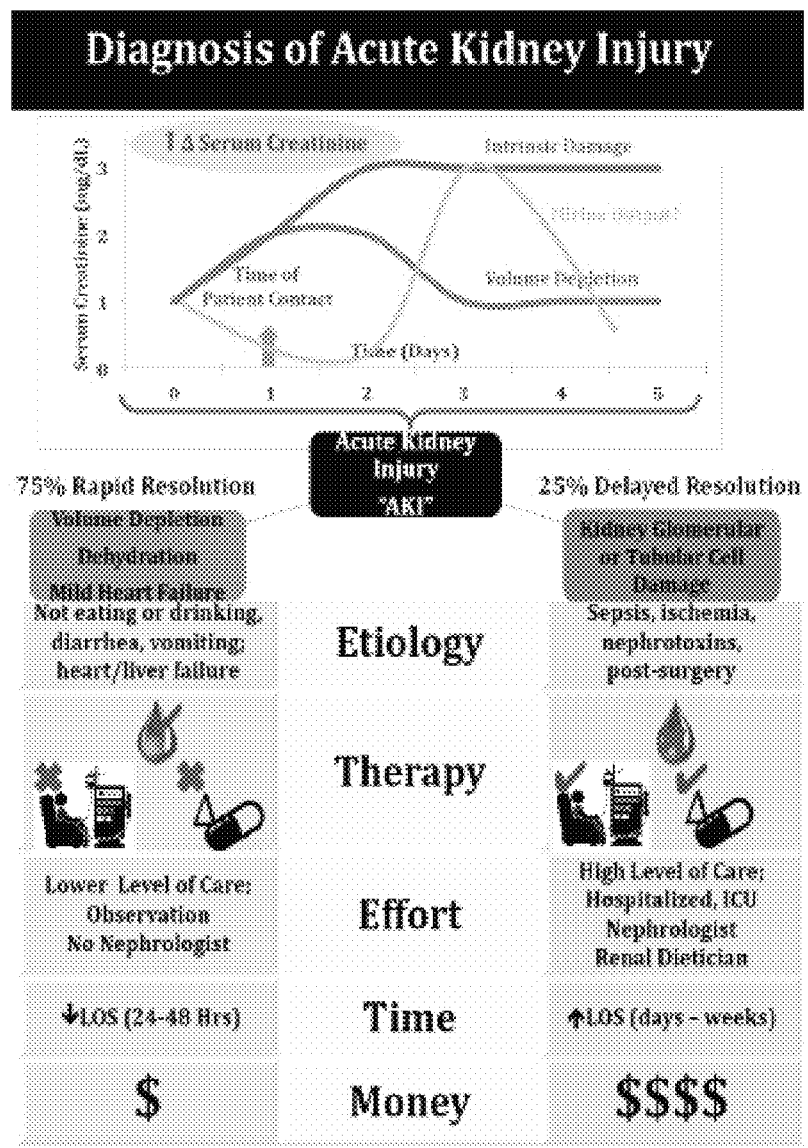
FIG. 1. Diagnosis of Acute Kidney Injury

The present invention relates to divergent AKI transcriptomes, specifically gene signatures in pre-renal/volume depletion/hemodynamic fluctuations versus ischemic kidney injury. The definition of acute kidney failure is undergoing a revision. Serum creatinine (sCr) is currently the only marker. Yet it elevates in pre-renal/volume depletion/hemodynamic fluctuations and in ischemic damage.

In one aspect, the invention provides a method for treating volume-dependent acute kidney injury (vAKI) in a subject in need thereof, the method comprising: a) determining the level of full-length PAPPA2 protein in a urine sample from the subject; and b) administering fluids to the subject if full-length PAPPA2 protein is present in the urine sample from the subject in a higher amount than in a urine sample from a subject that does not have Acute Kidney Injury (AKI).

In another aspect, the invention provides a method for treating vAKI in a subject in need thereof, the method comprising: a) determining the level of full-length PAPPA2 protein in a urine sample from the subject; b) determining the level of NGAL, KRT20, or TACSTD2 protein, or a combination thereof, in the urine sample from the subject; c) determining the ratio of full-length PAPPA2/NGAL, full-length PAPPA2/KRT20, or full-length PAPPA2/TACSTD2 in the urine sample from the subject; d) determining the level of full-length PAPPA2 protein in a urine sample from a subject that does not have AKI; e) determining the level of NGAL, KRT20, or TACSTD2 protein, or a combination thereof, in a urine sample from a subject that does not have AKI; f) determining the ratio of full-length PAPPA2/NGAL, full-length PAPPA2/KRT20, or full-length PAPPA2/TACSTD2 in the urine sample from the subject that does not have AKI; and g) administering fluids to the subject if the ratio of full-length PAPPA2/NGAL, full-length PAPPA2/KRT20, or full-length PAPPA2/TACSTD2 in the urine sample from the subject is greater than the ratio of full-length PAPPA2/NGAL, full-length PAPPA2/KRT20, or full-length PAPPA2/TACSTD2 in the urine sample from a subject that does not have AKI, respectively.

In another aspect, the invention provides a method for treating ischemic acute kidney injury (iAKI) in a subject in need thereof, the method comprising: a) determining the level of NGAL, KRT20, or TACSTD2 protein, or a combination thereof, in a urine sample from the subject; and b) administering treatment for kidney damage to the subject if NGAL, KRT20, or TACSTD2 protein, or a combination thereof, is present in the urine sample from the subject in a higher amount than in a urine sample from a subject that does not have AKI.

In one aspect, the invention provides a method for treating iAKI in a subject in need thereof, the method comprising: a) determining the level of full-length PAPPA2 protein in a urine sample from the subject; b) determining the level of NGAL, KRT20, or TACSTD2 protein, or a combination thereof, in the urine sample from the subject; c) determining the ratio of NGAL/full-length PAPPA2, KRT20/full-length PAPPA2, or TACSTD2/full-length PAPPA2 in the urine sample from the subject; d) determining the level of full-length PAPPA2 protein in a urine sample from a subject that does not have AKI; e) determining the level of NGAL, KRT20, or TACSTD2 protein, or a combination thereof, in the urine sample from the subject that does not have AKI; f) determining the ratio of NGAL/full-length PAPPA2, KRT20/full-length PAPPA2, or TACSTD2/full-length PAPPA2 in the urine sample from the subject that does not have AKI; and g) administering treatment for kidney damage to the subject if the ratio of NGAL/full-length PAPPA2, KRT20/full-length PAPPA2, or TACSTD2/full-length PAPPA2 in the urine sample from the subject is greater than the ratio of NGAL/full-length PAPPA2, KRT20/full-length PAPPA2, or TACSTD2/full-length PAPPA2 in the urine sample from the subject that does not have AKI, respectively.

In another aspect, the invention provides a method for treating iAKI in a subject in need thereof, the method comprising: a) determining the level of proteolytically cleaved PAPPA2 protein in a urine sample from the subject; and b) administering treatment for kidney damage to the subject if proteolytically cleaved PAPPA2 protein is present in the urine sample from the subject in a higher amount than in a urine sample from a subject that does not have AKI.

In one embodiment, the size of full-length PAPPA2 is equal to or above 180 kDa. In another embodiment, the size of proteolytically cleaved PAPPA2 is equal to or below 130 kDa.

In one embodiment, the method further comprises determining the level of serum creatinine in the subject. In one embodiment, the level of serum creatinine is determined before the administering step. In another embodiment, an elevated level of serum creatinine is above 0.5 mg/dL.

In one embodiment, treatment is administered if the subject has an elevated level of serum creatinine. In another embodiment, the treatment for kidney damage comprises withholding fluids, administering dialysis, or a combination thereof. In one embodiment, the method further comprises testing and treating the subject for hyperkalemia, hyponatremia, hyperphosphatemia or acidosis.

In one embodiment, the method comprises prior to step a), reducing a urine sample from a subject with a reducing agent to generate a reduced urine sample, filtering the reduced urine sample with a 300 KDa filter to produce a retentate and a filtrate, wherein step a) and/or d) is then performed on the retentate. In another embodiment, the reducing agent is beta-mercaptoethanol.

In one embodiment, the level of full-length PAPPA2, proteolytically cleaved PAPPA2, NGAL, KRT20, or TACSTD2 protein is determined by ELISA, immunoblot, Western blot, or lateral flow dip stick. In another embodiment, the level of full-length PAPPA2, proteolytically cleaved PAPPA2, NGAL, KRT20, or TACSTD2 protein is determined using an antibody that specifically binds to full-length PAPPA2, proteolytically cleaved PAPPA2, NGAL, KRT20, or TACSTD2 protein, respectively, or a fragment thereof.

In one aspect, the invention provides a diagnostic kit for determining whether a urine sample from a subject contains full-length PAPPA2, proteolytically cleaved PAPPA2, NGAL, KRT20, or TACSTD2 protein, or a combination thereof, the kit comprising at least one antibody that specifically binds to full-length PAPPA2, proteolytically cleaved PAPPA2, NGAL, KRT20, or TACSTD2 protein, or a fragment thereof.

In another aspect, the invention provides a diagnostic kit for determining whether a urine sample from a subject contains full-length PAPPA2, proteolytically cleaved PAPPA2, NGAL, KRT20, or TACSTD2 protein, or a combination thereof, the kit comprising at least one antibody that specifically binds to a protein comprising SEQ ID NO: 1, 2, 5, 7, or 9.

In another aspect, the invention provides a method for detecting the presence of a full-length PAPPA2, proteolytically cleaved PAPPA2, NGAL, KRT20, or TACSTD2 protein in a urine sample from a subject, the method comprising: (a) obtaining a urine sample from the subject; and (b) measuring full-length PAPPA2, proteolytically cleaved PAPPA2, NGAL, KRT20, or TACSTD2 protein levels by ELISA using an antibody directed to SEQ ID NO: 1, 2, 5, 7, or 9; or by western blot using an antibody directed to SEQ ID NO: 1, 2, 5, 7, or 9; or by mass spectroscopy; or by isoelectric focusing, or a combination thereof.

In another aspect, the invention provides a method of diagnosing vAKI in a subject in need thereof, the method comprising: a) determining the level of full-length PAPPA2 protein in a urine sample from the subject; and b) diagnosing the subject with vAKI if full-length PAPPA2 protein is present in the urine sample from the subject in a higher amount than in a urine sample from a subject that does not have AKI.

In one aspect, the invention provides a method of diagnosing vAKI in a subject in need thereof, the method comprising: a) determining the level of full-length PAPPA2 protein in a urine sample from the subject; b) determining the level of NGAL, KRT20, or TACSTD2 protein, or a combination thereof, in the urine sample from the subject; c) determining the ratio of full-length PAPPA2/NGAL, full-length PAPPA2/KRT20, or full-length PAPPA2/TACSTD2 in the urine sample from the subject; d) determining the level of full-length PAPPA2 protein in a urine sample from a subject that does not have AKI; e) determining the level of NGAL, KRT20, or TACSTD2 protein, or a combination thereof, in the urine sample from the subject that does not have AKI; f) determining the ratio of full-length PAPPA2/NGAL, full-length PAPPA2/KRT20, or full-length PAPPA2/TACSTD2 in the urine sample from the subject that does not have AKI; g) diagnosing the subject with vAKI if the ratio of full-length PAPPA2/NGAL, full-length PAPPA2/KRT20, or full-length PAPPA2/TACSTD2 in the urine sample from the subject is greater than the ratio of full-length PAPPA2/NGAL, full-length PAPPA2/KRT20, or full-length PAPPA2/TACSTD2 in the urine sample from a subject that does not have AKI, respectively.

In another aspect, the invention provides a method of diagnosing iAKI in a subject in need thereof, the method comprising: a) determining the level of NGAL, KRT20, or TACSTD2 protein, or a combination thereof, in a urine sample from the subject; and b) diagnosing the subject with iAKI if NGAL, KRT20, or TACSTD2 protein, or a combination thereof, is present in the urine sample from the subject in a higher amount than in a urine sample from a subject that does not have AKI.

In one aspect, the invention provides a method of diagnosing iAKI in a subject in need thereof, the method comprising: a) determining the level of full-length PAPPA2 protein in a urine sample from the subject; b) determining the level of NGAL, KRT20, or TACSTD2 protein, or a combination thereof, in the urine sample from the subject; c) determining the ratio of NGAL/full-length PAPPA2, KRT20/full-length PAPPA2, or TACSTD2/full-length PAPPA2 in the urine sample from the subject; d) determining the level of full-length PAPPA2 protein in a urine sample from a subject that does not have AKI; e) determining the level of NGAL, KRT20, or TACSTD2 protein, or a combination thereof, in the urine sample from the subject that does not have AKI; f) determining the ratio of NGAL/full-length PAPPA2, KRT20/full-length PAPPA2, or TACSTD2/full-length PAPPA2 in the urine sample from the subject that does not have AKI; g) diagnosing the subject with iAKI if the ratio of NGAL/full-length PAPPA2, KRT20/full-length PAPPA2, or TACSTD2/full-length PAPPA2 in the urine sample from the subject is greater than the ratio of NGAL/full-length PAPPA2, KRT20/full-length PAPPA2, or TACSTD2/full-length PAPPA2 in the urine sample from the subject that does not have AKI, respectively.

In another aspect, the invention provides a method for diagnosing iAKI in a subject in need thereof, the method comprising: a) determining the level of proteolytically cleaved PAPPA2 protein in a urine sample from the subject; and b) diagnosing the subject with iAKI if proteolytically cleaved PAPPA2 protein is present in the urine sample from the subject in a higher amount than in a urine sample from a subject that does not have AKI.

In one embodiment, the size of full-length PAPPA2 is equal to or above 180 kDa. In another embodiment, the size of proteolytically cleaved PAPPA2 is equal to or below 130 kDa.

In one embodiment, the method comprises administering fluids to the subject if the subject is diagnosed with vAKI. In another embodiment, the method comprises administering treatment for kidney damage if the subject is diagnosed with iAKI.

In one embodiment, the method comprises determining the level of serum creatinine in the subject. In another embodiment, the level of serum creatinine is determined before the diagnosing step. In one embodiment, an elevated level of serum creatinine is above 0.5 mg/dL.

In one embodiment, the subject is diagnosed with vAKI or iAKI if the subject also has an elevated level of serum creatinine.

In one embodiment, the treatment for kidney damage comprises withholding fluids, administering dialysis, or a combination thereof. In another embodiment, the method further comprises testing and treating the subject for hyperkalemia, hyponatremia, hyperphosphatemia or acidosis if the subject is diagnosed with iAKI.

In one embodiment, the method further comprises, prior to step a), reducing a urine sample from a subject with a reducing agent to generate a reduced urine sample, filtering the reduced urine sample with a 300 kDa filter to produce a retentate and a filtrate, wherein step a) and/or d) is then performed on the retentate. In another embodiment, the reducing agent is beta-mercaptoethanol.

In one embodiment, the level of full-length PAPPA2, proteolytically cleaved PAPPA2, NGAL, KRT20, or TACSTD2 protein is determined by ELISA, immunoblot, Western blot, or lateral flow dip stick. In another embodiment, the level of full-length PAPPA2, proteolytically cleaved PAPPA2, NGAL, KRT20, or TACSTD2 protein is determined using an antibody that specifically binds to full-length PAPPA2, proteolytically cleaved PAPPA2, NGAL, KRT20, or TACSTD2 protein, respectively, or a fragment thereof.

In one embodiment, the subject is a human subject.

In one aspect, the invention provides a device for determining whether a urine sample from a subject contains full-length PAPPA2, proteolytically cleaved PAPPA2, NGAL, KRT20, or TACSTD2 protein, or a combination thereof, the device comprising at least one antibody that specifically binds to full-length PAPPA2, proteolytically cleaved PAPPA2, NGAL, KRT20, or TACSTD2 protein, or a fragment thereof.

DETAILED DESCRIPTION

All patent applications, published patent applications, issued and granted patents, texts, and literature references cited in this specification are hereby incorporated herein by reference in their entirety to more fully describe the state of the art to which the present disclosed subject matter pertains.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Described herein are specific gene markers for volume depletion of the kidney (i.e. vAKI) and for kidney ischemic damage (i.e. iAKI) that have been identified. Specific gene markers were identified for volume depletion (i.e. vAKI), and specific gene markers were identified for ischemic damage (i.e. iAKI).

The terms "effective amount" and "effective to treat," as used herein, refer to an amount or a concentration of one or more compounds or a pharmaceutical composition described herein utilized for a period of time (including in vitro and in vivo acute or chronic administration and periodic or continuous administration) that is effective within the context of its administration for causing an intended effect or physiological outcome.

The term "subject" is used throughout the specification to describe an animal, human or non-human, to whom treatment according to the methods of the present invention is provided. A subject may be, for example, a mammal such as a dog, a cat, a cow, a horse, a rabbit, a monkey, a pig, a sheep, a goat, a mouse, a rat, or a human.

The singular forms "a," "an," and "the" include plural reference unless the context clearly dictates otherwise.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein the term "variant" covers nucleotide or amino acid sequence variants which have about 95%, about 90%, about 85%, about 80%, about 85%, about 80%, about 75%, about 70%, or about 65% nucleotide identity, or about 95%, about 90%, about 85%, about 80%, about 85%, about 80%, about 75%, or about 70% amino acid identity, including but not limited to variants comprising conservative, or non-conservative substitutions, deletions, insertions, duplications, or any other modification. The term variant as used herein includes functional and non-functional variants, and variants with reduced or altered activity.

As used herein "AKI" refers to Acute Kidney Injury.

As used herein "vAKI" and "pAKI" refer to volume-dependent Acute Kidney Injury, also referred to as pre-renal/volume depletion/hemodynamic fluctuations. vAKI (or pAKI) is defined by an increase in serum creatinine that is rapidly reversible by fluids. vAKI (or pAKI) is commonly due to volume depletion, heart failure, or liver failure, and is considered a transient condition.

As used herein "iAKI" refers to ischemic Acute Kidney Injury, or nephrotoxic Acute Kidney Injury, also referred to as intrinsic tubular damage, ischemic damage, direct damage to the kidney tubule, tubular injury, and intrinsic tubular damage. iAKI is a direct injury to the kidney tubules, or kidney vasculature. iAKI is not reversible with fluids, typically lasts more than two days, and is considered a more prolonged condition.

As used herein "sCr" refers to serum creatinine, and "Pcr" refers to plasma creatinine or P-creatinine. The terms sCr and Pcr and the terms "serum creatinine" and "plasma creatinine" and "P-creatinine" can be used interchangeably.

vAKI and iAKI

Acute kidney failure was traditionally categorized by etiology including prerenal/transient kidney failure, intrinsic/prolonged kidney failure (ATN), or postrenal kidney failure. In contrast, more recent classifications focus on two metrics, the rise in serum creatinine (sCr) or a decrease in urine output as tantamount to kidney injury (Acute Kidney Injury, "AKI"), without emphasis on its potential etiologies or on clinical heterogeneity. While any form of AKI worsens patient outcomes, it has remained an open question how hemodynamic or volume 'vAKI' is related to intrinsic tubular damage 'iAKI'.

The critical function of the kidney is the preservation of water and electrolytes. These functions are conserved throughout the animal kingdom from planaria to mammals. When Na+ and water are scarce ("volume depletion"), the kidney's excretory responses decrease, causing Na+, water, and urea retention. When volume depletion is more severe, the serum creatinine, sCr, is also retained. A similar scenario occurs in the setting of non-renal diseases that mimic volume depletion such as severe congestive heart and liver failure, because similar drivers (angiotensin-aldosterone systems) and effectors of volume retention (ENac, Na/KAT-Pase and osmolytes) are activated (currently called "cardio-renal and hepato-renal" syndromes). Adding further complexity, destruction of kidney epithelia by toxic stimuli (e.g. ischemia, sepsis, nephrotoxins) also blocks water, electrolyte, urea, and sCr excretion. Hence, it is not surprising that increases in urea and sCr of different etiologies are associated with poor prognoses, but it remains challenging to prospectively distinguish subtypes of diminished excretion on the basis of current blood or urine measurements.

Described herein is a method directed to a core issue in patient management on presentation to the clinic or to the hospital—whether the patient has a kidney injury. P-creatinine (Pcr) can be elevated because of volume depletion, but an elevated Pcr can also be found because of direct damage to the kidney tubule.

In the case of volume depletion or vAKI, fluids (saline, blood, albumin infusions) are administered, but in the case of injury or iAKI the same fluids should be withheld. In the case of volume depletion or vAKI, all medications, including medications that the patient may already be taking, do not need to be withheld or dose-adjusted. In the case of injury or iAKI, all medications, including medications that the patient may already be taking, need to be withheld or dose-adjusted. In the case of volume depletion or vAKI, the patient can be discharged, but in the case of injury or iAKI, the patient must remain in the hospital. In the case of volume depletion or vAKI, electrolyte imbalance is rare, but in the case of injury or iAKI, it is routine.

Because it is not possible to prospectively know whether an elevated Pcr is due to volume depletion (vAKI) or due to kidney damage (iAKI), mistakes in the treatment of these conditions are routine. For example, if the patient is volume depleted but does not get fluids, different organs can be damaged further. If the patient has kidney damage or injury already and receives fluids, the patient could become so fluid-overload that they go into pulmonary edema, and may need dialysis and intensive care admission. Described herein, is a method to diagnose, distinguish, and treat volume depletion or vAKI from kidney injury or iAKI.

Described herein is the identification of a combination of proteins in the urine which on measurement can distinguish the mechanism of the elevated Pcr at the time of patient contact, allowing prospective diagnosis, triage and treatment. Depending on the levels of proteins, treatment regimens are as follows.

Pappa 2 is a marker for volume depletion Acute Kidney Injury (vAKI). When there is elevated Pcr and positive Pappa2 in the urine, a patient is diagnosed with vAKI, and treated by immediate administration with fluids, such as saline, albumin and blood.

NGAL, TACSTD1 (Trop2) and Cytokeratin 20 (Krt20) are markers identified herein for ischemic Acute Kidney Injury (iAKI). When there is elevated Pcr and negative Pappa2, but positive NGAL, Cytokeratin 20 (Krt20), or TACSTD1 (Trop2), a patient is diagnosed with iAKI, is not treated with fluids, and doses of medications, including medications the patient may already be on, must be withheld or dose-adjusted. Further treatment of a patient with elevated Pcr, negative Pappa2, and positive NGAL, Cytokeratin 20 (Krt20), or TACSTD1 (Trop2) includes monitoring for and potentially administering dialysis, repeating blood tests, and testing for hyperkalemia, hyponatremia, and acidosis, each of which must be treated immediately.

If the patient has hyperkalemia, then potassium levels must be lowered, by administering to the patient kayexolate-sodium polystyrene sulfonate or sodium bicarbonate. If the patient has hyponatremia, then sodium chloride or sodium bicarbonate must be administered to the patient. If the patient has acidosis, then sodium bicarbonate must be administered to the patient. If the patient has hyperphosphatemia, then oral phosphate binders including aluminum and calcium and iron based binders must be administered to the patient.

Possible commercial applications include applications in heart failure/liver failure versus tubular damage of kidney versus nephrotoxicity. More specifically, the methods described herein can be used to distinguish heart and liver failure, which typically start with vAKI, from tubular damage of kidney and nephrotoxicity, which typically starts with iAKI. The methods can be used singularly or in combination.

Molecules of the Invention

The practice of aspects of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual, 3rd Ed., ed. by Sambrook (2001), Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription and Translation (B. D. Hames & S. J. Higgins eds. 1984); Culture Of Animal Cells (R. I. Freshney, Alan R. Liss, Inc., 1987); Immobilized Cells and Enzymes (IRL Press, 1986); B. Perbal, A Practical Guide To Molecular Cloning (1984); the series, Methods In Enzymology (Academic Press, Inc., N.Y.), specifically, Methods In Enzymology, Vols. 154 and 155 (Wu et al. eds.); Gene Transfer Vectors For Mammalian Cells (J. H. Miller and M. P. Calos eds., 1987, Cold Spring Harbor Laboratory); Immunochemical Methods In Cell And Molecular Biology (Caner and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986). All patents, patent applications and references cited herein are incorporated by reference in their entireties.

One skilled in the art can obtain a protein in several ways, which include, but are not limited to, isolating the protein via biochemical means or expressing a nucleotide sequence encoding the protein of interest by genetic engineering methods.

A protein is encoded by a nucleic acid (including, for example, genomic DNA, complementary DNA (cDNA), synthetic DNA, as well as any form of corresponding RNA). For example, it can be encoded by a recombinant nucleic acid of a gene. The proteins of the invention can be obtained from various sources and can be produced according to various techniques known in the art. For example, a nucleic acid that encodes a protein can be obtained by screening DNA libraries, or by amplification from a natural source. A protein can be a fragment or portion thereof. The nucleic acids encoding a protein can be produced via recombinant DNA technology and such recombinant nucleic acids can be prepared by conventional techniques, including chemical synthesis, genetic engineering, enzymatic techniques, or a combination thereof.

The Genbank ID for the PAPPA2 gene is 60676. PAPPA2 is also referred to as pappalysin-2, PAPPE, PLAC3, PAPP-E, and PAPP-A2. These alternative names for PAPPA2 may be used interchangeably herein. Unless stated otherwise, the term "PAPPA2", as used herein, includes any PAPPA2 protein, or fragment thereof. PAPPA2 is a member of the pappalysin family of metzincin metalloproteinases. The encoded protein cleaves insulin-like growth factor-binding protein 5 and is thought to be a local regulator of insulin-like growth factor (IGF) bioavailability. Alternative splicing of PAPPA2 results in multiple transcript variants. The Genbank Accession No for the PAPPA2 genomic DNA is NG 023390.1. Two isoforms are listed on Genbank for PAPPA2, e.g., having Genebank Accession Nos. NP_064714.2 (corresponding nucleotide sequence NM_020318.2); NP_068755.2 (corresponding to NM_021936.2).

SEQ ID NO: 1 is the PAPPA2 Amino Acid Sequence, Isoform 1 precursor (NP_064714.2; 1791 aa).

```
   1  mmclkilris lailagwalc sanselgwtr kkslverehl nqvllegerc wlgakvrrpr
  61  aspqhhlfgv ypsragnylr pypvgeqeih htgrskpdte gnavslvppd ltenpaglrg
 121  aveepaapwv gdspigqsel lgdddaylgn qrskeslgea giqkgsamaa ttttaifttl
 181  nepkpetqrr gwaksrqrrq vwkrraedgq gdsgisshfq pwpkhslkhr vkksppeesn
 241  qnggegsyre aetfnsqvgl pilyfsgrre rlllrpevla eipreaftve awvkpeggqn
 301  npaiiagvfd ncshtvsdkg walgirsgkd kgkrdarfff slctdrvkka tilishsryq
 361  pgtwthvaat ydgrhmalyv dgtqvassld qsgplnspfm ascrslllgg dssedghyfr
 421  ghlgtlvfws talpqshfqh ssqhssgeee atdlvltasf epvntewvpf rdekyprlev
 481  lqgfepepei lsplqpplcg qtvcdnveli sqyngywplr gekviryqvv nicddeglnp
 541  ivseeqirlq healneafsr yniswqlsvh qvhnstlrhr vvlvncepsk igndhcdpec
 601  ehpltgydgg dcrlqgrcys wnrrdglchv ecnnmlndfd dgdccdpqva dvrktcfdpd
 661  spkraymsvk elkealqlns thflniyfas svredlagaa twpwdkdavt hlggivlspa
 721  yygmpghtdt mihevghvlg lyhvfkgvse rescndpcke tvpsmetgdl cadtaptpks
 781  elcrepepts dtcgftrfpg apftnymsyt ddnctdnftp nqvarmhcyl dlvyqqwtes
 841  rkptpipipp mviqqtnksl tihwlppisg vvydrasgsl cgactedgtf rqyvhtassr
 901  rvcdssgywt peeavgppdv dqpcepslqa wspevhlyhm nmtvpcpteg cslellfqhp
 961  vqadtltlwv tsffmessqv lfdteillen kesvhlgpld tfcdipltik lhvdgkvsgv
1021  kvytfderie idaalltsqp hsplcsgcrp vryqvlrdpp fasglpvvvt hshrkftdve
1081  vtpgqmyqyq vlaeaggelg easpplnhih gapycgdgkv serlgeecdd gdlvsgdgcs
1141  kvceleegfn cvgepslcym yegdgicepf erktsivdcg iytpkgyldq watraysshe
1201  dkkkcpvslv tgephslict syhpdlpnhr pltgwfpcva senetqddrs eqpegslkke
1261  devwlkvcfn rpgearaifi flttdglvpg ehqqptvtly ltdvrgsnhs lgtyglscqh
1321  npliinvthh qnvlfhhtts vllnfssprv gisavalrts sriglsapsn cisedegqnh
1381  qgqscihrpc gkqdscpsll ldhadvvnct sigpglmkca itcqrgfalq assgqyirpm
1441  qkeilltcss ghwdqnvscl pvdcgvpdps lvnyanfscs egtkflkrcs iscvppaklq
1501  glspwltcle dglwslpevy cklecdappi ilnanlllph clqdnhdvgt ickyeckpgy
1561  yvaesaegkv rnkllkiqcl eggiweggsc ipvvceppppp vfegmyectn gfsldsqcvl
```

-continued

```
1621  ncnqereklp ilctkeglwt qefklcenlq gecppppsel nsveykceqg ygigavcspl
1681  cvippsdpvm lpenitadtl ehwmepvkvq sivctgrrqw hpdpvlvhci qscepfqadg
1741  wcdtinnray chydggdccs stlsskkvip faadcdldec tcrdpkaeen q
```

SEQ ID NO: 2 is the PAPPA2 Amino Acid Sequence, Isoform 2 precursor (NP_068755.2; 827 aa).

```
  1  mmclkilris lailagwalc sanselgwtr kkslverehl nqvllegerc wlgakvrrpr
 61  aspqhhlfgv ypsragnylr pypvgeqeih htgrskpdte gnavslvppd ltenpaglrg
121  aveepaapwv gdspigqsel lgdddaylgn qrskeslgea giqkgsamaa ttttaifttl
181  nepkpetqrr gwaksrqrrq vwkrraedgq gdsgisshfq pwpkhslkhr vkksppeesn
241  qnggegsyre aetfnsqvgl pilyfsgrre rlllrpevla eipreaftve awvkpeggqn
301  npaiiagvfd ncshtvsdkg walgirsgkd kgkrdarfff slctdrvkka tilishsryq
361  pgtwthvaat ydgrhmalyv dgtqvassld qsgplnspfm ascrslllgg dssedghyfr
421  ghlgtlvfws talpqshfqh ssqhssgeee atdlvltasf epvntewvpf rdekyprlev
481  lqgfepepei lsplqpplcg qtvcdnveli sqyngywplr gekviryqvv nicddeglnp
541  ivseeqirlq healneafsr yniswqlsvh qvhnstlrhr vvlvncepsk igndhcdpec
601  ehpltgydgg dcrlqgrcys wnrrdglchv ecnnmlndfd dgdccdpqva dvrktcfdpd
661  spkraymsvk elkealqlns thflniyfas svredlagaa twpwdkdavt hlggivlspa
721  yygmpghtdt mihevghvlg lyhvfkgvse rescndpcke tvpsmetgdl cadtaptpks
781  elcrepepts dtcgftrfpg apftnymsyt gittvlfcfl lrihggl
```

SEQ ID NO: 3 is the PAPPA2 mRNA or cDNA Nucleotide Sequence, transcript variant 1 (NM_020318.2; 6940 bp).

```
  1  gggcatgact ctctctcttg agtaggcaca cactcccttt tctcgggtgt gtacttttg
 61  ctttgtgata catctctgca ctttcagtat tttccaactc atccttaaat tccttctcac
121  aacagtgtca agagcctgga cgccagccag gattgaggtc ctacgggtgt ttggggacct
181  ccccaagccc acgagtatca atggcagtat caattgtctg tgacagtgat taaggagcaa
241  aacacttgga acccacaaga ctcccagaag gtgaagttaa gagctcccag actcataagg
301  ttattagaac agcaaactgg caccccaaag aactttacgg agacttgcaa cctatcaaca
361  agttggatga gggattaaaa gccttcaaca accaacaacc ccaagcatca aactgaagga
421  aacattctaa ccttcacaga cagactggag gctggatggg gacctggctg aagacatctg
481  gagaatgaaa gttaagtacc agcttgcatt tttgtgcccc tagattattt ttgcattta
541  aaataagaag catcaaattg cgtgtctctg tgtaaaagtt ctagcaattt gttttaaggt
601  gaacttattt tggcttaggg actacaaaaa gagaaggtaa ttcctaggga aggaagaaga
661  gaaagaaatg aaaattagag aataagatta ttttgaatga cttcaggtag cgaggagtgt
721  gtgtttgtga gtgtgtattt gagagacttg gctcatgcct gtgggtcttc tcttctagta
781  tcagtgaggg gagggattac tgaagaagaa gggggaaaa aaaagaaag aaatctgagc
841  tttctgggag gaaattcaaa ggaaccaaga gaaattaact tcgttctgca aggactaaag
901  tacagcaaga ggagagaggt caagcgagaa gcgtgcggga agcacatgcc ctggggaggc
961  atagaagcca cactggcaga gcggccagca caggtagcca gcagaggcat tcttgggct
```

-continued

```
1021  atttgaaaaa gtttggtctg tgaacaaaac agtttccctg gtgactgcaa atccattgct
1081  agctgcctct ttctcgtctg cccatcactc tggtgtggta cccagaagtt gacttctggt
1141  tctgtagaaa gagctagggg aggtatgatg tgcttaaaga tcctaagaat aagcctggcg
1201  attttggctg ggtgggcact ctgttctgcc aactctgagc tgggctggac acgcaagaaa
1261  tccttggttg agagggaaca cctgaatcag gtgctgttgg aaggagaacg ttgttggctg
1321  ggggccaagg ttcgaagacc cagagcttct ccacagcatc acctctttgg agtctacccc
1381  agcagggctg ggaactacct aaggccctac cccgtggggg agcaagaaat ccatcataca
1441  ggacgcagca aaccagacac tgaaggaaat gctgtgagcc ttgttccccc agacctgact
1501  gaaaatccag caggactgag gggtgcagtt gaagagccgg ctgccccatg ggtagggat
1561  agtcctattg gcaatctga ctgctggga gatgatgacg cttatctcgg caatcaaaga
1621  tccaaggagt ctctaggtga ggccgggatt cagaaaggct cagccatggc tgccactact
1681  accaccgcca ttttcacaac cctgaacgaa cccaaaccag agacccaaag gaggggctgg
1741  gccaagtcca ggcagcgtcg ccaagtgtgg aagagcgggg cggaagatgg gcaggagac
1801  tccggtatct cttcacattt ccaaccttgg cccaagcatt cccttaaaca cagggtcaaa
1861  aagagtccac cggaggaaag caaccaaaat ggtggagagg gctcctaccg agaagcagag
1921  acctttaact cccaagtagg actgcccatc ttatacttct ctgggaggcg ggagcggctg
1981  ctgctgcgtc agaagtgct ggctgagatt ccccgggagg cgttcacagt ggaagcctgg
2041  gttaaaccgg agggaggaca gaacaaccca gccatcatcg caggtgtgtt tgataactgc
2101  tcccacactg tcagtgacaa aggctgggcc ctggggatcc gctcagggaa ggacaaggga
2161  aagcgggatg ctcgcttctt cttctccctc tgcaccgacc gcgtgaagaa agccaccatc
2221  ttgattagcc acagtcgcta ccaaccaggc acatggaccc atgtggcagc cacttacgat
2281  ggacggcaca tggccctgta tgtggatggc actcaggtgg ctagcagtct agaccagtct
2341  ggtccccctga acagcccctt catggcatct tgccgctctt tgctcctggg gggagacagc
2401  tctgaggatg ggcactattt ccgtggacac ctgggcacac tggttttctg gtcgaccgcc
2461  ctgccacaaa gccattttca gcacagttct cagcattcaa gtgggagga ggaagcgact
2521  gacttggtcc tgacagcgag ctttgagcct gtgaacacag agtgggttcc ctttagagat
2581  gagaagtacc cacgacttga ggttctccag ggctttgagc cagagcctga gattctgtcg
2641  cctttgcagc ccccactctg tgggcaaaca gtctgtgaca atgtggaatt gatctcccag
2701  tacaatggat actggcccct tcggggagag aaggtgatac gctaccaggt ggtgaacatc
2761  tgtgatgatg agggcctaaa ccccattgtg agtgaggagc agattcgtct gcagcacgag
2821  gcactgaatg aggccttcag ccgctacaac atcagctggc agctgagcgt ccaccaggtc
2881  cacaattcca ccctgcgaca ccgggttgtg cttgtgaact gtgagcccag caagattggc
2941  aatgaccatt gtgaccccga gtgtgagcac ccactcacag gctatgatgg gggtgactgc
3001  cgcctgcagg gccgctgcta ctcctggaac cgcagggatg ggctctgtca cgtggagtgt
3061  aacaacatgc tgaacgactt tgacgacgga gactgctgcg accccaggt ggctgatgtg
3121  cgcaagacct gctttgaccc tgactcaccc aagagggcat acatgagtgt gaaggagctg
3181  aaggaggccc tgcagctgaa cagtactcac ttcctcaaca tctactttgc cagctcagtg
3241  cgggaagacc ttgcaggtgc tgccacctgg ccttgggaca ggacgctgt cactcacctg
3301  ggtggcattg tcctcagccc agcatattat gggatgcctg ccacaccga caccatgatc
3361  catgaagtgg acatgttcct gggactctac catgtcttta aggagtcag tgaaagaaa
3421  tcctgcaatg accccctgcaa ggagacagtg ccatccatgg aaacgggaga cctctgtgcc
```

-continued

```
3481  gacaccgccc ccactcccaa gagtgagctg tgccgggaac cagagcccac tagtgacacc
3541  tgtggcttca ctcgcttccc aggggctccg ttcaccaact acatgagcta cacggatgat
3601  aactgcactg acaacttcac tcctaaccaa gtggcccgaa tgcattgcta tttggaccta
3661  gtctatcagc agtggactga aagcagaaag cccaccccca tccccattcc acctatggtc
3721  atcggacaga ccaacaagtc cctcactatc cactggctgc ctcctattag tggagttgta
3781  tatgacaggg cctcaggcag cttgtgtggc gcttgcactg aagatgggac ctttcgtcag
3841  tatgtgcaca cagcttcctc ccggcgggtg tgtgactcct caggttattg accccagag
3901  gaggctgtgg ggcctcctga tgtggatcag ccctgcgagc caagcttaca ggcctggagc
3961  cctgaggtcc acctgtacca catgaacatg acggtcccct gccccacaga aggctgtagc
4021  ttggagctgc tcttccaaca cccggtccaa gccgacaccc tcaccctgtg ggtcacttcc
4081  ttcttcatgg agtcctcgca ggtcctcttt gacacagaga tcttgctgga aaacaaggag
4141  tcagtgcacc tgggcccctt agacactttc tgtgacatcc cactcaccat caaactgcac
4201  gtggatggga aggtgtcggg ggtgaaagtc tacacctttg atgagaggat agagattgat
4261  gcagcactcc tgacttctca gccccacagt cccttgtgct ctggctgcag gcctgtgagg
4321  taccaggttc tccgcgatcc cccatttgcc agtggtttgc ccgtggtggt gacacattct
4381  cacaggaagt tcacggacgt ggaggtcaca cctggacaga tgtatcagta ccaagttcta
4441  gctgaagctg gaggagaact gggagaagct tcgcctcctc tgaaccacat tcatggagct
4501  ccttattgtg agatgggaa ggtgtcagag agactgggag aagagtgtga tgatggagac
4561  cttgtgagcg gagatggctg ctccaaggtg tgtgagctgg aggaaggttt caactgtgta
4621  ggagagccaa gcctttgcta catgtatgag ggagatggca tatgtgaacc ttttgagaga
4681  aaaaccagca ttgtagactg tggcatctac actcccaaag gatacttgga tcaatgggct
4741  acccgggctt actcctctca tgaagacaag aagaagtgtc ctgtttcctt ggtaactgga
4801  gaacctcatt ccctaatttg cacatcatac catccagatt tacccaacca ccgtccccta
4861  actgctggt ttccctgtgt tgccagtgaa atgaaactc aggatgacag gagtgaacag
4921  ccagaaggta gcctgaagaa agaggatgag gtttggctca aagtgtgttt caatagacca
4981  ggagaggcca gagcaatttt tattttttttg acaactgatg gcctagttcc cggagagcat
5041  cagcagccga cagtgactct ctacctgacc gatgtccgtg aagcaaacca ctctcttgga
5101  acctatggac tgtcatgcca gcataatcca ctgattatca atgtgaccca tcaccagaat
5161  gtcctttccc accataccac ctcagtgctg ctgaatttct catccccacg ggtcggcatc
5221  tcagctgtgg ctctaaggac atcctcccgc attggtcttt cggctcccag taactgcatc
5281  tcagaggacg aggggcagaa tcatcaggga cagagctgta tccatcggcc ctgtgggaag
5341  caggacagct gtccgtcatt gctgcttgat catgctgatg tggtgaactg tacctctata
5401  ggcccaggtc tcatgaagtg tgctatcact tgtcaaaggg gatttgccct tcaggccagc
5461  agtgggcagt acatcaggcc catgcagaag gaaattctgc tcacatgttc ttctgggcac
5521  tgggaccaga atgtgagctg ccttcccgtg gactgcggtg ttcccgaccc gtctttggtg
5581  aactatgcaa acttctcctg ctcagaggga accaaatttc tgaaacgctg ctcaatctct
5641  tgtgtcccac cagccaagct gcaaggactg agcccatggc tgacatgtct tgaagatggt
5701  ctctggtctc tccctgaagt ctactgcaag ttggagtgtg atgctccccc tattattctg
5761  aatgccaact tgctcctgcc tcactgcctc caggacaacc acgacgtggg caccatctgc
5821  aaatatgaat gcaaaccagg gtactatgtg gcagaaagtg cagagggtaa agtcaggaac
```

-continued

```
5881  aagctcctga agatacaatg cctggaaggt ggaatctggg agcaaggcag ctgcattcct
5941  gtggtgtgtg agccacccce tectgtgttt gaaggcatgt atgaatgtac caatggcttc
6001  agcctggaca gccagtgtgt gctcaactgt aaccaggaac gtgaaaagct tcccatcctc
6061  tgcactaaag agggcctgtg gacccaggag tttaagttgt gtgagaatct gcaaggagaa
6121  tgcccaccac cccectcaga gctgaattct gtggagtaca aatgtgaaca aggatatggg
6181  attggtgcag tgtgttcccc attgtgtgta atcccccccca gtgaccccgt gatgctacct
6241  gagaatatca ctgctgacac tctggagcac tggatggaac ctgtcaaagt ccagagcatt
6301  gtgtgcactg gccggcgtca atggcaccca gacccegtct tagtccactg catccagtca
6361  tgtgagccct tccaagcaga tggttggtgt gacactatca acaaccgagc ctactgccac
6421  tatgacgggg gagactgctg ctcttccaca ctctcctcca agaaggtcat tccatttgct
6481  gctgactgtg acctggatga gtgcacctgc cgggacccca aggcagaaga aaatcagtaa
6541  ctgtgggaac aagcccctcc ctccactgcc tcagaggcag taagaaagag aggccgaccc
6601  aggaggaaac aaagggtgaa tgaagaagaa caatcatgaa atggaagaag gaggaagagc
6661  atgaaggatc ttataagaaa tgcaagagga tattgatagg tgtgaactag ttcatcaagt
6721  agcccaagta ggagagaatc ataggcaaaa gtttctttaa agtggcagtt gattaacatg
6781  gaaggggaaa tatgatagat atataaggac cctcctccct cacttatatt ctattaaatc
6841  ctatcctcaa ctcttgccct gctctccgct ccacccectg ccaactactc agtcccaccc
6901  aacttgtaaa ccaataccaa aaaaaaaaaa aaaaaaaaa
```

SEQ ID NO: 4 is the PAPPA2 mRNA or cDNA Nucleotide Sequence, transcript variant 2 (NM_021936.2; 4370 bp).

```
   1  gggcatgact ctctctcttg agtaggcaca cactcccttt tctcgggtgt gtacttttg
  61  ctttgtgata catctctgca ctttcagtat tttccaactc atccttaaat tccttctcac
 121  aacagtgtca agagcctgga cgccagccag gattgaggtc ctacgggtgt ttggggacct
 181  ccccaagccc acgagtatca atggcagtat caattgtctg tgacagtgat taaggagcaa
 241  aacacttgga acccacaaga ctcccagaag gtgaagttaa gagctcccag actcataagg
 301  ttattagaac agcaaactgg caccccaaag aactttacgg agacttgcaa cctatcaaca
 361  agttggatga gggattaaaa gccttcaaca accaacaacc ccaagcatca aactgaagga
 421  aacattctaa ccttcacaga cagactggag gctggatggg gacctggctg aagacatctg
 481  gagaatgaaa gttaagtacc agcttgcatt tttgtgcccc tagattattt ttgcatttta
 541  aaataagaag catcaaattg cgtgtctctg tgtaaaagtt ctagcaattt gttttaaggt
 601  gaacttatttt tggcttaggg actacaaaaa gagaaggtaa ttcctaggga aggaagaaga
 661  gaaagaaatg aaaattagag aataagatta ttttgaatga cttcaggtag cgaggagtgt
 721  gtgtttgtga gtgtgtattt gagagacttg gctcatgcct gtgggtcttc tcttctagta
 781  tcagtgaggg gagggattac tgaagaagaa ggggggaaaa aaaaagaaag aaatctgagc
 841  tttctgggag gaaattcaaa ggaaccaaga gaaattaact tcgttctgca aggactaaag
 901  tacagcaaga ggagagaggt caagcgagaa gcgtgcggga agcacatgcc ctggggaggc
 961  atagaagcca cactggcaga gcggccagca caggtagcca gcagaggcat tcttggggct
1021  atttgaaaaa gtttggtctg tgaacaaaac agtttccctg tgactgcaa atccattgct
1081  agctgcctct ttctcgtctg cccatcactc tggtgtggta cccagaagtt gacttctggt
```

```
-continued
1141  tctgtagaaa gagctagggg aggtatgatg tgcttaaaga tcctaagaat aagcctggcg
1201  attttggctg ggtgggcact ctgttctgcc aactctgagc tgggctggac acgcaagaaa
1261  tccttggttg agagggaaca cctgaatcag gtgctgttgg aaggagaacg ttgttggctg
1321  ggggccaagg ttcgaagacc cagagcttct ccacagcatc acctctttgg agtctacccc
1381  agcagggctg gaactacct aaggccctac cccgtggggg agcaagaaat ccatcataca
1441  ggacgcagca aaccagacac tgaaggaaat gctgtgagcc ttgttccccc agacctgact
1501  gaaaatccag caggactgag gggtgcagtt gaagagccgg ctgccccatg ggtagggat
1561  agtcctattg gcaatctga gctgctggga gatgatgacg cttatctcgg caatcaaaga
1621  tccaaggagt ctctaggtga ggccgggatt cagaaaggct cagccatggc tgccactact
1681  accaccgcca ttttcacaac cctgaacgaa cccaaaccag agacccaaag gaggggctgg
1741  gccaagtcca ggcagcgtcg ccaagtgtgg aagaggcggg cggaagatgg gcaggagac
1801  tccggtatct cttcacattt ccaaccttgg cccaagcatt cccttaaaca cagggtcaaa
1861  aagagtccac cggaggaaag caaccaaaat ggtggagagg ctcctaccg agaagcagag
1921  acctttaact cccaagtagg actgcccatc ttatacttct ctgggaggcg ggagcggctg
1981  ctgctgcgtc agaagtgct ggctgagatt ccccgggagg cgttcacagt ggaagcctgg
2041  gttaaaccgg agggaggaca gaacaaccca gccatcatcg caggtgtgtt tgataactgc
2101  tcccacactg tcagtgacaa aggctgggcc ctggggatcc gctcagggaa ggacaaggga
2161  aagcgggatg ctcgcttctt cttctccctc tgcaccgacc gcgtgaagaa agccaccatc
2221  ttgattagcc acagtcgcta ccaaccaggc acatggaccc atgtggcagc cacttacgat
2281  ggacggcaca tggccctgta tgtggatggc actcaggtgg ctagcagtct agaccagtct
2341  ggtcccctga acagccctt catggcatct tgccgctctt tgctcctggg gggagacagc
2401  tctgaggatg ggcactattt ccgtggacac ctgggcacac tggttttctg gtcgaccgcc
2461  ctgccacaaa gccatttca gcacagttct cagcattcaa gtggggagga ggaagcgact
2521  gacttggtcc tgacagcgag ctttgagcct gtgaacacag agtgggttcc ctttagagat
2581  gagaagtacc cacgacttga ggttctccag ggctttgagc cagagcctga gattctgtcg
2641  cctttgcagc ccccactctg tgggcaaaca gtctgtgaca atgtggaatt gatctcccag
2701  tacaatggat actggcccct tcggggagag aaggtgatac gctaccaggt ggtgaacatc
2761  tgtgatgatg agggcctaaa ccccattgtg agtgaggagc agattcgtct gcagcacgag
2821  gcactgaatg aggccttcag ccgctacaac atcagctggc agctgagcgt ccaccaggtc
2881  cacaattcca ccctgcgaca ccgggttgtg cttgtgaact gtgagcccag caagattggc
2941  aatgaccatt gtgaccccga gtgtgagcac ccactcacag gctatgatgg gggtgactgc
3001  cgcctgcagg gccgctgcta ctcctggaac cgcagggatg gctctgtca cgtggagtgt
3061  aacaacatgc tgaacgactt tgacgacgga gactgctgcg accccaggt ggctgatgtg
3121  cgcaagacct gctttgaccc tgactcaccc aagagggcat acatgagtgt gaaggagctg
3181  aaggaggccc tgcagctgaa cagtactcac ttcctcaaca tctactttgc cagctcagtg
3241  cgggaagacc ttgcaggtgc tgccacctgg ccttgggaca aggacgctgt cactcacctg
3301  gtggcattg tcctcagccc agcatattat ggatgcctg ccacaccga caccatgatc
3361  catgaagtgg acatgttct ggactctac catgtcttta aggagtcag tgaaagaaa
3421  tcctgcaatg acccctgcaa ggagacagtg ccatccatgg aaacgggaga cctctgtgcc
3481  gacaccgccc ccactcccaa gagtgagctg tgccgggaac cagagcccac tagtgacacc
3541  tgtggcttca ctcgcttccc aggggctccg ttcaccaact acatgagcta cacgggtatc
```

-continued

```
3601  accactgtct tgttttgttt tctgttaaga atacatgggg gcctttgaga gctgggaggg 3661  tggaggtgtg ggagctgatg ggagaatgat taagtggtca tttgtgtcgg agagttgaag 3721  tgtatttatt ataaggtatt attattttt catgtctttg aagaacttga agaaatactg 3781  acatattaag gtactttgtt cactgaattc tcctctacta gatattttaa aatatacttc 3841  tatcctcgat agtaaaaaag gcacagagcc aaaagccctc ttgtgatccc cttgacttct 3901  agaatgtggt tattcttatt tttgcccgca ttcttagaca tttactctga agaagagtcc 3961  aatggaaata aaggaaaaga gtttatgggt caaggtggcc cattgtactg tttttgaagt 4021  tggtcaacaa ggtggcttgg ttaatttagg ctcagcatgt tttactgtat gttactaaaa 4081  aaaaaaaaaa aaaaaatcag attctctttt tccagcacta gtcaagcaca aattcttagc 4141  tgcctaccac cctttcccca ccaaaaggtg acatctaatt ttaaaaaaat ggcatcttcc 4201  tggccctcgg aaaaacttgt catctggtct ttcttgcctt aattcagctt ctgtattatt 4261  cttcgctgtc tctcacgcct tccttgtttc ttgtgaaaag taatagtgac tggtttccta 4321  taatggactc aaagttatcc ctaaaattaa agacttattt gatgacctag
```

The Genbank ID for the KRT20 gene is 54474. KRT20 is also referred to as keratin 20, K20, CD20, CK20, CK-20, KRT21, and cytokeratin 20. These alternative names for KRT20 may be used interchangeably herein. Unless stated otherwise, the term "KRT20", as used herein, includes any KRT20 protein, or fragment thereof. The protein encoded by this gene is a member of the keratin family. The keratins are intermediate filament proteins responsible for the structural integrity of epithelial cells and are subdivided into cytokeratins and hair keratins. The type I cytokeratins consist of acidic proteins which are arranged in pairs of heterotypic keratin chains. This cytokeratin is a major cellular protein of mature enterocytes and goblet cells and is specifically expressed in the gastric and intestinal mucosa. The type I cytokeratin genes are clustered in a region of chromosome 17q12-q21. The Genbank Accession No for the KRT20 genomic DNA is NG 012286.1. One isoform is listed on Genbank for KRT20, e.g., having Genebank Accession Nos. NP_061883.1 (corresponding nucleotide sequence NM_019010.2).

SEQ ID NO: 5 is the KRT20 Amino Acid Sequence (NP_061883.1; 424 aa).

```
  1  mdfsrrsfhr slssslqapv vstvgmqrlg ttpsvyggag grgirisnsr htvnygsdlt
 61  gggdlfvgne kmamqnlndr lasylekvrt leqsnsklev qikqwyetna pragrdysay
121  yrqieelrsq ikdaqlqnar cvlqidnakl aaedfrlkye tergirltve adlqglnkvf
181  ddltlhktdl eiqieelnkd lallkkehqe evdglhkhlg ntvnvevdaa pglnlgvimn
241  emrqkyevma qknlqeakeq ferqtavlqq qvtvnteelk gtevqltelr rtsqsleiel
301  qshlsmkesl ehtleetkar yssqlanlqs llssleaqlm qirsnmerqn neyhilldik
361  trleqeiaty rrllegedvk tteyqlstle erdikktrki ktvvqevvdg kvvssevkev
421  eeni
```

SEQ ID NO: 6 is the KRT20 mRNA or cDNA Nucleotide Sequence (NM_019010.2; 1805 bp).

```
  1  gagacacact ctgccccaac catcctgaag ctacaggtgc tccctcctgg aatctccaat 61  ggatttcagt cgcagaagct tccacagaag cctgagctcc tccttgcagg ccctgtagt 121  cagtacagtg ggcatgcagc gcctcggac gacacccagc gtttatgggg gtgctggagg 181  ccggggcatc cgcatctcca actccagaca cacggtgaac tatgggagcg atctcacagg 241  cggcggggac ctgtttgttg gcaatgagaa aatggccatg cagaacctaa atgaccgtct 301  agcgagctac ctagaaaagg tgcggaccct ggagcagtcc aactccaaac ttgaagtgca 361  aatcaagcag tggtacgaaa ccaacgcccc gagggctggt cgcgactaca gtgcatatta 421  cagacaaatt gaagagctgc gaagtcagat taaggatgct caactgcaaa atgctcggtg
```

-continued

```
 481   tgtcctgcaa attgataatg ctaaactggc tgctgaggac ttcagactga agtatgagac
 541   tgagagagga atacgtctaa cagtggaagc tgatctccaa ggcctgaata aggtctttga
 601   tgacctaacc ctacataaaa cagatttgga gattcaaatt gaagaactga ataaagacct
 661   agctctcctc aaaaaggagc atcaggagga agtcgatggc ctacacaagc atctgggcaa
 721   cactgtcaat gtggaggttg atgctgctcc aggcctgaac cttggcgtca tcatgaatga
 781   aatgaggcag aagtatgaag tcatggccca gaagaacctt caagaggcca agaacagtt
 841   tgagagacag actgcagttc tgcagcaaca ggtcacagtg aatactgaag aattaaaagg
 901   aactgaggtt caactaacgg agctgagacg cacctcccag agccttgaga tagaactcca
 961   gtcccatctc agcatgaaag agtctttgga gcacactcta gaggagacca aggcccgtta
1021   cagcagccag ttagccaacc tccagtcgct gttgagctct ctggaggccc aactgatgca
1081   gattcggagt aacatggaac gccagaacaa cgaataccat atccttcttg acataaagac
1141   tcgacttgaa caggaaattg ctacttaccg ccgccttctg gaaggagaag acgtaaaaac
1201   tacagaatat cagttaagca ccctggaaga gagagatata aagaaaacca ggaagattaa
1261   gacagtcgtg caagaagtag tggatggcaa ggtcgtgtca tctgaagtca aagaggtgga
1321   agaaaatatc taaatagcta ccagaaggag atgctgctga ggttttgaaa gaaatttggc
1381   tataatctta tctttgctcc ctgcaagaaa tcagccataa gaaagcacta ttaatactct
1441   gcagtgatta gaagggggtgg ggtggcggga atcctattta tcagactctg taattgaata
1501   taaatgtttt actcagagga gctgcaaatt gcctgcaaaa atgaaatcca gtgagcacta
1561   gaatatttaa aacatcatta ctgccatctt tatcatgaag cacatcaatt acaagctgta
1621   gaccacctaa tatcaatttg taggtaatgt tcctgaaaat tgcaatacat ttcaattata
1681   ctaaacctca caaagtagag gaatccatgt aaaattgcaaa taaaccactt tctaattttt
1741   tcctgtttct gaattgtaaa accccctttg ggagtccctg gtttcttatt gagccaattt
1801   ctggg
```

The Genbank ID for the TACSTD2 gene is 4070. TACSTD2 is also referred to as tumor-associated calcium signal transducer 2, EGP1, GP50, M1S1, EGP-1, TROP2, GA7331, GA733-1. These alternative names for TACSTD2 may be used interchangeably herein. Unless stated otherwise, the term "TACSTD2", as used herein, includes any TACSTD2 protein, or fragment thereof. This intronless gene encodes a carcinoma-associated antigen. This antigen is a cell surface receptor that transduces calcium signals. Mutations of this gene have been associated with gelatinous drop-like corneal dystrophy. The Genbank Accession No for the TACSTD2 genomic DNA is NG 016237.1. One isoform is listed on Genbank for TACSTD2, e.g., having Genebank Accession Nos. NP_002344.2 (corresponding nucleotide sequence NM_002353.2).

SEQ ID NO: 7 is the TACSTD2 Amino Acid Sequence (NP_002344.2; 323 aa).

```
  1   margpglapp plrlplllv laavtghtaa qdnctcptnk mtvcspdgpg grcqcralgs
 61   gmavdcstlt skclllkarm sapknartlv rpsehalvdn dglydpdcdp egrfkarqcn
121   qtsvcwcvns vgvrrtdkgd lslrcdelvr thhilidlrh rptagafnhs dldaelrrlf
181   reryrlhpkf vaavhyeqpt iqielrqnts qkaagdvdig daayyferdi kgeslfqgrg
241   gldlrvrgep lqvertliyy ldeippkfsm krltagliav ivvvvalva gmavlvitnr
301   rksgkykkve ikelgelrke psl
```

SEQ ID NO: 8 is the TACSTD2 mRNA or cDNA Nucleotide Sequence (NM_002353.2; 2080 bp).

```
  1   gcgggtcccc agaagcctac aggtgagtat cggttctccc cttcccggct ttcggtccgg
 61   aggaggcggg agcagcttcc ctgttctgat cctatcgcgg gcggcgcagg gccggcttgg
```

```
-continued
 121   ccttccgtgg gacggggagg ggggcgggat gtgtcaccca ataccagtg gggacggtcg 181   gtggtggaac cagccgggca ggtcgggtag agtataagag ccggagggag cggccgggcg 241   gcagacgcct gcagaccatc ccagacgccg gagcccgagc cccgacgagt ccccgcgcct 301   catccgcccg cgtccggtcc gcgttcctcc gccccaccat ggctcgggc cccggcctcg 361   cgccgccacc gctgcggctg ccgctgctgc tgctggtgct ggcggcggtg accggccaca 421   cggccgcgca ggacaactgc acgtgtccca ccaacaagat gaccgtgtgc agccccgacg 481   gccccggcgg ccgctgccag tgccgcgcgc tgggctcggg catggcggtc gactgctcca 541   cgctgaccte caagtgtctg ctgctcaagg cgcgcatgag cgcccccaag aacgcccgca 601   cgctggtgcg gccgagtgag cacgcgctcg tggacaacga tggcctctac gaccccgact 661   gcgacccccga gggccgcttc aaggcgcgcc agtgcaacca gacgtcggtg tgctggtgcg 721   tgaactcggt gggcgtgcgc cgcacggaca agggcgacct gagcctacgc tgcgatgagc 781   tggtgcgcac ccaccacatc ctcattgacc tgcgccaccg ccccaccgcc ggcgccttca 841   accactcaga cctggacgcc gagctgaggc ggctcttccg cgagcgctat cggctgcacc 901   ccaagttcgt ggcggccgtg cactacgagc agcccaccat ccagatcgag ctgcggcaga 961   acacgtctca gaaggccgcc ggtgacgtgg atatcggcga tgccgcctac tacttcgaga 1021   gggacatcaa gggcgagtct ctattccagg gccgcggcgg cctggacttg cgcgtgcgcg 1081   gagaacccct gcaggtggag cgcacgctca tctattacct ggacgagatt ccccgaagt 1141   tctccatgaa gcgcctcacc gccggcctca tcgccgtcat cgtggtggtc gtggtggccc 1201   tcgtcgccgg catggccgtc ctggtgatca ccaaccgag aaagtcgggg aagtacaaga 1261   aggtggagat caaggaactg ggggagttga gaaaggaacc gagcttgtag gtacccggcg 1321   gggcagggga tggggtgggg taccggatt cggtatcgtc ccagacccaa gtgagtcacg 1381   cttcctgatt cctcggcgca aaggagacgt ttatcctttc aaattcctgc cttcccccctc 1441   cctttgcgc acacaccagg tttaatagat cctgcctca gggtctcctt tctttctcac 1501   ttctgtcttg aaggaagcat ttctaaaatg tatccccttt cggtccaaca acaggaaacc 1561   tgactggggc agtgaaggaa gggatggcat agcgttatgt gtaaaaaca agtatctgta 1621   tgacaacccg ggatcgtttg caagtaactg aatccattgc gacattgtga aggcttaaat 1681   gagtttagat gggaaatagc gttgttatcg ccttgggttt aaattatttg atgagttcca 1741   cttgtatcat ggcctacccg aggagaagag gagtttgtta actgggccta tgtagtagcc 1801   tcatttacca tcgtttgtat tactgaccac atatgcttgt cactgggaaa gaagcctgtt 1861   tcagctgcct gaacgcagtt tggatgtctt tgaggacaga cattgcccgg aaactcagtc 1921   tatttattct tcagcttgcc cttactgcca ctgatattgg taatgttctt ttttgtaaaa 1981   tgtttgtaca tatgttgtct ttgataatgt tgctgtaatt ttttaaaata aaacacgaat 2041   ttaataaaat atgggaaagg cacaaaccag aaaaaaaaaa
```

The Genbank ID for the NGAL gene is 3934. The abbreviation "NGAL" refers to Neutrophil Gelatinase Associated Lipocalin. NGAL is also referred to in the art as human neutrophil lipocalin, siderocalin, a-micropglobulin related protein, Scn-NGAL, lipocalin 2, 24p3, superinducible protein 24 (SIP24), uterocalin, neu-related lipocalin, LCN2, p25, 24p3, and MSFI. This gene encodes a protein that belongs to the lipocalin family. These alternative names for NGAL may be used interchangeably herein. Unless stated otherwise, the term "NGAL", as used herein, includes any NGAL protein, or fragment thereof. The Genbank Accession No for the NGAL genomic DNA is NC 000009.12. One isoform is listed on Genbank for NGAL, e.g., having Genebank Accession Nos. NP_005555.2 (corresponding nucleotide sequence NM_005564.4).

NGAL is a small protein with a molecular weight of about 22kD and is a siderophore binding protein. A siderophore is an organic molecule that binds to and chelates iron. Bacteria produce the siderophore enterochelin, and mammals endogenously express a similar type, but simpler molecule called catechol. Enterochelin has an extremely high affinity for iron, and wild type NGAL has a high affinity for the enterochelin-iron complex. The enterochelin-iron-NGAL complex is pH insensitive and the bound iron is redox inactive. Thus the iron bound by such NGAL complexes is not available to catalyze oxygen radical formation, making NGAL an ideal iron chelator for in vivo use.

NGAL, and once produced in cells, is secreted into extracellular space and quickly cleared by kidney with a half-life of 10 minutes. Serum and urine levels of the protein can become very high in a number of disease models. The NGAL protein is transported into the kidney of healthy humans and can pass the filtration barrier of the glomerulus (the cut-off size of filtration is about 70kD) to enter the primary urine, but then NGAL is efficiently reabsorbed by megalin or megalin-cubilin-cubilin receptors localized on the apical side of the epithelia of the proximal tubules. Megalin is a universal receptor with broad substrate specificity and is expressed at the apical surface of the proximal tubules of the kidney where it is involved in protein reabsorption. The binding of megalin to its substrates is mediated by ionic interactions, and its negative charged substrate binding domains can efficiently bind to the positively charged surfaces of proteins in the urinary filtrate. Once absorbed and endocytosed, NGAL is trafficked to lysosomes, where it is degraded. Once degraded, the iron which NGAL transported to the kidney is reabsorbed.

SEQ ID NO: 9 is the NGAL Amino Acid Sequence (NP_005555.2; 198 aa).

shown in SEQ ID NOs: 1 or 2, or can comprise the nucleic acid sequence shown in SEQ ID NOs: 3 or 4. A PAPPA2 molecule can include a variant of the above described examples, such as a fragment thereof.

As used herein, a "KRT20 molecule" can be a nucleic acid (e.g., synthetic, purified, and/or recombinant) which encodes a polypeptide corresponding to a KRT20 protein, or a KRT20 protein, or fragment thereof. For example, a KRT20 molecule can comprise the amino acid sequence shown in SEQ ID NO: 5, or can comprise the nucleic acid sequence shown in SEQ ID NO: 6. A KRT20 molecule can include a variant of the above described examples, such as a fragment thereof.

As used herein, a "TACSTD2 molecule" can be a nucleic acid (e.g., synthetic, purified, and/or recombinant) which encodes a polypeptide corresponding to a TACSTD2 protein, or a TACSTD2 protein, or fragment thereof. For example, a TACSTD2 molecule can comprise the amino acid sequence shown in SEQ ID NO: 7, or can comprise the nucleic acid sequence shown in SEQ ID NO: 8. A TACSTD2 molecule can include a variant of the above described examples, such as a fragment thereof.

As used herein, a "NGAL molecule" can be a nucleic acid (e.g., synthetic, purified, and/or recombinant) which encodes a polypeptide corresponding to a NGAL protein, or a NGAL

```
  1  mplgllwlgl  allgalhaqa  qdstsdlipa  pplskvplqq  nfqdnqfqgk  wyvvglagna
 61  ilredkdpqk  myatiyelke  dksynvtsvl  frkkkcdywi  rtfvpgcqpg  eftlgniksy
121  pgltsylvrv  vstnynqham  vffkkvsqnr  eyfkitlygr  tkeltselke  nfirfskslg
181  lpenhivfpv  pidqcidg
```

SEQ ID NO: 10 is the NGAL mRNA or cDNA Nucleotide Sequence (NM_002353.2; 2080 bp).

protein, or fragment thereof. For example, a NGAL molecule can comprise the amino acid sequence shown in SEQ

```
  1 agggccaccc  aggtgagcct  ctcactcgcc  acctcctctt  ccaccctgc   caggcccagc
 61 agccaccaca  gcgcctgctt  cctcggccct  gaaatcatgc  ccctaggtct  cctgtggctg
121 ggcctagccc  tgttgggggc  tctgcatgcc  caggcccagg  actccacctc  agacctgatc
181 ccagccccac  ctctgagcaa  ggtccctctg  cagcagaact  tccaggacaa  ccaattccag
241 gggaagtggt  atgtggtagg  cctggcaggg  aatgcaattc  tcagagaaga  caaagacccg
301 caaaagatgt  atgccaccat  ctatgagctg  aaagaagaca  agagctacaa  tgtcacctcc
361 gtcctgttta  ggaaaaagaa  gtgtgactac  tggatcagga  cttttgttcc  aggttgccag
421 cccggcgagt  tcacgctggg  caacattaag  agttaccctg  gattaacgag  ttacctcgtc
481 cgagtggtga  gcaccaacta  caaccagcat  gctatggtgt  tcttcaagaa  agtttctcaa
541 aacagggagt  acttcaagat  caccctctac  gggagaacca  aggagctgac  ttcggaacta
601 aaggagaact  tcatccgctt  ctccaaatct  ctgggcctcc  ctgaaaacca  catcgtcttc
661 cctgtcccaa  tcgaccagtg  tatcgacggc  tgagtgcaca  ggtgccgcca  gctgccgcac
721 cagcccgaac  accattgagg  gagctgggag  accctcccca  cagtgccacc  catgcagctg
781 ctccccaggc  cacccgctg   atggagcccc  accttgtctg  ctaaataaac  atgtgccctc
841 aggccaaaaa  aaaaaaaaaa  aaa
```

As used herein, a "PAPPA2 molecule" can be a nucleic acid (e.g., synthetic, purified, and/or recombinant) which encodes a polypeptide corresponding to a PAPPA2 protein, or a PAPPA2 protein, or fragment thereof. For example, a PAPPA2 molecule can comprise the amino acid sequence ID NO: 9, or can comprise the nucleic acid sequence shown in SEQ ID NO: 10. A NGAL molecule can include a variant of the above described examples, such as a fragment thereof.

The nucleic acid can be any type of nucleic acid, including genomic DNA, complementary DNA (cDNA), recombinant DNA, synthetic or semi-synthetic DNA, as well as any form of corresponding RNA. A cDNA is a form of DNA artificially synthesized from a messenger RNA template and is used to produce gene clones. A synthetic DNA is free of modifications that can be found in cellular nucleic acids, including, but not limited to, histones and methylation. For example, a nucleic acid encoding a molecule of the invention can comprise a recombinant nucleic acid encoding such a protein. The nucleic acid can be a non-naturally occurring nucleic acid created artificially (such as by assembling, cutting, ligating or amplifying sequences). It can be double-stranded or single-stranded.

The invention further provides for nucleic acids that are complementary to a PAPPA2, KRT20, TACSTD2, or NGAL molecule. Complementary nucleic acids can hybridize to the nucleic acid sequence described above under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

According to the invention, protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture.

In one embodiment, a molecule of the invention comprises a protein or polypeptide, such as the sequences shown in SEQ ID NOS: 1-2, 5, 7, or 9. In some embodiments, the protein or polypeptide is about 70%, about 75%, about 80%, about 85%, about 90%, about 93%, about 95%, about 97%, about 98%, or about 99% identical to SEQ ID NOS: 1-2, 5, 7, or 9. In another embodiment, the polypeptide can be modified, such as by glycosylations and/or acetylations and/or chemical reaction or coupling, and can contain one or several non-natural or synthetic amino acids. In another embodiment, a molecule of the invention can be a fragment of a protein. For example, the molecule of the invention can encompass any portion of at least about 8 consecutive amino acids of SEQ ID NOS: 1-2, 5, 7, or 9. The fragment can comprise at least about 10 amino acids, a least about 20 amino acids, at least about 30 amino acids, at least about 40 amino acids, a least about 50 amino acids, at least about 60 amino acids, or at least about 75 amino acids of SEQ ID NOS: 1-2, 5, 7, or 9. Fragments include all possible amino acid lengths between about 8 and 100 about amino acids, for example, lengths between about 10 and 100 amino acids, between about 15 and 100 amino acids, between about 20 and 100 amino acids, between about 35 and 100 amino acids, between about 40 and 100 amino acids, between about 50 and 100 amino acids, between about 70 and 100 amino acids, between about 75 and 100 amino acids, or between about 80 and 100 amino acids.

Chemical Synthesis. Nucleic acid sequences encoding a molecule can be synthesized, in whole or in part, using chemical methods known in the art. Alternatively, a polypeptide can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer).

Optionally, polypeptides fragments can be separately synthesized and combined using chemical methods to produce a full-length molecule. For example, these methods can be utilized to synthesize a protein of the invention.

Obtaining, Purifying and Detecting PAPPA2, KRT20, TACSTD2, and NGAL molecules. A polypeptide, such as PAPPA2, KRT20, TACSTD2, or NGAL, can be obtained by purification from a sample. Non-limiting purification methods include size exclusion chromatography, ammonium sulfate fractionation, ion exchange chromatography, affinity chromatography, and preparative gel electrophoresis.

The expression of a polypeptide can be measured or detected using either polyclonal or monoclonal antibodies specific for the polypeptide. Non-limiting examples include enzyme-linked immunosorbent assay (ELISA), and radio-immunoassay (RIA). A two-site, monoclonal-based immunoassay using monoclonal antibodies reactive to two non-interfering epitopes on a polypeptide can be used, or a competitive binding assay can be employed.

Labeling and conjugation techniques are known by those skilled in the art and can be used in various nucleic acid and amino acid assays. Methods for producing labeled hybridization or PCR probes for detecting sequences related to nucleic acid sequences encoding a protein, include, but are not limited to, oligolabeling, nick translation, end-labeling, or PCR amplification using a labeled nucleotide. Alternatively, nucleic acid sequences, can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, and/or magnetic particles.

A fragment can be a fragment of a protein, such as a PAPPA2, KRT20, TACSTD2, or NGAL protein. For example, a fragment of a PAPPA2, KRT20, TACSTD2, or NGAL molecule can encompass any portion of at least about 8 consecutive amino acids of SEQ ID NOs: 1-2, 5, 7, or 9. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 75 consecutive amino acids, at least about 80 consecutive amino acids, at least about 85 consecutive amino acids, at least about 90 consecutive amino acids, at least about 95 consecutive amino acids, at least about 100 consecutive amino acids, at least about 200 consecutive amino acids, at least about 300 consecutive amino acids, at least about 400 consecutive amino acids, at least about 500 consecutive amino acids, at least about 600 consecutive amino acids, at least about 700 consecutive amino acids, or at least about 800 consecutive amino acids of SEQ ID NOs: 1-2, 5, 7, or 9. Fragments include all possible amino acid lengths between about 8 and 100 about amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids.

Polypeptides of the present invention comprising fragments of at least 8 contiguous amino acids, often at least 15 contiguous amino acids, are useful as immunogens for raising antibodies that recognize polypeptides of the present invention. See, e.g., Lerner, Nature 299: 592-596 (1982); Shinnick et al., Annu. Rev. Microbiol. 37: 425-46 (1983); Sutcliffe et al., Science 219: 660-6 (1983). As further described in the references cited herein, 8-mers, conjugated to a carrier, such as a protein, prove immunogenic and are capable of eliciting antibody for the conjugated peptide; accordingly, fragments of at least 8 amino acids of the polypeptides of the present invention have utility as immunogens.

Polypeptides comprising fragments of at least 8, 9, 10 or 12 contiguous amino acids are also useful as competitive inhibitors of binding of the entire polypeptide, or a portion thereof, to antibodies (as in epitope mapping), and to natural binding partners, such as subunits in a multimeric complex or to receptors or ligands of the subject protein; this competitive inhibition permits identification and separation of molecules that bind specifically to the polypeptide of interest. See U.S. Pat. Nos. 5,539,084 and 5,783,674, incorporated herein by reference in their entireties.

The polypeptides of the present invention thus can be at least 6 amino acids in length, at least 8 amino acids in length, at least 9 amino acids in length, at least 10 amino acids in length, at least 12 amino acids in length, at least 15 amino acids in length, at least 20 amino acids in length, at least 25 amino acids in length, at least 30 amino acids in length, at least 35 amino acids in length, at least 50 amino acids in length, at least 75 amino acids in length, at least 100 amino acids in length, or at least 150 amino acids in length. Polypeptides of the present invention can also be larger and comprise a full-length protein and/or an epitope tag and/or a fusion protein.

One having ordinary skill in the art can produce fragments by truncating the nucleic acid molecule, encoding the polypeptide and then expressing it recombinantly. Alternatively, one can produce a fragment by chemically synthesizing a portion of the full-length polypeptide. One can also produce a fragment by enzymatically cleaving a recombinant polypeptide or an isolated naturally occurring polypeptide. Methods of producing polypeptide fragments are well known in the art. See, e.g., Sambrook (1989), supra; Sambrook (2001), supra; Ausubel (1992), supra; and Ausubel (1999), supra. In one embodiment, a polypeptide comprising only a fragment can be produced by chemical or enzymatic cleavage of a polypeptide.

Polypeptides of the present invention are also inclusive of mutants, fusion proteins, homologous proteins and allelic variants.

A mutant protein can have the same or different properties compared to a naturally occurring polypeptide and comprises at least one amino acid insertion, duplication, deletion, rearrangement or substitution compared to the amino acid sequence of a native polypeptide. Small deletions and insertions can often be found that do not alter the function of a protein. The mutant protein can be a polypeptide that comprises at least one amino acid insertion, duplication, deletion, rearrangement or substitution compared to the amino acid sequence of SEQ ID NO: 1-2, 5, 7, or 9. Accordingly, in one embodiment, the mutant protein is one that exhibits at least 60% sequence identity, at least 70%, or at least 80% sequence identity, at least 85% sequence identity, at least 90% sequence identity, at least 95% sequence identity, at least 97%, sequence identity at least 985, sequence identity at least 99% or sequence identity at least 99.5% to SEQ ID NO: 1-2, 5, 7, or 9.

The invention also contemplates polypeptides that are homologous to a polypeptide of the invention. By homologous polypeptide it is meant one that exhibits significant sequence identity to a PAPPA2, NGAL, KRT20, or TAC-STD2 protein. By significant sequence identity it is meant that the homologous polypeptide exhibits at least exhibits at least 60% sequence identity, at least 70%, or at least 80% sequence identity, at least 85% sequence identity, at least 90% sequence identity, at least 95% sequence identity, at least 97%, sequence identity at least 985, sequence identity at least 99% or sequence identity at least 99.5% to a PAPPA2, NGAL, KRT20, or TACSTD2 protein. In one embodiment, the amino acid substitutions of the homologous polypeptide are conservative amino acid substitutions.

Homologous polypeptides of the present invention can be naturally occurring and derived from another species, especially one derived from another primate, such as chimpanzee, gorilla, rhesus macaque, or baboon, wherein the homologous polypeptide comprises an amino acid sequence that exhibits significant sequence identity to a polypeptide of the invention. The homologous polypeptide can also be a naturally occurring polypeptide from a human, when the PAPPA2, NGAL, KRT20, or TACSTD2 protein is a member of a family of polypeptides. The homologous polypeptide can also be a naturally occurring polypeptide derived from a non-primate, mammalian species, including without limitation, domesticated species, e.g., dog, cat, mouse, rat, rabbit, guinea pig, hamster, cow, horse, goat or pig. The homologous polypeptide can also be a naturally occurring polypeptide derived from a non-mammalian species, such as birds or reptiles. The naturally occurring homologous protein can be isolated directly from humans or other species. Alternatively, the nucleic acid molecule encoding the naturally occurring homologous polypeptide can be isolated and used to express the homologous polypeptide recombinantly. The homologous polypeptide can also be one that is experimentally produced by random mutation of a nucleic acid molecule and subsequent expression of the nucleic acid molecule. Alternatively, the homologous polypeptide can be one that is experimentally produced by directed mutation of one or more codons to alter the encoded amino acid of a PAPPA2, NGAL, KRT20, or TACSTD2 protein.

Relatedness of proteins can also be characterized using a second functional test, the ability of a first protein competitively to inhibit the binding of a second protein to an antibody. It is, therefore, another aspect of the present invention to provide isolated polypeptide not only identical in sequence to those described herein, but also to provide isolated polypeptide ("cross-reactive proteins") that can competitively inhibit the binding of antibodies to all or to a portion of various of the isolated polypeptides of the present invention. Such competitive inhibition can readily be determined using immunoassays well known in the art.

As discussed herein, single nucleotide polymorphisms (SNPs) occur frequently in eukaryotic genomes, and the sequence determined from one individual of a species can differ from other allelic forms present within the population. Thus, polypeptides of the present invention are also inclusive of those encoded by an allelic variant of a nucleic acid molecule encoding a PAPPA2, NGAL, KRT20, or TAC-STD2 protein.

Polypeptides of the present invention are also inclusive of derivative polypeptides encoded by a nucleic acid molecule according to the invention. Also inclusive are derivative polypeptides having an amino acid sequence selected from the group consisting of SEQ ID NOs: 1, 2, 5, 7, and 9 and which has been acetylated, carboxylated, phosphorylated, glycosylated, ubiquitinated or other post-translational modifications. In another embodiment, the derivative has been labeled with, e.g., radioactive isotopes such as 125I, 32P, 35S, and 3H. In another embodiment, the derivative has been labeled with fluorophores, chemiluminescent agents, enzymes, and antiligands that can serve as specific binding pair members for a labeled ligand.

Polypeptide modifications are well known to those of skill and have been described in detail in the scientific literature. Several common modifications, such as glycosylation, lipid attachment, sulfation, gamma-carboxylation of glutamic acid residues, hydroxylation and ADP-ribosylation, for instance, are described in most basic texts, such as, for instance Creighton, Protein Structure and Molecular Properties, 2nd ed., W. H. Freeman and Company (1993). Many detailed reviews are available on this subject, such as, for example, those provided by Wold, in Johnson (ed.), Post-translational Covalent Modification of Proteins, pgs. 1-12, Academic Press (1983); Seifter et al., Meth. Enzymol. 182: 626-646 (1990) and Rattan et al., Ann. N.Y. Acad. Sci. 663: 48-62 (1992).

One can determine whether a polypeptide of the invention will be post-translationally modified by analyzing the sequence of the polypeptide to determine if there are peptide motifs indicative of sites for post-translational modification. There are a number of computer programs that permit prediction of post-translational modifications. See, e.g., expasy with the extension .org of the world wide web (accessed Nov. 11, 2002), which includes PSORT, for prediction of protein sorting signals and localization sites, SignalP, for prediction of signal peptide cleavage sites, MITOPROT and Predotar, for prediction of mitochondrial targeting sequences, NetOGlyc, for prediction of type O-glycosylation sites in mammalian proteins, big-PI Predictor and DGPI, for prediction of prenylation-anchor and cleavage sites, and NetPhos, for prediction of Ser, Thr and Tyr phosphorylation sites in eukaryotic proteins. Other computer programs, such as those included in GCG, also can be used to determine post-translational modification peptide motifs.

Examples of types of post-translational modifications include, but are not limited to: (Z)-dehydrobutyrine; 1-chondroitin sulfate-L-aspartic acid ester; 1'-glycosyl-L-tryptophan; 1'-phospho-L-histidine; 1-thioglycine; 2'-(S-L-cysteinyl)-L-histidine; 2'-[3-carboxamido (trimethylammonio) propyl]-L-histidine; 2'-alpha-mannosyl-L-tryptophan; 2-methyl-L-glutamine; 2-oxobutanoic acid; 2-pyrrolidone carboxylic acid; 3'-(r-L-histidyl)-L-tyrosine; 3'-(8alpha-FAD)-L-histidine; 3'-(S-L-cysteinyl)-L-tyrosine; 3', 3", 5'-triiodo-L-thyronine; 3'-4'-phospho-L-tyrosine; 3-hydroxy-L-proline; 3'-methyl-L-histidine; 3-methyl-L-lanthionine; 3'-phospho-L-histidine; 4'-(L-tryptophan)-L-tryptophyl quinone; 42 N-cysteinyl-glycosylphosphatidylinositolethanolamine; 43-(T-L-histidyl)-L-tyrosine; 4-hydroxy-L-arginine; 4-hydroxy-L-lysine; 4-hydroxy-L-proline; 5'-(N6-L-lysine)-L-topaquinone; 5-hydroxy-L-lysine; 5-methyl-L-arginine; alpha-1-microglobulin-Ig alpha complex chromophore; bis-L-cysteinyl bis-L-histidino diiron disulfide; bis-L-cysteinyl-L-N3'-histidino-L-serinyl tetrairon' tetrasulfide; chondroitin sulfate D-glucuronyl-D-galactosyl-D-galactosyl-D-xylosyl-L-serine; //D-alanine; D-allo-isoleucine; D-asparagine; dehydroalanine; dehydrotyrosine; dermatan 4-sulfate D-glucuronyl-D-galactosyl-D-galactosyl-D-xylosyl-L-serine; D-glucuronyl-N-glycine; dipyrrolylmethanemethyl-L-cysteine; D-leucine; D-methionine; D-phenylalanine; D-serine; D-tryptophan; glycine amide; glycine oxazolecarboxylic acid; glycine thiazolecarboxylic acid; heme P450-bis-L-cysteine-L-tyrosine; heme-bis-L-cysteine; hemediol-L-aspartyl ester-L-glutamyl ester; hemediol-L-aspartyl ester-L-glutamyl ester-L-methionine sulfonium; heme-L-cysteine; heme-L-histidine; heparan sulfate D-glucuronyl-D-galactosyl-D-galactosyl-D-xylosyl-L-serine; heme P450-bis-L-cysteine-L-lysine; hexakis-L-cysteinyl hexairon hexasulfide; keratan sulfate D-glucuronyl-D-galactosyl-D-galactosyl-D-xylosyl-L-threonine; L oxoalanine-lactic acid; L phenyllactic acid; 1'-(8alpha-FAD)-L-histidine; L-2'.4',5'-topaquinone; L-3',4'-dihydroxyphenylalanine; L-3'.4'.5'-trihydroxyphenylalanine; L-4'-bromophenylalanine; L-6'-bromotryptophan; L-alanine amide; L-alanyl imidazolinone glycine; L-allysine; L-arginine amide; L-asparagine amide; L-aspartic 4-phosphoric anhydride; L-aspartic acid 1-amide; L-beta-methylthioaspartic acid; L-bromohistidine; L-citrulline; L-cysteine amide; L-cysteine glutathione disulfide; L-cysteine methyl disulfide; L-cysteine methyl ester; L-cysteine oxazolecarboxylic acid; L-cysteine oxazolinecarboxylic acid; L-cysteine persulfide; L-cysteine sulfenic acid; L-cysteine sulfinic acid; L-cysteine thiazolecarboxylic acid; L-cysteinyl homocitryl molybdenum-heptairon-nonasulfide; L-cysteinyl imidazolinone glycine; L-cysteinyl molybdopterin; L-cysteinyl molybdopterin guanine dinucleotide; L-cystine; L-erythro-beta-hydroxyasparagine; L-erythro-beta-hydroxyaspartic acid; L-gamma-carboxyglutamic acid; L-glutamic acid 1-amide; L-glutamic acid 5-methyl ester; L-glutamine amide; L-glutamyl 5-glycerylphosphoryletha-nolamine; L-histidine amide; L-isoglutamyl-polyglutamic acid; L-isoglutamyl-polyglycine; L-isoleucine amide; L-lanthionine; L-leucine amide; L-lysine amide; L-lysine thiazolecarboxylic acid; L-lysinoalanine; L-methionine amide; L-methionine sulfone; L-phenyalanine thiazolecarboxylic acid; L-phenylalanine amide; L-proline amide; L-selenocysteine; L-selenocysteinyl molybdopterin guanine dinucleotide; L-serine amide; L-serine thiazolecarboxylic acid; L-seryl imidazolinone glycine; L-T-bromophenylalanine; L-T-bromophenylalanine; L-threonine amide; L-thyroxine; L-tryptophan amide; L-tryptophyl quinone; L-tyrosine amide; L-valine amide; meso-lanthionine; N-(L-glutamyl)-L-tyrosine; N-(L-isoaspartyl)-glycine; N-(L-isoaspartyl)-L-cysteine; N,N,N-trimethyl-L-alanine; N,N-dimethyl-L-proline; N2-acetyl-L-lysine; N2-succinyl-L-tryptophan; N4-(ADP-ribosyl)-L-asparagine; N4-glycosyl-L-asparagine; N4-hydroxymethyl-L-asparagine; N4-methyl-L-asparagine; N5-methyl-L-glutamine; N6-1-carboxyethyl-L-lysine; N6-(4-amino hydroxybutyl)-L-lysine; N6-(L-isoglutamyl)-L-lysine; N6-(phospho-5'-adenosine)-L-lysine; N6-(phospho-5'-guanosine)-L-lysine; N6,N6,N6-trimethyl-L-lysine; N6,N6-dimethyl-L-lysine; N6-acetyl-L-lysine; N6-biotinyl-L-lysine; N6-carboxy-L-lysine; N6-formyl-L-lysine; N6-glycyl-L-lysine; N6-lipoyl-L-lysine; N6-methyl-L-lysine; N6-methyl-N6-poly(N-methyl-propylamine)-L-lysine; N6-mureinyl-L-lysine; N6-myristoyl-L-lysine; N6-palmitoyl-L-lysine; N6-pyridoxal phosphate-L-lysine; N6-pyruvic acid 2-iminyl-L-lysine; N6-retinal-L-lysine;

N-acetylglycine; N-acetyl-L-glutamine; N-acetyl-L-alanine; N-acetyl-L-aspartic acid; N-acetyl-L-cysteine; N-acetyl-L-glutamic acid; N-acetyl-L-isoleucine; N-acetyl-L-methionine; N-acetyl-L-proline; N-acetyl-L-serine; N-acetyl-L-threonine; N-acetyl-L-tyrosine; N-acetyl-L-valine; N-alanyl-glycosylphosphatidylinositolethanolamine; N-asparaginyl-glycosylphosphatidylinositolethanolamine; N-aspartyl-glycosylphosphatidylinositolethanolamine; N-formylglycine; N-formyl-L-methionine; N-glycyl-glycosylphosphatidylinositolethanolamine; N-L-glutamyl-poly-L-glutamic acid; N-methylglycine; N-methyl-L-alanine; N-methyl-L-methionine; N-methyl-L-phenylalanine; N-myristoyl-glycine; N-palmitoyl-L-cysteine; N-pyruvic acid 2-iminyl-L-cysteine; N-pyruvic acid 2-iminyl-L-valine; N-seryl-glycosylphosphatidylinositolethanolamine; N-seryl-glycosy OSPhingolipidinositolethanolamine; O-(ADP-ribosyl)-L-serine; O-(phospho-5'-adenosine)-L-threonine; O-(phospho-5'-DNA)-L-serine; O-(phospho-5'-DNA)-L-threonine; O-(phospho-5'rRNA)-L-serine; O-(phosphoribosyl dephospho-coenzyme A)-L-serine; O-(sn-1-glycerophosphoryl)-L-serine; O4'-(8alpha-FAD)-L-tyrosine; O4'-(phospho-5'-adenosine)-L-tyrosine; O4'-(phospho-5'-DNA)-L-tyrosine; O4'-(phospho-5'-RNA)-L-tyrosine; O4'-(phospho-5'-uridine)-L-tyrosine; O4-glycosyl-L-hydroxyproline; O4'-glycosyl-L-tyrosine; O4'-sulfo-L-tyrosine; O5-glycosyl-hydroxylysine; O-glycosyl-L-serine; O-glycosyl-L-threonine; omega-N-(ADP-ribosyl)-L-arginine; omega-N-omega-N'-dimethyl-L-arginine; omega-N-methyl-L-arginine; omega-N-omega-N-dimethyl-L-arginine; omega-N-phospho-L-arginine; O'octanoyl-L-serine; O-palmitoyl-L-serine; O-palmitoyl-L-threonine; O-phospho-L-serine; O-phospho-L-threonine; O-phospho-pantetheine-L-serine; phycoerythrobilin-bis-L-cysteine; phycourobilin-bis-L-cysteine; pyrroloquinoline quinone; pyruvic acid; S hydroxycinnamyl-L-cysteine; S-(2-aminovinyl)methyl-D-cysteine; S-(2-aminovinyl)-D-cysteine; S-(6-FW-L-cysteine; S-(8alpha-FAD)-L-cysteine; S-(ADP-ribosyl)-L-cysteine; S-(L-isoglutamyl)-L-cysteine; S-12-hydroxyfarnesyl-L-cysteine; S-acetyl-L-cysteine; S-diacylglycerol-L-cysteine; S-diphytanylglycerot diether-L-cysteine; S-farnesyl-L-cysteine; S-geranylgeranyl-L-cysteine; S-glycosyl-L-cysteine; S-glycyl-L-cysteine; S-methyl-L-cysteine; S-nitrosyl-L-cysteine; S-palmitoyl-L-cysteine; S-phospho-L-cysteine; S-phycobiliviolin-L-cysteine; S-phycocyanobilin-L-cysteine; S-phycoerythrobilin-L-cysteine; S-phytochromobilin-L-cysteine; S-selenyl-L-cysteine; S-sulfo-L-cysteine; tetrakis-L-cysteinyl diiron disulfide; tetrakis-L-cysteinyl iron; tetrakis-L-cysteinyl tetrairon tetrasulfide; trans-2,3-cis 4-dihydroxy-L-proline; tris-L-cysteinyl triiron tetrasulfide; tris-L-cysteinyl triiron trisulfide; tris-L-cysteinyl-L-aspartato tetrairon tetrasulfide; tris-L-cysteinyl-L-cysteine persulfido-bis-L-glutamato-L-histidino tetrairon disulfide trioxide; tris-L-cysteinyl-L-N3'-histidino tetrairon tetrasulfide; tris-L-cysteinyl-L-NM'-histidino tetrairon tetrasulfide; and tris-L-cysteinyl-L-serinyl tetrairon tetrasulfide.

Additional examples of post translational modifications can be found in web sites such as the Delta Mass database based on Krishna, R. G. and F. Wold (1998). Posttranslational Modifications. Proteins—Analysis and Design. R. H. Angeletti. San Diego, Academic Press. 1: 121-206; Methods in Enzymology, 193, J. A. McClosky (ed) (1990), pages 647-660; Methods in Protein Sequence Analysis edited by Kazutomo Imahori and Fumio Sakiyama, Plenum Press, (1993) "Post-translational modifications of proteins" R. G. Krishna and F. Wold pages 167-172; "GlycoSuiteDB: a new curated relational database of glycoprotein glycan structures and their biological sources" Cooper et al. Nucleic Acids Res. 29; 332-335 (2001) "O-GLYCBASE version 4.0: a revised database of O-glycosylated proteins" Gupta et al. Nucleic Acids Research, 27: 370-372 (1999) and "PhosphoBase, a database of phosphorylation sites: release 2.0.", Kreegipuu et al. Nucleic Acids Res 27(1):237-239 (1999) see also, WO 02/21139A2, the disclosure of which is incorporated herein by reference in its entirety.

Disease states are often accompanied by alterations in the post-translational modifications of proteins. Thus, in another embodiment, the invention provides polypeptides from diseased cells or tissues that have altered post-translational modifications compared to the post-translational modifications of polypeptides from normal cells or tissues. A number of altered post-translational modifications are known. One common alteration is a change in phosphorylation state, wherein the polypeptide from the diseased cell or tissue is hyperphosphorylated or hypophosphorylated compared to the polypeptide from a normal tissue, or wherein the polypeptide is phosphorylated on different residues than the polypeptide from a normal cell. Another common alteration is a change in glycosylation state, wherein the polypeptide from the diseased cell or tissue has more or less glycosylation than the polypeptide from a normal tissue, and/or wherein the polypeptide from the diseased cell or tissue has a different type of glycosylation than the polypeptide from a non-diseased cell or tissue.

Another post-translational modification that can be altered in diseased cells is prenylation. Prenylation is the covalent attachment of a hydrophobic prenyl group (farnesyl or geranylgeranyl) to a polypeptide. Prenylation is required for localizing a protein to a cell membrane and is often required for polypeptide function. For instance, the Ras superfamily of GTPase signalling proteins must be prenylated for function in a cell. See, e.g., Prendergast et al., Semin. Cancer Biol. 10: 443-452 (2000) and Khwaja et al., Lancet 355: 741-744 (2000).

Other post-translation modifications that can be altered in diseased cells include, without limitation, polypeptide methylation, acetylation, arginylation or racemization of amino acid residues. In these cases, the polypeptide from the diseased cell can exhibit increased or decreased amounts of the post-translational modification compared to the corresponding polypeptides from non-diseased cells.

Other polypeptide alterations in diseased cells include abnormal polypeptide cleavage of proteins and aberrant protein-protein interactions. Abnormal polypeptide cleavage can be cleavage of a polypeptide in a diseased cell that does not usually occur in a normal cell, or a lack of cleavage in a diseased cell, wherein the polypeptide is cleaved in a normal cell. Aberrant protein-protein interactions can be covalent cross-linking or non-covalent binding between proteins that do not normally bind to each other. Alternatively, in a diseased cell, a protein can fail to bind to another protein to which it is bound in a non-diseased cell. Alterations in cleavage or in protein-protein interactions can be due to over- or underproduction of a polypeptide in a diseased cell compared to that in a normal cell, or can be due to alterations in post-translational modifications of one or more proteins in the diseased cell. See, e.g., Henschen-Edman, Ann. N.Y. Acad. Sci. 936: 580-593 (2001).

Alterations in polypeptide post-translational modifications, as well as changes in polypeptide cleavage and protein-protein interactions, can be determined by any method known in the art. For instance, alterations in phosphorylation can be determined by using anti-phosphoserine, anti-phosphothreonine or anti-phosphotyrosine antibodies or by amino acid analysis. Glycosylation alterations can be determined using antibodies specific for different sugar residues, by carbohydrate sequencing, or by alterations in the size of the glycoprotein, which can be determined by, e.g., SDS polyacrylamide gel electrophoresis (PAGE). Other alterations of post-translational modifications, such as prenylation, racemization, methylation, acetylation and arginylation, can be determined by chemical analysis, protein sequencing, amino acid analysis, or by using antibodies that bind a post-translational modification. Changes in protein-protein interactions and in polypeptide cleavage can be analyzed by any method known in the art including, without limitation, non-denaturing PAGE (for non-covalent protein-protein interactions), SDS PAGE (for covalent protein-protein interactions and protein cleavage), chemical cleavage, protein sequencing or immunoassays.

In another embodiment, the invention provides polypeptides that have been post-translationally modified. In one embodiment, polypeptides can be modified enzymatically or chemically, by addition or removal of a post-translational modification. For example, a polypeptide can be glycosylated or deglycosylated enzymatically. Similarly, polypeptides can be phosphorylated using a purified kinase, such as a MAP kinase (e.g, p38, ERK, or JNK) or a tyrosine kinase (e.g., Src or erbB2). A polypeptide can also be modified through synthetic chemistry. Alternatively, one can isolate the polypeptide of interest from a cell or tissue that expresses the polypeptide with the desired post-translational modification. In another embodiment, a nucleic acid molecule encoding the polypeptide of interest is introduced into a host cell that is capable of post-translationally modifying the encoded polypeptide in the desired fashion. If the polypeptide does not contain a motif for a desired post-translational modification, one can alter the post-translational modification by mutating the nucleic acid sequence of a nucleic acid molecule encoding the polypeptide so that it contains a site for the desired post-translational modification. Amino acid sequences that can be post-translationally modified are known in the art. See, e.g., the programs described herein on the Expasy website. The nucleic acid molecule can also be introduced into a host cell that is capable of post-translationally modifying the encoded polypeptide. Similarly, one can delete sites that are post-translationally modified by mutating the nucleic acid sequence so that the encoded polypeptide does not contain the post-translational modification motif, or by introducing the native nucleic acid molecule into a host cell that is not capable of post-translationally modifying the encoded polypeptide.

Polypeptides are not always entirely linear. For instance, polypeptides can be branched as a result of ubiquitination, and they can be circular, with or without branching, as a result of posttranslation events, including natural processing event and events brought about by human manipulation which do not occur naturally. Circular, branched and branched circular polypeptides can be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications can be present in polypeptides of the present invention, as well. For instance, the amino terminal residue of polypeptides made in E. coli, prior to proteolytic processing, almost invariably will be N-formylmethionine.

Useful post-synthetic (and post-translational) modifications include conjugation to detectable labels, such as fluorophores. A wide variety of amine-reactive and thiol-reactive fluorophore derivatives have been synthesized that react under nondenaturing conditions with N-terminal amino groups and epsilon amino groups of lysine residues, on the one hand, and with free thiol groups of cysteine residues, on the other.

Kits are available commercially that permit conjugation of proteins to a variety of amine-reactive or thiol-reactive fluorophores: Molecular Probes, Inc. (Eugene, Oreg., USA), e.g., offers kits for conjugating proteins to Alexa Fluor 350, Alexa Fluor 430, Fluorescein-EX, Alexa Fluor 488, Oregon Green 488, Alexa Fluor 532, Alexa Fluor 546, Alexa Fluor 546, Alexa Fluor 568, Alexa Fluor 594, and Texas Red-X A wide variety of other amine-reactive and thiol-reactive fluorophores are available commercially (Molecular Probes, Inc., Eugene, Oreg., USA), including Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA).

The polypeptides of the present invention can also be conjugated to fluorophores, other proteins, and other macromolecules, using bifunctional linking reagents. Common homobifunctional reagents include, e.g., APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS (available from Pierce, Rockford, Ill., USA); common heterobifunctional cross-linkers include ABH, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, M2C2H, MPBH, MSA, NHS-ASA, PDPH, PMPI, SADP, SAED, SAND, SANPAH, SASD, SATP, SBAP, SFAD, SIA, SLAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS, Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS (available Pierce, Rockford, Ill., USA).

Polypeptides of the present invention, including full length polypeptides, fragments and fusion proteins, can be conjugated, using such cross-linking reagents, to fluorophores that are not amine- or thiol-reactive. Other labels that usefully can be conjugated to polypeptides of the present invention include radioactive labels, echosonographic contrast reagents, and MRI contrast agents.

Polypeptides of the present invention, including full length polypeptide, fragments and fusion proteins, can also usefully be conjugated using cross-linking agents to carrier proteins, such as KLH, bovine thyroglobulin, and even bovine serum albumin (BSA), to increase immunogenicity for raising anti-PAPPA2, anti-NGAL, anti-KRT20, or anti-TACSTD2 protein antibodies.

Polypeptides of the present invention, including full length polypeptide, fragments and fusion proteins, can also usefully be conjugated to polyethylene glycol (PEG); PEGylation increases the serum half life of proteins administered intravenously for replacement therapy. Delgado et al., Crit. Rev. Ther. Drug Carrier Syst. 9(3-4): 249-304 (1992); Scott et al., Curr. Pharm. Des. 4(6): 423-38 (1998); DeSantis et al., Curr. Opin. Biotechnol. 10(4): 324-30 (1999). PEG monomers can be attached to the protein directly or through a linker, with PEGylation using PEG monomers activated with tresyl chloride (2,2,2-trifluoroethanesulphonyl chloride) permitting direct attachment under mild conditions.

Methods of Treatment and Diagnosis

In one embodiment, the method comprises detecting the presence of PAPPA2 in a sample obtained from a subject, the presence of the PAPPA2 being indicative of a vAKI, and, administering to the subject in need a therapeutic treatment for vAKI. In some embodiments, the sample is incubated with an agent that binds to PAPPA2, such as an antibody, a probe, a nucleic acid primer, and the like.

In one embodiment, the method comprises detecting the presence of NGAL, KRT20, TACSTD2, or a combination thereof, in a sample obtained from a subject, the presence of the NGAL, KRT20, TACSTD2, or a combination thereof, being indicative of a iAKI, and, administering to the subject in need a therapeutic treatment for iAKI. In some embodiments, the sample is incubated with an agent that binds to NGAL, KRT20, or TACSTD2, such as an antibody, a probe, a nucleic acid primer, and the like.

In one aspect, the invention provides a method for treating volume-dependent acute kidney injury (vAKI) in a subject in need thereof, the method comprising: a) determining the level of full-length PAPPA2 protein in a urine sample from the subject; and b) administering fluids to the subject if full-length PAPPA2 protein is present in the urine sample from the subject in a higher amount than in a urine sample from a subject that does not have Acute Kidney Injury (AKI).

In another aspect, the invention provides a method for treating vAKI in a subject in need thereof, the method comprising: a) determining the level of full-length PAPPA2 protein in a urine sample from the subject; b) determining the level of NGAL, KRT20, or TACSTD2 protein, or a combination thereof, in the urine sample from the subject; c) determining the ratio of full-length PAPPA2/NGAL, full-length PAPPA2/KRT20, or full-length PAPPA2/TACSTD2 in the urine sample from the subject; d) determining the level of full-length PAPPA2 protein in a urine sample from a subject that does not have AKI; e) determining the level of NGAL, KRT20, or TACSTD2 protein, or a combination thereof, in a urine sample from a subject that does not have AKI; f) determining the ratio of full-length PAPPA2/NGAL, full-length PAPPA2/KRT20, or full-length PAPPA2/TACSTD2 in the urine sample from the subject that does not have AKI; and g) administering fluids to the subject if the ratio of full-length PAPPA2/NGAL, full-length PAPPA2/KRT20, or full-length PAPPA2/TACSTD2 in the urine sample from the subject is greater than the ratio of full-length PAPPA2/NGAL, full-length PAPPA2/KRT20, or full-length PAPPA2/TACSTD2 in the urine sample from a subject that does not have vAKI, respectively.

In another aspect, the invention provides a method for treating ischemic acute kidney injury (iAKI) in a subject in need thereof, the method comprising: a) determining the level of NGAL, KRT20, or TACSTD2 protein, or a combination thereof, in a urine sample from the subject; and b) administering treatment for kidney damage to the subject if NGAL, KRT20, or TACSTD2 protein, or a combination thereof, is present in the urine sample from the subject in a higher amount than in a urine sample from a subject that does not have AKI.

In one aspect, the invention provides a method for treating iAKI in a subject in need thereof, the method comprising: a) determining the level of full-length PAPPA2 protein in a urine sample from the subject; b) determining the level of NGAL, KRT20, or TACSTD2 protein, or a combination thereof, in the urine sample from the subject; c) determining the ratio of NGAL/full-length PAPPA2, KRT20/full-length PAPPA2, or TACSTD2/full-length PAPPA2 in the urine sample from the subject; d) determining the level of full-length PAPPA2 protein in a urine sample from a subject that does not have AKI; e) determining the level of NGAL, KRT20, or TACSTD2 protein, or a combination thereof, in the urine sample from the subject that does not have AKI; f) determining the ratio of NGAL/full-length PAPPA2, KRT20/full-length PAPPA2, or TACSTD2/full-length PAPPA2 in the urine sample from the subject that does not have AKI; and g) administering treatment for kidney damage to the subject if the ratio of NGAL/full-length PAPPA2, KRT20/full-length PAPPA2, or TACSTD2/full-length PAPPA2 in the urine sample from the subject is greater than the ratio of NGAL/full-length PAPPA2, KRT20/full-length PAPPA2, or TACSTD2/full-length PAPPA2 in the urine sample from the subject that does not have AKI, respectively.

In another aspect, the invention provides a method for treating iAKI in a subject in need thereof, the method comprising: a) determining the level of proteolytically cleaved PAPPA2 protein in a urine sample from the subject; and b) administering treatment for kidney damage to the subject if proteolytically cleaved PAPPA2 protein is present in the urine sample from the subject in a higher amount than in a urine sample from a subject that does not have AKI.

In one embodiment, the size of full-length PAPPA2 is equal to or above 100 kDa, 110 kDa, 120 kDa, 130 kDa, 135 kDa, 140 kDa, 150 kDa, 160 kDa, 170 kDa, 180 kDa, 190 kDa, 200 kDa, 210 kDa or 220 kDa.

In one embodiment, the size of proteolytically cleaved PAPPA2 is equal to or below 200 kDa, 190 kDa, 180 kDa, 170 kDa, 160 kDa, 150 kDa, 140 kDa, 130 kDa, 120 kDa, 110 kDa, 100 kDa, 90 kDa, 80 kDa, 75 kDa, 70 kDa, 65 kDa, 60 kDa, 55 kDa, or 50 kDa.

In one embodiment, the method further comprises determining the level of serum creatinine in the subject. In one embodiment, the level of serum creatinine is determined before the administering step. In another embodiment, In one embodiment, the level of serum creatinine is determined after the administering step.

In one embodiment, an elevated level of serum creatinine is equal to or above 0.1 mg/dL, 0.2 mg/dL, 0.3 mg/dL, 0.4 mg/dL, 0.5 mg/dL, 0.6 mg/dL, 0.7 mg/dL, 0.8 mg/dL, 0.9 mg/dL or 1 mg/dL.

In one embodiment, treatment is administered if the subject has an elevated level of serum creatinine. In another embodiment, the treatment for kidney damage comprises withholding fluids, administering dialysis, or a combination thereof. In one embodiment, the method further comprises testing and treating the subject for hyperkalemia, hyponatremia, hyperphosphatemia or acidosis.

In one embodiment, the method comprises prior to step a), reducing a urine sample from a subject with a reducing agent to generate a reduced urine sample, filtering the reduced urine sample with a 300 KDa filter to produce a retentate and a filtrate, wherein step a) and/or d) is then performed on the retentate. In another embodiment, the reducing agent is beta-mercaptoethanol.

In one embodiment, the level of full-length PAPPA2, proteolytically cleaved PAPPA2, NGAL, KRT20, or TACSTD2 protein is determined by ELISA, immunoblot, Western blot, or lateral flow dip stick. In another embodiment, the level of full-length PAPPA2, proteolytically cleaved PAPPA2, NGAL, KRT20, or TACSTD2 protein is determined using an antibody that specifically binds to full-length PAPPA2, proteolytically cleaved PAPPA2, NGAL, KRT20, or TACSTD2 protein, respectively, or a fragment thereof.

In one embodiment, the subject is a human subject.

For vAKI, the administering step in each of the claimed methods can comprise a fluid, blood or albumin administration, or a drug administration. In another embodiment, administration of the therapy improves the volume capacity of the kidney and the volume status (extracellular fluid volume or the circulating volume) of the body.

In one embodiment, the biological sample comprises urine. In another embodiment, the biological sample comprises neuronal cells, serum, bone marrow, blood, peripheral blood, lymph nodes, cerebro-spinal fluid, urine, a saliva sample, a buccal swab, a serum sample, a sputum sample, a lacrimal secretion sample, a semen sample, a vaginal secretion sample, a fetal tissue sample, or a combination thereof.

A PAPPA2, NGAL, KRT20, or TACSTD2 molecule, can be determined at the level of the DNA, RNA, or polypeptide. Optionally, detection can be determined by performing an oligonucleotide ligation assay, a confirmation based assay, a hybridization assay, a sequencing assay, an allele-specific amplification assay, a microsequencing assay, a melting curve analysis, a denaturing high performance liquid chromatography (DHPLC) assay (for example, see Jones et al, (2000) Hum Genet., 106(6):663-8), or a combination thereof. In another embodiment, the detection or determination comprises protein expression analysis, for example by western blot analysis, ELISA, or other antibody detection methods.

The present invention provides a method for treating vAKI in a subject in need thereof. In one embodiment, the method comprises obtaining a sample from the subject to determine the level of PAPPA2 in the subject. In some embodiments, the sample is incubated with an agent that binds to PAPPA2, such as an antibody, a probe, a nucleic acid primer, and the like. In another embodiment, the detection or determination comprises nucleic acid sequencing, selective hybridization, selective amplification, gene expression analysis, or a combination thereof. In another embodiment, the detection or determination comprises protein expression analysis, for example by western blot analysis, ELISA, or other antibody detection methods. In some embodiments, the method further comprises assessing whether to administer treatment for vAKI based on the expression pattern of the subject. In further embodiments, the method comprises administering a vAKI treatment to the subject.

The present invention provides a method for treating iAKI in a subject in need thereof. In one embodiment, the method comprises obtaining a sample from the subject to determine the level of NGAL, KRT20, or TACSTD2 in the subject. In some embodiments, the sample is incubated with an agent that binds to NGAL, KRT20, or TACSTD2, such as an antibody, a probe, a nucleic acid primer, and the like. In another embodiment, the detection or determination comprises nucleic acid sequencing, selective hybridization, selective amplification, gene expression analysis, or a combination thereof. In another embodiment, the detection or determination comprises protein expression analysis, for example by western blot analysis, ELISA, or other antibody detection methods. In some embodiments, the method further comprises assessing whether to administer treatment for iAKI based on the expression pattern of the subject. In further embodiments, the method comprises administering an iAKI treatment to the subject.

Various techniques known in the art can be used to detect or quantify PAPPA2, NGAL, KRT20, or TACSTD2. Detection methods can require the use of a ligand specific for the polypeptide, for example, the use of a specific antibody.

Specific Ligand Binding.

As discussed herein, a PAPPA2, NGAL, KRT20, or TACSTD2 protein can be detected by screening for the expression level of a polypeptide. Different types of ligands can be used, such as specific antibodies. In one embodiment, the sample is contacted with an antibody specific for a PAPPA2, NGAL, KRT20, or TACSTD2 protein and the formation of an immune complex is subsequently determined. Various methods for detecting an immune complex can be used, such as ELISA, radioimmunoassays (RIA) and immuno-enzymatic assays (IEMA).

For example, an antibody can be a polyclonal antibody, a monoclonal antibody, as well as fragments or derivatives thereof having substantially the same antigen specificity. Fragments include Fab, Fab'2, or CDR regions. Derivatives include single-chain antibodies, humanized antibodies, or poly-functional antibodies. An antibody specific for a PAPPA2, NGAL, KRT20, or TACSTD2 protein can be an antibody that selectively binds such a polypeptide. In one embodiment, the antibody is raised against a PAPPA2, NGAL, KRT20, or TACSTD2 protein or an epitope-containing fragment thereof. Although non-specific binding towards other antigens can occur, binding to the target polypeptide occurs with a higher affinity and can be reliably discriminated from non-specific binding. In one embodiment, the method can comprise contacting a sample from the subject with an antibody specific for a PAPPA2, NGAL, KRT20, or TACSTD2 protein, and determining the presence of an immune complex. Optionally, the sample can be contacted to a support coated with antibody specific for a PAPPA2, NGAL, KRT20, or TACSTD2 protein. In one embodiment, the sample can be contacted simultaneously, or in parallel, or sequentially, with various antibodies specific for PAPPA2, NGAL, KRT20, or TACSTD2.

The invention also provides for a diagnostic kit comprising products and reagents for detecting in a sample from a subject the presence of a PAPPA2, NGAL, KRT20, or TACSTD2 protein, or the presence of PAPPA2, NGAL, KRT20, or TACSTD2 nucleic acid. The kit can be useful for determining whether a sample from a subject exhibits increased or reduced expression of a PAPPA2, NGAL, KRT20, or TACSTD2 protein or PAPPA2, NGAL, KRT20, or TACSTD2 nucleic acid. For example, the diagnostic kit according to the present invention comprises any primer, any pair of primers, any nucleic acid probe and/or any ligand, or any antibody directed specifically to a PAPPA2, NGAL, KRT20, or TACSTD2 protein, or a PAPPA2, NGAL, KRT20, or TACSTD2 nucleic acid. The diagnostic kit according to the present invention can further comprise reagents and/or protocols for performing a hybridization, amplification, or antigen-antibody immune reaction. In some embodiments, the kit comprises an antibody that specifically binds to a PAPPA2, NGAL, KRT20, or TACSTD2 protein comprising SEQ ID NO: 1, 2, 5, 7, or 9.

The diagnosis methods can be performed in vitro, ex vivo, or in vivo. These methods utilize a sample from the subject in order to assess the status of vAKI or iAKI. The sample can be any biological sample derived from a subject, which contains nucleic acids or polypeptides. Examples of such samples include, but are not limited to, fluids, tissues, cell samples, organs, and tissue biopsies. Non-limiting examples of samples include blood, liver, plasma, serum, saliva, urine, or seminal fluid. The sample can be collected according to conventional techniques and used directly for diagnosis or stored. The sample can be treated prior to performing the method, in order to render or improve availability of nucleic acids or polypeptides for testing. Treatments include, for instance, lysis (e.g., mechanical, physical, or chemical), centrifugation. The nucleic acids and/or polypeptides can be pre-purified or enriched by conventional techniques, and/or reduced in complexity. Nucleic acids and polypeptides can also be treated with enzymes or other chemical or physical treatments to produce fragments thereof. In one embodiment, the sample is contacted with reagents, such as probes, primers, or ligands, in order to assess the presence of a PAPPA2, NGAL, KRT20, or TACSTD2 protein, or PAPPA2, NGAL, KRT20, or TACSTD2 nucleic acid. Contacting can be performed in any suitable device, such as a plate, tube, well, or glass. In some embodiments, the contacting is performed on a substrate coated with the reagent, such as an antibody or epitope binding fragment of an antibody. The substrate can be a solid or semi-solid substrate such as any support comprising glass, plastic, nylon, paper, metal, or polymers. The substrate can be of various forms and sizes, such as a slide, a membrane, a bead, a column, or a gel. The contacting can be made under any condition suitable for a complex to be formed between the reagent and the nucleic acids or polypeptides of the sample.

Methods of Detection and Kits of the Invention

In one aspect, the invention provides a diagnostic kit for determining whether a urine sample from a subject contains full-length PAPPA2, proteolytically cleaved PAPPA2, NGAL, KRT20, or TACSTD2 protein, or a combination thereof, the kit comprising at least one antibody that specifically binds to full-length PAPPA2, proteolytically cleaved PAPPA2, NGAL, KRT20, or TACSTD2 protein, or a fragment thereof.

In another aspect, the invention provides a diagnostic kit for determining whether a urine sample from a subject contains full-length PAPPA2, proteolytically cleaved PAPPA2, NGAL, KRT20, or TACSTD2 protein, or a combination thereof, the kit comprising at least one antibody that specifically binds to a protein comprising SEQ ID NO: 1, 2, 5, 7, or 9.

In another aspect, the invention provides a method for detecting the presence of a full-length PAPPA2, proteolytically cleaved PAPPA2, NGAL, KRT20, or TACSTD2 protein in a urine sample from a subject, the method comprising: (a) obtaining a urine sample from the subject; and (b) measuring full-length PAPPA2, proteolytically cleaved PAPPA2, NGAL, KRT20, or TACSTD2 protein levels by ELISA using an antibody directed to SEQ ID NO: 1, 2, 5, 7, or 9; or by western blot using an antibody directed to SEQ ID NO: 1, 2, 5, 7, or 9; or by mass spectroscopy; or by isoelectric focusing, or a combination thereof.

In another aspect, the invention provides a method of diagnosing vAKI in a subject in need thereof, the method comprising: a) determining the level of full-length PAPPA2 protein in a urine sample from the subject; and b) diagnosing the subject with vAKI if full-length PAPPA2 protein is present in the urine sample from the subject in a higher amount than in a urine sample from a subject that does not have AKI.

In one aspect, the invention provides a method of diagnosing vAKI in a subject in need thereof, the method comprising: a) determining the level of full-length PAPPA2 protein in a urine sample from the subject; b) determining the level of NGAL, KRT20, or TACSTD2 protein, or a combination thereof, in the urine sample from the subject; c) determining the ratio of full-length PAPPA2/NGAL, full-length PAPPA2/KRT20, or full-length PAPPA2/TACSTD2 in the urine sample from the subject; d) determining the level of full-length PAPPA2 protein in a urine sample from a subject that does not have AKI; e) determining the level of NGAL, KRT20, or TACSTD2 protein, or a combination thereof, in the urine sample from the subject that does not have AKI; f) determining the ratio of full-length PAPPA2/NGAL, full-length PAPPA2/KRT20, or full-length PAPPA2/TACSTD2 in the urine sample from the subject that does not have AKI; g) diagnosing the subject with vAKI if the ratio of full-length PAPPA2/NGAL, full-length PAPPA2/KRT20, or full-length PAPPA2/TACSTD2 in the urine sample from the subject is greater than the ratio of full-length PAPPA2/NGAL, full-length PAPPA2/KRT20, or full-length PAPPA2/TACSTD2 in the urine sample from a subject that does not have AKI, respectively.

In another aspect, the invention provides a method of diagnosing iAKI in a subject in need thereof, the method comprising: a) determining the level of NGAL, KRT20, or TACSTD2 protein, or a combination thereof, in a urine sample from the subject; and b) diagnosing the subject with iAKI if NGAL, KRT20, or TACSTD2 protein, or a combination thereof, is present in the urine sample from the subject in a higher amount than in a urine sample from a subject that does not have AKI.

In one aspect, the invention provides a method of diagnosing iAKI in a subject in need thereof, the method comprising: a) determining the level of full-length PAPPA2 protein in a urine sample from the subject; b) determining the level of NGAL, KRT20, or TACSTD2 protein, or a combination thereof, in the urine sample from the subject; c) determining the ratio of NGAL/full-length PAPPA2, KRT20/full-length PAPPA2, or TACSTD2/full-length PAPPA2 in the urine sample from the subject; d) determining the level of full-length PAPPA2 protein in a urine sample from a subject that does not have AKI; e) determining the level of NGAL, KRT20, or TACSTD2 protein, or a combination thereof, in the urine sample from the subject that does not have AKI; f) determining the ratio of NGAL/full-length PAPPA2, KRT20/full-length PAPPA2, or TACSTD2/full-length PAPPA2 in the urine sample from the subject that does not have AKI; g) diagnosing the subject with iAKI if the ratio of NGAL/full-length PAPPA2, KRT20/full-length PAPPA2, or TACSTD2/full-length PAPPA2 in the urine sample from the subject is greater than the ratio of NGAL/full-length PAPPA2, KRT20/full-length PAPPA2, or TACSTD2/full-length PAPPA2 in the urine sample from the subject that does not have AKI, respectively.

In another aspect, the invention provides a method for diagnosing iAKI in a subject in need thereof, the method comprising: a) determining the level of proteolytically cleaved PAPPA2 protein in a urine sample from the subject; and b) diagnosing the subject with iAKI if proteolytically cleaved PAPPA2 protein is present in the urine sample from the subject in a higher amount than in a urine sample from a subject that does not have AKI.

In one embodiment, the size of full-length PAPPA2 is equal to or above 100 kDa, 110 kDa, 120 kDa, 130 kDa, 135 kDa, 140 kDa, 150 kDa, 160 kDa, 170 kDa, 180 kDa, 190 kDa, 200 kDa, 210 kDa or 220 kDa.

In one embodiment, the size of proteolytically cleaved PAPPA2 is equal to or below 200 kDa, 190 kDa, 180 kDa, 170 kDa, 160 kDa, 150 kDa, 140 kDa, 130 kDa, 120 kDa, 110 kDa, 100 kDa, 90 kDa, 80 kDa, 75 kDa, 70 kDa, 65 kDa, 60 kDa, 55 kDa, or 50 kDa.

In one embodiment, the method comprises administering fluids to the subject if the subject is diagnosed with vAKI. In another embodiment, the method comprises administering treatment for kidney damage if the subject is diagnosed with iAKI.

In one embodiment, the method comprises determining the level of serum creatinine in the subject. In another embodiment, the level of serum creatinine is determined before the diagnosing step.

In one embodiment, an elevated level of serum creatinine is equal to or above 0.1 mg/dL, 0.2 mg/dL, 0.3 mg/dL, 0.4 mg/dL, 0.5 mg/dL, 0.6 mg/dL, 0.7 mg/dL, 0.8 mg/dL, 0.9 mg/dL or 1 mg/dL.

In one embodiment, the subject is diagnosed with vAKI or iAKI if the subject also has an elevated level of serum creatinine.

In one embodiment, the treatment for kidney damage comprises withholding fluids, administering dialysis, or a combination thereof. In another embodiment, the method further comprises testing and treating the subject for hyperkalemia, hyponatremia, hyperphosphatemia or acidosis if the subject is diagnosed with iAKI.

In one embodiment, the method further comprises, prior to step a), reducing a urine sample from a subject with a reducing agent to generate a reduced urine sample, filtering the reduced urine sample with a 300 kDa filter to produce a retentate and a filtrate, wherein step a) and/or d) is then performed on the retentate. In another embodiment, the reducing agent is beta-mercaptoethanol.

In one embodiment, the level of full-length PAPPA2, proteolytically cleaved PAPPA2, NGAL, KRT20, or TACSTD2 protein is determined by ELISA, immunoblot, Western blot, or lateral flow dip stick. In another embodiment, the level of full-length PAPPA2, proteolytically cleaved PAPPA2, NGAL, KRT20, or TACSTD2 protein is determined using an antibody that specifically binds to full-length PAPPA2, proteolytically cleaved PAPPA2, NGAL, KRT20, or TACSTD2 protein, respectively, or a fragment thereof.

In one embodiment, the subject is a human subject.

Embodiments of the invention provide for detecting expression of PAPPA2, NGAL, KRT20, or TACSTD2 protein, or PAPPA2, NGAL, KRT20, or TACSTD2 nucleic acid. In one embodiment, increased or reduced protein expression and/or activity, or increased or reduced nucleic acid expression can be detected. The detection can be performed at the level of the DNA, RNA, or polypeptide.

In some embodiments, the detection comprises detecting in a biological sample whether there is a reduction in an mRNA encoding an PAPPA2, NGAL, KRT20, or TACSTD2 protein, or a reduction in a PAPPA2, NGAL, KRT20, or TACSTD2 protein, or a combination thereof. In further embodiments, the detection comprises detecting in a biological sample whether there is an increase in an mRNA encoding an PAPPA2, NGAL, KRT20, or TACSTD2 protein, or an increase in an PAPPA2, NGAL, KRT20, or TACSTD2 protein, or a combination thereof.

Methods for detecting and quantifying PAPPA2, NGAL, KRT20, or TACSTD2 molecules in biological samples are known the art. For example, protocols for detecting and measuring a PAPPA2, NGAL, KRT20, or TACSTD2 protein molecule using either polyclonal or monoclonal antibodies specific for the polypeptide are well established. Non-limiting examples include Western blot, enzyme-linked immunosorbent assay (ELISA), radioimmunoassay (RIA), and fluorescence activated cell sorting (FACS).

In one aspect, the invention provides a device for determining whether a sample from a subject contains PAPPA2, NGAL, KRT20, or TACSTD2 protein, or a combination thereof, the device comprising at least one antibody that specifically binds to PAPPA2, NGAL, KRT20, or TACSTD2 protein, or a fragment thereof. In another aspect, the invention provides a device for determining whether a sample from a subject contains PAPPA2, NGAL, KRT20, or TACSTD2 nucleic acid, or a combination thereof, the device comprising at least one primer, primer pair, or nucleic acid probe, that specifically binds to PAPPA2, NGAL, KRT20, or TACSTD2 nucleic acid, or a fragment thereof.

In one embodiment, a biological sample comprises, a blood sample, serum, cells (including whole cells, cell fractions, cell extracts, and cultured cells or cell lines), tissues (including tissues obtained by biopsy), body fluids (e.g., urine, sputum, amniotic fluid, synovial fluid), or from media (from cultured cells or cell lines). The methods of detecting or quantifying a PAPPA2, NGAL, KRT20, or TACSTD2 molecule include, but are not limited to, amplification-based assays with (signal amplification) hybridization based assays and combination amplification-hybridization assays. For detecting and quantifying a PAPPA2, NGAL, KRT20, or TACSTD2 molecule, an exemplary method is an immunoassay that utilizes an antibody or other binding agents that specifically bind to an ILDR2 protein or epitope of such, for example, Western blot or ELISA assays.

Antibodies to PAPPA2, NGAL, KRT20, or TACSTD2

In one aspect, the invention provides antibody that binds to a PAPPA2, NGAL, KRT20, or TACSTD2. In one aspect, the invention provides antibody that binds to an epitope of the polypeptide of SEQ ID NO: 1, 2, 5, 7, or 9.

In another aspect, the antibodies of the invention are isolated. The antibodies of the invention can be monoclonal or polyclonal. Methods for making polyclonal and monoclonal antibodies are well known in the art. Antibodies of the invention can be produced by methods known in the art in any suitable animal host such as but not limited to rabbit, goat, mouse, sheep. In one embodiment, the antibodies can be chimeric, i.e. a combination of sequences of more than one species. In another embodiment, the antibodies can be fully-human or humanized Abs. Humanized antibodies contain complementarity determining regions that are derived from non-human species immunoglobulin, while the rest of the antibody molecule is derived from human immunoglobulin. Fully-human or humanized antibodies avoid certain problems of antibodies that possess non-human regions which can trigger host immune response leading to rapid antibody clearance. In still another embodiment, antibodies of the invention can be produced by immunizing a non-human animal with an immunogenic composition comprising a polypeptide of the invention in the monomeric form. In other embodiments, dimeric or multimeric forms can be used. The immunogenic composition can also comprise other components that can increase the antigenicity of the inventive peptide. In one embodiment the non-human animal is a transgenic mouse model, for e.g., the HuMAb-Mouse™ or the Xenomouse®, which can produce human antibodies. Neutralizing antibodies against peptides of interest and the cells producing such antibodies can be identified and isolated by methods know in the art.

Making of monoclonal antibodies is well known in the art. In one embodiment, the monoclonal antibodies of the invention are made by harvesting spleen tissue from a rabbit which produces a polyclonal antibody. Harvested cells are fused with the immortalized myeloma cell line partner. After an initial period of growth of the fused cells, single antibody producing clones are isolated by cell purification, grown and analyzed separately using a binding assay (e.g., ELISA, or Western). Hybridomas can be selected based on the ability of their secreted antibody to bind to a peptide interest, including a polypeptide comprising SEQ ID NO: 1, 2, 5, 7, or 9. Variable regions can be cloned from the hybridomas by PCR and the sequence of the epitope binding region can be determined by sequencing methods known in the art.

The invention provides antibodies and antibody fragments of various isotypes. The recombined immunoglobulin (Ig) genes, for example the variable region genes, can be isolated from the deposited hybridomas, by methods known in the art, and cloned into an Ig recombination vector that codes for human Ig constant region genes of both heavy and light chains. The antibodies can be generated of any isotype such as IgG1, IgG2, IgG3, IgG4, IgD, IgE, IgM, IgA1, IgA2, or sIgA isotype. The invention provides isotypes found in non-human species as well such as but not limited to IgY in birds and sharks. Vectors encoding the constant regions of various isotypes are known and previously described. (See, for example, Preston et al. Production and characterization of a set of mouse-human chimeric immunoglobulin G (IgG) subclass and IgA monoclonal antibodies with identical variable regions specific for P. aeruginosa serogroup O6 lipopolysaccharide. Infect Immun. 1998 September; 66(9):4137-42; Coloma et al. Novel vectors for the expression of antibody molecules using variable regions generated by polymerase chain reaction. J Immunol Methods. 1992 Jul. 31; 152(1):89-104; Guttieri et al. Cassette vectors for conversion of Fab fragments into full-length human IgG1 monoclonal antibodies by expression in stably transformed insect cells. Hybrid Hybridomics. 2003 June; 22(3):135-45; McLean et al. Human and murine immunoglobulin expression vector cassettes. Mol Immunol. 2000 October; 37(14):837-45; Walls et al. Vectors for the expression of PCR-amplified immunoglobulin variable domains with human constant regions. Nucleic Acids Res. 1993 Jun. 25; 21(12):2921-9; Norderhaug et al. Versatile vectors for transient and stable expression of recombinant antibody molecules in mammalian cells. J Immunol Methods. 1997 Can 12; 204(1):77-87.)

The antibodies of the invention bind to a polypeptide comprising the sequence of any of SEQ ID NOs: 1, 2, 5, 7, and 9, comprised in a longer polypeptide, in a specific manner. In one embodiment, the antibodies, or antibody fragments of the invention bind specifically to a peptide of SEQ ID NO: 1, 2, 5, 7, or 9. In one embodiment, the antibodies, or antibody fragments of the invention bind specifically to a peptide of SEQ ID NO: 1, 2, 5, 7, or 9. For example, antibodies that bind specifically to a peptide that comprises a sequence shown in any of SEQ ID NOs: 1, 2, 5, 7, and 9 will not bind to polypeptides which do not comprise the amino acid sequence of any of SEQ ID NOs: 1, 2, 5, 7, or 9 to the same extent and with the same affinity as they bind to a peptide that comprises a sequence shown in any of SEQ ID NOs: 1, 2, 5, 7, or 9.

The present invention provides specific monoclonal antibodies, including but not limited to rabbit, mouse and human, which recognize a peptide of SEQ ID NO: 1, 2, 5, 7, or 9. When used in vivo in humans, human monoclonal antibodies are far less likely to be immunogenic (as compared to antibodies from another species).

Variable region nucleic acids for the heavy and light chains of the antibodies can be cloned into an human Ig expression vector that contain any suitable constant region, for example (i.e., TCAE6) that contains the IgG1 (gamma 1) constant region coding sequences for the heavy chain and the lambda constant region for the light chains. (See, for example, Preston et al. Production and characterization of a set of mouse-human chimeric immunoglobulin G (IgG) subclass and IgA monoclonal antibodies with identical variable regions specific for P. aeruginosa serogroup O6 lipopolysaccharide. Infect Immun. 1998 September; 66(9):4137-42.) The variable regions can be placed in any vector that encodes constant region coding sequences. For example, human Ig heavy-chain constant-region expression vectors containing genomic clones of the human IgG2, IgG3, IgG4 and IgA heavy-chain constant-region genes and lacking variable-region genes have been described in Coloma, et al. 1992 J. Immunol. Methods 152:89-104.) These expression vectors can then be transfected into cells (e.g., CHO DG44 cells), the cells are grown in vitro, and IgG1 are subsequently harvested from the supernatant. Resultant antibodies can be generated to posses human variable regions and human IgG1 and lambda constant regions. In other embodiments, the Fc portions of the antibodies of the invention can be replaced so as to produce IgM.

In other embodiments, the antibody of the invention also includes an antibody fragment. It is well-known in the art, only a portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford; and Pier G B, Lyczak J B, Wetzler L M, (eds). Immunology, Infection and Immunity (2004) 1st Ed. American Society for Microbiology Press, Washington D.C.). The pFc' and Fc regions of the antibody, for example, are effectors of the complement cascade and can mediate binding to Fc receptors on phagocytic cells, but are not involved in antigen binding. An antibody from which the pFc' region has been enzymatically cleaved, or which has been produced without the pFc' region, e.g. an F(ab')2 fragment, retains both of the antigen binding sites of an intact antibody. An isolated F(ab')2 fragment is referred to as a bivalent monoclonal fragment because of its two antigen binding sites. Similarly, an antibody from which the Fc region has been enzymatically cleaved, or which has been produced without the Fc region, e.g. an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment can be associated with up to ten different light chains without altering antibody specificity) and Fd fragments retain epitope-binding ability in isolation. An antibody fragment is a polypeptide which can be targeted to the nucleus. Methods to modify polypeptides for targeting to the nucleus are known in the art.

Additional methods of producing and using antibodies and antibody fragments comprising Fab, Fc, pFc', F(ab')2 and Fv regions are well known in the art [Klein, Immunology (John Wiley, New York, N.Y., 1982); Clark, W. R. (1986) The Experimental Foundations of Modern Immunology (Wiley & Sons, Inc., New York); Roitt, I. (1991)

Essential Immunology, 7th Ed., (Blackwell Scientific Publications, Oxford); and Pier G B, Lyczak J B, Wetzler L M, (eds). Immunology, Infection and Immunity (2004) 1st Ed. American Society for Microbiology Press, Washington D.C.].

Usually the CDR regions in humanized antibodies are substantially identical, and more usually, identical to the corresponding CDR regions of the donor antibody. However, in certain embodiments, it can be desirable to modify one or more CDR regions to modify the antigen binding specificity of the antibody and/or reduce the immunogenicity of the antibody. One or more residues of a CDR can be altered to modify binding to achieve a more favored on-rate of binding, a more favored off-rate of binding, or both, such that an idealized binding constant is achieved. Using this strategy, an antibody having high or ultra high binding affinity of can be achieved. Briefly, the donor CDR sequence is referred to as a base sequence from which one or more residues are then altered. Affinity maturation techniques can be used to alter the CDR region(s) followed by screening of the resultant binding molecules for the desired change in binding. The method can also be used to alter the donor CDR to be less immunogenic such that a potential chimeric antibody response is minimized or avoided. Accordingly, as CDR(s) are altered, changes in binding affinity as well as immunogenicity can be monitored and scored such that an antibody optimized for the best combined binding and low immunogenicity are achieved (see, e.g., U.S. Pat. No. 6,656, 467 and U.S. Pat. Pub. Nos: US20020164326A1; US20040110226A1; US20060121042A1).

The antibodies of the invention can be used in a variety of applications including, but not limited to, methods for vAKI and iAKI in a subject, wherein the antibody is used to determine different levels of PAPPA2, NGAL, KRT20, or TACSTD2 in a urine or other tissue sample, which can be compared to the level of PAPPA2, NGAL, KRT20, or TACSTD2 from a control subject, or sample that does not have vAKI or iAKI. Additionally, such antibodies could be used to detect shed molecules in the circulation as a diagnostic.

In one aspect, the antibodies that specifically bind a polypeptide of SEQ ID NO: 1, 2, 5, 7, or 9, or a polypeptide which comprises the corresponding peptide, can be used in a screening method to evaluate agents designed to affect the levels of PAPPA2, NGAL, KRT20, or TACSTD2 protein. The antibody can be used to quantitate protein levels and expression, protein localization, or protein modification of PAPPA2, NGAL, KRT20, or TACSTD2 protein.

The antibodies of the present invention, including fragments and derivatives thereof, can be labeled. It is, therefore, another aspect of the present invention to provide labeled antibodies that bind specifically to one or more of the polypeptides of the present invention, to one or more of the polypeptides encoded by the isolated nucleic acid molecules of the present invention, or the binding of which can be competitively inhibited by one or more of the polypeptides of the present invention or one or more of the polypeptides encoded by the isolated nucleic acid molecules of the present invention. The choice of label depends, in part, upon the desired use.

For example, when the antibodies of the present invention are used for immunohistochemical staining of tissue samples, the label can usefully be an enzyme that catalyzes production and local deposition of a detectable product. Enzymes useful as conjugates to antibodies to permit antibody detection are well known. Exemplary conjugataes are alkaline phosphatase, p-galactosidase, glucose oxidase, horseradish peroxidase (HRP), and urease. Exemplary substrates for production and deposition of visually detectable products are o-nitrophenyl-beta-D-galactopyranoside (ONPG); o-phenylenediamine dihydrochloride (OPD); p-nitrophenyl phosphate (NPP); p-nitrophenyl-beta-D-galactopryanoside (PNPG); 3',3'-diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Other substrates can be used to produce luminescent products for local deposition. For example, in the presence of hydrogen peroxide (H2O2), horseradish peroxidase (HRP) can catalyze the oxidation of cyclic diacylhydrazides, such as luminol. Immediately following the oxidation, the luminol is in an excited state (intermediate reaction product), which decays to the ground state by emitting light. Strong enhancement of the light emission is produced by enhancers, such as phenolic compounds. Advantages include high sensitivity, high resolution, and rapid detection without radioactivity and requiring only small amounts of antibody. See, e.g., Thorpe et al., Methods Enzymol. 133: 331-53 (1986); Kricka et al., J. Immmunoassay 17(1): 67-83 (1996); and Lundqvist et al., J. Biolumin. Chemiluimin. 10(6): 353-9 (1995). Kits for such enhanced chemiluminescent detection (ECL) are available commercially. The antibodies can also be labeled using colloidal gold.

As another example, when the antibodies of the present invention are used, e.g., for flow cytometric detection, for scanning laser cytometric detection, or for fluorescent immunoassay, they can usefully be labeled with fluorophores. There are a wide variety of fluorophore labels that can usefully be attached to the antibodies of the present invention. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCP-Cy5.5, PE-Cy5, PE-Cy5.5, PE-Cy7, PE-Texas Red, and APC-Cy7.

Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention. For secondary detection using labeled avidin, streptavidin, captavidin or neutravidin, the antibodies of the present invention can usefully be labeled with biotin.

When the antibodies of the present invention are used, e.g., for western blotting applications, they can usefully be labeled with radioisotopes, such as 33P, 32P, 35S, 3H, and 125I. As another example, when the antibodies of the present invention are used for radioimmunotherapy, the label can usefully be 228Th, 227Ac, 225Ac, 223Ra, 213Bi, 212Pb, 212Bi, 211At, 203Pb, 194Os, 188Re, 186Re, 153Sm, 149Tb, 131I, 125I, 111In, 105Rh, 99mTc, 97Ru, 90Y, 90Sr, 88Y, 72Se, 67Cu, or 47Sc.

As another example, when the antibodies of the present invention are to be used for in vivo diagnostic use, they can be rendered detectable by conjugation to MRI contrast agents, such as gadolinium diethylenetriaminepentaacetic acid (DTPA), Lauffer et al., Radiology 207(2): 529-38 (1998), or by radioisotopic labeling.

The antibodies of the present invention, including fragments and derivatives thereof, can also be conjugated to toxins, in order to target the toxin's ablative action to cells that display and/or express the polypeptides of the present invention. The antibody in such immunotoxins is conjugated to *Pseudomonas* exotoxin A, diphtheria toxin, shiga toxin A, anthrax toxin lethal factor, or ricin. See Hall (ed.), Immunotoxin Methods and Protocols (Methods in Molecular Biology, vol. 166), Humana Press (2000); and Frankel et al. (eds.), Clinical Applications of Immunotoxins, Springer-Verlag (1998).

In one aspect, the invention provides a device for determining whether a urine sample from a subject contains full-length PAPPA2, proteolytically cleaved PAPPA2, NGAL, KRT20, or TACSTD2 protein, or a combination thereof, the device comprising at least one antibody that specifically binds to full-length PAPPA2, proteolytically cleaved PAPPA2, NGAL, KRT20, or TACSTD2 protein, or a fragment thereof.

The antibodies of the present invention can usefully be attached to a substrate of a device, and it is, therefore, another aspect of the invention to provide antibodies that bind specifically to one or more of the polypeptides of the present invention, to one or more of the polypeptides encoded by the isolated nucleic acid molecules of the present invention, or the binding of which can be competitively inhibited by one or more of the polypeptides of the present invention or one or more of the polypeptides encoded by the isolated nucleic acid molecules of the present invention, attached to a substrate. Substrates can be porous or nonporous, planar or nonplanar. For example, the antibodies of the present invention can usefully be conjugated to filtration media, such as NHS-activated Sepharose or CNBr-activated Sepharose for purposes of immunoaffinity chromatography. For example, the antibodies of the present invention can usefully be attached to paramagnetic microspheres by, for example, biotin-streptavidin interaction. The microsphere can then be used for isolation of one or more cells that express or display the polypeptides of the present invention. As another example, the antibodies of the present invention can be attached to the surface of a microtiter plate for ELISA.

As noted herein, the antibodies of the present invention can be produced in prokaryotic and eukaryotic cells. It is, therefore, another aspect of the present invention to provide cells that express the antibodies of the present invention, including hybridoma cells, Beta cells, plasma cells, and host cells recombinantly modified to express the antibodies of the present invention.

In yet a further aspect, the present invention provides aptamers evolved to bind specifically to one or more of the PAPPA2, NGAL, KRT20, or TACSTD2 proteins of the present invention or to polypeptides encoded by the nucleic acids of the invention.

In sum, one of skill in the art, provided with the teachings of this invention, has available a variety of methods which can be used to alter the biological properties of the antibodies of this invention including methods which can increase or decrease the stability or half-life, immunogenicity, toxicity, affinity or yield of a given antibody molecule, or to alter it in any other way that can render it more suitable for a particular application.

Pharmaceutical Compositions and Administration for Therapy

The treatments described herein can be administered to the subject once (e.g., as a single injection or deposition). Alternatively, treatments can be administered once or twice daily to a subject in need thereof for a period of from about two to about twenty-eight days, or from about seven to about ten days. A treatment can also be administered once or twice daily to a subject for a period of 1, 2, 3, 4, 5, 6, 7, 8, 9, 10, 11, 12 times per year, or a combination thereof. Furthermore, therapeutics can be co-administrated with another therapeutic.

The treatments of this invention can be formulated and administered to reduce the symptoms associated with vAKI or iAKI. Treatments can be administered by any conventional means available for use in conjunction with pharmaceuticals. Treatments can be administered alone, but are generally administered with a pharmaceutical carrier selected on the basis of the chosen route of administration and standard pharmaceutical practice.

A therapeutically effective treatment can depend upon a number of factors known to those or ordinary skill in the art. The dose(s) of a treatment inhibitor can vary, for example, depending upon the identity, size, and condition of the subject or sample being treated, further depending upon the route by which the treatment is to be administered. These amounts can be readily determined by a skilled artisan. Any of the therapeutic applications described herein can be applied to any subject in need of such therapy, including, for example, a mammal such as a dog, a cat, a cow, a horse, a rabbit, a monkey, a pig, a sheep, a goat, or a human.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa. (20th Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation or ingestion), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the inhibitor (e.g., a polypeptide or antibody or small molecule) of the invention in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier and subsequently swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—a Point-of-Care Test that Distinguishes Non-Fatal Volume Depletion from Fatal Tubular Injury of the Kidney Abstract Nephrology is the only field in Medicine that uses a single analyte—serum creatinine (sCr)—to suggest organ injury. Yet the rise of sCr trails the injury by 24 hrs, if not by days, and it is insensitive to <50% damage. Most vexing is the fact that common volume depletion (75%) and tubular injury ("ATN" 25%) both increase sCr, meaning that therapy is not based on a prospective physiological assay. The consequence of unguided decisions includes unacceptable morbidity, multiple testing, escalation of care—LOS and increased aggregate costs of $7500 ppt. Described herein is a solution: while the damaged kidney does not produce a symptom like chest pain, it announces its injury by releasing proteins into the urine that have been detected by massive sequencing, and that when assayed together, distinguishes volume depletion from tubular injury at the time of patient contact. The assay is a point of care (POC) Urine Dip-Chip, or other rapid measurement devices including, but not limited to, microfluidics, lateral flow dip sticks, and rapid western blotting technology, administered by the clinician, applied to all patients with elevated s-Cr levels. Modeling indicates that the invention described herein will not only modify the "cycle of care" but save US Hospitals $3.6-$5.7B because of the huge population at risk (5-7% of all Emergency patients) that are managed today only by a $7 test for sCr.

Section I—Clinical Context: Does a True Umet Cinical Need Exist?

Summary Statement of Unmet Need:

There is currently a need to prospectively distinguish potentially fatal from nonfatal changes in kidney function at the point of patient contact, thereby correcting mismatches between clinical urgency, level of care, and costs.

Discovery of the Unmet Clinical Need:

Imagine presenting to the Emergency Department (ED), and a few hours after a patients blood is drawn, the physician informs the patient that they have Acute Kidney Injury (AKI) and that they must stay in the hospital because of this perilous condition. Chances are that the patient will receive intravenous fluids or be placed on a near starvation diet. If the patient's presentation included fever, the concern would be Septic or Ischemic-AKI, or if the patient takes certain medications, the concern would be Nephrotoxic-AKI, both potentially fatal (Septic or Ischemic or Nephrotoxic AKI=Tubular Damage). At this point, the doctor mentions the possibility of dialysis. Now imagine that the patient's blood is taken again at 24 hrs and 48 hrs. Will these new levels show that the doctor was correct, or that his concern was misplaced? From studies of >3000 patients[1], the Barasch lab knows that the discussions were premature (>75% of cases) and that the initial therapy was misapplied (>25% of cases). Does this ever happen? Unfortunately it is commonplace for the 12.4M patients presenting to the ED (7% of admitted patients have elevated serum creatinine (sCr)) diagnosed with fatal or non-fatal AKI[1] and for some hospitalized in ICUs (30-50% of critical care patients have increased sCr)[2-4].

The genesis of the problem is clear: Nephrology depends on a single analyte, the serum creatinine test, sCr which unfortunately is elevated both in cases of simple volume depletion "non-fatal AKI" (FIG. 1), as well as in cases of tubular damage "fatal AKI" (FIG. 1), despite the fact that every other attribute differs between these drivers of elevated sCr (FIG. 1—bottom). Nor can urine output help (FIG. 1). The medical need for better diagnostics is deep, because not treating volume depletion can result in ischemic tubular damage but treating tubular damage causes drowning. Most distressing, the problem cannot be resolved for 48-72 hrs.

Figure 2:
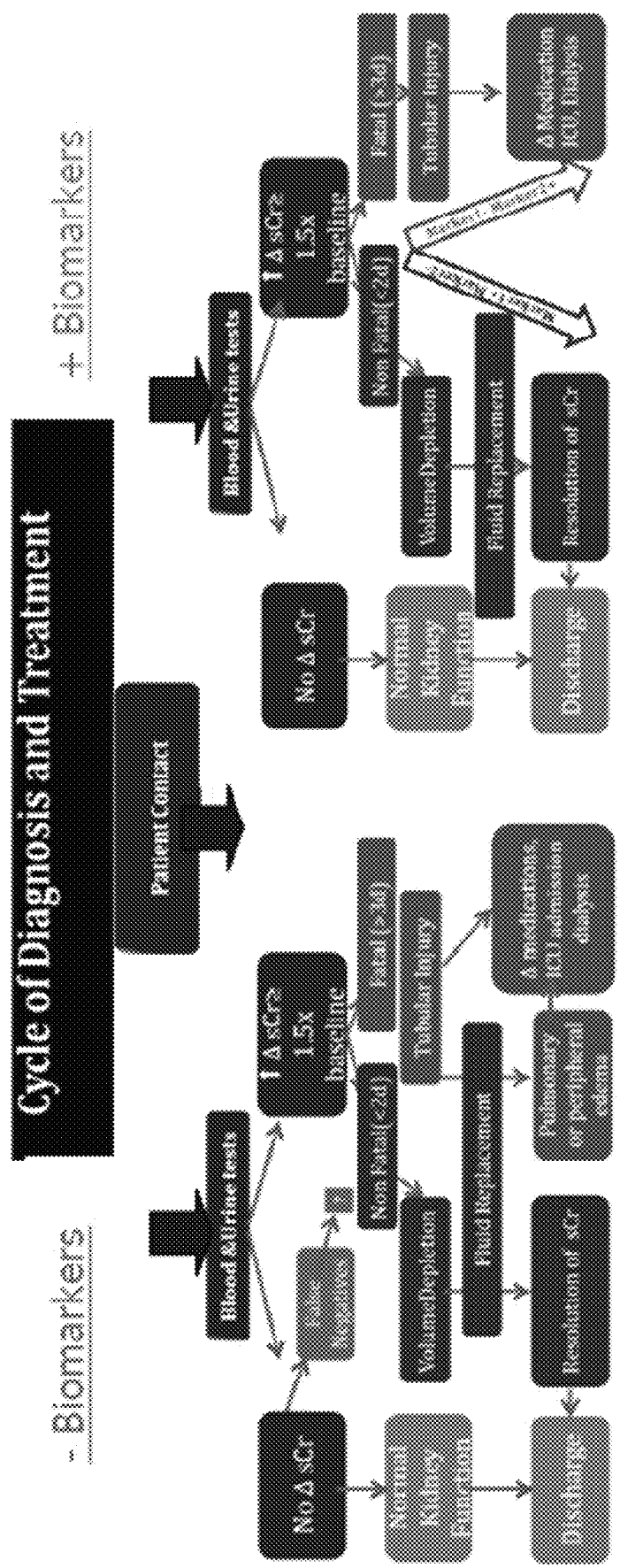
FIG. 2. Cycle of Diagnosis and Treatment

Current Cycle of Care is shown in FIG. 2, Left (No Biomarker). Patients are tested by physicians in the ED or Clinics or Post-Op for many analytes including sCr, but unlike those other tests, a rise in sCr generally invokes a singular therapy, the injection of saline. Volume depletion might resolve (56% of the cohort (in blue)) but yet pulmonary edema, ICU admission and dialysis may be needed in patients with Tubular Damage (19% of the cohort (in red)) who cannot be found prospectively due to the non-specificity of sCr. Even FalseNegative sCr tests are prevalent (25% of the cohort (in bright red)).

Stakeholder Analysis:

(i) Patients would support the diagnostic tool described herein—the Urine Dip-Chip, or other rapid measurement devices including, but not limited to, microfluidics, lateral flow dip sticks, and rapid western blotting technology, because they are a non-invasive method that reduces unintended risks, reduces LOS and opportunity costs, and fewer changes in medications/treatments due to delayed diagnosis. (ii) Physicians and nephrologists can support the method of diagnosis and treatment described herein because it enhances workflow and guides therapy, reducing malpractice risk by prospectively directing medication adjustments, transfusions, electrolyte treatments and preparation for dialysis. Reduced referrals may be a risk for nephrologists, but interpretation of reciprocal biomarker values in the context of ΔsCr can support even greater numbers of referrals. Downcoding of some patients can also reduce enthusiasm and provide a barrier, but this depends on payers (see Value). (iii) Hospitals will appreciate the increased efficiency and turnover in the ED/ICU/Post-Op due to matching illness with the level of care, providing cost avoidance, reducing LOS, and obviating downcoding (see Value) (iv) Clinical Labs will not be adverse to the Urine Dip-Chip, or other rapid measurement devices including, but not limited to, microfluidics, lateral flow dip sticks, and rapid western blotting technology, because they are an add-on rather than a substitute for sCr. In fact, CPT codes already exist for biomarkers of other diseases and for related lab techniques such as ELISA and Immunoblot. A significant issue arises if there is a demand for "gold standard levels" from a clinical lab analyzer, but given the paucity of kidney diagnostics to date, and the clarity of the findings described herein, it is expected that this demand can be downstream of the introduction of the new biomarkers described herein. In addition, while it is understood that training and maintenance would increase cost, it is the case that labs currently service the ubiquitous Abbott iSTAT POC, (v) Biotech and Investors will enter an entirely new space with new devices that have the flexibility to configure different biomarkers identified herein, providing many alternative opportunities (vi) Payers and Insurance (see Value) will be supportive, because based on primary research, biomarkers reduce costs ($408-522 ppt)5 because they circumvent unnecessary treatments and LOS.

Customer Discovery Validates the Unmet Need and Identifies Investors. Key Opinion Leaders Validate the Unmet Need and agree that volume depletion and tubular damage need to be distinguished6. The ED is obligated to treat all comers (Emergency Medical Treatment and Active Labor Law), but cannot bill for observational stays, a problem compounded by fact that these patients cannot meet the two-midnight rule if admitted. Consequently, key opinion leaders are supportive if one can rapidly identify correctable volume depleted patients to help reduce his census. Some have pointed out that the current flu epidemic (Flu.gov) is a case in point where an elevated sCr may represent volume depletion or septic AKI, both common occurrences with the flu. Hence, they were supportive that the device described herein will help triage patients in anticipation of ICU admission, particularly because increasing nursing staff from 2:1 to 1:1 is required for dialysis. The culture in the ICU is accepting of POC. One key opinion leader who manages the POC, was accepting, if the device described herein matched the results of a Clinical Lab Analyzer (which requires an investment) in thorough clinical trials. In addition, it was indicated that extensive optimization of sample preparation was needed7. Another was supportive as the technology described herein allows physicians to concentrate on higher acuity patients, which result in higher reimbursement. Furthermore, while DRGs and older CPT codes combine AKI patients, fractionation into lower cost volume depletion and higher cost tubular injury could result in profitability under "shared savings models" with insurers. It was also stressed that a hospital's biggest liabilities are Standard of Care targets and thus the biomarkers described herein will have to be incorporated into SOC. One nephrologist stressed that "AKI" bills at a high acuity, but down-coding to volume depletion is a barrier, which could be compensated by saving on DRG/ACO mandates and increasing consultations.

Section II—Value Proposition

State-of-the Art:

(#1) sCr (since 1929)8 purports to meet the unmet need but cannot provide adequate guidance because of its intrinsic characteristics: Delay: A positive test requires accumulating grams of creatinine in the blood, and this process usually requires >24-48 hours. The delay confounds care plans. Sensitivity: Tubular damage may not elevate sCr because >50% of renal mass must be damaged9. Misdiagnosis: sCr also increases in volume depletion (FIG. 1). (#2) The urine Na (1970's)10 purports to meet the unmet need, but it has fallen out of favor because a negative value is non-interpretable and it does not meet its own guidelines in many adults and failed in studies1,11. In fact, sCr and urine Na together could not retrospectively classify 25% of ED patients, highlighting the diagnostic dilemma1. Growth of AKI diagnoses (1.2 million new cases/yr)12 emphasizes the unmet need.

Emerging Solutions and Investments:

The goal is to find biomarkers with the following test characteristics: higher sensitivity than sCr, rapid expression in urine or blood and specificity for potentially non-fatal (volume) vs fatal (ischemic, septic) presentations1,4. NGAL13,14 has a number of these attributes, but it is expressed as a continuous logarithmic function, meaning that volume depleted patients have a 2 fold elevation (injury >10 fold) debating its specificity. In addition, because its expression is so rapid, before sCr rise, the dissociation of NGAL with sCr has lead authors to suggest a complex 4 fold characterization: normal (sCr−NGAL−), "loss of function without injury" (sCr+NGAL−), "damage without loss of function" (sCr−NGAL+) and finally "damage with loss of function" (sCr+NGAL+). While such embellishments can be useful, the scheme does not recognize the distinction between volume depletion and intrinsic injury. Assay platforms include the NGAL Test™ ($33/test) (BioPorto) and the Architect NGAL assay (~$35/test) (Abbott, JAPAN). Kim1 is another injury biomarker, but it is expressed 12 hrs after the event, and it is difficult to measure (pg range) because it fragments in the urine. Kim1 may not be dose responsive with injury. Timp2×IGFBP7 is a combination of new biomarkers used in NephroCheck POC, but non-specificity (50% false positive rate according to FDA)15 is problematic.

Figure 3A:
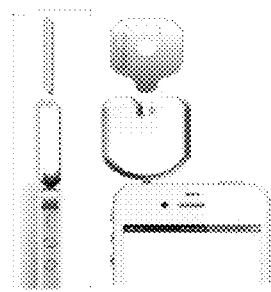
FIGS. 3A-C. mChip (or other rapid measurement devices including, but not limited to, microfluidics, lateral flow dip sticks, rapid western blotting technology), "dongle" and smartphone (A) Device and flow chart for self-running a test. (B) Prototype run in Rwanda and tested samples (C) ROC curves for HIV and 2 syphilis markers.
Figure 3B:
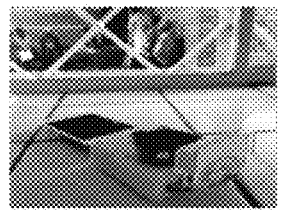
Figure 3C:
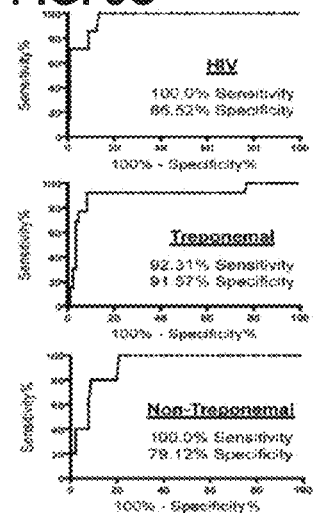
Figure 4:
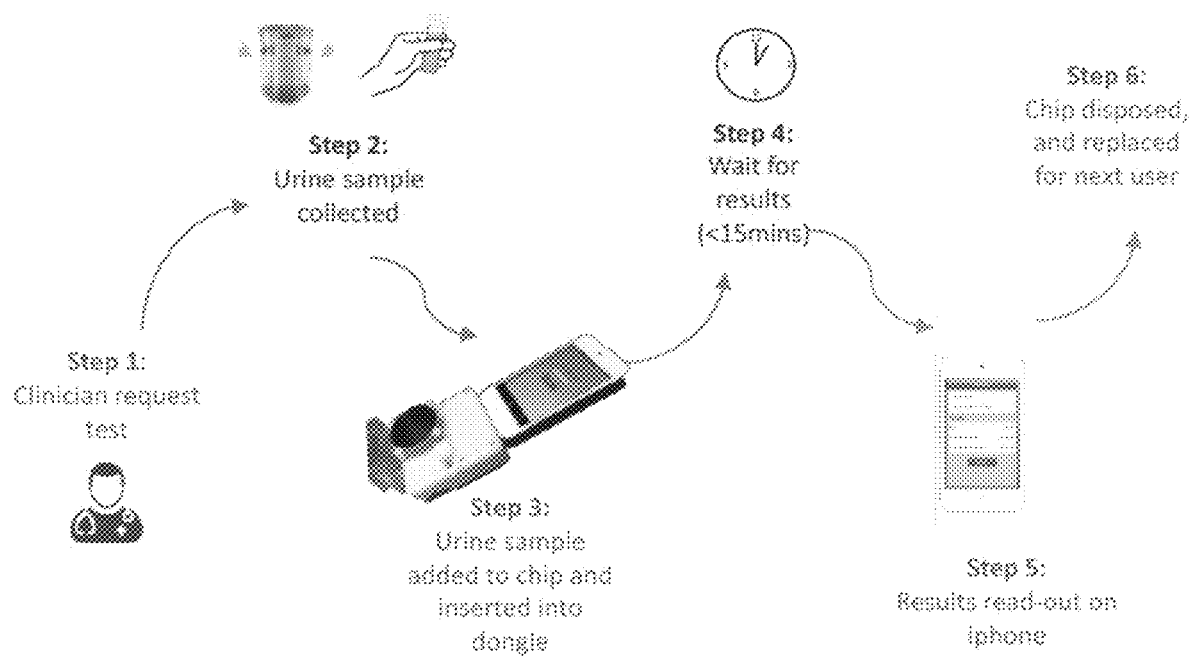
FIG. 4. Workflow for Diagnostic Test

Envisioned Product:

The product described herein is an automated diagnostic test that distinguishes volume depletion from tubular injury. The platform, called the mChip, can run a diagnostic test from start to finish using 1 L of urine, replicating all the key steps of ELISA and POC (or other rapid measurement devices including, but not limited to, microfluidics, lateral flow dip sticks, and rapid western blotting technology), but at low cost without complex instrumentation. Initial versions of mChip have been field-tested to detect HIV and sexually transmitted diseases 16-18. Most recently, this device was moved into a form factor that is cheaper, smaller, and easier-to-use including a $34 "dongle" (replacing a $100, 000 instrument) which connects to Smartphones and a mChip ($1.44 ppt) to read out what were otherwise traditionally sophisticated ELISA tests (FIG. 3A). The worth of the technology was proven in field testing in Rwanda, building on previous global initiatives (FIG. 3B). Rwandan healthcare workers utilized a custom-built Smartphone-app, and ran a blinded study on finger-pricked whole blood. Three antigens (HIV, treponemal-specific syphilis, and a non-treponemal activity marker) can be detected accurately (FIG. 3C). An exemplary workflow is shown in FIG. 4.

Enabling Innovation:

By massive sequencing of transcriptome and proteome of mouse and human analytes were identified which address: Delay in Diagnosis: The markers described herein are activated within 3 hrs of AKI. Lack of Sensitivity: Only nanogram quantities of urine proteins are required. Misdiagnosis: One biomarker responds to volume depletion (PAPPA2) while the others respond to tubular damage (Cytokeratin20, Tacstd2, NGAL); because the markers are mutually exclusive, the ratio between the two biomarkers enhances specificity for the diagnosis in either direction (e.g. volume depletion+, tubular damage− or volume depletion−, tubular damage+). Combination of markers (volume depletion+, tubular damage+) would indicate damage. Hence, the technology described herein (FIG. 2, R+Biomarker,) stratifies sCr, resolves false-negative tests, and restricts volume resuscitation to deficient patients. Therefore, the "Urine Dip-Chip" (or other rapid measurement devices including, but not limited to, microfluidics, lateral flow dip sticks, and rapid western blotting technology) provides a prospective diagnosis allowing immediate, appropriate treatment, decreasing morbidity.

The Smartphone mChip platform is perfectly suited to urine diagnostics because it matches the performance of lab ELISA systems in quantitative readout, high sensitivity due to log order amplification chemistry and multiplexing capability. Other suitable platforms can be used but lateral flow tests are hindered by subjective interpretation of bands, low sensitivity and lack of multiplexing.

Figure 5:
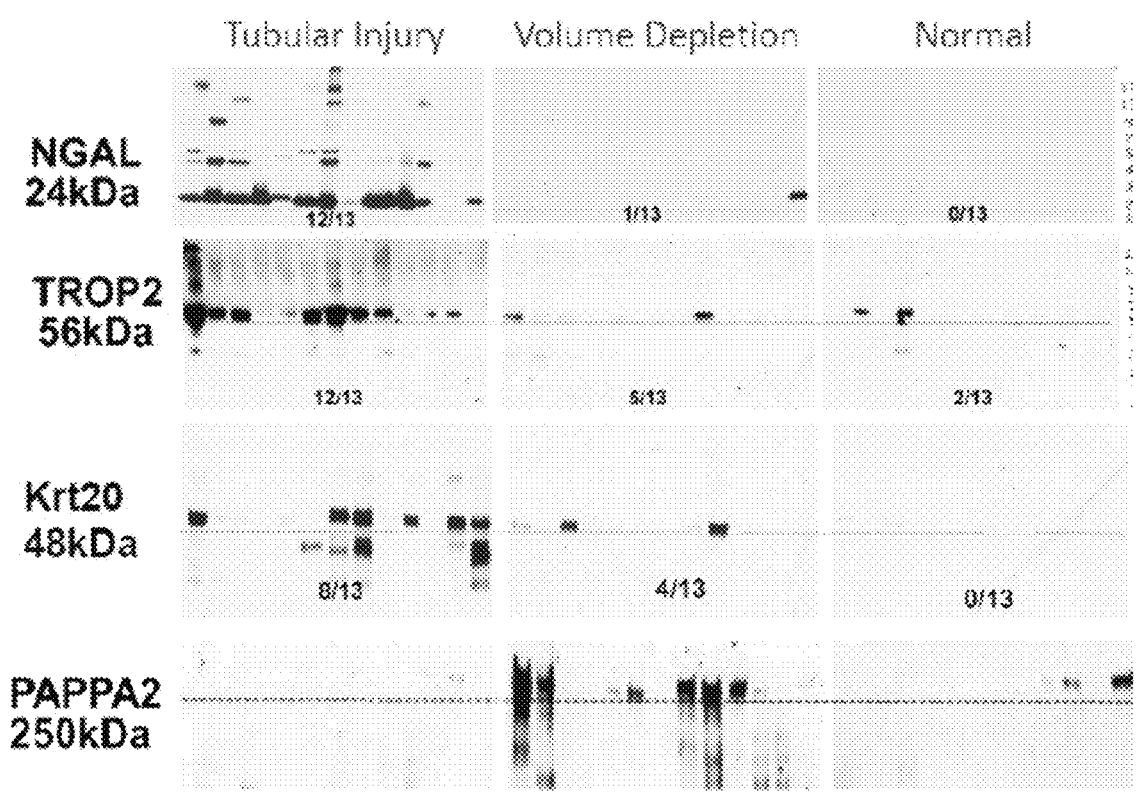
FIG. 5. Biomarkers of Injury

Preliminary Results:

The anticipated limits of detection and required cutoffs (ng/mL) are well within the capabilities of the mChip platform. The reproducibility of mChip has matched those of ELISA, with quantitative performance at 3 ng/mL t-PSA. Excellent agreement with the gold-standard Siemens ADVIA Centaur assay was found. And of course mChip platform has been tested head-to-head against lateral flow tests, with superior sensitivity. FIG. 5 demonstrates biomarkers of injury, NGAL, TACSTD1 (Trop2), Krt20 and the first known marker of volume depletion, PAPPA2. Note the reciprocal expression of PAPPA2 and these other proteins.

Value Proposition:

Excellent preliminary data (suggesting disruptive refocusing of nephrology) and low costs for the technology described herein are drivers of the Value Proposition herein. In addition, each stakeholder has idiosyncratic value added: (A) Hospitals are the Key Customers: On the basis of health economics research, the Urine Dip-Chip, or other rapid measurement devices including, but not limited to, microfluidics, lateral flow dip sticks, and rapid western blotting technology, would provide cost-avoidance and net revenue increases. (i) If a patient is diagnosed with Tubular Damage, yet sCr rapidly returns to normal (e.g. volume depletion), then the admission would be down-coded to observation, a 60% loss of revenue for community hospitals, and additionally an unnecessary consumption of nursing and administrative coverage. Moreover a case of greater severity would not be awarded a hospital bed if such a patient were admitted (which is required at Columbia where observation cannot be billed), an opportunity loss. Even when the patient remains in the ED until the sCr has resolved, such a patient blocks more acute patients from occupying the ED, which then must divert patients (Columbia ED >300% of capacity).

Given that ED evaluation is mandated by EMTALA, confusion over AKI diagnoses looses money. (ii) Lack of diagnostic clarity in hospitalized patients increases effort and LOS with repetitive testing to meet SOC. This scenario was modeled±biomarkers of injury5 and it was found that while treatment costs were $50 pp higher upon the addition of a NGAL, NGAL+Scr resulted in 1,578-1,973/10,000 fewer patients with delayed diagnosis and treatment than Scr alone (calculated retrospectively). Consequently, total costs declined by $408-$522 pp (av $465). Therefore, the Urine Dip-Chip described herein, or other rapid measurement devices including, but not limited to, microfluidics, lateral flow dip sticks, rapid western blotting technology, with two biomarkers, would avoid those costs and reduce length of stay by prospectively providing diagnosis. (B) Healthcare Providers: Allows triage towards higher acuity with greater accuracy. In addition, if the payee model is bundled, or a "shared savings model" the hospital and the providers share in the savings. (C) Payers: Potential to share in cost savings achieved by the hospital through the "shared savings model". Reduction in unnecessary treatments helps payers justify reimbursement for therapies. (D) Investors: Opportunity to invest in an area of diagnostics with limited competition through innovative POC technology; significant scope to expand market by moving into other settings (clinics/homecare POC). (E) Regulatory: Non-invasive rapid point-of-care testing on routine samples; current SOC needs improvement.

REFERENCES FOR EXAMPLE 1

1. Nickolas, T. L. et al. Sensitivity and specificity of a single emergency department measurement of urinary neutrophil gelatinase-associated lipocalin for diagnosing acute kidney injury. *Ann. Intern. Med.* 148, 810-819 (2008).
2. Centers for Disease Control and Prevention. National Center for Health Statistics: Emergency Department Visits. at www.cdc.gov/nchs/fastats/emergency-department.htm
3. Philip R. Lee Institute for Health Policy Studies. ICU Outcomes (Mortality and Length of Stay) Methods, Data Collection Tool and Data. at www.healthpolicy.ucsf.edu/content/icu-outcomes.
4. Mandelbaum, T. et al. Outcome of critically ill patients with acute kidney injury using the Acute Kidney Injury Network criteria*. *Crit. Care Med.* 39, (2011).
5. A., P., J., R., D., C. & T., N. Does NGAL reduce costs? A cost analysis of urine NGAL (UNGAL) and serum creatinine (SCR) for acute kidney injury (AKI) diagnosis. *Crit. Care Med.* 38, A106 (2010).
6. Yuen, P. S. T., Jo, S.-K., Holly, M. K., Hu, X. & Star, R. A. Ischemic and nephrotoxic acute renal failure are distinguished by their broad transcriptomic responses. *Physiol. Genomics* 25, 375-86 (2006).
7. Rai, A. J. The Urinary Proteome: Methods and Protocols (Methods in Molecular Biology, 641). *Springer* 1-362 (2010). at <papers2://publication/uuid/F8636D6E-36B2-4196-87D2-7B401B614D67>
8. Jaffe, M. Ueber den Niederschlag welchen Pikrinsa¨ure in normalen Ham erzeugt and u¨ber eine neuereaction des Kreatinins. *Z Physiol Chem* 10, 391-400 (1886).
9. Sise, M. E. et al. Urine neutrophil gelatinase-associated lipocalin identifies unilateral and bilateral urinary tract obstruction. *Nephrol. Dial. Transplant* 26, 4132-5 (2011).
10. Schrier, R. W. Diagnostic value of urinary sodium, chloride, urea, and flow. *J. Am. Soc. Nephrol.* 22, 1610-3 (2011).
11. Nickolas, T. L. et al. Article Annals of Internal Medicine Sensitivity and Specificity of a Single Emergency Department Measurement of Urinary Neutrophil Gelatinase—Associated Lipocalin for Diagnosing Acute Kidney Injury. *Ann. Intern. Med.* 148, 810-819 (2008).
12. Kidney Disease Statistics for the United States|National Institute of Diabetes and Digestive and Kidney Diseases (NIDDK). at www.niddk.nih.gov/health-information/healthstatistics/Pages/kidney-disease-statistics-united-states.aspx#8
13. Mishra, J. et al. Neutrophil gelatinase-associated lipocalin: A novel early urinary biomarker for cisplatin nephrotoxicity. *Am. J. Nephrol.* 24, 307-315 (2004).
14. Mishra, J. et al. Identification of neutrophil gelatinase-associated lipocalin as a novel early urinary biomarker for ischemic renal injury. *J. Am. Soc. Nephrol.* 14, 2534-2543 (2003).
15. FDA. Press Announcements—FDA allows marketing of the first test to assess risk of developing acute kidney injury. at www.fda.gov/newsevents/newsroom/pressannouncements/ucm412910.htm
16. Chin, C. D. et al. Microfluidics-based diagnostics of infectious diseases in the developing world. *Nat. Med.* 17, 1015-9 (2011).
17. Chin, C. D. et al. Mobile device for disease diagnosis and data tracking in resource-limited settings. *Clin. Chem.* 59, 629-40 (2013).
18. Laksanasopin, T. et al. A smartphone dongle for diagnosis of infectious diseases at the point of care. *Sci. Transl. Med.* 7, 273re1 (2015).
19. Chertow, G. M., Burdick, E., Honour, M., Bonventre, J. V & Bates, D. W. Acute kidney injury, mortality, length of stay, and costs in hospitalized patients. *J. Am. Soc. Nephrol.* 16, 3365-70 (2005).
20. Rewa, 0. & Bagshaw, S. M. Acute kidney injury-epidemiology, outcomes and economics. *Nat. Rev. Nephrol.* 10, 193-207 (2014).
21. Kalorama. The United States Market for In Vitro Diagnostic Tests: Market Research Report. At www.kaloramainformation.com/United-States-Vitro-8079142/
22. Hsu, C.-Y. et al. Community-based incidence of acute renal failure. *Kidney Int.* 72, 208-12 (2007).
23. Siew, E. D. et al. Predictors of Recurrent AKI. *J. Am. Soc. Nephrol.* (2015). doi:10.1681/ASN.2014121218
24. Kalorama. The World Market for Point of Care (POC) Diagnostics: Market Research Report Example 2—Unique Transcriptional Programs Identify Subtypes of "Acute Kidney Injury"

Abstract

Acute kidney failure was traditionally categorized by etiology including prerenal/transient kidney failure, intrinsic/prolonged kidney failure (ATN), or postrenal kidney failure. In contrast, more recent classifications focus on two metrics, the rise in serum creatinine (sCr) or a decrease in urine output as tantamount to kidney injury (Acute Kidney Injury, "AKI"), without emphasis on its potential etiologies or on clinical heterogeneity. While any form of AKI worsens patient outcomes, it has remained an open question how hemodynamic or volume 'vAKI' is related to intrinsic tubular damage 'iAKI'. To clarify their relationship, transcriptional profiling was performed in mouse models with matched sCr levels. Thousands of genes responding specifically to vAKI or to iAKI were found, but very few responded to both stimuli. These gene sets were not only members of different signal transduction pathways and were functionally unrelated, but they were expressed by different regions of the kidney. Moreover some of these proteins demonstrated distinctive patterns in human urine as potential biomarkers of either vAKI or iAKI. Hence, despite similar sCr levels, vAKI and iAKI in the models herein were biologically distinct, implying that tests for these genes could refine and enhance current definitions of acute injury of the kidney.

The critical function of the kidney is the preservation of water and electrolytes. These functions are conserved throughout the animal kingdom from planaria to mammals[1,2]. When Na+ and water are scarce ("volume depletion"), the kidney's excretory responses decrease, causing Na+, water, and urea retention[3-6]. When volume depletion is more severe, the serum creatinine, sCr, is also retained. A similar scenario occurs in the setting of non-renal diseases that mimic volume depletion such as severe congestive heart and liver failure, because similar drivers (angiotensin-aldosterone systems) and effectors of volume retention (ENac, Na/KATPase and osmolytes) are activated (currently called "cardio-renal and hepato-renal" syndromes). Adding further complexity, destruction of kidney epithelia by toxic stimuli (e.g. ischemia, sepsis, nephrotoxins) also blocks water, electrolyte, urea, and sCr excretion. Hence, it is not surprising that increases in urea and sCr of different etiologies are associated with poor prognoses[7,8], but it remains challenging to prospectively distinguish subtypes of diminished excretion on the basis of current blood or urine measurements.

It may be the case that different forms of diminished kidney excretory activity are highly related to one another, as indicated by the application of the RIFLE, the Acute Kidney Injury Network, and the Kidney Disease Improving Global Outcomes[9] scales to a wide range of clinical settings[7]. These scales focus on sCr as the principal metric of acute injury to the kidney ("AKI"), since sCr has an unequivocal dose-responsive relationship with clinical outcomes[7]. In this light, equivalent levels of sCr should be associated with similar patterns of cellular damage. Less severe elevations of sCr should be a forme-fruste of more severe elevations, expressing attenuated, but similar patterns of cellular responses. On the other hand, it is also possible that the relationship between sCr and tissue damage differs across etiologies and varies during the course of an acute illness, for example as a result of changing extracellular volume[10]. By this logic, different etiologies could induce different types of epithelial damage, and different types of protective and repair mechanisms (e.g. prostaglandins, NO, HIF)[8,11-15] at similar levels of sCr. Mapping the nephron may be required to understand the relationship between elevated sCr and cellular responses.

The inherent characteristics of sCr may also confound its association with a single cellular response. The level of sCr can only represent the extent of damage after a specific time interval has elapsed, because it accumulates at variable rates as a function of muscle mass[16], nutrition[17], body surface area, and Scr reabsorption[18,19] in fact complicating the relationship between sCr and GFR.[18,20-24] Moreover, recruitment of the "renal reserve"[25] may obscure the rise in sCr and limit detection of a significant loss of renal mass, even partial obstruction[26] or kidney donation[27] (called "subclinical AKI"[28]). Finally, different sCr metrics capture different patients[29,30] and false positive AKI diagnoses in up to 30% of cases have been modeled. Hence, it is not surprising that sCr dissociates from renal histology in critical care.[8,31,32] In sum, in kinetically active, non-steady state conditions, the level of sCr may not reflect the level of acute injury.

To examine the relationship between sCr and cellular responses, mouse models of volume depletion ("vAKI") and ischemia ("iAKI") were compared at matched levels of sCr. Kidney histology, serum measurements, and the regional expression of thousands of genes were divergent. These data translated to human AKI because the different genes could distinguish subsets of patients with elevated sCr. In sum, the extra-renal environment elicited specific cellular and molecular responses in specific domains of the kidney, which could not have been directly predicted by the level of sCr.

Results

Figure 6:
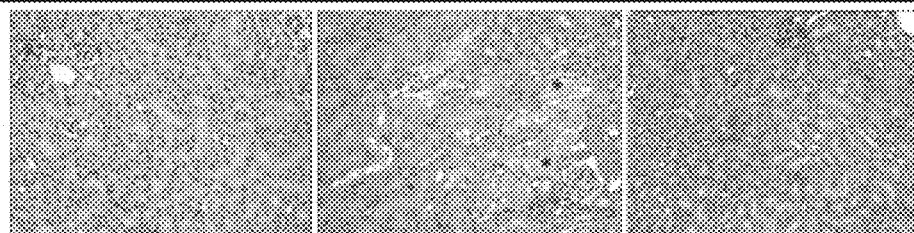
FIG. 6. Basic metabolic profiles of AKI models. iAKI (10 min ischemia, 24 hrs of reperfusion) versus vAKI (72 hr volume depletion) demonstrate similar RIFL-R levels of sCr (control: n=3; ischemia: n=6; volume depletion: n=7). Nonetheless, histopathology (H&E) demonstrates acute tubular injury particularly in the outer stripe of the outer medulla (denoted by *straight S3 proximal tubule) in iAKI, but no evidence of acute kidney injury in vAKI. Bars=250 μm.

Differential Responses to vAKI and iAKI in Mouse Models:

iAKI was induced by 10 minutes of bilateral renal artery ischemia which raised sCr 1.5 fold at the 24 hr point (p<0.03). vAKI was induced by 72 hours of water deprivation[33] and reduced food intake (6.2±0.3 vs 1.2±0.4 g on day 3; p<0.001) which raised sCr 1.9 fold (p<0.01). Nonetheless, despite achieving similar sCr at RIFLE-'R' levels (p=NS), the models differed in clinical, serum, and histologic measurements. iAKI mice maintained activity, whereas the vAKI mice appeared lethargic. iAKI mice maintained weight (17.8±1.2 g vs 15.2±1.1 g; NS) and a normal BUN/Cr ratio, whereas volume depleted mice lost ~20% weight (18.5±0.2 g vs 14.6±0.5 g; p<0.001) and became azotemic, hypernatremic and hemoconcentrated. The iAKI kidneys consistently demonstrated regions of coagulative necrosis at the outer edge of the outer stripe of the outer medulla (OSOM), a region known to be most sensitive to ischemic damage[34], while vAKI kidneys failed to demonstrate cellular derangements (FIG. 6).

To examine transcriptional differences in microanatomic regions of the kidney, laser capture microdissection (LCM) of unfixed frozen sections from vAKI (n=5), iAKI (n=3), and control (n=3) whole kidney, glomeruli, cortex, outer stripe of the outer medulla (OSOM), and inner stripe of the outer medulla (ISOM) (50 independent samples) was used. Both RNA sequencing and quantitative real-time PCR confirmed the appropriate enrichment of segment specific genes from podocytes, proximal, and distal tubules[35,36] in the captured RNA pools (FIG. 11). For example, OSOM was accurately isolated based on the absence of Slc5a2[37] and Alpl[38]. Moreover, whole kidney extracts mirrored cortical genes and recapitulated prior studies[39].

Figure 7:
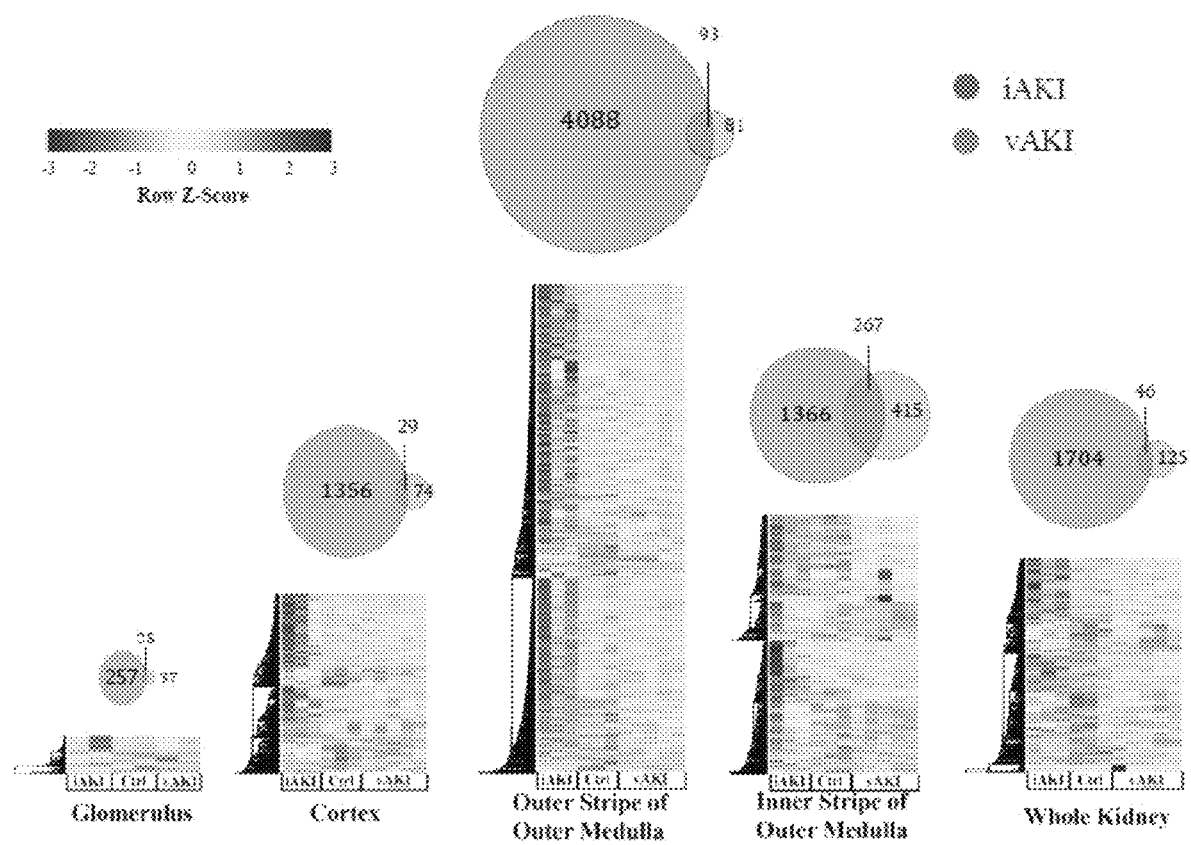
FIG. 7. Limited overlap of gene expression between iAKI and vAKI. Differential gene expression (q-value<0.01) was most prominent in the OSOM in the iAKI model and in the ISOM in vAKI model. The heatmaps portray only the significant differentially expressed genes. Genes were hierarchically clustered and fold ranked and row normalized, and gene level expression values were z-score transformed on a per-gene basis FIG. 8A. Functional analysis using Gene Set Enrichment Analysis (GSEA) against KEGG, Reactome, Biocarta, and PID Pathway databases show different patterning of iAKI and vAKI pathways. Each row (thin lines) demonstrates a pathway found in one or more of the queried databases. Significant pathway enrichment is represented in a binary manner (enrichment=red; de-enrichment=blue; unchanged in white).
Figure 8B:
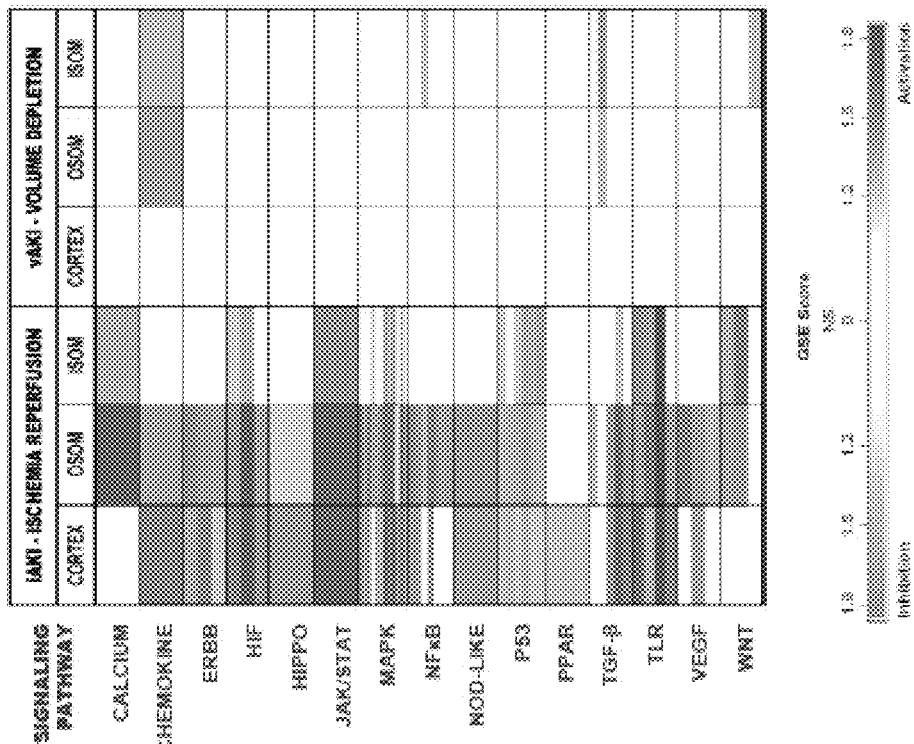
FIG. 8B. Functional analysis using GSEA was supplemented with Signaling Pathway Impact Analysis (SPIA) of canonical signaling pathways to demonstrate biochemical pathways with topological information. Each division demonstrates a well described signaling pathway and each row within the division (thin lines) demonstrates a pathway found one or more of the queried databases. Significant pathway activation is represented in red, whereas inhibition is in green as computed with GSE Score guide. The degree of GSEA enrichment or de-enrichment is reflected in the shade of red or green.
Figure 8A:
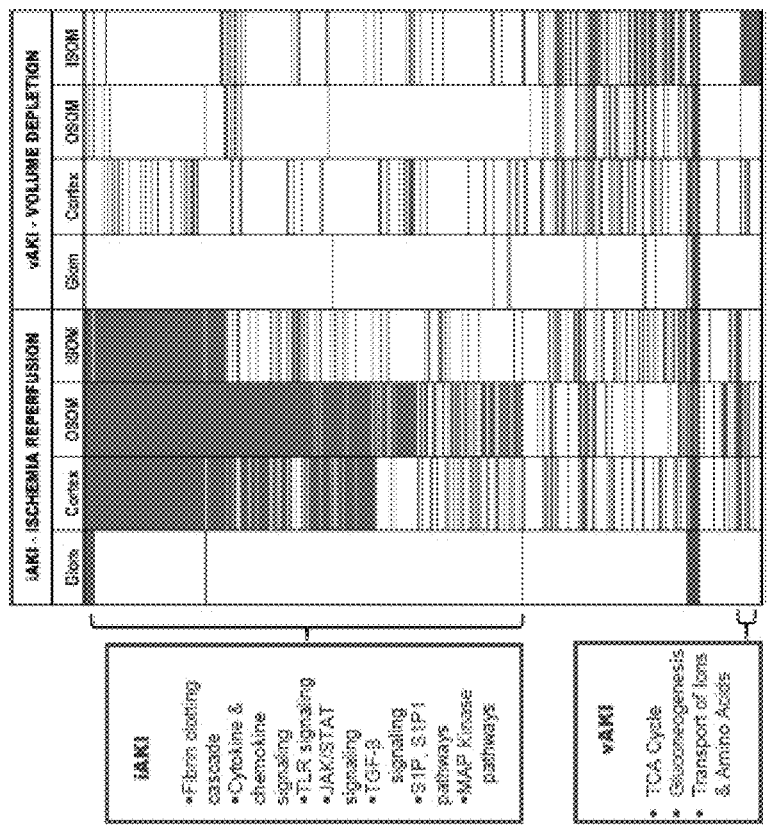
Figure 12:
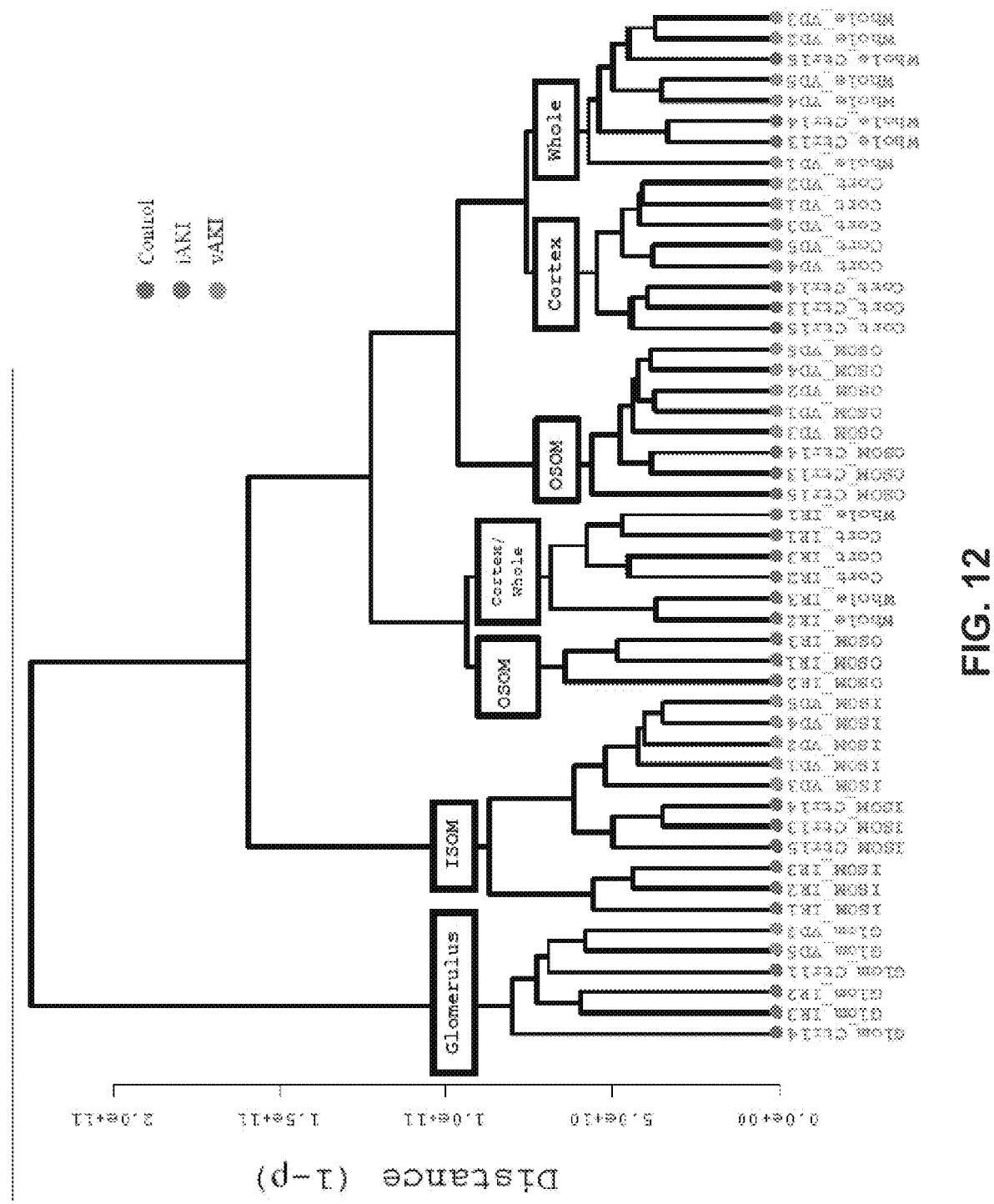
FIG. 12. iAKI and vAKI models demonstrated unique and regional specific transcriptional profiles in an unsupervised hierarchical clustering analysis of mRNA sequencing of glomerulus, cortex, outer stripe of outer medulla, inner stripe of outer medulla, and whole kidney. Distance is expressed as 1—Spearman correlation (ρ). Note that genes stratified by the specific stimulus in different microanatomical regions (glomerulus and ISOM). iAKI agglomerated both the cortex and OSOM. vAKI (n=5), iAKI (n=3) and control (n=3) kidneys (i.e. 50 independent samples).

To determine the relationship between different kidney regions and their responses to stimuli, an unsupervised hierarchical clustering analysis (FIG. 12) was performed. The transcriptional profiles clustered by anatomic regions and separated according to etiology of the rise in sCr. iAKI induced 12× more differentially expressed genes than vAKI (q-value<0.01). Most remarkably, iAKI DEGs localized to the OSOM whereas vAKI DEGs localized to the ISOM (FIG. 7). To infer the functional consequences of these condition specific transcriptional profiles, gene-set enrichment analyses (GSEA; FDR=25%; q=0.01) were performed[40]. As shown in FIG. 8A, the iAKI protocol yielded many more significantly induced gene-sets than vAKI, including classical injury/repair (HIPPO, ERBB, MAPK) and inflammatory (JAK/STAT, NOD-Like, NFκb, TLR, and Chemokine) pathways. In addition, the Signaling Pathway Impact Analysis[41] (SPIA; q=0.01), which provides directionality to gene interactions, identified novel Wnt and PPAR pathways in iAKI (FIG. 8B). In contrast, none of these pathways were modulated by vAKI protocols. Instead, vAKI induced metabolic (TCA, Gluconeogenesis, Oxidative Phosphorylation, Respiratory Electron Transport), transport (Metal Transport), and osmoregulatory (sulfur amino acid, glycine-serine-threonine pathways) gene sets, the latter regulating the metabolism of betaine, an organic osmolyte elevated by osmotic stress[42].

Differential Expression of Known and Novel AKI Genes:

To identify specific genes that might distinguish iAKI from vAKI, known biomarkers of kidney tubular injury[43] upregulated >2-fold (p-value<10-5) after 10 min of ischemia (FIG. 24) were first examined. Prominent iAKI genes included Spp1 (OPN), Cxcl1 (GRO-α), Lcn2 (NGAL) with p-values<10-21 and Clu, Havcr (Kim1), Timp1 with p-values<10-10. These genes were predominately expressed in OSOM. For example, Lcn2 RNA was intensely expressed by the TALH and Intercalated Cells after iAKI (FIG. 9A). On the other hand, none of these genes iAKI biomarkers were significantly upregulated by vAKI.

Figure 13:
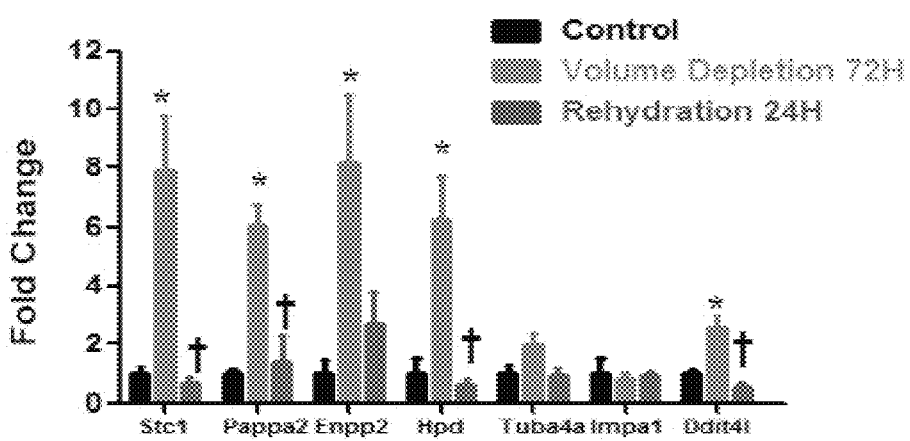
FIG. 13. Rehydration Reverses vAKI gene expression. vAKI mice (n=5) were water/food deprived for 72 hours followed by ad-libitum access to water for 24 hours. Differentially expressed vAKI genes (Stc1, Pappa2, Enpp2, Hpd) and sCr and sNa measurements returned to baseline after resuscitation.
Figure 25:
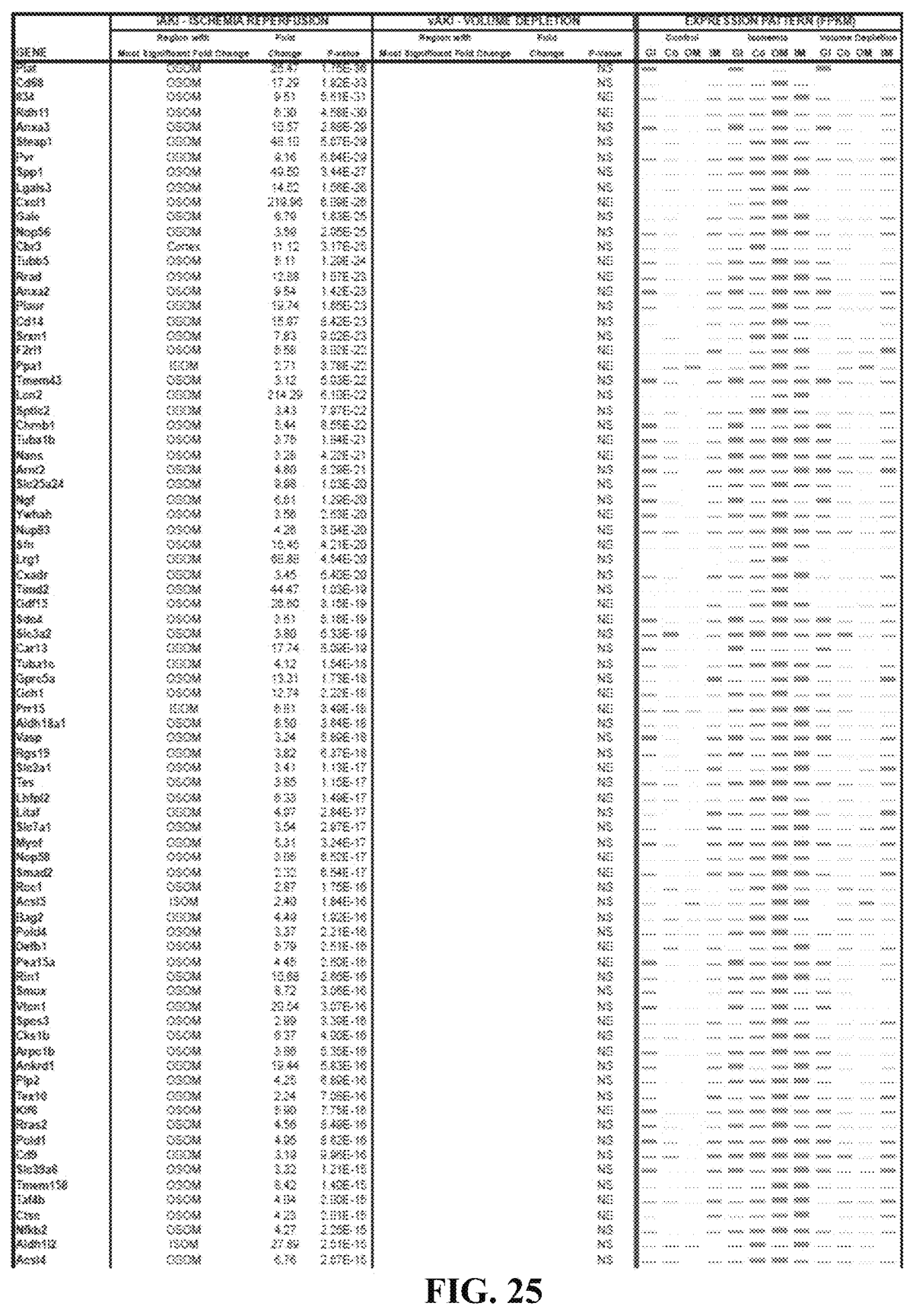
Figure 25:
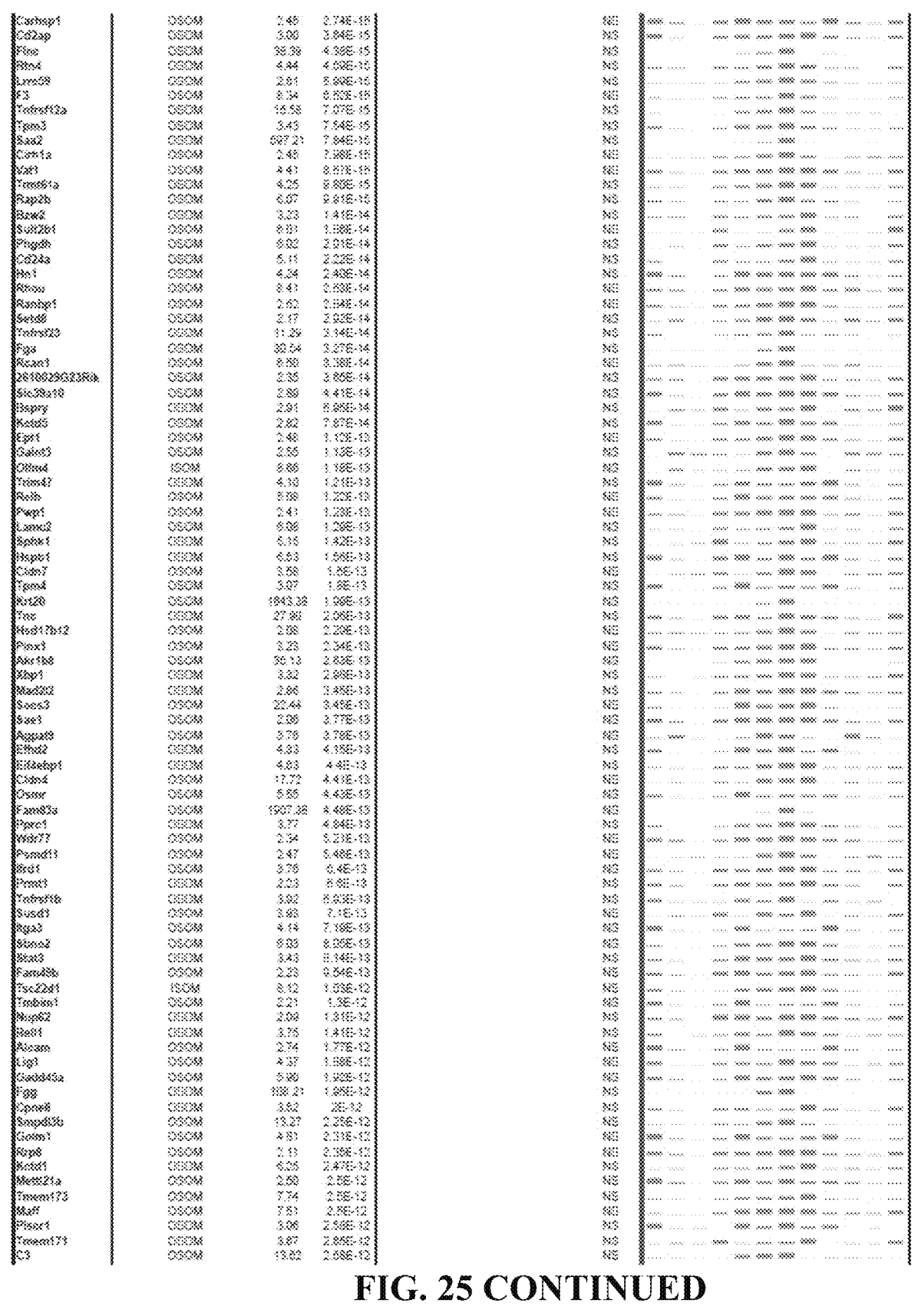
Figure 25:
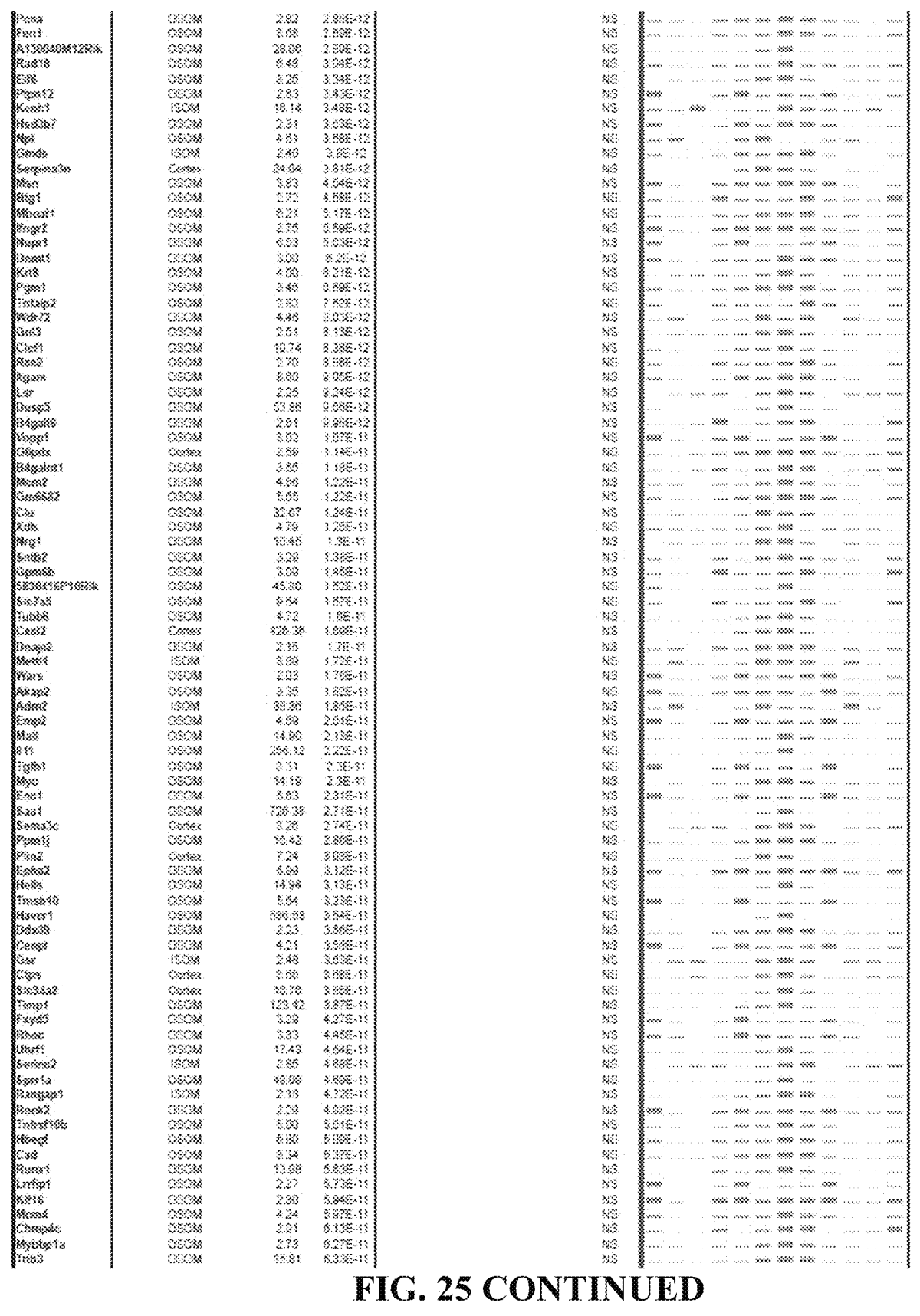
Figure 25:
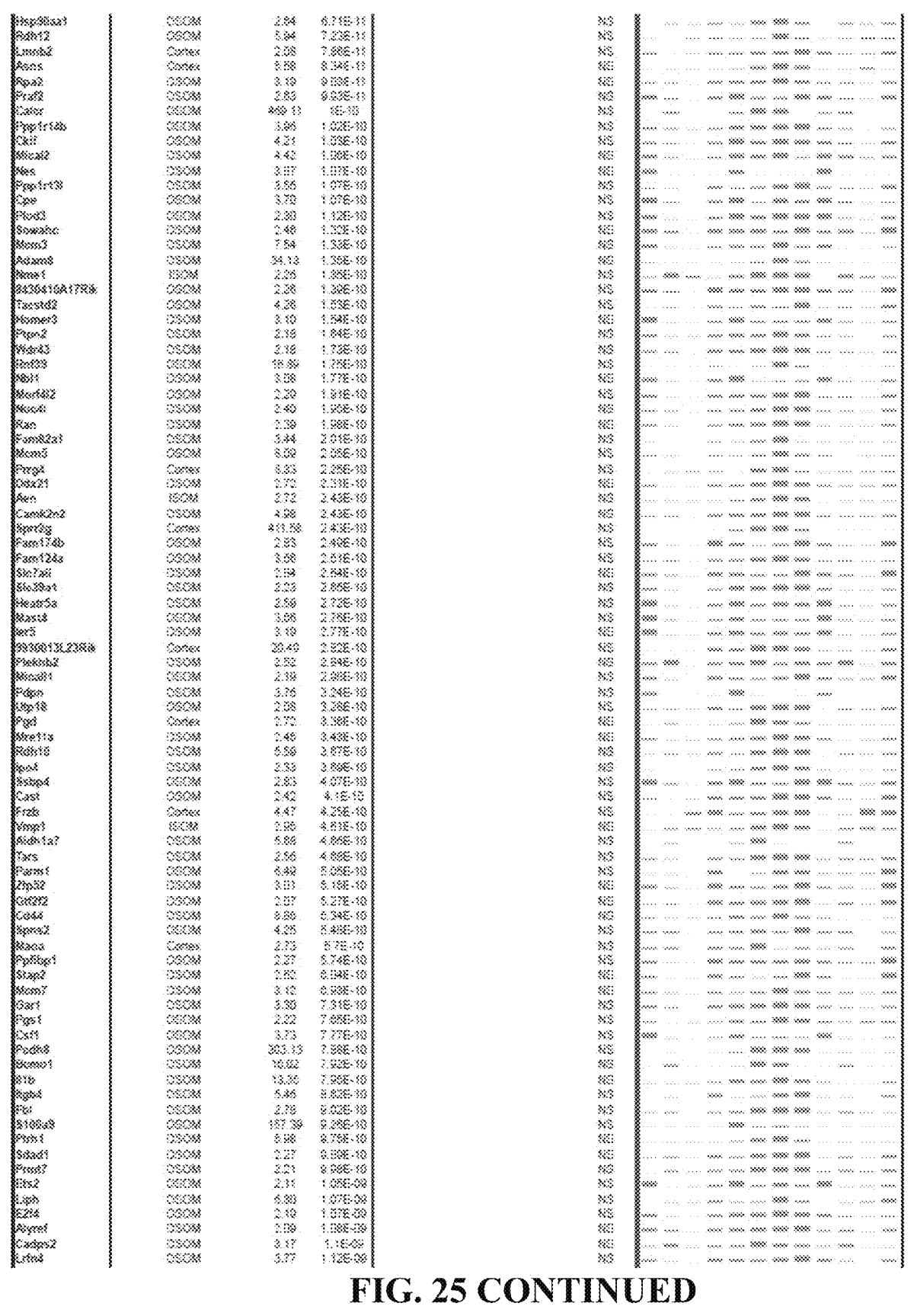
Figure 25:
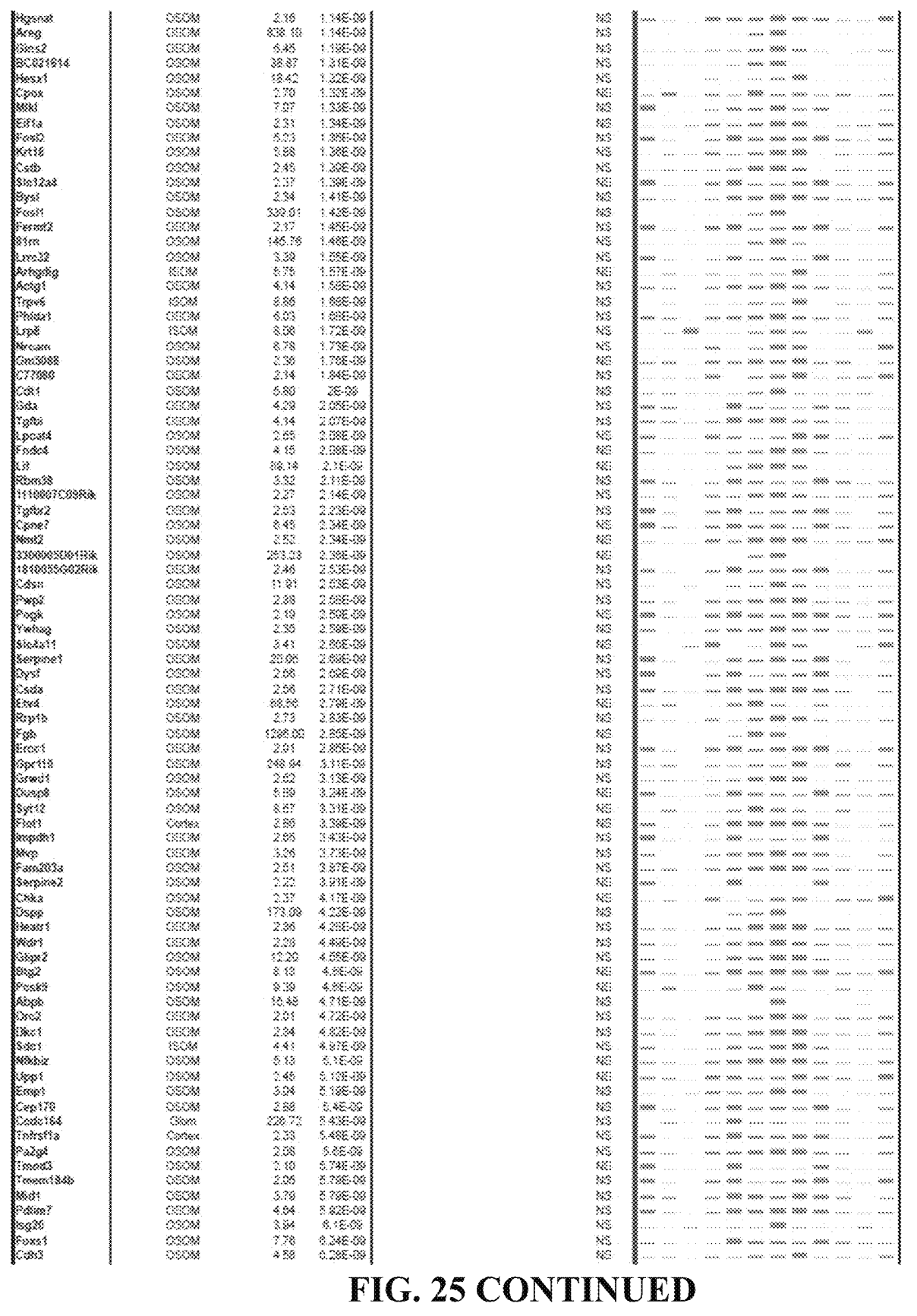
Figure 25:
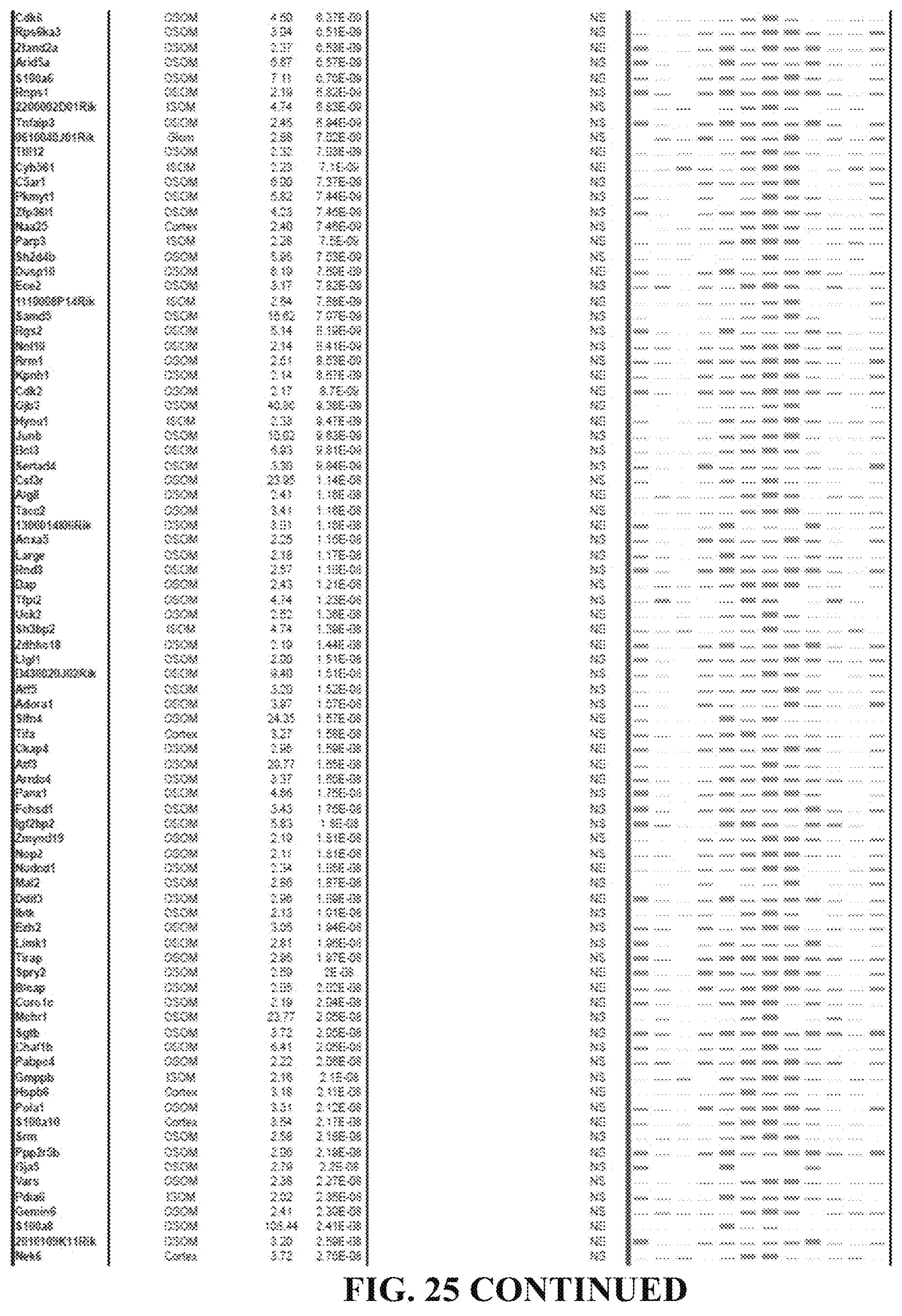
Figure 25:
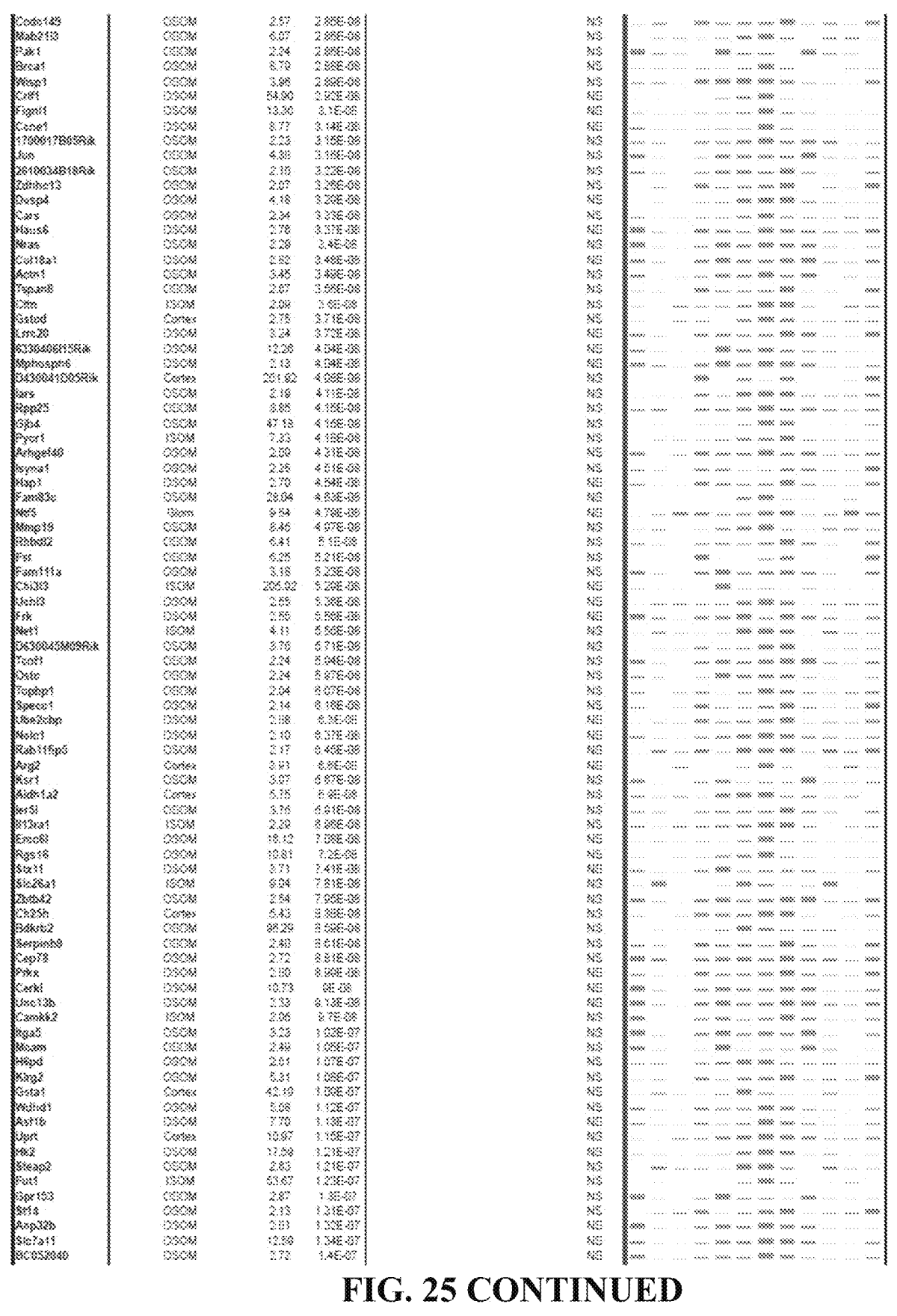
Figure 25:
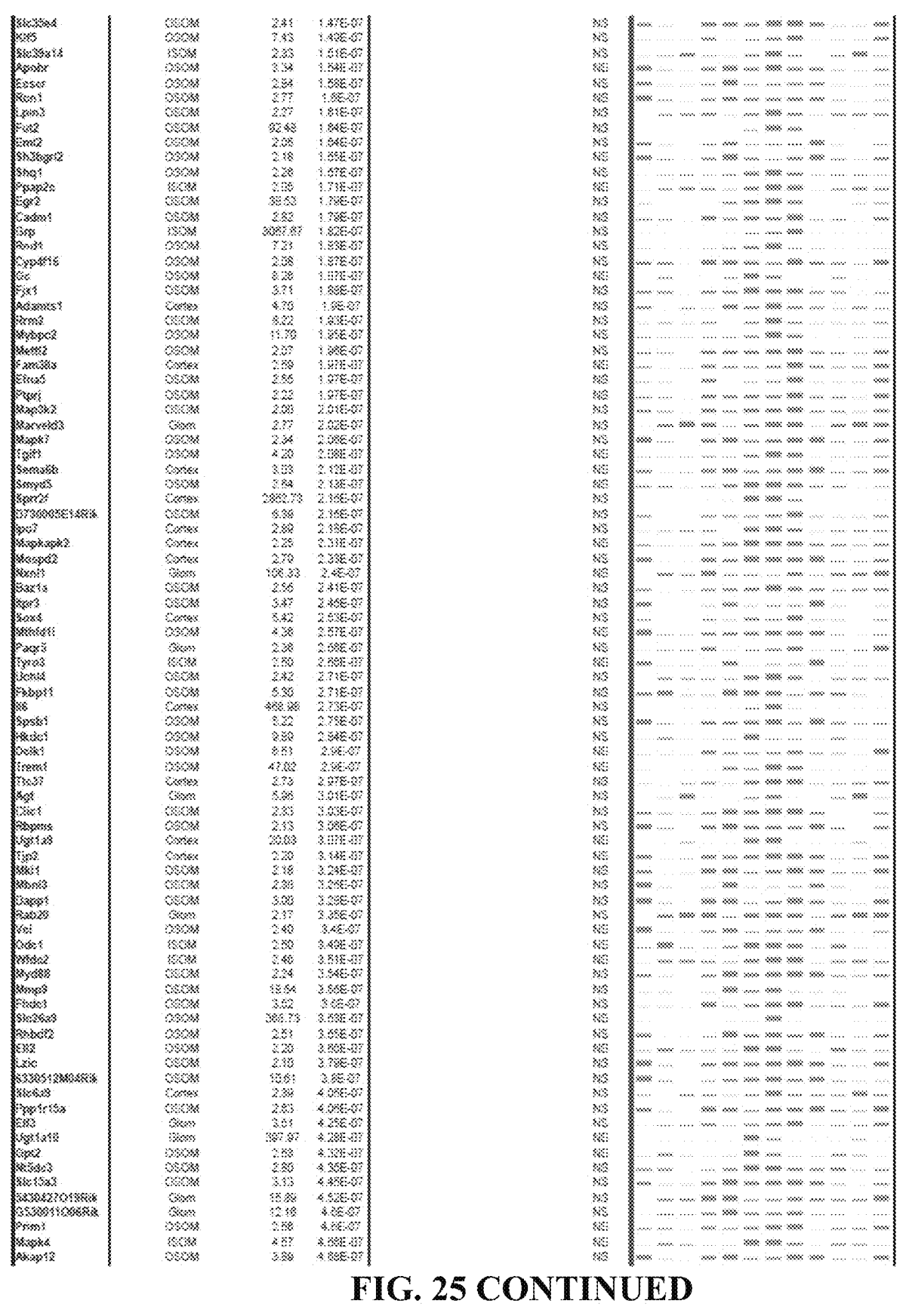
Figure 25:
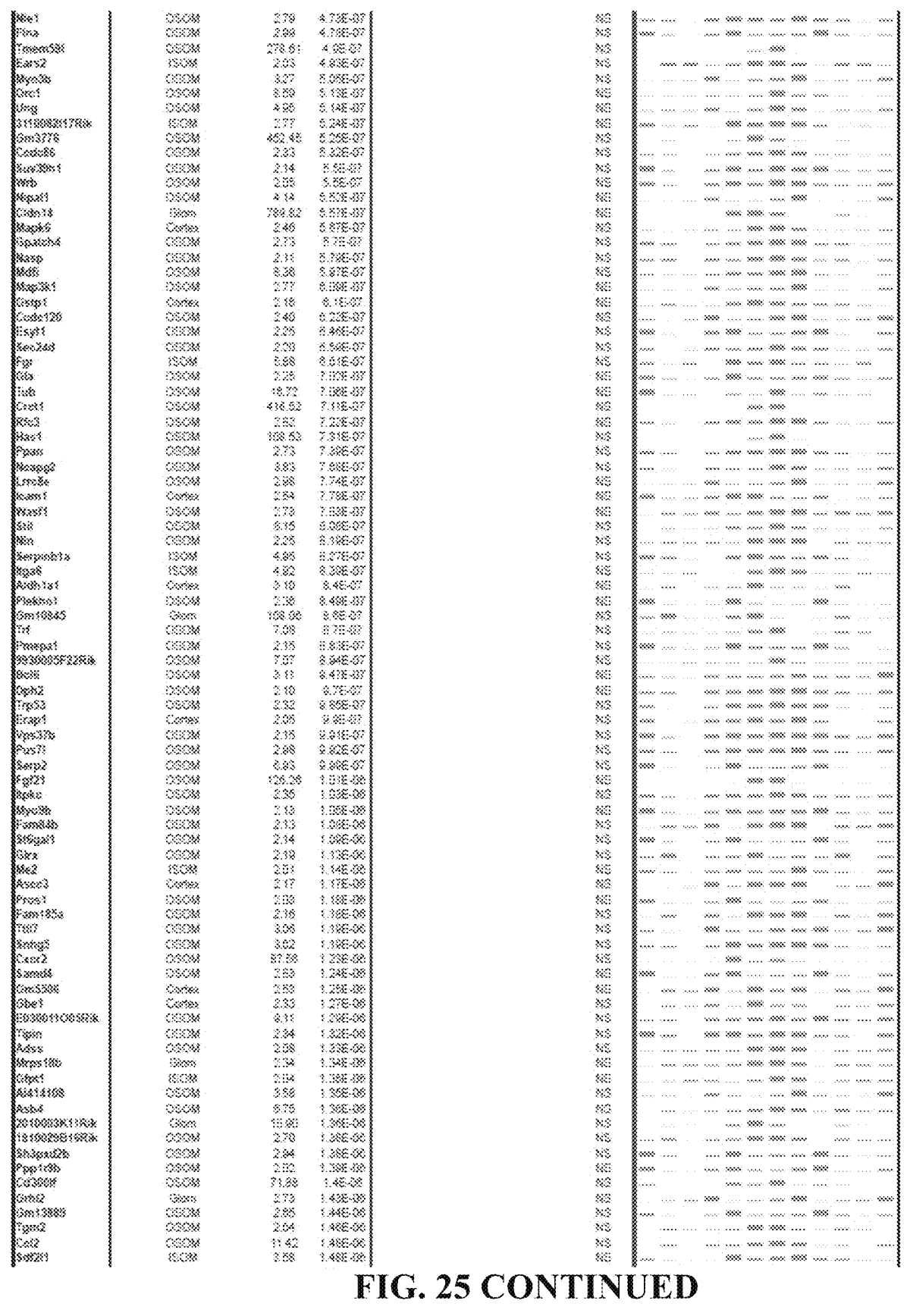
Figure 25:
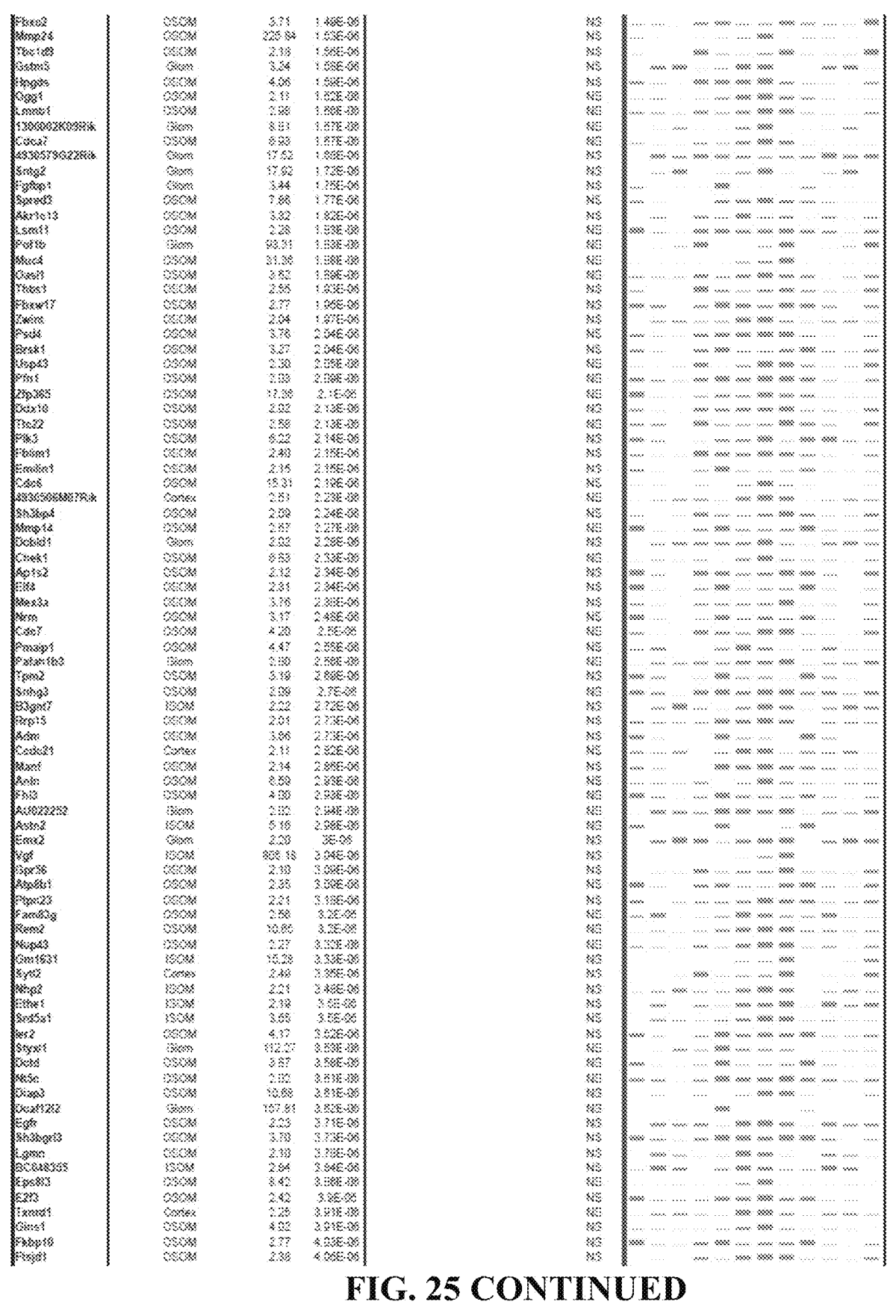
Figure 25:
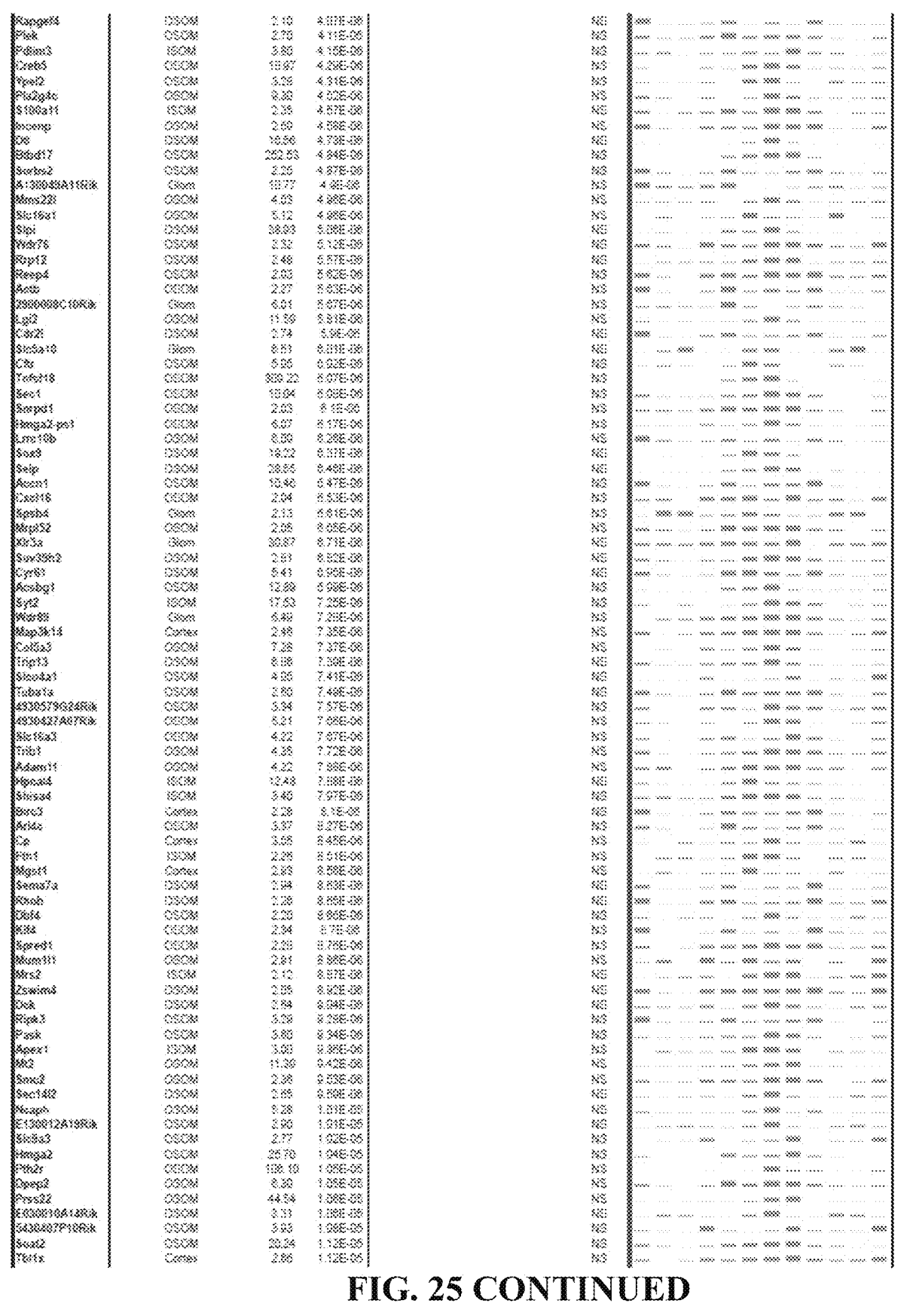
Figure 25:
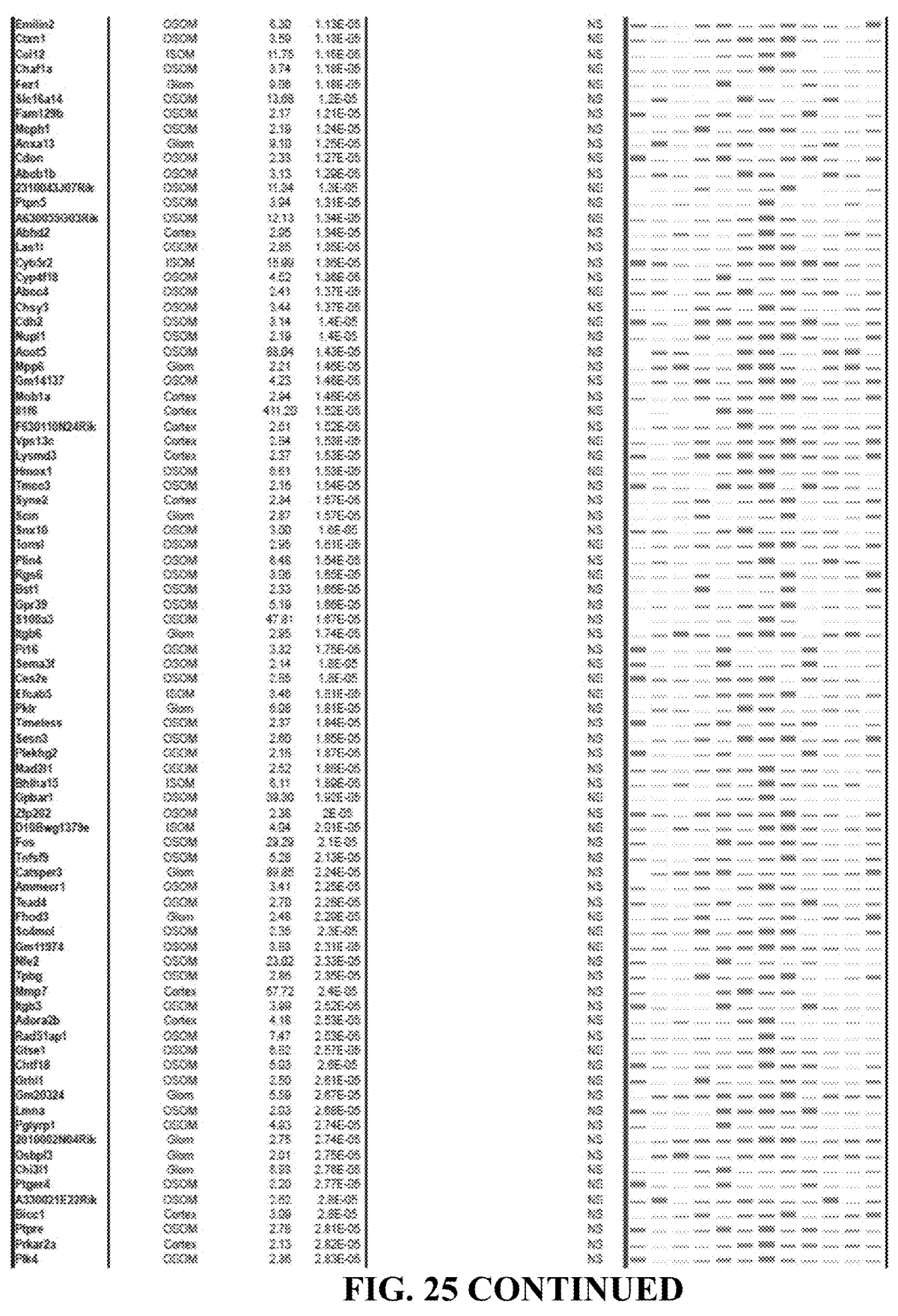
Figure 25:
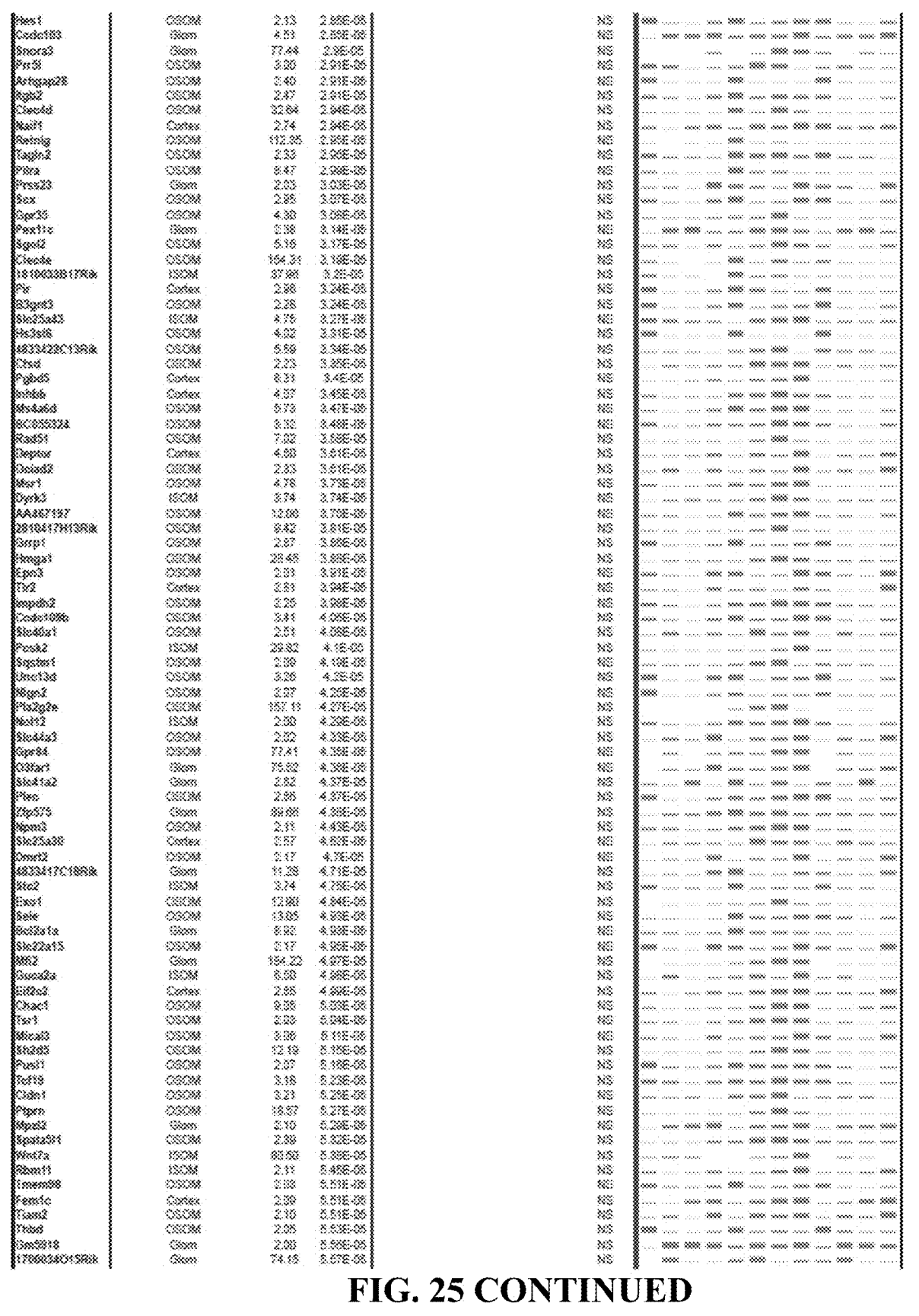
Figure 25:
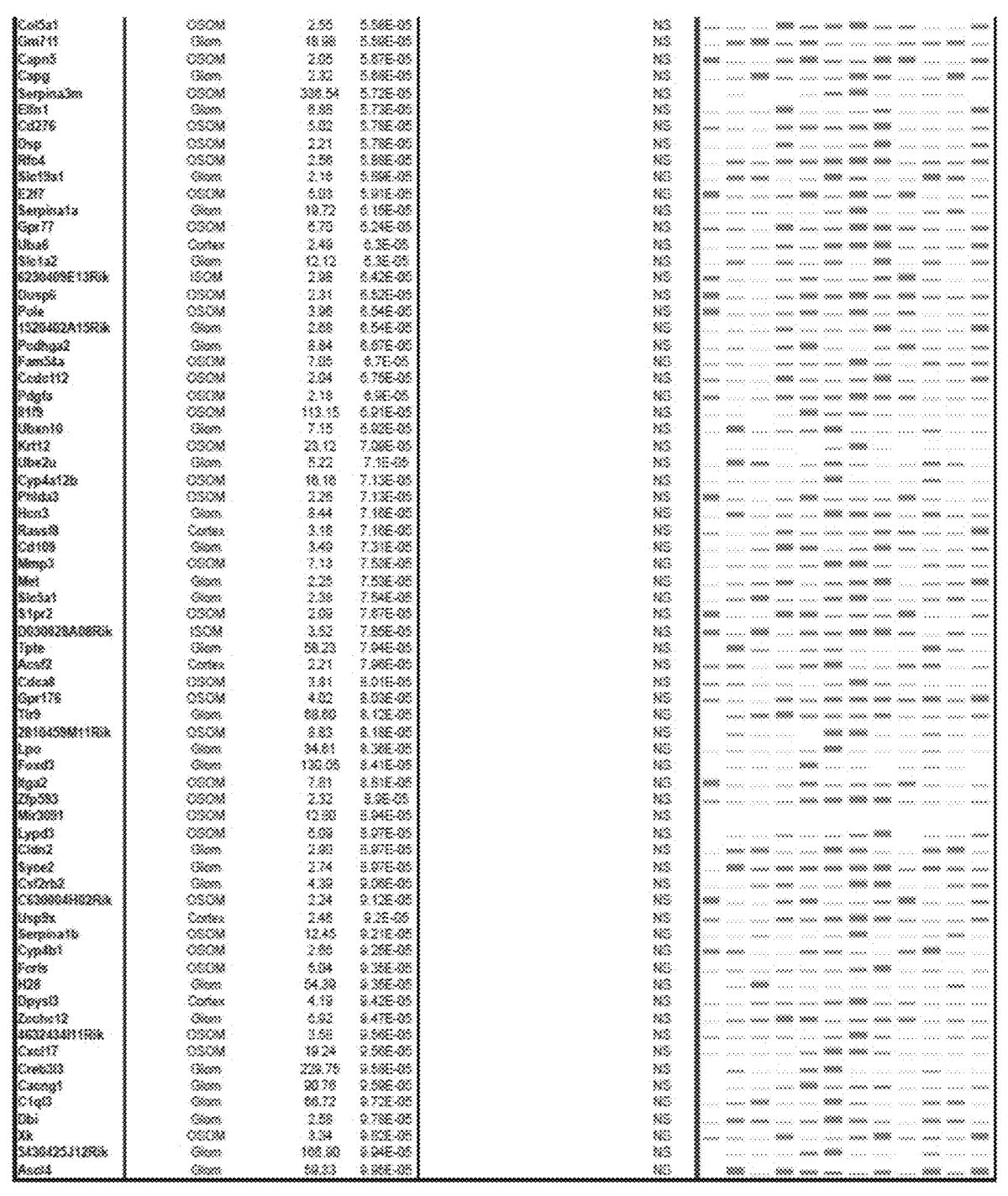
Figure 26:
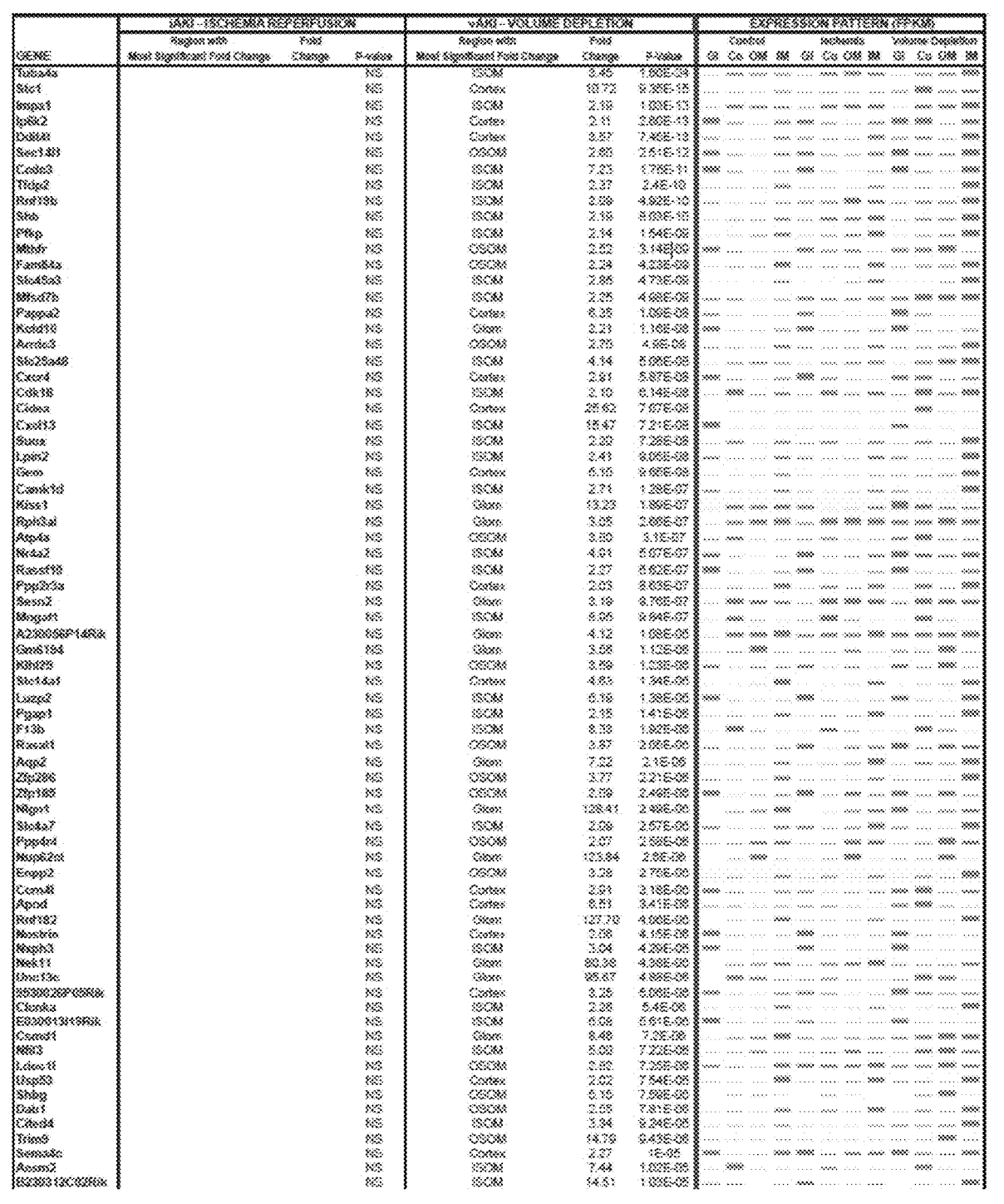
Figure 26:
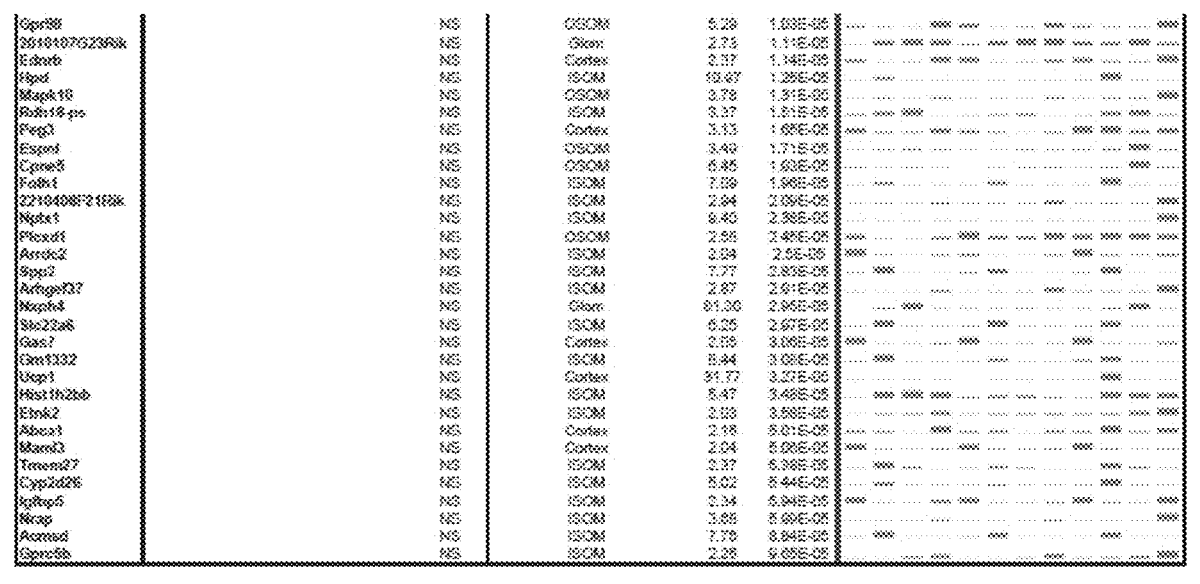

In contrast to the genes listed above, a subset of biomarkers were unchanged or downregulated (β2Microglobulin, Timp2, Netrin, Igfbp7, Tnfsf10, HGF) after 10 min of ischemia, in agreement with published date[44,45]. Consequently, to determine whether there were additional stimulus-specific genes, all upregulated genes (>2-fold; p-value<10-5) were cataloged and it was found 92.3% (1158) of iAKI regulated genes were not expressed in the vAKI model (FIG. 25) and conversely, 51.7% (103 genes) of vAKI regulated genes were not expressed in the iAKI model (FIG. 26). In addition, iAKI specific genes were generally localized to the OSOM (e.g. Trop2/Tactstd2, 4.26 fold, p<10-9 and Cytokeratin 20, 1643 fold, p<10-12) demonstrating prominent expression (FIG. 9A), while vAKI genes were particularly localized to Cortex and ISOM (e.g. Pappa2, 6.35 fold, p<10-8 and Stc1, 10.72 fold, p<10-15). Distinct gene expression was validated in a related model (water and food deprivation combined with a single dose of furosemide; 50 mg/kg)[46,47] which elevated sCr 1.5 fold and induced vAKI (e.g. Pappa2) but not iAKI genes (e.g. NGAL, KIM1). To characterize the vAKI response further, we restored ad-libitum access to water (n=5) for 24 hours. Rehydration not only corrected both sNa and sCr (sNa: from 159.6±3.5 mmol/L to 131.4±2.5 mmol/L; p<0.001 and sCr: from 0.37±0.006 mg/dL to 0.28±0.09 mg/dL), but also normalized differentially expressed vAKI genes (n=5; FIG. 13).

Examination of vAKI and iAKI Genes in Human Urine:

Statistically significant, 2-fold upregulated mouse genes (p-value<10-5) were compared with the Secreted Protein Database and the Max Plank Unified Proteome to identify putatively secreted iAKI (267, FIG. 27) and vAKI (30, FIG. 28) proteins in human urine. Candidates from different regions of the kidney were tested using urine collected from patients in Emergency Departments[48,49]. Their clinical histories were previously adjudicated by strict criteria (see Methods; reference 48), including clinical history, time to resolution of elevated sCr (vAKI<72 hrs; iAKI≥7 days), and rapid response to volume challenges. Representative iAKI patients had acute illnesses due to obstructive uropathy, sepsis and rhabdomyolysis with a 2.56 fold rise in sCr at the time of admission from the Emergency Department and prolonged azotemia ≥7 days; these patients were seen by a renal consultant. Representative vAKI patients had an acute illness due to hyperglycemia, gastroenteritis, syncope, drug overdose with a 2.14 fold rise in sCr which resolved within <72 hrs, but were not visited by a renal consultant. Normal patients had acute illnesses due to gastroenteritis and cardiovascular disease and trauma with no rise in sCr.

Figure 10:
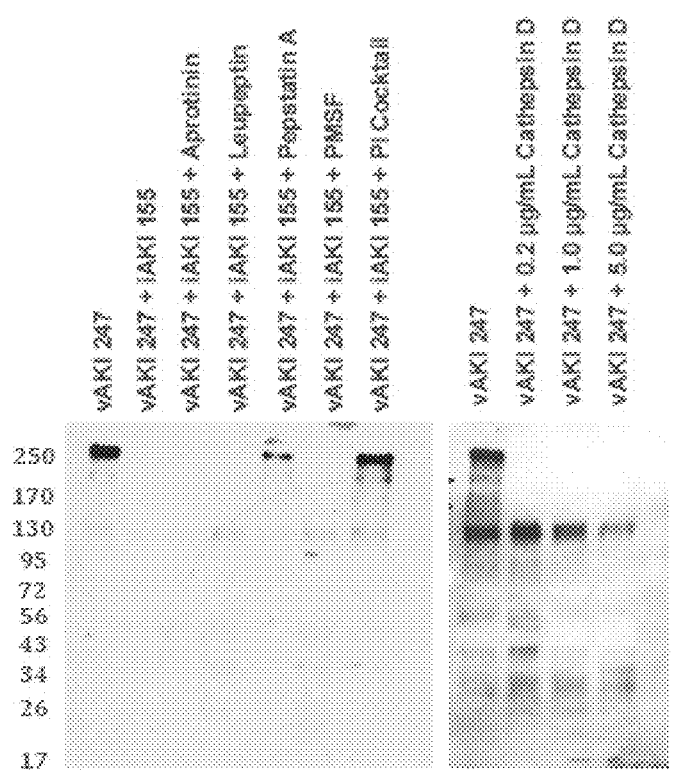
FIG. 10. Proteolysis of vAKI urinary PAPPA2 by iAKI urine was rescued by protease inhibitors especially pepstatin A and combinations of inhibitors. PAPPA2 was also degraded by Cathepsin D.

Chi3l1, Trop2 (Tacstd2), Plat, Krt20 (FIG. 9B) were prominently expressed in urine of patients who achieved the diagnosis of iAKI during their subsequent hospitalization, but these proteins were minimally or inconsistently expressed in patients diagnosed with volume reversible vAKI. NGAL, VitDBP[50], IGFBP7, TIMP2, shown for comparison had variable degrees of specificity for iAKI (FIG. 9C). In contrast, Pappa2 (FIG. 9B) was expressed in vAKI urine, but not in iAKI urine; rather, PAPPA2 immunoreactive fragments were found. To test whether iAKI urine contained proteases that cleaved PAPPA2, vAKI was coincubated with iAKI urines, and it was found that PAPPA2 was degraded, particularly when urine pH was acidic (pH5.5)[51] (FIG. 10). A preliminary proteomic analysis, validated by the abundance (spectral counts) of NGAL, OPN, CLU identified proteases known to be active in tubular damage (e.g. Cathepsin D[52], CathepsinB[53], AminopeptidaseN[54], MMP-9[55], MMP-8[56]). Consistently, the addition of cathepsin D to vAKI samples digested PAPPA2 and conversely, PAPPA2 immunoreactivity was preserved by the addition of Pepstatin A to the vAKI/iAKI coincubation. These data indicate that enhanced proteolysis increased the specificity of PAPPA2.

Prevalence of Transient vs Sustained Azotemia: Analysis of >2000 Emergency Department patients[48,49] demonstrated that prolonged sCr elevation associated with high levels of urinary biomarkers, whereas brief azotemia, including volume sensitive reversal of sCr, was far less inductive (e.g. NGAL remained in the normal range[57]). To identify the predominate kinetics of sCr in New York City, an algorithm was developed to detect baseline sCr values (available in 52,391 patients) and ≥0.3 mg/dL deflections above baseline (which occurred ≥1 time in 25,348 patients during the same hospitalization, i.e. 54,435 events) in the New York Presbyterian-Columbia University Clinical Data Warehouse (3.8 million patients). It was found that sCr resolved in 33% of patients after 1 day, 60% after 2 days and 73% after 3 days. In sum, increased sCr, definitional for AKI criteria, is elevated only briefly in the majority of cases, once the patient comes to medical attention.

Discussion

The failure to excrete of salt and water and even urea and sCr by the kidney is a common result of tubular injury, volume depletion and a myriad of other diseases including heart and liver failure. As a result, it can be quite challenging to distinguish these entities at the point of patient contact, especially at lower elevations of urea and sCr. Consequently, it can be the case that each of these entities invokes an etiologically indifferent 'final common pathway' best measured by sCr. On the other hand, if stimulus-specific genetic readouts accompanied elevations of sCr, one can obtain information reflecting pathogenesis and consequently revise definitions of AKI.

In fact, known biomarkers can demonstrate stimulus specific expression[60]. For example, numerous studies show that NGAL expression is linked to sepsis, nephrotoxicity, and ischemia in rats, mice, pigs, dogs[33,49,61] as well as in human neonates, children, adults[62] subject to poor outcomes[49,13], but in contrast, NGAL is poorly responsive to volume deficits[33,49] and to diuretics[33] which nonetheless elevate sCr in patients[49,63] and in animal models[33]. It was hypothesized that these discriminating characteristics were not specific to NGAL but rather intrinsic to AKI. Consequently, iAKI and vAKI models should express different cellular and genetic programs. In fact, kidney histology demonstrated that while tubular damage was obvious in iAKI, vAKI kidneys failed to show any evidence of injury. Study by RNA-seq, in situ hybridization, immunocytochemistry and immunoblotting human urine identifying hundreds of genes biased to either iAKI or vAKI, highlighted differences between the models. These data were supported by ongoing efforts in gene mapping, adapting the method of Gay et al. of cell specific labeling of RNA[64], using HoxB7-Cre-driven phosphoribosyltransferase to isolate the response of the collecting duct to iAKI and vAKI. 86.3% (139) of iAKI genes (>2-fold; p-value<0.05) were not expressed in vAKI model, and conversely, 95.9% (522) of vAKI genes were not expressed in the iAKI model, similar to LCM analysis of kidney domains. These findings are also in agreement with transcriptomic analysis by Star and colleagues[39] and with measurements of tubular cell energetics, which were preserved in vAKI but not in iAKI[58]. The data described herein are also reminders of the well-known mismatches between sCr and renal pathology[8,31,32], and the limited changes in sCr even when there is significant damage by partial obstruction[26] or even the loss of an entire kidney (donation)[27,59], a phenomenon that has been called "subclinical AKI"[28]. The data herein solves these conundrums by demonstrating that a specific level of sCr can reflect a variety of distinct genetic programs.

Hence, it was not shown that vAKI is an attenuated form of iAKI; rather, each activated a distinct genetic program despite a similar level of sCr. iAKI induced changes in inflammatory, epithelial growth and repair genes. These included the Hippo-signaling pathway, in particular, YAP, an anti-apoptotic transcription cofactor, 1.7-fold (p<105) increased while its inactivator, LATS2, 0.65-fold downregulated (p<104), suggesting mechanisms of epithelial regeneration after injury. In addition, the iAKI model described herein (10 min of ischemia) activated Wnt7a 80.5-fold (p<104), an essential gene promoting tubular repair and regeneration[65], while driving AKI to CKD fibrosis when the pathway is sustained. Other classical inflammatory and repair pathways, such as MAPK, JAK/STAT, NFκB, TLR, and Chemokines were also markedly activated in iAKI, in agreement with many landmark studies. Yet none of these pathways were activated in the vAKI model, which instead reflected metabolic and osmotic regulatory pathways in the ISOM, consistent with food and water scarcity.

Perhaps the distinct patterning of gene expression may be the result of differential sensitivity of different nephron segments to potentially injurious stimuli. The patterning could also result from differentially expressed protective mechanisms. For example, PAPPA2 which is expressed in mouse and human vAKI is a metalloproteinase secreted by the TALH, that may play a role in salt sensitive volume stress66. PAPPA2 targets the IGFBP system, permitting IGF mediated cell survival and growth[67,68]. This protein appears to be lost in iAKI due to its own proteolysis, demonstrating the potential loss of a protective pathway.

While the iAKI and vAKI models diverged in clinical, transcriptional and biochemical assays, they can converge at a different time point, or if the severity of vAKI can be increased. Without being bound by theory, vAKI mice already manifest severe volume derangements over many days and cannot survive further volume depletion. Moreover, even if further manipulation of the vAKI model were possible, sCr would no longer be matched. It is also possible that other models of vAKI (e.g. bleeding, severe heart failure) might better overlap iAKI, yet this remains to be tested, especially since the two models (±diuretics) which are consistent with human presentations to Emergency Departments induced the same volume sensitive genes. In this light, vAKI and iAKI can converge only because vAKI sensitizes the kidney to a "second hit", for example by increasing the risk of nephrotoxicity69, contrast70, chemotherapy[71], and sepsis induced AKI[54].

The distinct patterning of vAKI and iAKI genes has a number of clinical applications including the possible utility of a new class of biomarkers responsive to reversible volume stresses. Pending the testing of the multitude of secreted vAKI genes, simple ratios (iAKI/vAKI genes) can detect the mechanism of sCr elevation in patients. Additionally, since the vAKI genes rapidly reversed with volume resuscitation, these proteins can also serve as reporters to guide rehydration therapy and limit water/volume intoxication.

Finally, the data described herein provide an explanation for the dissociation of biomarkers of iAKI with sCr at lower levels of RIFL, AKIN, KDIGO scores. Elevation of sCr by volume depletion (which causes lower levels of elevation) should not be compared with an iAKI biomarker, but rather with vAKI induced proteins. Pooling molecularly and spatially distinct programs reduces the utility of iAKI biomarkers, since these proteins are minimally expressed when sCr rises due to volume depletion.

In sum, the kidney has a fine tuned response to environmental challenges based on different genetic readouts in different cells in different parts of the nephron. Transient elevation of sCr dominates our hospital records, and if these rapid fluctuations are due to volume sensitivity as was indicated by our Emergency Department series, then new tools specific to iAKI or vAKI may permit prospective diagnoses and treatments at the point of patient contact. Based on clinical, pathological, transcriptional and proteomic data shown here there is evidence that these new tools that may refine our understanding of the AKI syndromes.

Concise Methods

Clinical Samples:

Emergency Room urine samples were selected at random from a multicenter prospective cohort study49, using published criteria for iAKI, vAKI and control. In brief, the total cohort was followed solely by sCr kinetics, and in a separate analysis, the cohort was adjudicated using strict criteria aimed at identifying only "gold standard" patients, to identify normals (no fluctuations in sCr, no history of exposure to agents that might cause iAKI such as nephrotoxins, sepsis, obstructive uropathy, rhabdomyolysis), vAKI (≥RIFL-R and historical or clinical data suggesting decreased renal perfusion for example due to hyperglycemia, diarrhea, but no history of exposure to agents that might cause iAKI such as nephrotoxins, sepsis, obstructive uropathy, rhabdomyolysis and time limited resolution <3 days with fluid therapy or diuretic withdrawal), and finally iAKI (≥RIFL-R, with evidence of exposure to stimuli known to induce AKI, but lack of resolution for ≥168 hrs). Patients in the later category were more likely to require a renal consultant and undergo dialysis. Hence the iAKI and vAKI cohorts differed by time to resolution but also by their history and severity of clinical outcome. Patients with documented urinary tract infections and chronic kidney disease were excluded. Standard blood chemistries were collected each day for 7 days post admission as previously published49.

Mouse Husbandry:

Female wild-type C57Bl/6 mice, aged 10-12 weeks (Jackson Labs, Bar Harbor, Me.) were used according to approved protocols.

Renal Ischemia Reperfusion Injury Model:

Mice were anesthetized with isoflurane and placed on a warming table to maintain a rectal temperature of 37° C. Left and right renal pedicles were clamped using microvascular clamps (Fine Science Tools, Foster City, Calif.) for 10 minutes. After the clamps were removed, reperfusion of the kidneys was visually confirmed. The kidneys and blood were harvested at 24 hrs.

Renal Volume Depletion Model:

Water was withheld from mice for 72 hours. Body weight and food intake were measured daily. Food intake was determined by weighing chow pellets and spillage. Kidneys were harvested and blood was collected at 72 hrs or mice were rehydrated for an additional 24 hrs.

Clinical Measurements:

Serum creatinine, sodium and blood urea nitrogen, were measured using Creatinine and EC8+ cartridges read by an i-STAT Handheld (Abbott Point of Care, Princeton, N.J.).

Immunohistochemistry:

Kidneys were fixed (4% PFA/0.1M PB at 4° C. overnight), transferred to 30% sucrose/0.1M PB (4° C. overnight), and embedded in O.C.T. Compound (Tissue-Tek). Frozen sections of 20 µm were used for immunofluorescence staining with rabbit anti-KRT20 (1:200; ab118574; Abcam), goat anti-AQP2 (1:400; sc-9880; Santa Cruz Biotechnology), and Fluorescein-labeled Lotus Tetragonolobus Lectin (1:200; FL-1321; Vector Laboratories). Fluorescent secondary antibodies, Alexa Fluor® 594-AffiniPure F(ab')2 Fragment Donkey Anti-Rabbit IgG and Alexa Fluor® 647-AffiniPure F(ab')2 Fragment Donkey Anti-Goat IgG (1:1000; Jackson Immunoresearch Laboratories), were used for KRT20 and AQP2 identification, respectively. All slides were co-stained with 4',6-diamidino-2-phenylindole to identify nuclei.

Laser Capture Microdissection:

Kidneys were embedded in O.C.T. Compound (Tissue-Tek) and immediately snap frozen in dry ice and kept in −80° C. until time of sectioning. Sections of 8-10 µm (20 µm for glomeruli) were collected on nuclease-free glass slides covered with a thin membrane (Zeiss Microscopy, Thornwood, N.Y.), fixed in 70% ethanol for 30 seconds, stained with 1% cresyl violet acetate solution and dehydrated in 70% and 100% ethanol followed by air-drying for 30 minutes. Regions of interest were identified morphologically and 15-20 cross sections (for Cortex, OSOM, ISOM) or ~1500 cross sections (glomerulus) were microdissected (PALM MicroBeam, Zeiss Microscopy, Thornwood, N.Y.).

RNA extraction and RNA sequencing: Total RNA was isolated from segment-specific laser captured kidney sections using Ambion RNAqueous® Micro Kit (Life Technologies, Carlsbad, Calif.). RNA concentration and integrity for each sample were assessed on RNA 6000 Chips using an Agilent 2100 Bioanalyzer (Agilent Technologies, Santa Clara, Calif.). Poly-A pull-down was used to enrich mRNAs (200 ng-1 ug per sample, sample RIN was above 8.0) and then libraries were prepared using single-end 100 bp reads for each sample with Illumina TruSeq® RNA prep kits (Illumina, San Diego, Calif.). Libraries were sequenced using Illumina HiSeq2000. Illumina RTA was used to perform base calling whilst CASAVA (version 1.8.2) for converting base call files (.BCL) to FASTQ format and also perform sequence adaptor trimming. Reads were then mapped to the mouse reference genome (mm9) using Tophat72 (version 2.0.4) allowing 4 mismatches (--read-mismatches=4) and a maximum of 10 multiple hits (--max-multihits=10). The relative expression was calculated using cufflinks73 (version 2.0.2) with default settings. Gene expression levels were normalized by library size and gene length into FPKMs74 and log 2 transformed. Counts tables were generated with HTSeq (www.huber.embl.de/users/anders/HTSeq) version 0.6.1. Transcripts with 0 counts across all samples were removed and mathematical artifacts (e.g. negative infinites) were replaced with "NA". Statistical analysis was performed in R version 3.1.0 and additional Bioconductor packages were part of release 2.14. Unsupervised cluster analysis was performed on log 2 transformed FPKM values using Spearman correlation as distance and complete linkage as similarity method. No significant differences were seen in mRNA integrity (RIN Agilent 2100 Bioanalyzer) from different samplings and all samples passed the quality controls on post sequencing analysis.

Generation of Heatmaps:

Genes that were differentially expressed in iAKI vs. control and vAKI vs. control were included. The expression data shown is the variance stabilized data generated using the DESeq package from Bioconductor according to the DESeq vignette (bioconductor.org/packages/release/bioc/html/DESeq.html, bioconductor.org/packages/release/bioc/vignettes/DESeq/inst/doc/DESeq.pdf). Hierarchical clustering used Pearson Correlation distance plus single linkage. The variance stabilized expression values were visualized with heatmap.2 (gplots package, cran.r-project.org/web/packages/gplots/index.html).

Identification of Genes and Pathways:

Differentially expressed genes were identified using edgeR package75 version 3.6. The Benjamini & Hochberg76 procedure was used for controlling false discovery rate (FDR) of the multiple tests and accepted as significant a q-value<0.01. Enrichment analysis was performed using PathwayGuide (Advaita Corporation www.advaitabio.com/) 20 against KEGG77 and Reactome78 and GSEA19 against MSigDB canonical pathways from the curated gene sets v4.019.

Identification of Biomarkers:

Candidate biomarkers were filtered according to the Max Plank Unified Proteome (1542 proteins assessed Mar. 20, 2014), Secreted ProteinDB79, or by prediction (signal peptide and without a transmembrane domain—according to Ensembl80,81. The proteins that were exclusive to condition were identified, demonstrated ≥2-fold changed compared to control and were expressed with an FPKM>1.

Real-Time PCR Analysis:

Total RNA was isolated and first-strand cDNA was synthesized with Superscript III (Invitrogen). Real-time PCR was performed using LightCycler®96 (Roche) with a SYBR green Supermix reagent (Bio-Rad) and specific primers (Supplementary Table x). β-actin was quantified as an internal control. ΔΔCt was used to calculate fold amplification of transcripts.

Western Blot:

Urine (8.34) was loaded on 4-15% SDS-polyacrylamide-gel (Bio-Rad Laboratories), blotted using nitrocellulose (GE Healthcare, Pittsburgh, Pa.) and proteins detected using anti-human antibodies: polyclonal human CHI3L1 (1:1000;

AF2599; R&D Systems), polyclonal human TROP2 (1:1000; AF650; R&D Systems), monoclonal human TPA (PLAT) (1:1000; ab157469; Abcam), monoclonal human KRT20 (1:1000; ab118574; Abcam), polyclonal human PAPPA2 (1:1000; AF1668; R&D Systems), monoclonal human NGAL (1:1,000; BPD-HYB-211-01-02; Enzo Lifesciences), monoclonal human VITDBP (1:1000; MAB3778; R&D), polyclonal human IGFBP7 (1:1000; AF1334; R&D Systems), polyclonal human TIMP2 (1:1000; AF971; R&D Systems).

Probe Synthesis for In Situ Hybridization:

Mouse kidney mRNA was reverse transcribed using SuperScript® III First-Strand Synthesis SuperMix for qRT-PCR (Invitrogen), and target genes were amplified using the following primers: Timp2, Forward: 5'-gatcagagccaaagcagtgag-3' (SEQ ID NO: 11) and T7 embedded Reverse: 5'-ggattaccTAATACGACTCACTATAGGGttctctgtgacccagtccatc-3' (SEQ ID NO: 12); IGFBP7, Forward: 5'-ctctcctcttcctcctcttcg-3' (SEQ ID NO: 13) and T7 embedded Reverse: 5'-ggattaccTAATACGACTCAC-TATAGGGtgacctcacagctcaagaaca-3' (SEQ ID NO: 14); Ngal, Forward: 5'-aaaaacagaaggcagctttacg-3' (SEQ ID NO: 15) and T7 embedded Reverse: 5'-ggattaccTAATACGACT-CACTATAGGGaaagatggagtggcagacaga-3' (SEQ ID NO: 16); Pappa2, Forward: 5'-CAGAGGGAGGACAGAGCAA-3' (SEQ ID NO: 17) and T7 embedded Reverse: 5'-GGCCAGTGAATTGTAATACGACTCACTATAGG-GAGGCGG GTAAAGGTGACAGAATCTCAGG-3' (SEQ ID NO: 18); STC1, Forward: 5'-TGCTC-CAAAACTCAGCAGTG-3' (SEQ ID NO: 19), T7 embedded Reverse: 5'-GGCCAGTGAATTGTAATACGACT-CACTATAGGGAGGCGG CGCCTCCTATTGAAGTCAGC-3' (SEQ ID NO: 20); Trop2, Forward: 5'-GCAATGGGCTCACAGGTATT-3' (SEQ ID NO: 21), and T7-embedded Reverse: 5'-GGCCAGTGAATTGTAATACGACTCACTATAGG-GAGGCGG TTTGTATTTGCCCGACTTCC-3' (SEQ ID NO: 22). The PCR products were used as templates for in vitro transcription. Probes were synthesized by T7 RNA polymerase (Roche) and Digoxigenin (DIG)-labeled RNAs were subsequently purified by PureLink RNA Mini Kit (Life tech).

In situ hybridization for frozen sections: Kidneys fixed in 4% PFA, were sectioned (8 µm), air-dried for 1-3 hours, then refixed in 4% PFA for 10 minutes and treated with proteinase K (1 µg/ml), acetylated and prehybridized and hybridizations at 68-72° C. overnight in 50% formamide, 5×SSC, 5×Denhardts, 250 µg/ml baker's yeast RNA (Sigma), 500 µg/ml herring sperm DNA (Sigma). Washes were at 72° C. in 5×SSC for 5-10 minutes, then at 72° C. in 0.2×SSC for 1 hour. Sections were stained overnight with anti-digoxigenin antibody (Boehringer-Mannheim, 1:5000 dilution) and alkaline phosphatase activity detected with BCIP, NBT (Boehringer-Mannheim) and 0.25 mg/ml levamisole. Sections were dehydrated and mounted in Permount (Fisher Scientific).

REFERENCES FOR EXAMPLE 2

1. Laverty G, Skadhauge E. Adaptive strategies for postrenal handling of urine in birds. *Comp Biochem Physiol A Mol Integr Physiol.* 2008; 149(3):246-254. doi:10.1016/j.cbpa.2008.01.014.
2. Van Sant M J, Oufiero C E, Muñoz-Garcia A, Hammond K A, Williams J B. A phylogenetic approach to total evaporative water loss in mammals. *Physiol Biochem Zool.* 2012; 85(5):526-532. doi:10.1086/667579.
3. SMITH H W. The fate of sodium and water in the renal tubules. *Bull N Y Acad Med.* 1959; 35(5):293-316. www.pubmedcentral.nih.gov/articlerender.fcgi?artid=1806157&tool=pmcentrez&rendertype=abstract. Accessed May 5, 2016.
4. Brenner B M, Berliner R W. Relationship between extracellular volume and fluid reabsorption by the rat nephron. *Am J Physiol.* 1969; 217(1):6-12. www.ncbi.nlm.nih.gov/pubmed/5785902. Accessed May 6, 2016.
5. Skorecki K L, Brenner B M. Body fluid homeostasis in man. A contemporary overview. *Am J Med.* 1981; 70(1):77-88. www.ncbi.nlm.nih.gov/pubmed/7006395. Accessed May 5, 2016.
6. Feinstein E I, Quion-Verde H, Kaptein E M, Massry S G. Severe hyperuricemia in patients with volume depletion. *Am J Nephrol.* 1984; 4(2):77-80. www.ncbi.nlm.nih.gov/pubmed/6720757. Accessed May 5, 2016.
7. Uchino S, Bellomo R, Bagshaw S M, Goldsmith D. Transient azotaemia is associated with a high risk of death in hospitalized patients. *Nephrol Dial Transplant.* 2010; 25(6):1833-1839. doi:10.1093/ndt/gfp624.
8. Parikh C R, Coca S G. Acute kidney injury: defining prerenal azotemia in clinical practice and research. *Nat Rev Nephrol.* 2010; 6(11):641-642. doi:10.1038/nmeph.2010.128.
9. Kidney Disease: Improving Global Outcomes (KDIGO) Acute Kidney Injury Work Group. KDIGO Clinical Practice Guideline for Acute Kidney Injury. *Kidney Int Suppl.* 2012; 2:1-138.
10. Macedo E, Bouchard J, Soroko S H, et al. Fluid accumulation, recognition and staging of acute kidney injury in critically-ill patients. *Crit Care.* 2010; 14(3):R82. doi:10.1186/cc9004.
11. Arany I, Megyesi J K, Reusch J E B, Safirstein R L. CREB mediates ERK-induced survival of mouse renal tubular cells after oxidant stress. *Kidney Int.* 2005; 68(4):1573-1582. doi:10.1111/j.1523-1755.2005.00569.x.
12. di Mari J F, Davis R, Safirstein R L. MAPK activation determines renal epithelial cell survival during oxidative injury. *Am J Physiol.* 1999; 277(2 Pt 2):F195-F203. www.ncbi.nlm.nih.gov/pubmed/10444573. Accessed May 6, 2016.
13. Goldfarb M, Abassi Z, Rosen S, Shina A, Brezis M, Heyman S N. Compensated heart failure predisposes to outer medullary tubular injury: studies in rats. *Kidney Int.* 2001; 60(2):607-613. doi:10.1046/j.1523-1755.2001.060002607.x.
14. Gobé G, Willgoss D, Hogg N, Schoch E, Endre Z. Cell survival or death in renal tubular epithelium after ischemia-reperfusion injury. *Kidney Int.* 1999; 56(4):1299-1304. doi:10.1046/j.1523-1755.1999.00701.x.
15. Bonventre J V. Dedifferentiation and proliferation of surviving epithelial cells in acute renal failure. *J Am Soc Nephrol.* 2003; 14 Suppl 1:S55-S61. www.ncbi.nlm.nih.gov/pubmed/12761240. Accessed Mar. 24, 2016.
16. Moretti C, Frajese G V, Guccione L, et al. Androgens and body composition in the aging male. *J Endocrinol Invest.* 2005; 28(3 Suppl):56-64. www.ncbi.nlm.nih.gov/pubmed/16042362. Accessed May 6, 2016.
17. Kimmel P L, Lew S Q, Bosch J P. Nutrition, ageing and GFR: is age-associated decline inevitable? *Nephrol Dial Transplant.* 1996; 11 Suppl 9:85-88. www.ncbi.nlm.nih.gov/pubmed/9050040. Accessed May 6, 2016.
18. Musso C G, Michelángelo H, Vilas M, et al. Creatinine reabsorption by the aged kidney. *Int Urol Nephrol.* 2009; 41(3):727-731. doi:10.1007/s11255-008-9508-7.

19. Sjöström P A, Odlind B G, Wolgast M. Extensive tubular secretion and reabsorption of creatinine in humans. *Scand J Urol Nephrol.* 1988; 22(2):129-131. www.ncbi.nlm.nih.gov/pubmed/3206217. Accessed May 6, 2016.
20. Gault M H, Cockcroft D W. Letter: Creatinine clearance and age. *Lancet* (London, England). 1975; 2(7935):612-613.www.ncbi.nlm.nih.gov/pubmed/51444. Accessed May 6, 2016.
21. Cockcroft D W, Gault M H. Prediction of creatinine clearance from serum creatinine. Nephron. 1976; 16(1): 31-41. www.ncbi.nlm.nih.gov/pubmed/1244564. Accessed Feb. 26, 2015.
22. Inker L A, Schmid C H, Tighiouart H, et al. Estimating glomerular filtration rate from serum creatinine and cystatin C. *N Engl J Med.* 2012; 367(1):20-29. doi:10.1056/NEJMoa1114248.
23. Schaeffner E S, Ebert N, Delanaye P, et al. Two novel equations to estimate kidney function in persons aged 70 years or older. *Ann Intern Med.* 2012; 157(7):471-481. doi:10.7326/0003-4819-157-7-201210020-00003.
24. Sutherland S M, Byrnes J J, Kothari M, et al. AKI in hospitalized children: comparing the pRIFLE, AKIN, and KDIGO definitions. *Clin J Am Soc Nephrol.* 2015; 10(4): 554-561. doi:10.2215/CJN.01900214.
25. Sharma A, Mucino M J, Ronco C. Renal functional reserve and renal recovery after acute kidney injury. *Nephron Clin Pract.* 2014; 127(1-4):94-100. doi:10.1159/000363721.
26. Sise M E, Forster C, Singer E, et al. Urine neutrophil gelatinase-associated lipocalin identifies unilateral and bilateral urinary tract obstruction. *Nephrol Dial Transplant.* 2011; 26(12):4132-4135. doi:10.1093/ndt/gfr569.
27. Ramcharan T, Matas A J. Long-term (20-37 years) follow-up of living kidney donors. *Am J Transplant.* 2002; 2(10):959-964. www.ncbi.nlm.nih.gov/pubmed/12482149. Accessed May 6, 2016.
28. Haase M, Kellum J A, Ronco C. Subclinical AKI—an emerging syndrome with important consequences. *Nat Rev Nephrol.* 2012; 8(12):735-739. doi:10.1038/nmeph.2012.197.
29. Gamer A E, Lewington A J P, Barth J H. Detection of patients with acute kidney injury by the clinical laboratory using rises in serum creatinine: comparison of proposed definitions and a laboratory delta check. *Ann Clin Biochem.* 2012; 49(Pt 1):59-62. doi:10.1258/acb.2011.011125.
30. Lin J, Fernandez H, Shashaty M G S, et al. False-Positive Rate of AKI Using Consensus Creatinine-Based Criteria. *Clin J Am Soc Nephrol.* 2015; 10(10):1723-1731. doi:10.2215/CJN.02430315.
31. Labban B, Arora N, Restaino S, Markowitz G, Valeri A, Radhakrishnan J. The role of kidney biopsy in heart transplant candidates with kidney disease. Transplantation. 2010; 89(7):887-893. doi:10.1097/TP.0b013e3181cd4abb.
32. Bergler-Klein J, Pinch C, Laufer G, et al. The long-term effect of simultaneous heart and kidney transplantation on native renal function. *Transplantation.* 2001; 71(11): 1597-1600. www.ncbi.nlm.nih.gov/pubmed/11435971. Accessed May 6, 2016.
33. Paragas N, Qiu A, Zhang Q, et al. The Ngal reporter mouse detects the response of the kidney to injury in real time. *Nat Med.* 2011; 17(2):216-222. doi:10.1038/nm.2290.
34. Heyman S N, Evans R G, Rosen S, Rosenberger C. Cellular adaptive changes in AKI: mitigating renal hypoxic injury. *Nephrol Dial Transplant.* 2012; 27(5):1721-1728. doi:10.1093/ndt/gfs100.
35. Igarashi P. Kidney-specific gene targeting. *J Am Soc Nephrol.* 2004; 15(8):2237-2239. doi:10.1097/01.ASN.0000136298.09488.D7.
36. Dworniczak B, Skryabin B, Tchinda J, et al. Inducible Cre/loxP recombination in the mouse proximal tubule. *Nephron Exp Nephrol.* 2007; 106(1):e11-e20. doi:10.1159/000100554.
37. Mather A, Pollock C. Glucose handling by the kidney. *Kidney Int Suppl.* 2011; 79(120):S1-56. doi:10.1038/ki.2010.509.
38. Brière N, Martel M, Plante G, Petitclerc C. Heterogeneous distribution of alkaline phosphatase and gamma-glutamyl transpeptidase in the mouse nephron. *Acta Histochem.* 1984; 74(1):103-108. www.ncbi.nlm.nih.gov/pubmed/6145277. Accessed May 6, 2016.
39. Yuen P S T, Jo S-K, Holly M K, Hu X, Star R A. Ischemic and nephrotoxic acute renal failure are distinguished by their broad transcriptomic responses. *Physiol Genomics.* 2006; 25(3):375-386. doi:10.1152/physiolgenomics.00223.2005.
40. Subramanian A, Tamayo P, Mootha V K, et al. Gene set enrichment analysis: a knowledge-based approach for interpreting genome-wide expression profiles. *Proc Natl Acad Sci USA.* 2005; 102(43):15545-15550. doi:10.1073/pnas.0506580102.
41. Tarca A L, Draghici S, Khatri P, et al. A novel signaling pathway impact analysis. *Bioinformatics.* 2009; 25(1):75-82. doi:10.1093/bioinformatics/btn577.
42. Beck F-X, Neuhofer W. Response of renal medullary cells to osmotic stress. *Contrib Nephrol.* 2005; 148:21-34. doi:10.1159/000086041.
43. Vanmassenhove J, Vanholder R, Nagler E, Van Biesen W. Urinary and serum biomarkers for the diagnosis of acute kidney injury: an in-depth review of the literature. *Nephrol Dial Transplant.* 2013; 28(2):254-273. doi:10.1093/ndt/gfs380.
44. Gauer S, Sichler O, Obermüller N, et al. IL-18 is expressed in the intercalated cell of human kidney. *Kidney Int.* 2007; 72(9):1081-1087. doi:10.1038/sj.ki.5002473.
45. Mar D, Gharib S A, Zager R A, Johnson A, Denisenko O, Bomsztyk K. Heterogeneity of epigenetic changes at ischemia/reperfusion- and endotoxin-induced acute kidney injury genes. *Kidney Int.* 2015; 88(4):734-744. doi:10.1038/ki.2015.164.
46. Dennen P, Altmann C, Kaufman J, et al. Urine interleukin-6 is an early biomarker of acute kidney injury in children undergoing cardiac surgery. *Crit Care.* 2010; 14(5):R181. doi:10.1186/cc9289.
47. Lee C-T, Chen H-C, Lai L-W, Yong K-C, Lien Y-H H. Effects of furosemide on renal calcium handling. *Am J Physiol Renal Physiol.* 2007; 293(4):F1231-F1237. doi:10.1152/ajprenal.00038.2007.
48. Nickolas T L, Schmidt-Ott K M, Canetta P, et al. Diagnostic and prognostic stratification in the emergency department using urinary biomarkers of nephron damage: a multicenter prospective cohort study. *J Am Coll Cardiol.* 2012; 59(3):246-255. doi:10.1016/j.jacc.2011.10.854.
49. Nickolas T L, O'Rourke M J, Yang J, et al. Sensitivity and specificity of a single emergency department measurement of urinary neutrophil gelatinase-associated lipocalin for diagnosing acute kidney injury. *Ann Intern Med.* 2008; 148(11):810-819. doi:148/11/810 [pii].
50. Vicente-Vicente L, Ferreira L, González-Buitrago J M, López-Hernandez F J, López-Novoa J M, Morales A I. Increased urinary excretion of albumin, hemopexin, transferrin and VDBP correlates with chronic sensitization to gentamicin nephrotoxicity in rats. *Toxicology.* 2013; 304:83-91. doi:10.1016/j.tox.2012.12.006.
51. Banay-Schwartz M, Bracco F, Dahl D, Deguzman T, Turk V, Lajtha A. The pH dependence of breakdown of various purified brain proteins by cathepsin D preparations. *Neurochem Int.* 1985; 7(4):607-614. www.ncbi.nlm.nih.gov/pubmed/20492966. Accessed May 12, 2016.
52. Aregger F, Uehlinger D E, Witowski J, et al. Identification of IGFBP-7 by urinary proteomics as a novel prognostic marker in early acute kidney injury. *Kidney Int.* 2014; 85(4):909-919. doi:10.1038/ki.2013.363.
53. Svara T, Pogacnik M, Juntes P. Distribution and amount of cathepsin B in gentamicin-induced acute kidney injury in rats. *Pol J Vet Sci.* 2010; 13(1):75-82. www.ncbi.nlm.nih.gov/pubmed/21077434. Accessed May 10, 2016.
54. Bagshaw S M, Uchino S, Bellomo R, et al. Septic acute kidney injury in critically ill patients: clinical characteristics and outcomes. *Clin J Am Soc Nephrol.* 2007; 2(3):431-439. doi:10.2215/CJN.03681106.
55. Bengatta S, Arnould C, Letavernier E, et al. MMP9 and SCF protect from apoptosis in acute kidney injury. *J Am Soc Nephrol.* 2009; 20(4):787-797. doi:10.1681/ASN.2008050515.
56. Basu R K, Wang Y, Wong H R, Chawla L S, Wheeler D S, Goldstein S L. Incorporation of biomarkers with the renal angina index for prediction of severe AKI in critically ill children. *Clin J Am Soc Nephrol.* 2014; 9(4):654-662. doi:10.2215/CJN.09720913.
57. Nejat M, Pickering J W, Devarajan P, et al. Some biomarkers of acute kidney injury are increased in pre-renal acute injury. *Kidney Int.* 2012; 81(12):1254-1262. doi:10.1038/ki.2012.23.
58. Zager R A. Alterations of intravascular volume: influence on renal susceptibility to ischemic injury. *J Lab Clin Med.* 1986; 108(1):60-69. www.ncbi.nlm.nih.gov/pubmed/3711726. Accessed May 12, 2016.
59. Hood B, Attman P O, Ahlmén J, Jagenburg R. Renal hemodynamics and limitations of creatinine clearance in determining filtration rate in glomerular disease. *Scand J Urol Nephrol.* 1971; 5(2):154-161. doi:10.3109/00365597109133594.
60. Murray P T, Mehta R L, Shaw A, et al. Potential use of biomarkers in acute kidney injury: report and summary of recommendations from the 10th Acute Dialysis Quality Initiative consensus conference. *Kidney Int.* 2014; 85(3):513-521. doi:10.1038/ki.2013.374.
61. Parravicini E, Nemerofsky S L, Michelson K A, et al. Urinary neutrophil gelatinase-associated lipocalin is a promising biomarker for late onset culture-positive sepsis in very low birth weight infants. *Pediatr Res.* 2010; 67(6):636-640. doi:10.1203/PDR.0b013e3181da75c1.
62. Haase-Fielitz A, Haase M, Devarajan P. Neutrophil gelatinase-associated lipocalin as a biomarker of acute kidney injury: a critical evaluation of current status. *Ann Clin Biochem.* 2014; 51(Pt 3):335-351. doi:10.1177/0004563214521795.
63. Basu R K, Wong H R, Krawczeski C D, et al. Combining functional and tubular damage biomarkers improves diagnostic precision for acute kidney injury after cardiac surgery. *J Am Coll Cardiol.* 2014; 64(25):2753-2762. doi:10.1016/j.jacc.2014.09.066.
64. Gay L, Miller M R, Ventura P B, et al. Mouse T U tagging: a chemical/genetic intersectional method for purifying cell type-specific nascent RNA. *Genes Dev.* 2013; 27(1):98-115. doi:10.1101/gad.205278.112.
65. Humphreys B D, Valerius M T, Kobayashi A, et al. Intrinsic epithelial cells repair the kidney after injury. *Cell Stem Cell.* 2008; 2(3):284-291. doi:10.1016/j.stem.2008.01.014.
66. Cowley A W, Yang C, Kumar V, et al. Pappa2 is linked to salt-sensitive hypertension in Dahl S rats. *Physiol Genomics.* 2016; 48(1):62-72. doi:10.1152/physiolgenomics.00097.2015.
67. Christians J K, Bath A K, Amiri N. Pappa2 deletion alters IGFBPs but has little effect on glucose disposal or adiposity. *Growth Horm IGF Res.* 2015; 25(5):232-239. doi:10.1016/j.ghir.2015.07.001.
68. Yan X, Baxter R C, Firth S M. Involvement of pregnancy-associated plasma protein-A2 in insulin-like growth factor (IGF) binding protein-5 proteolysis during pregnancy: a potential mechanism for increasing IGF bioavailability. *J Clin Endocrinol Metab.* 2010; 95(3):1412-1420. doi:10.1210/jc.2009-2277.
69. Ghane Shahrbaf F, Assadi F. Drug-induced renal disorders. *J Ren Inj Prev.* 2015; 4(3):57-60. doi:10.12861/jrip.2015.12.
70. Goldfarb S, McCullough P A, McDermott J, Gay S B. Contrast-induced acute kidney injury: specialty-specific protocols for interventional radiology, diagnostic computed tomography radiology, and interventional cardiology. *Mayo Clin Proc.* 2009; 84(2):170-179. doi:10.1016/S0025-6196(11)60825-2.
71. Perazella M A. Onco-nephrology: renal toxicities of chemotherapeutic agents. *Clin J Am Soc Nephrol.* 2012; 7(10):1713-1721. doi:10.2215/CJN.02780312.
72. Trapnell C, Pachter L, Salzberg S L. TopHat: discovering splice junctions with RNA-Seq. *Bioinformatics.* 2009; 25(9):1105-1111. doi:10.1093/bioinformatics/btp120.
73. Trapnell C, Williams B A, Pertea G, et al. Transcript assembly and quantification by RNA-Seq reveals unannotated transcripts and isoform switching during cell differentiation. *Nat Biotechnol.* 2010; 28(5):511-515. doi:10.1038/nbt.1621.
74. Mortazavi A, Williams B A, McCue K, Schaeffer L, Wold B. Mapping and quantifying mammalian transcriptomes by RNA-Seq. *Nat Methods.* 2008; 5(7):621-628. doi:10.1038/nmeth.1226.
75. Robinson T J, Dinan M A, Dewhirst M, Garcia-Blanco M A, Pearson J L. SplicerAV: a tool for mining microarray expression data for changes in RNA processing. *BMC Bioinformatics.* 2010; 11(1):108. doi:10.1186/1471-2105-11-108.
76. Benjamini Y, Hochberg Y. Controlling the False Discovery Rate: A Practical and Powerful Approach to Multiple Testing. *J R Stat Soc Ser B.* 1995; 57(1):289-300. www.jstor.org/stable/2346101.
77. Kanehisa M. KEGG: Kyoto Encyclopedia of Genes and Genomes. *Nucleic Acids Res.* 2000; 28(1):27-30. doi:10.1093/nar/28.1.27.
78. Croft D, Mundo A F, Haw R, et al. The Reactome pathway knowledgebase. *Nucleic Acids Res.* 2014; 42(Database issue):D472-D477. doi:10.1093/nar/gkt1102.
79. Chen Y, Zhang Y, Yin Y, et al. SPD—a web-based secreted protein database. *Nucleic Acids Res.* 2005; 33(Database issue):D169-D173. doi:10.1093/nar/gki093.
80. Flicek P, Amode M R, Barrell D, et al. Ensembl 2014. *Nucleic Acids Res.* 2014; 42(Database issue):D749-D755. doi:10.1093/nar/gkt1196.
81. Activities at the Universal Protein Resource (UniProt). *Nucleic Acids Res.* 2014; 42(Database issue):D191-D198. doi:10.1093/nar/gkt1140.

Example 3—Novel Kidney Biomarker for Volume Depletion, with Sample Preparation

Figure 14:
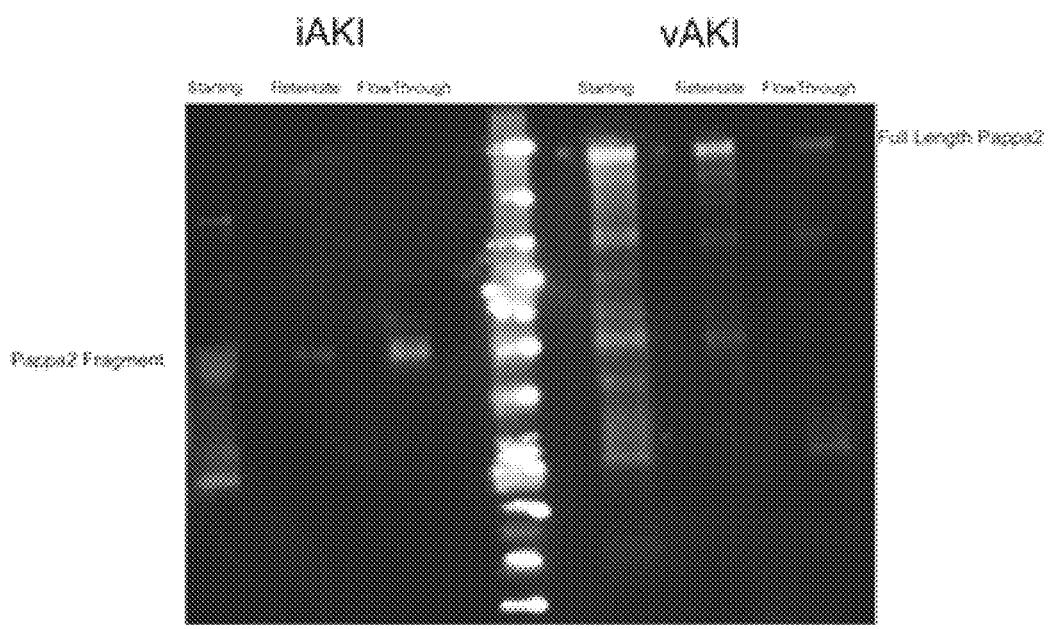
FIG. 14. Gel showing expression of PAPPA-2 in iAKI and vAKI.

As described herein, Pappa2 was identified as a marker of volume depletion. The molecular weight is approximately 250 KDa when studied in volume depletion (vAKI). In ischemic or toxic AKI (iAKI) on the other hand the 250 KDa protein appears to be degraded to 50 KDa-70 KDa (FIG. 14).

To separate these forms for analysis of the two different clinical states of vAKI and iAKI the following protocol was identified:
1. Human urine is reduced with 5% beta-mercatoethanol for 10 min at Room Temperature.
2. The sample is then subjected to filtration in a 300 KDa centrifugal device.
3. The fragment 50 KDa-70 KDa mostly passes through the filtration unit while the full length Pappa2 mostly remains in the retentate.
4. Consequently the retentate is used for assay of vAKI.

Example 4—Unique Transcriptional Programs Identify Subtypes of Acute Kidney Injury Abstract Acute kidney failure was traditionally categorized as prerenal/transient, intrinsic/prolonged (ATN), or postrenal in etiology. However, current metrics rely solely on a rise in serum creatinine (sCr), considered tantamount to Acute Kidney Injury (AKI), without distinguishing its potential etiologies or its biological heterogeneity. While there is no doubt that each form of AKI worsens patient outcomes and raises some biomarkers (1), it has remained an open question how volume related or transient 'pAKI' is related to intrinsic or prolonged 'iAKI'. Given that the biomarker NGAL (Siderocalin) is strictly predictive of iAKI rather than pAKI2-7, the alternative hypothesis is that these entities are biologically independent. To clarify their relationship, transcriptional profiling was performed in mouse models with matched sCr levels using laser capture microscopy. Thousands of genes responding to pAKI and to iAKI were found, but very few responded to both stimuli. In addition, pAKI and iAKI genes were expressed by different regions of the kidney, were members of different signal transduction pathways, were functionally unrelated, and demonstrated distinctive patterns in human urine. Hence, despite similar sCr levels, pAKI and iAKI were biologically unrelated, implying that tests for these genes will refine the definition of acute kidney failure.

The critical function of the kidney is the preservation of water and electrolytes. These functions are conserved throughout the animal kingdom from planaria to mammals[33,34]. When Na+ and water are scarce ("volume depletion"), the kidney's excretory responses decrease, causing Na+, water, and urea retention. When volume depletion is more severe, the serum creatinine, sCr, is also retained. A similar scenario occurs in the setting of non-renal diseases that mimic volume depletion such as severe congestive heart and liver failure, because similar drivers (angiotensin-aldosterone systems) and effectors of volume retention (ENac Na/KATPase and osmolytes) are activated. Adding further complexity, direct destruction of kidney epithelia by toxic stimuli (e.g. ischemia, sepsis, nephrotoxins) also blocks water, electrolyte, urea, and sCr excretion. Hence, it is not surprising that increases in urea and sCr of any etiology are associated with poor prognoses (Uchino; Chirag), but it remains challenging to prospectively distinguish these subtypes. It also remains unclear whether they induce similar types of damage to the nephron.

The duration of elevated sCr can also be quite variable. Using a series of algorithms to study 68,000 patients at the NY Presbyterian Hospital, it was found that transient azotemia (often due to volume sensitive AKI) is more common than prolonged azotemia. Transient azotemia was associated with lower rates of hyperkalemia, hyponatremia and acidosis, nephrology consult and renal replacement therapy, suggesting limited nephron dysfunction. Yet it remains unclear whether the duration of azotemia reflects different types of tubular damage.

It may be the case that elevated sCr of any etiology or duration reflects a stereotyped pattern of injured cells, and that pAKI is simply a forme-fruste of iAKI rather than an independent entity (KDIGO)[33]. Kidney biomarkers however, may begin to distinguish these subtypes (Murray and Mehta). For example, numerous studies show that NGAL is an iAKI biomarker[3,4,8] but it is poorly responsive to transient increases in sCr (≤48 hrs), or to volume deficits in patients (4)[36] or animal models[2,4]. Consequently, elevated NGAL predicted poor patient outcomes, including renal replacement therapy and in-hospital mortality[3,11] typical of iAKI, whereas low levels of NGAL was more likely associated with transient pAKI. These data implied that different AKI stimuli regulate different genetic responses.

Figure 19:
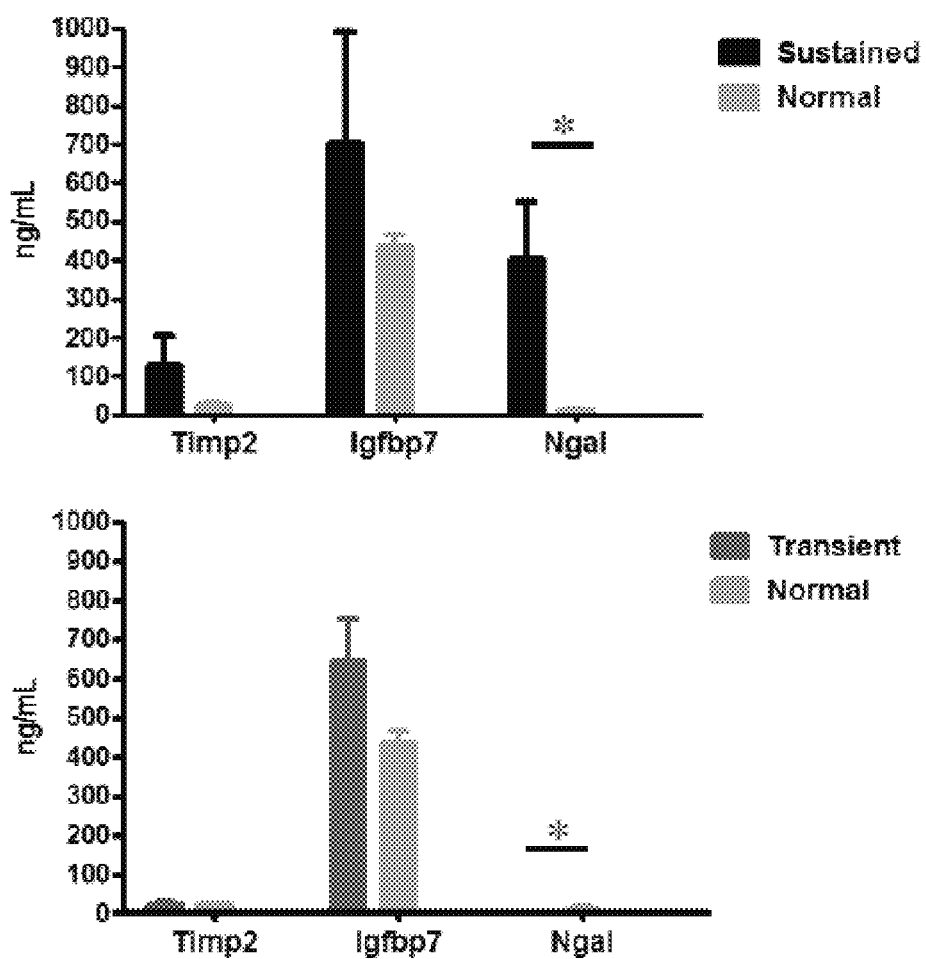
FIG. 19. Urine samples were collected from patients after surgery, while sCr kinetics were determined from the pre-operative day zero to post-operative day 7. Elevations of sCr≤48 hrs, "transient" (n=17) were analyzed separately from elevations>48 hrs "sustained" (n=11) and from patients with unchanging sCr levels "normal" (n=140). Higher levels of NGAL were associated with "sustained" increases in sCr (401±149 ng/ml) rather than "transient" (undetectable) or constant levels of sCr (12±5 ng/ml), whereas IGFBP7 and TIMP2 did not associate with either form of AKI. *p<0.05.

Additional biomarkers including Timp2 and IGFBP7 were examined in 168 general surgical patients. Immunoblots were used to identify the canonical gene products among the different molecular forms, but while NGAL correlated with sustained elevations of sCr, Timp2 and IGFBP7 could not be significantly associated with either sustained or transient elevations of sCr (FIG. 19). To better resolve these conflicting data, the kidney transcriptome was assayed at matched "RIFL-R" level of sCr, induced by either bilateral renal artery ischemia (sCr rose 1.5 fold; p=0.05) or by water deprivation[4] which in turn reduced food intake (6.2±0.3 vs 1.2±0.4 g/day; p<0.001) and raised sCr 1.9 fold (p=0.05). A variation of this model included a single dose of furosemide (50 mg/kg), which elevated sCr 1.4 fold. Remarkably, while each AKI cohort had similar sCr (p=0.18), they differed in metabolic, histologic and transcriptomic responses.

Figure 15:
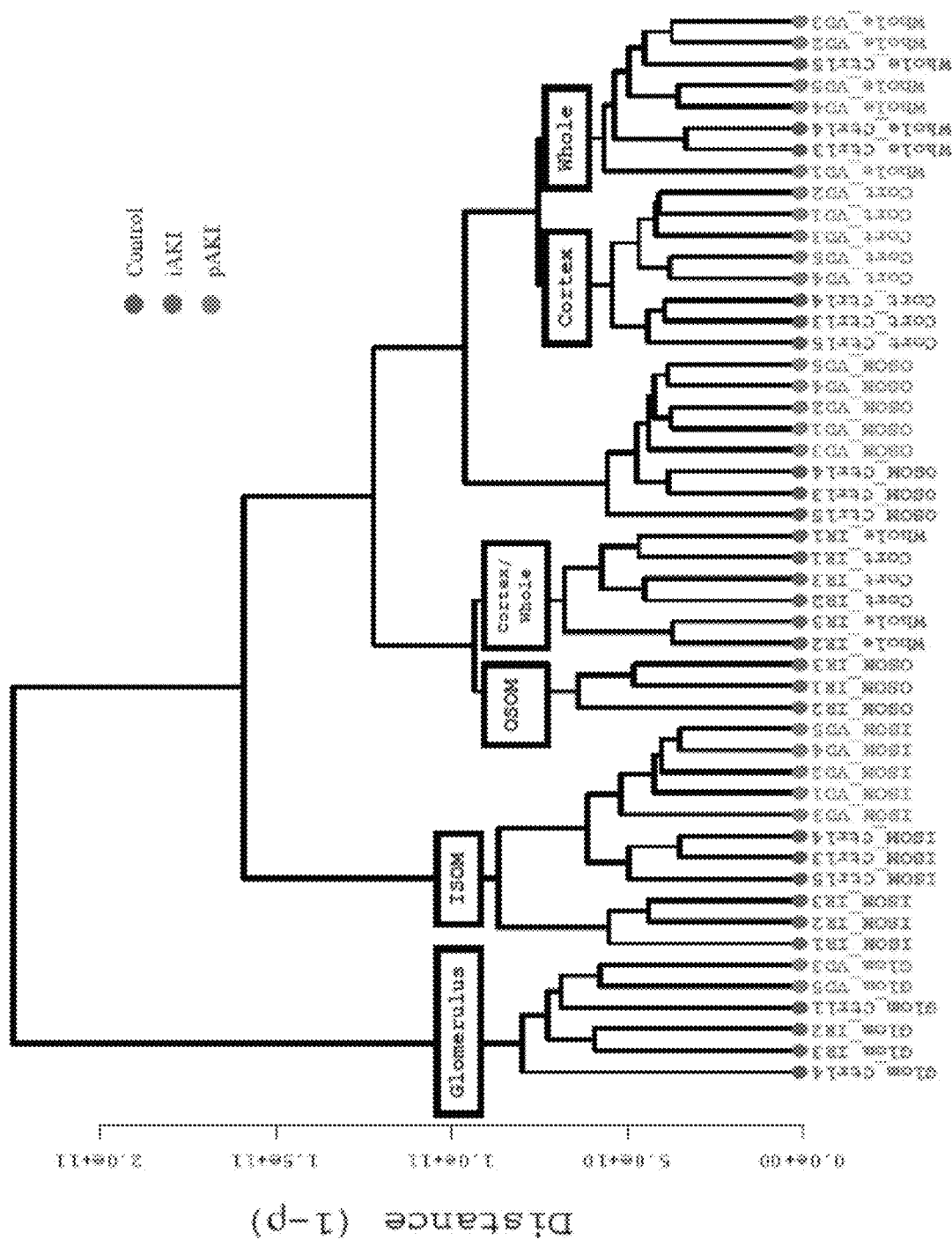
FIG. 15. Transcriptional profiles of AKI models. iAKI and pAKI models demonstrate unique and regional specific transcriptional profiles. Unsupervised hierarchical clustering analysis of mRNA sequencing of glomerulus, cortex, outer stripe of outer medulla, inner stripe of outer medulla, and whole kidney in control, after 72 hrs of volume depletion, and 24 hrs post 10 min ischemia reperfusion injury. Distance is expressed as 1—Spearman correlation (ρ). Note that genes were stratified by the specific AKI stimulus in different microanatomical regions (glomerulus and ISOM). iAKI agglomerated both the cortex and OSOM. pAKI (n=5), iAKI (n=3), and control (n=3) kidneys (50 independent samples).
Figure 16:
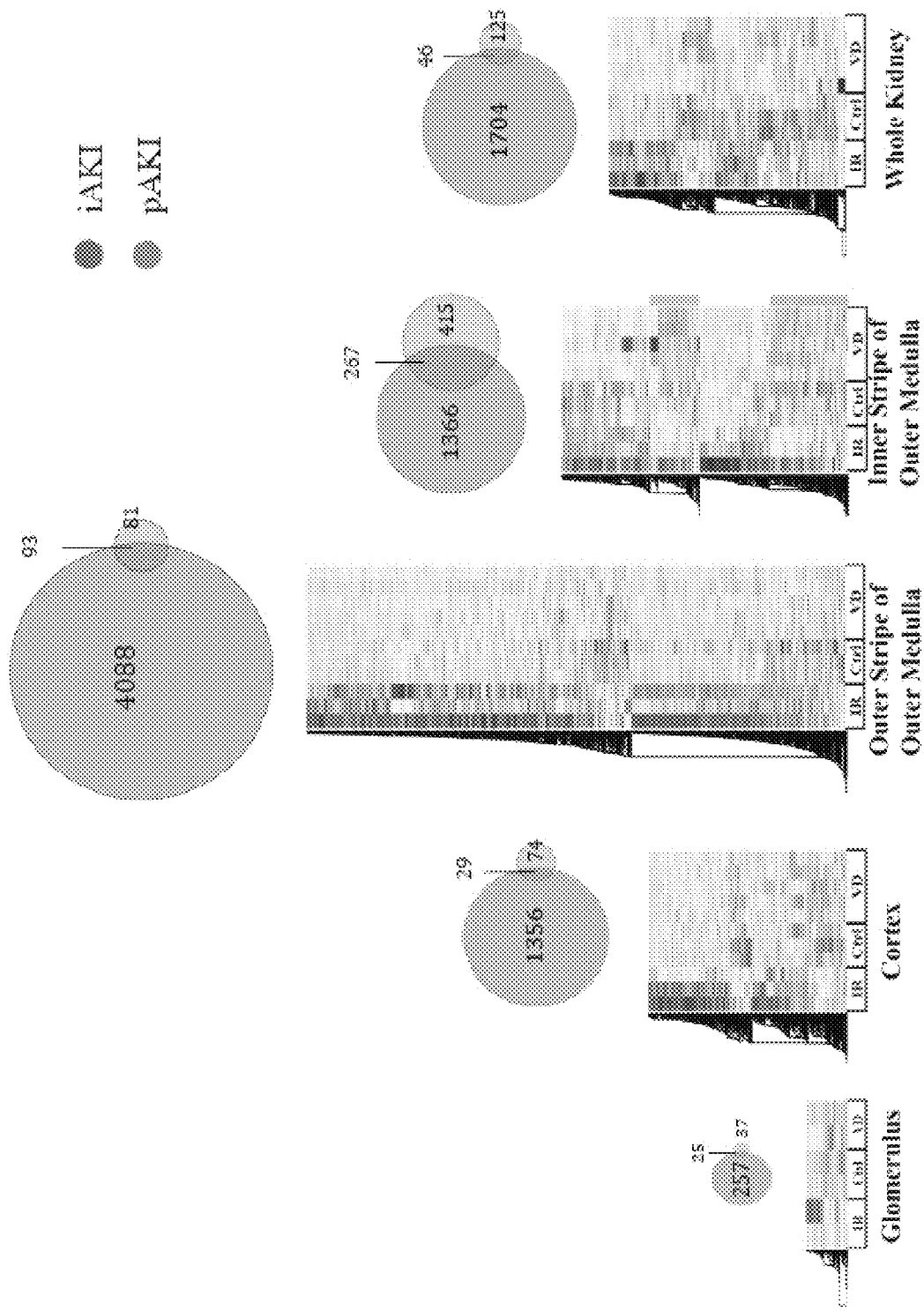
FIG. 16. Limited overlap of gene expression changes between iAKI and pAKI. Gene expression changes (q-value<0.01) localize particularly to the OSOM in iAKI and to the ISOM in pAKI. The heatmaps portray only the significant genes differentially expressed in iAKI vs. control and pAKI vs. control. Genes were hierarchically clustered and fold ranked and row normalized, and gene level expression values were z-score transformed.
Figure 17A:
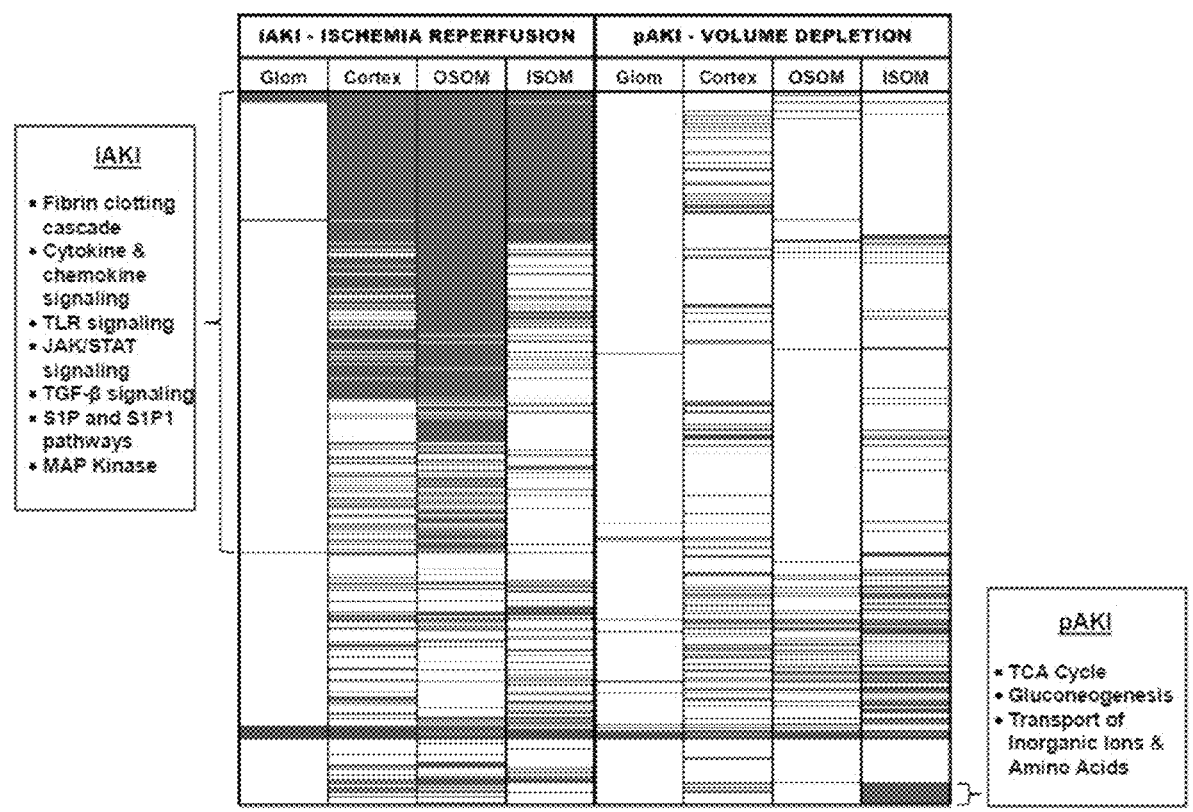
FIG. 17A. Functional analysis using Gene Set Enrichment Analysis (GSEA) against KEGG, Reactome, Biocarta, and PID Pathway Databases show different patterning of iAKI and pAKI pathways. Significant pathway enrichment is represented in red, whereas de-enrichment is represented in blue as computed with pathway guide.
Figure 17B:
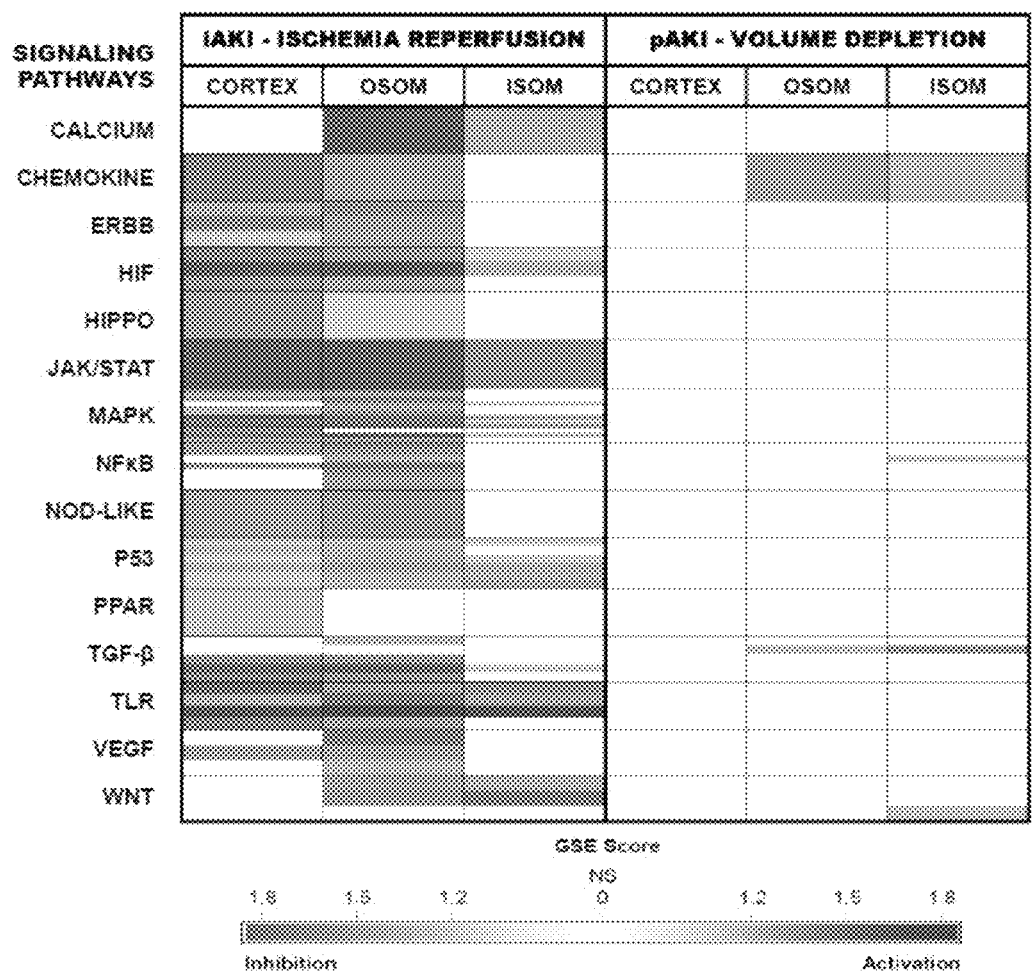
FIG. 17B. Pathway enrichment and activation analysis using GSEA and Signaling Pathway Impact Analysis (SPIA) of canonical signaling pathways. Significant pathway activation is represented in red, whereas inhibition is in green as computed with GSE Score guide. The degree of GSEA enrichment or de-enrichment is reflected in the shade of red or green.
Figure 20:
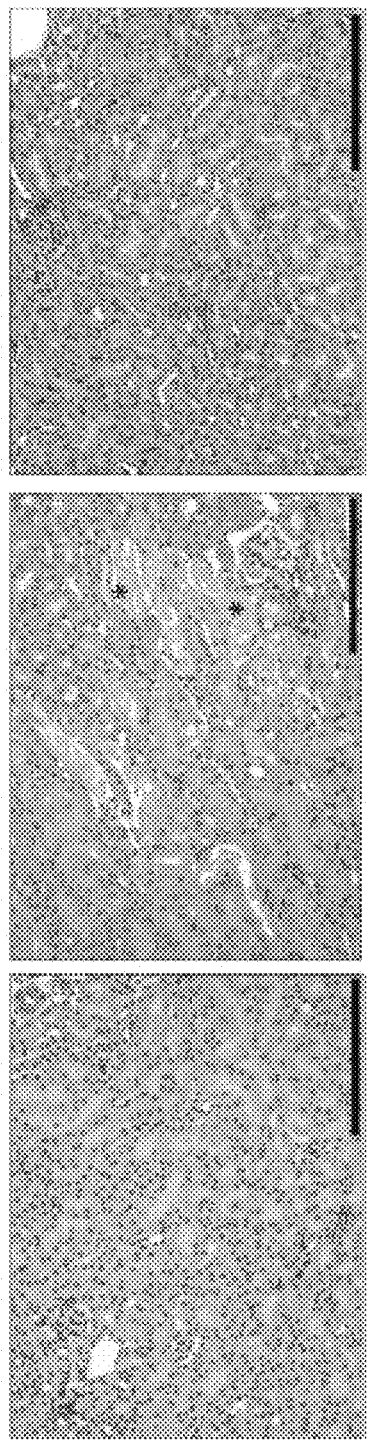
FIG. 20. Basic metabolic profiles of AKI models. 10 min ischemia 24 hrs of reperfusion versus 72 hr volume depletion demonstrate similar RIFL-R levels of sCr (control: n=3; ischemia: n=6; volume depletion: n=7). * p<0.05 vs. control; † p<0.05 vs. ischemia. Histopathology (H&E) of 10 min ischemia reperfusion demonstrate acute tubular injury, most severe in the outer stripe of the outer medulla (denoted by *straight S3 proximal tubule). In contrast, volume depletion models and littermate controls do not show evidence of acute kidney injury. Bar=250 µm.
Figure 21A:
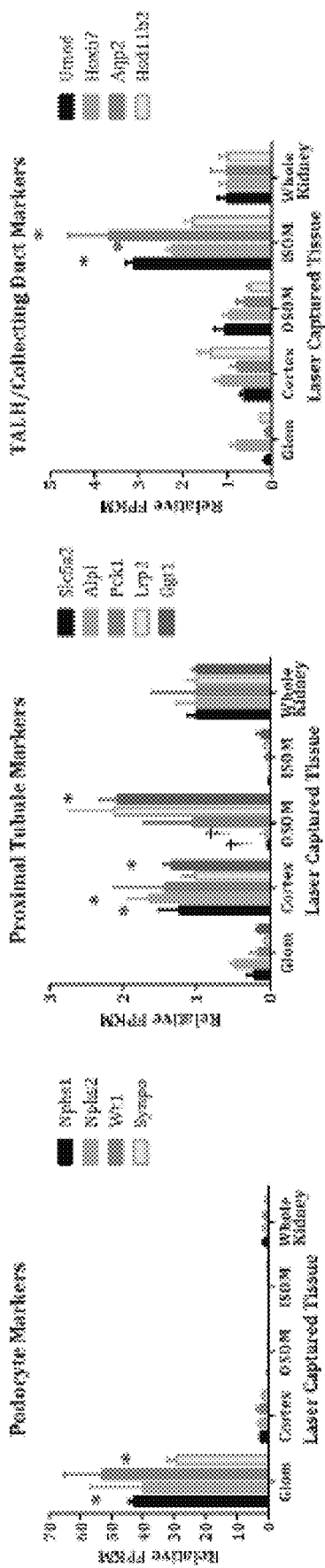
FIGS. 21A-B. Segment-Specific Markers in Laser Captured Tissues.
Figure 21B:
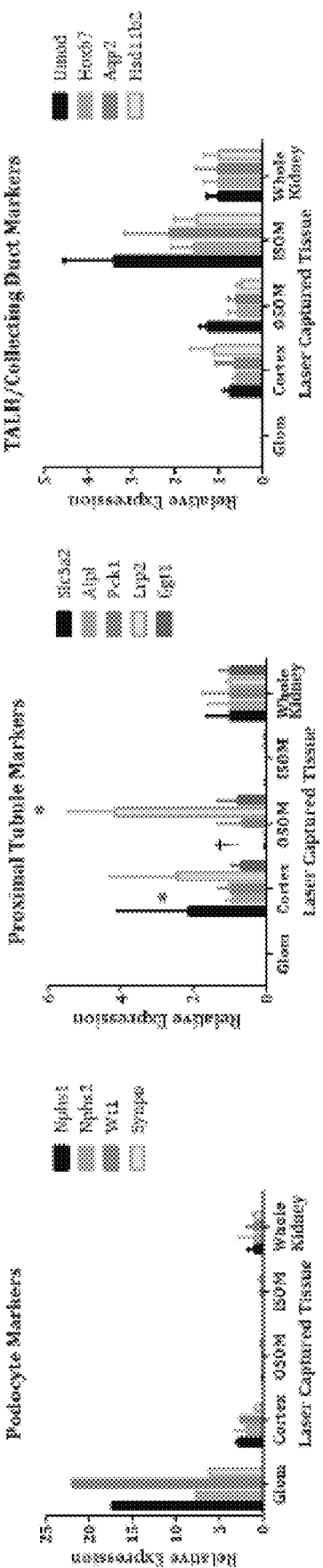

First, ischemic iAKI mice maintained weight (17.8±1.2 g vs 15.2±1.1 g; NS) and a normal BUN/Cr ratio, whereas volume depleted mice lost 21% weight (18.5±0.2 g vs 14.6±0.5 g; p<0.001), and were azotemic, hypernatremic and hemoconcentrated. Second, iAKI kidneys demonstrated coagulative necrosis at the outer edge of the OSOM, a region sensitive to ischemic damage, whereas pAKI kidneys lacked any evidence of cellular abnormalities (FIG. 20). Third, iAKI and pAKI kidneys demonstrated radically different gene profiles, which were deduced by laser capture microdissection followed by RNA-seq and comparison with segmental markers[14,15] (FIG. 21) and published transcriptomes[16] (50 independent samples were tested). Ischemic injury was the dominant agglomerative factor in Cortex, OSOM, and ISOM, whereas pAKI genes aggregated with the control set (FIG. 15). iAKI not only induced 12× more differentially expressed genes (DEGs) than did pAKI (q-value<0.01), but they were enriched in different domains (iAKI=OSOM and pAKI=ISOM) (FIG. 16). To infer functional distinctions, gene-set enrichment analysed[17] was performed (FIG. 17A) and Signaling Pathway Impact Analysis[18] which provided topological evidence of activation (FIG. 17B). iAKI modulated injury (HIPPO, ERBB, MAPK) and inflammatory (JAK/STAT, NOD Like, NFκb, TLR, and Chemokine) pathways, as well as novel Wnt and PPAR signaling, but pAKI modulated none of these pathways. Rather, a unique cluster of metabolic and mitochondrial genes mediating gluconeogenesis, citric acid cycle and amino acid metabolism involved in the organic osmolyte (betaine) response to osmotic stress[19] were enriched in the pAKI ISOM.

Figure 18A:
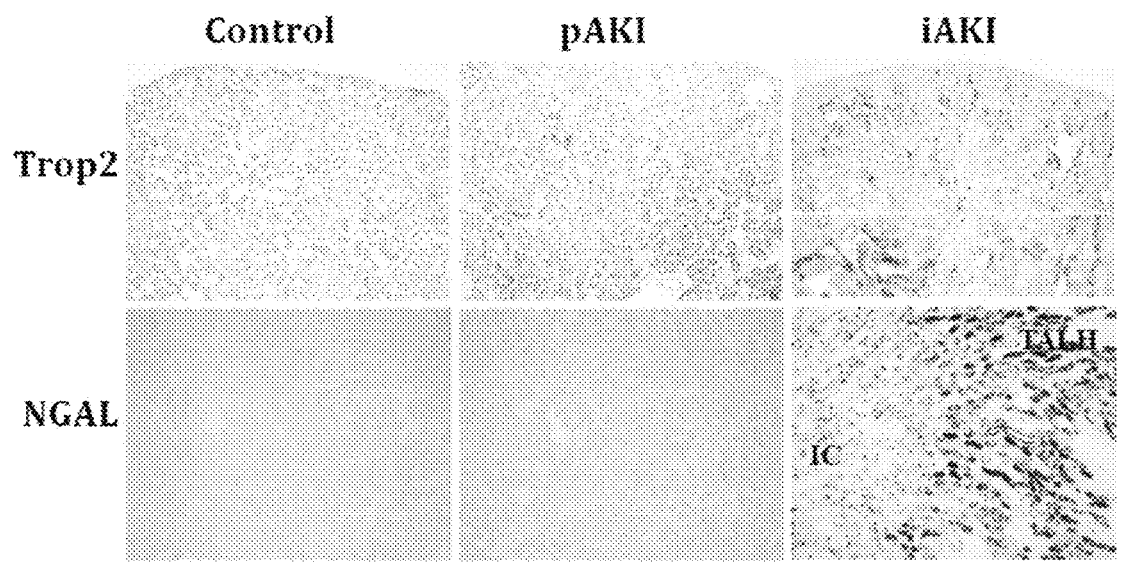
FIG. 18A. Trop2 and NGAL RNA are expressed by cortical and corticomedullary tubules after ischemia but not volume depletion, pAKI. NGAL+ tubules were identifiable as Thick Ascending Limbs of Henle (TALH) as well as Intercalated Cells (IC) of the Collecting Ducts.
Figure 18B:
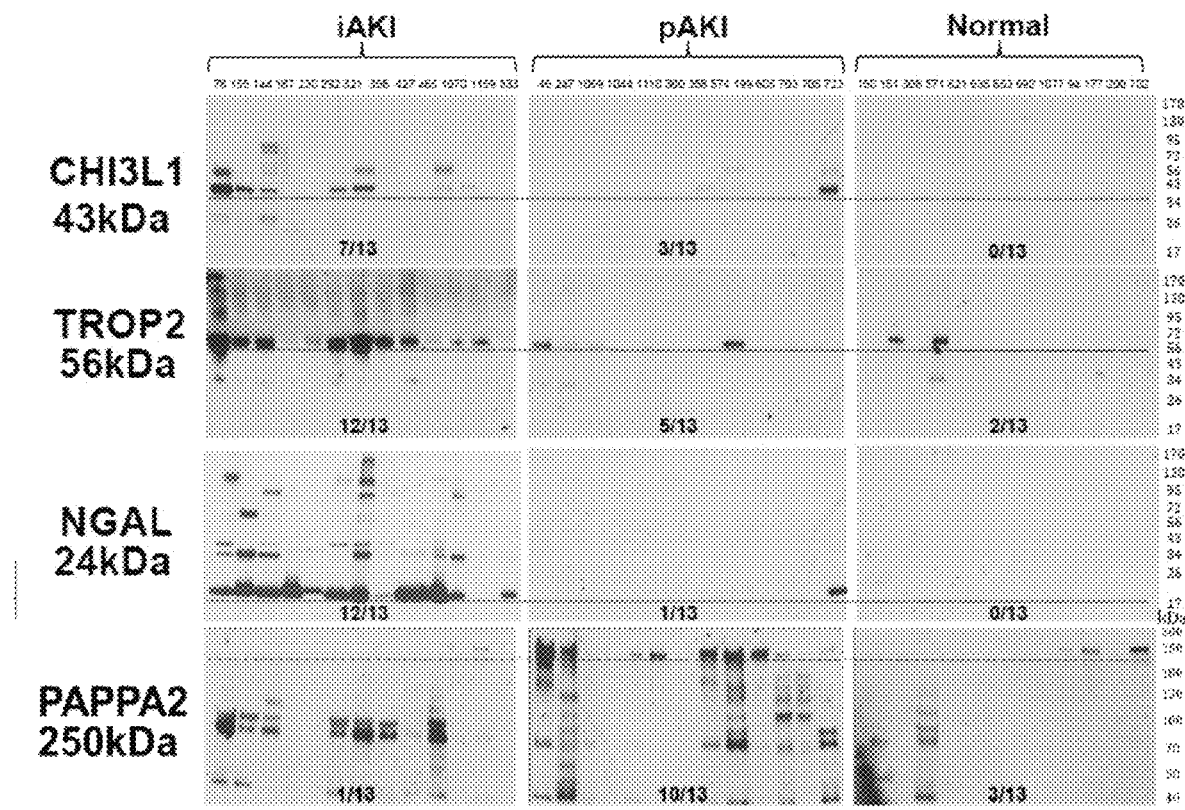
FIG. 18B. Secreted proteins (CHI3L1, TROP2, NGAL) are elevated in the urine of iAKI patients from the Emergency Department compared to pAKI patients. Conversely, secreted protein PAPPA2 is elevated in the urine of pAKI patients from the Emergency Department compared to iAKI patients.
Figure 18C:
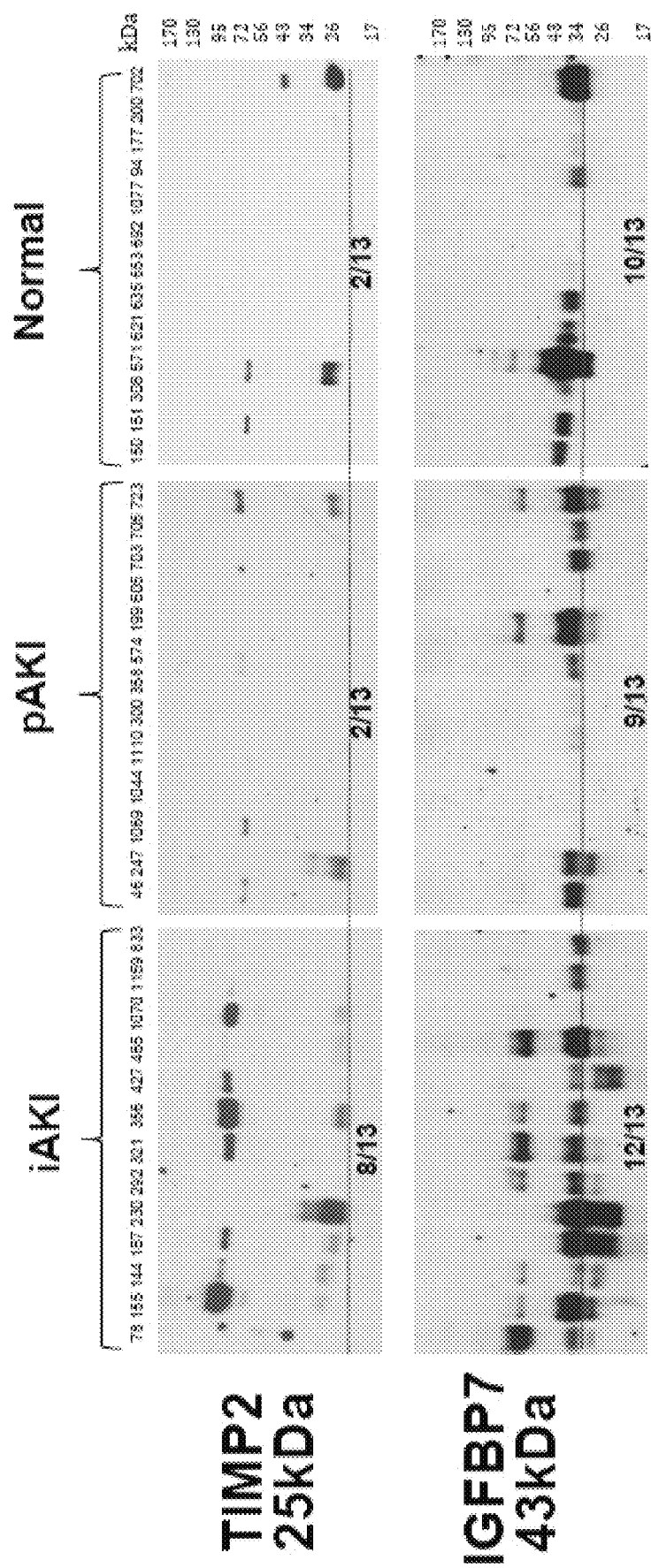
FIG. 18C. Secreted proteins (TIMP2, IGFBP7) are elevated in the urine of both iAKI and pAKI and some patients without changes in sCr from the Emergency Department.
Figure 22:
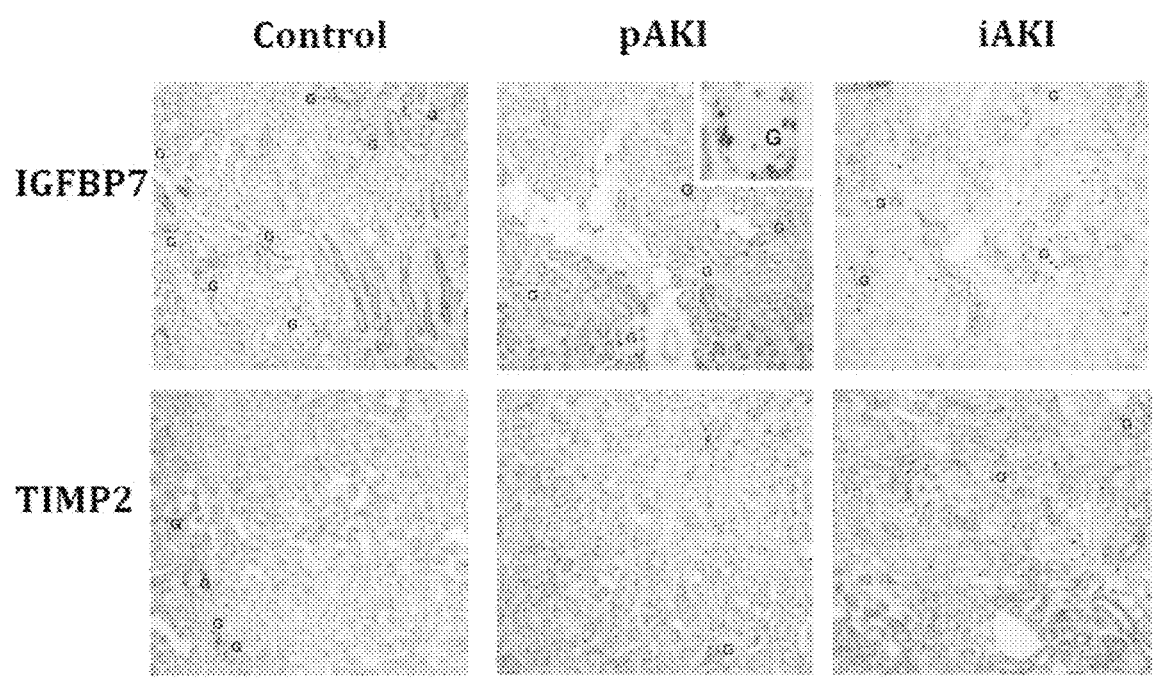
FIG. 22. In situ hybridization demonstrated no modulation of IGFBP7 and TIMP2 RNA in iAKI or pAKI. Note specific expression of these genes in scattered glomerular cells.
Figure 24:
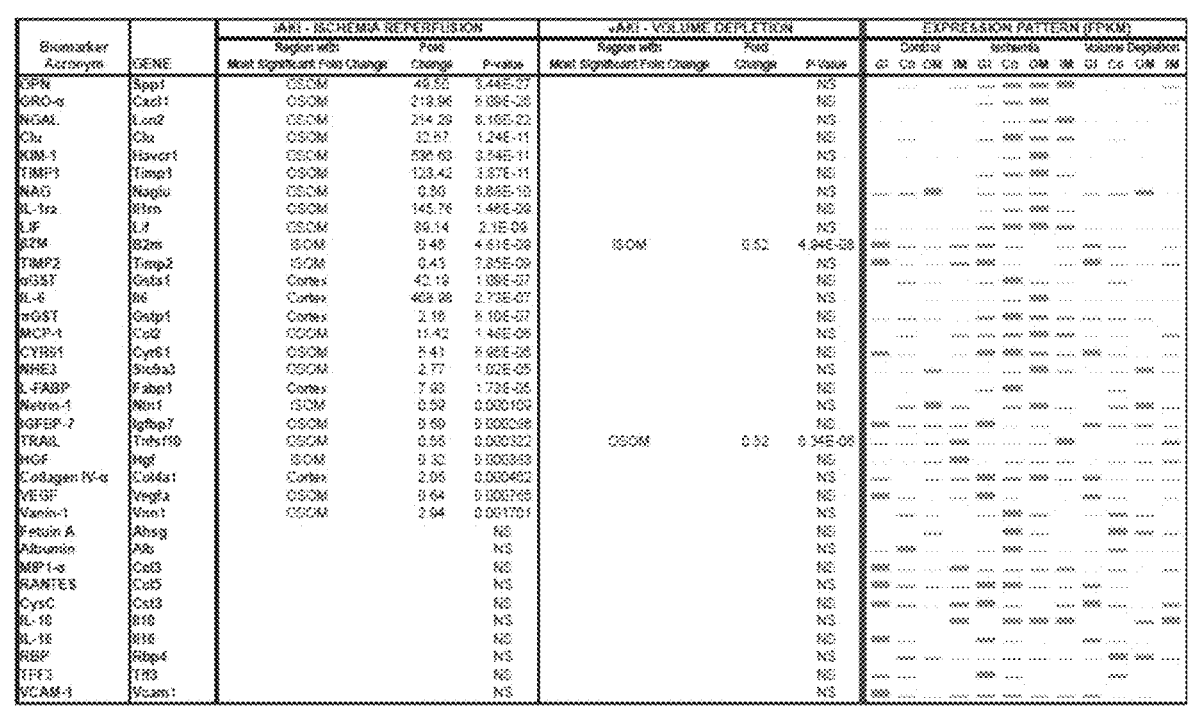
Figure 29:
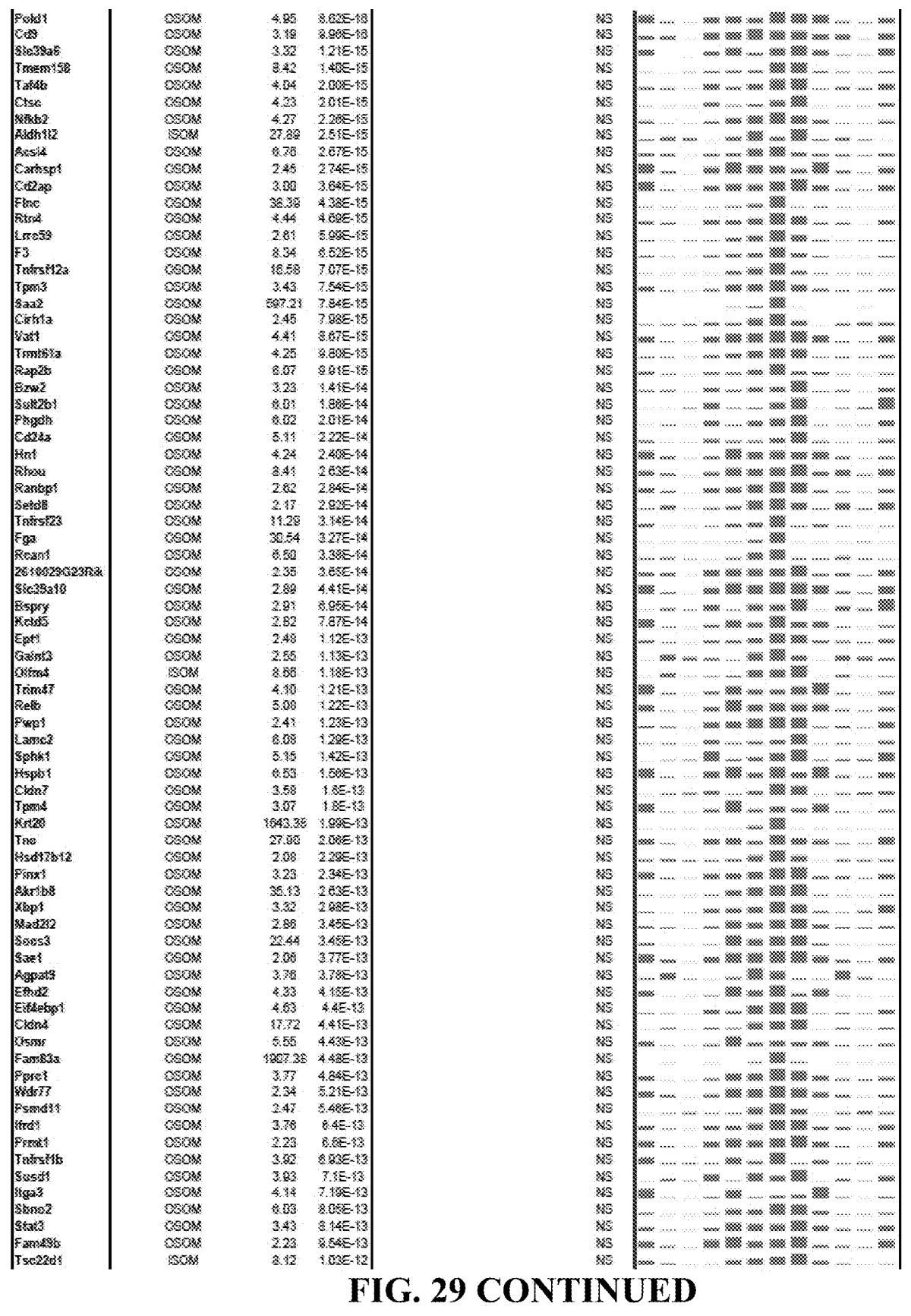
Figure 29:
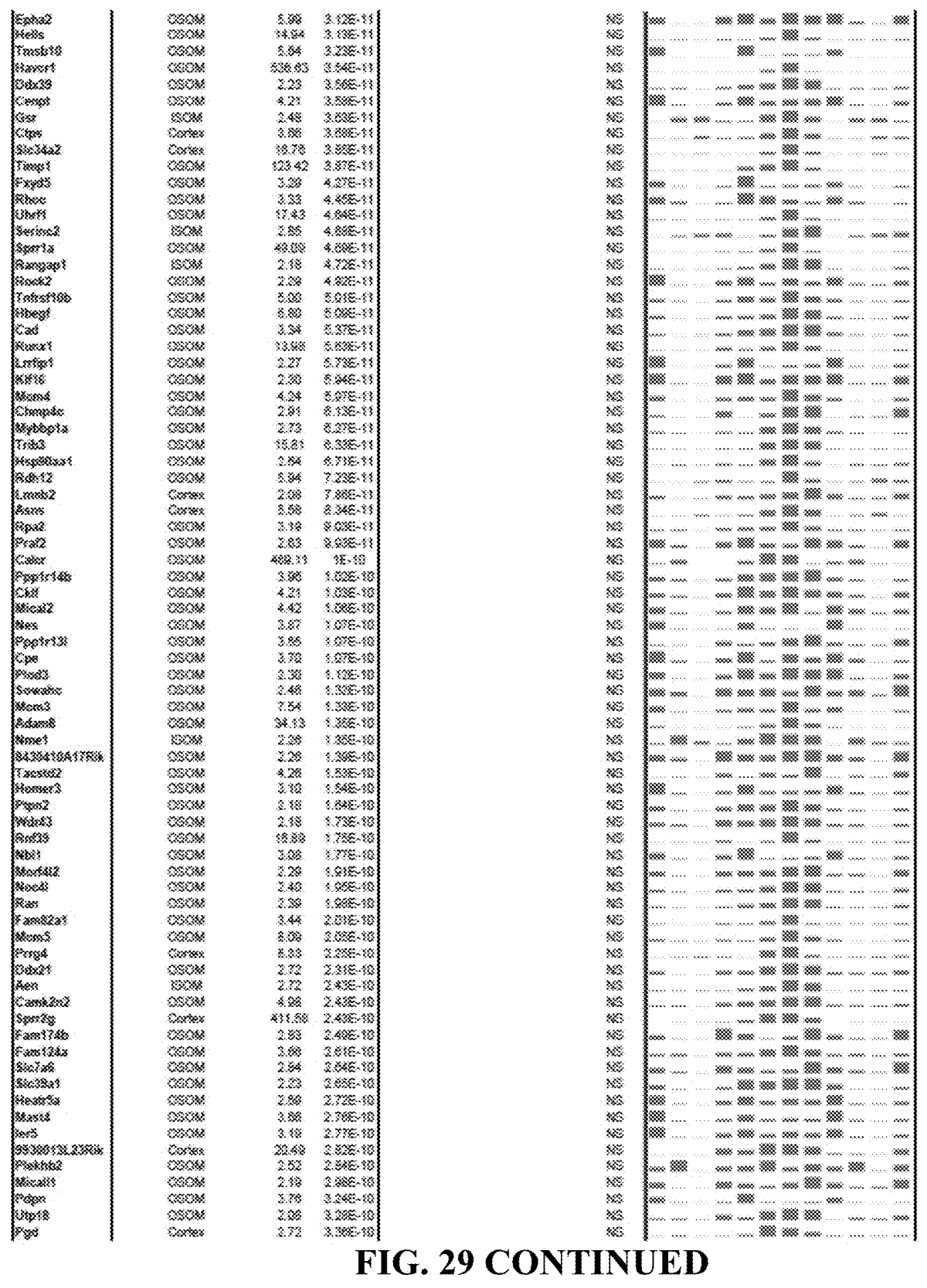
Figure 29:
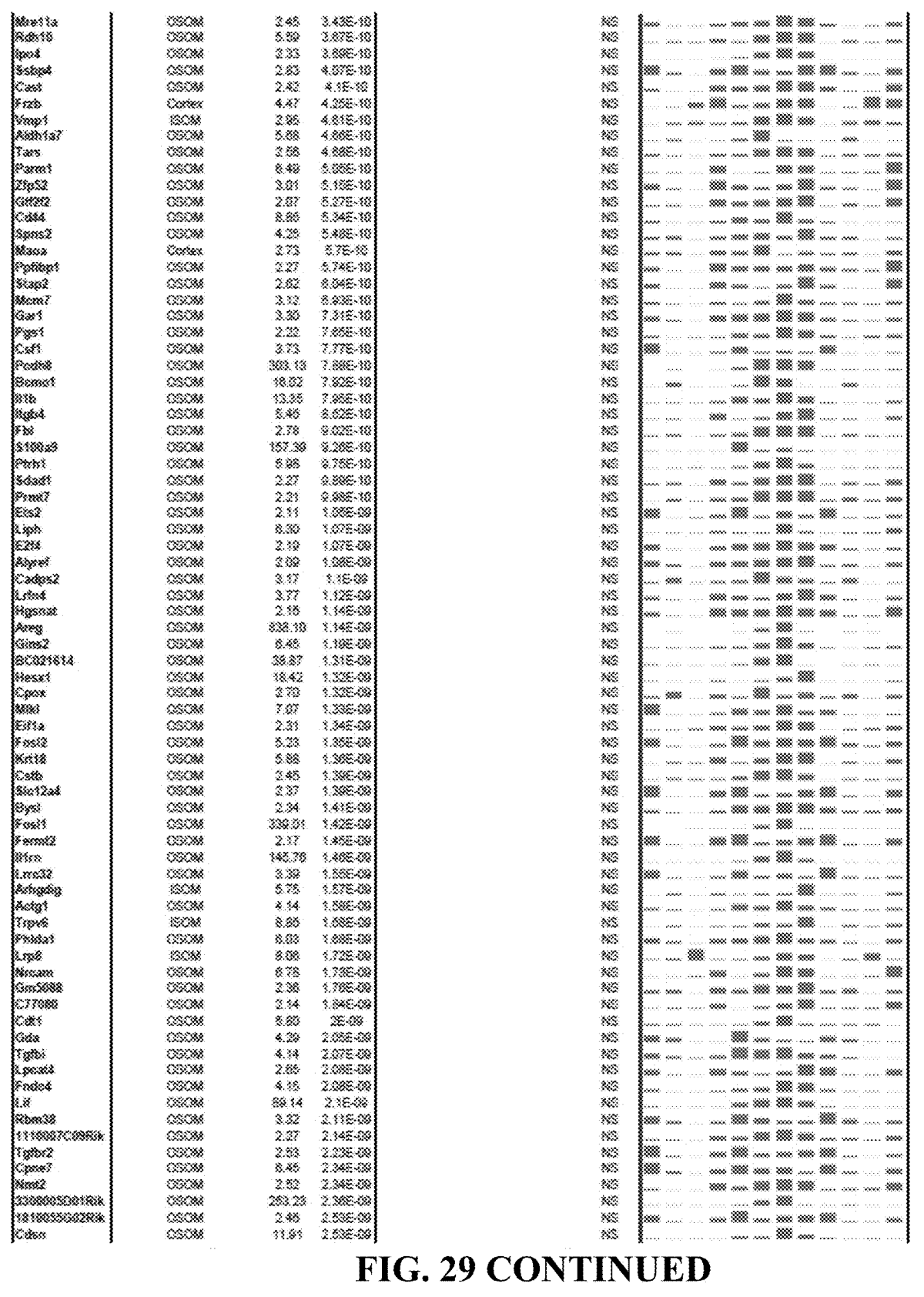

The distinction between iAKI and pAKI was confirmed by comparison with published biomarkers[20] (FIG. 24). Whereas genes with glomerular expression, Timp2, Igfbp7, Vegf, and ☐2M were surprisingly down-regulated by ischemia (FIG. 24, right), as confirmed by in situ hybridization and by urinary blots (FIG. 22), all other known biomarkers including Spp1 (OPN), Cxcl1 (GRO-α), Lcn2 (NGAL) with p-values<10-21, followed by Clu (Clusterin), Havcr1 (KIM1) and Timp1 with p-values<10-10, as well as 1,158 novel DEG's (upregulated >2-fold; p-value<10-5) were expressed by OSOM and were strictly iAKI specific (FIG. 29; FIG. 18A-C).

Figure 23:
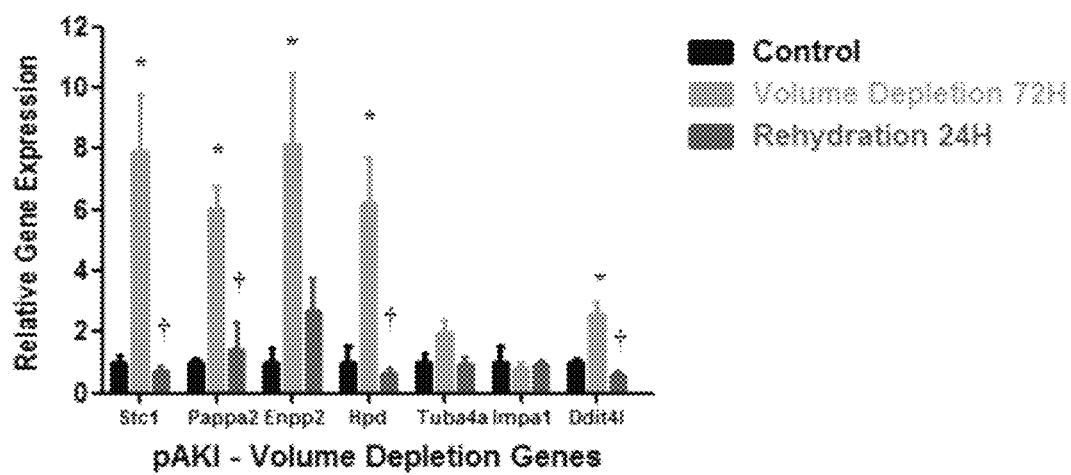
FIG. 23. Rehydration Reverses pAKI. pAKI mice (n=5) were water/food deprived for 72 hours followed by ad-libitum access to water for 24 hours. Differentially expressed pAKI genes (Stc1, Pappa2, Hpd, Enpp2) and sCr and sNa measurements returned to baseline after resuscitation.

The specificity of iAKI biomarkers raised the possibility of pAKI specific biomarkers. 103 novel pAKI DEGs were predominately associated with ISOM (FIG. 30) including Tuba4a, Stc1, Impa1, Ip6k2, Ddit4l Pappa2, Enpp2, Hpd. A model using furosemide reproducibly elevated the same pAKI genes, but not any iAKI genes. Consistent with the clinical characteristics of pAKI, refeeding and rehydration rapidly reverted pAKI genes, the sCr, and the sNa to baseline (n=5; p<0.05; FIG. 23).

Figure 31:
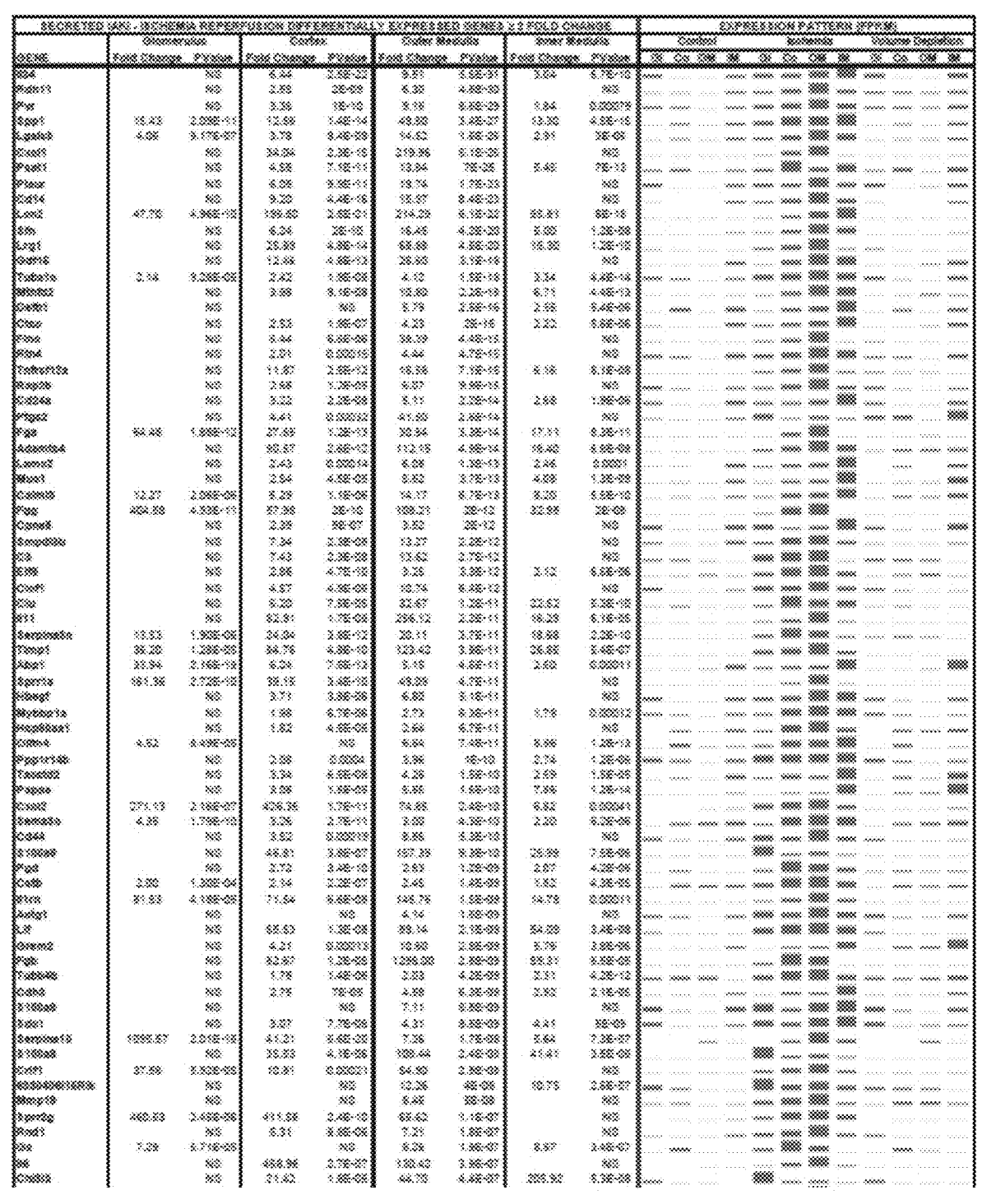
Figure 31:
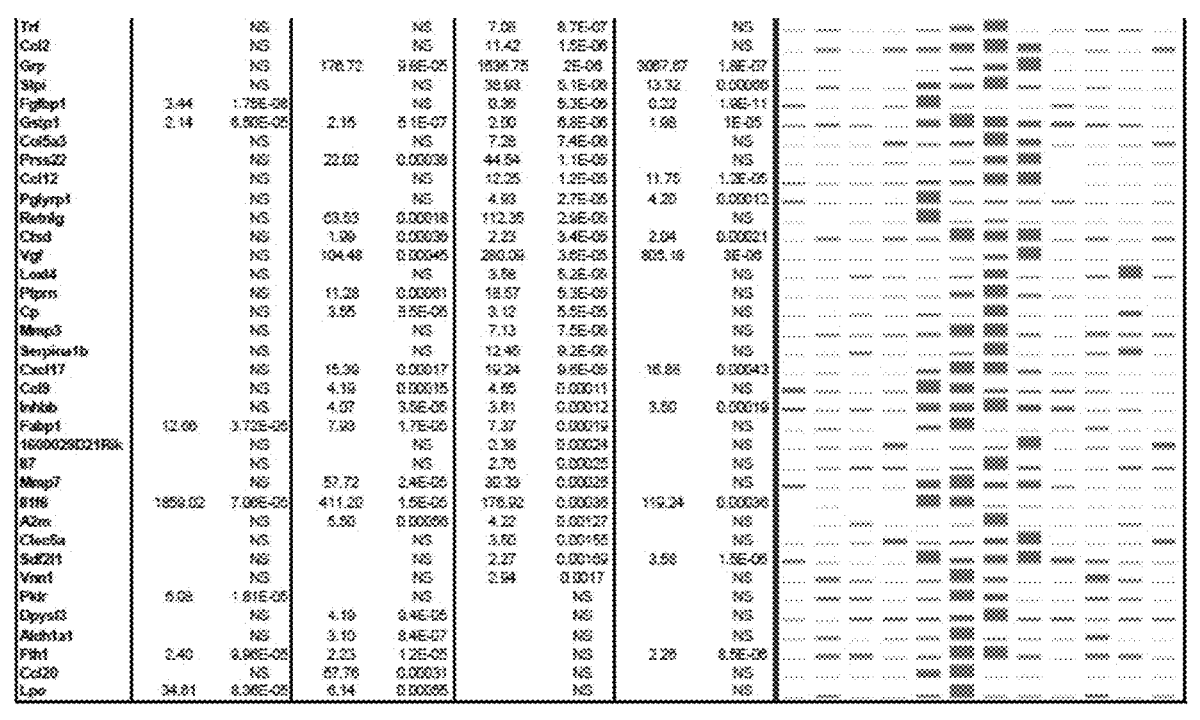

To examine whether iAKI and pAKI genes were relevant to diverse clinical presentations, the general surgery cohort as well as our extensive urinary studies in Emergency Departments and screened genes (upregulated >2-fold; p-value<$10^{-5}$) that were also referenced in the Secreted Protein Database or in the Max Plank Unified Proteome were used. 108 iAKI (FIG. 31) and 10 pAKI (FIG. 32) secreted proteins were identified. For example, iAKI candidates NGAL and CHI3L1 and TROP2 (Tacstd2) were prominently expressed by mouse iAKI kidneys (FIG. 18A) and by patients who achieved the diagnosis of iAKI rather than pAKI (FIG. 19, FIGS. 18B-C), while conversely pAKI candidate PAPPA2 was expressed in pAKI and in some normal patients but not in iAKI. TIMP2, IGFBP7 and STC1 did not demonstrate specificity.

sCr currently defines kidney injury (RIFL, AKIN, KDIGO scales)[21,22]. Yet, while tubular damage was obvious in iAKI, pAKI kidneys failed to show any evidence of injury at the same level of sCr and despite the prolonged course of our pAKI model. These findings are consistent with well known mismatches between sCr and renal pathology[33,34,35] including data that partial obstruction[33] or even kidney donation[33] may produce modest changes in Scr[41] ("subclinical AKI"[42]).

iAKI activated inflammatory and proliferation genes compatible with the repopulation of denuded cells[12] in the OSOM (1,158 novel and known iAKI genes), whereas pAKI activated metabolic and osmotic regulatory pathways, consistent with food and water scarcity in the ISOM. The specific responses of different cell types is consistent with a myriad of studies including in situ hybridization, reporter gene constructs, RNA-seq analysis, and urine measurements in mice and humans (confirmed in this paper)[2-7] as well as in rats, pigs, dogs demonstrating that NGAL was induced strictly in the ischemic domain (ie after ligation of a polar artery), by specialized intercalated and TALH cells. Hence, different environmental signals are sensed by different cells of the nephron and these cells express specific genetic programs relevant to the stimulus.

It is possible that the iAKI and pAKI models converge at a different time point or after increasing severity of pAKI. Nonetheless, it could be argued that the pAKI mice already manifest severe volume derangements already over many days. Moreover, even if further manipulation of the pAKI model were possible, sCr will no longer be matched. It is also possible that other models of pAKI (i.e. bleeding, severe heart failure) might better overlap iAKI, yet this remains to be tested especially since our two models (±diuretics) induced the same volume sensitive genes.

The distinct patterning of pAKI and iAKI genes has a number of applications including a new class of kidney biomarkers responsive to reversible volume stresses. The pAKI and iAKI genes can be tested in new bioassays for example in simple ratios of iAKI/pAKI genes (e.g. the data herein shows that sCr$^+$ and the NGAL$^-$/Pappa2$^+$ ratio rules out iAKI and indicates pAKI, whereas sCr$^+$ and NGAL$^+$/Pappa2$^-$ ratio indicates iAKI). Secondly, the data herein explains the dissociation between sCr and condition specific biomarkers. For example, the elevation of sCr by volume depletion should not be compared with an iAKI biomarker, which is not even expressed in this setting. This indiscriminate matching of different stimuli with different transcriptomes (that are molecularly and spatially distinct) inappropriately limits interpretation of these analytes. Finally, since the pAKI genes rapidly reversed with volume resuscitation, these proteins may serve as reporters to avoid fluid intoxication. In sum, the clinical, pathological, and transcriptional data provides biological evidence for new tools in the precision diagnosis in acute kidney disease.

Concise Methods

Clinical Samples.

Emergency Room urine samples were selected at random from our multicenter prospective cohort study[43], using published criteria for iAKI, pAKI and control. Patients with documented urinary tract infections and chronic kidney disease were excluded. Standard blood chemistries were collected each day for 7 days post admission. General Surgical urine samples were collected within 2-3 hours following the procedures for abdominal surgery (Whipple procedure, exploratory laparotomy, colectomy or gastric bypass surgery) or orthopedic surgery (total knee or total hip replacement and open reduction and internal fixation of hip fractures) using our published criteria for iAKI, pAKI and control. Standard blood chemistries were collected each day for 7 days post admission. Patients with evidence of UTI or chronic kidney disease were excluded.

Mouse Husbandry

Female wild-type C57Bl/6 mice, aged 10-12 weeks (Jackson Labs, Bar harbor, ME) were used according to approved protocols.

Renal Ischemia Reperfusion Injury Model

Mice were anesthetized with isoflurane and placed on a warming table to maintain a rectal temperature of 37° C. Left and right renal pedicles were clamped using microvascular clamps (Fine Science Tools, Foster City, Calif.) for 10 minutes. After the clamps were removed, reperfusion of the kidneys was visually confirmed. The kidneys and blood were harvested at 24 hrs.

Renal Volume Depletion Model.

Water was withheld from mice for 72 hours. Body weight and food intake were measured daily. Food intake was determined by weighing chow pellets and chow spillage. Kidneys were harvested and blood was collected at 72 hrs or mice were rehydrated for an additional 24 hrs.

Clinical Measurements

Serum creatinine, sodium and blood urea nitrogen, were measured using Creatinine and EC8+ cartridges read by an i-STAT Handheld (Abbott Point of Care, Princeton, N.J.).

Laser Capture Microdissection

Kidneys were fixed (4% PFA/0.1M PB at 4° C. overnight), transferred to 30% sucrose/0.1M PB (4° C. overnight), embedded in O.C.T. Compound (Tissue-Tek) and kept in −80° C. until time of sectioning. Sections of 8-10 µm (20 µm for glomeruli) were collected on nuclease-free glass slides covered with a thin membrane (Zeiss Microscopy, Thornwood, N.Y.), fixed in 70% ethanol for 30 seconds, stained with 1% cresyl violet acetate solution and dehydrated in 70% and 100% ethanol followed by air-drying for 30 minutes. Regions of interest (cortex, inner medulla, outer medulla, or glomerulus) were identified morphologically and 15-20 cross sections (for Cortex, OSOM, ISOM) or ~1500 cross sections (glomerulus) were microdissected (PALM MicroBeam, Zeiss Microscopy, Thornwood, N.Y.).

RNA Extraction and RNA Sequencing

Total RNA was isolated from segment-specific laser captured kidney sections using Ambion RNAqueous® Micro Kit (Life Technologies, Carlsbad, Calif.). RNA concentration and integrity for each sample were assessed on RNA 6000 Chips using an Agilent 2100 Bioanalyzer (Agilent Technologies, Santa Clara, Calif.). Poly-A pull-down was used to enrich mRNAs (200 ng-1 ug per sample, sample RIN was above 8.0) and then libraries were prepared using single-end 100 bp reads for each sample with Illumina TruSeq® RNA prep kits (Illumina, San Diego, Calif.). Libraries were sequenced using Illumina HiSeq2000 at Columbia Genome Center. Illumina RTA was used to perform base calling whilst CASAVA (version 1.8.2) for converting base call files (.BCL) to FASTQ format and also perform sequence adaptor trimming. Reads were then mapped to the mouse reference genome (mm9) using Tophat[23] (version 2.0.4) allowing 4 mismatches (--read-mismatches=4) and a maximum of 10 multiple hits (--max-multihits=10). The relative expression was calculated using cufflinks[24] (version 2.0.2) with default settings. Gene expression levels were normalized by library size and gene length into FPKMs[25] and log 2 transformed. Transcripts with 0 counts across all samples were removed and mathematical artifacts (e.g. negative infinites) were replaced with "NA". Statistical analysis was performed in R version 3.1.0 and additional Bioconductor packages were part of release 2.14. Unsupervised cluster analysis was performed on log 2 transformed FPKM values using Spearman correlation as distance and complete linkage as similarity method. No significant differences were seen in mRNA integrity (RIN Agilent 2100 Bioanalyzer) from different samplings and all samples passed the quality controls on post sequencing analysis.

Generation of Heatmaps

Genes that were differentially expressed in iAKI vs. control and pAKI vs. control were included. The expression data shown is the variance stabilized data generated using the DESeq package from Bioconductor according to the DESeq vignette (bioconductor.org/packages/release/bioc/html/DESeq.html, /bioconductor.org/packages/release/bioc/vignettes/DESeq/inst/doc/DESeq.pdf). Hierarchical clustering used Pearson Correlation distance plus single linkage. The variance stabilized expression values were visualized with heatmap.2 (gplots package, cran.r-project.org/web/packages/gplots/index.html).

Identification of Genes and Pathways

Differentially expressed genes were identified using edgeR package[26] version 3.6. We used Benjamini & Hochberg[27] procedure for controlling false discovery rate (FDR) of the multiple tests and accepted as significant a q-value<0.01. Enrichment analysis was performed using PathwayGuide (Advaita Corporation www.advaitabio.com/)[18] against KEGG[28] and Reactome[29] and GSEA[17] against MSigDB canonical pathways from the curated gene sets v4.0[17].

Identification of Biomarkers

Candidate biomarkers were filtered according to the Max Plank Unified Proteome, Secreted ProteinDB[30], or by prediction (signal peptide and/or without a transmembrane domain—according to Ensembl![31, 32].

Real-Time PCR Analysis

Total RNA was isolated and first-strand cDNA was synthesized with Superscript III (Invitrogen). Real-time PCR was performed using LightCycler®96 (Roche) with a SYBR green Supermix reagent (Bio-Rad) and specific primers. β-actin was quantified as an internal control. ΔΔCt was used to calculate fold amplification of transcripts.

Western Blot

Western blots used polyclonal antibodies. Briefly, Urine (8.34) was loaded on 4-15% SDS-polyacrylamide-gel, blotted using nitrocellulose (GE Healthcare, Pittsburgh, Pa.) and proteins detected using polyclonal antibodies.

Probe Synthesis for In Situ Hybridization

Mouse kidney mRNA was reverse transcribed using SuperScript® III First-Strand Synthesis SuperMix for qRT-PCR (Invitrogen), and target genes were amplified using the following primers: Timp2, Forward: 5'-gatcagagccaaagcagtgag-3' (SEQ ID NO: 11) and T7 embedded Reverse: 5'-ggattaccTAATACGACTCACTATAGGGttctctgtgacccagtccatc-3' (SEQ ID NO: 12); IGFBP7, Forward: 5'-ctctcctcttcctcctcttcg-3' (SEQ ID NO: 13) and T7 embedded Reverse: 5'-ggattaccTAATACGACTCACTATAGGG tgacctcacagctcaagaaca-3' (SEQ ID NO: 14); Ngal, Forward: 5'-aaaaacagaaggcagctttacg-3' (SEQ ID NO: 15) and T7 embedded Reverse: 5'-ggattaccTAATACGACTCAC-TATAGGGaaagatggagtggcagacaga-3' (SEQ ID NO: 16); Pappa2, Forward: 5'-CAGAGGGAGGACAGAGCAA-3' (SEQ ID NO: 17) and T7 embedded Reverse: 5'-GGCCAGTGAATTGTAATACGACTCACTATAGG-GAGGCGG GTAAAGGTGACAGAATCTCAGG-3' (SEQ ID NO: 18); STC1, Forward: 5'-TGCTC-CAAAACTCAGCAGTG-3' (SEQ ID NO: 19), T7 embedded Reverse: 5'-GGCCAGTGAATTGTAATACGACT-CACTATAGGGAGGCGG CGCCTCCTATTGAAGTCAGC-3' (SEQ ID NO: 20); Trop2, Forward: 5'-GCAATGGGCTCACAGGTATT-3' (SEQ ID NO: 21), and T7-embedded Reverse: 5'-GGCCAGTGAATTGTAATACGACTCACTATAGG-GAGGCGG TTTGTATTTGCCCGACTTCC-3' (SEQ ID NO: 22). The PCR products were used as templates for in vitro transcription. Probes were synthesized by T7 RNA polymerase (Roche) and Digoxigenin (DIG)-labeled RNAs were subsequently purified by PureLink RNA Mini Kit (Life tech).

In Situ Hybridization for Frozen Sections

Kidneys fixed in 4% PFA, were sectioned (8 µm), air-dried for 1-3 hours, then refixed in 4% PFA for 10 minutes and treated with proteinase K (1 µg/ml), acetylated and prehybridized and hybridizations at 68-72° C. overnight in 50% formamide, 5×SSC, 5×Denhardts, 250 µg/ml baker's yeast RNA (Sigma), 500 µg/ml herring sperm DNA (Sigma). Washes were at 72° C. in 5×SSC for 5-10 minutes, then at 72° C. in 0.2×SSC for 1 hour. Sections were stained over-

REFERENCES FOR EXAMPLE 4

1. Endre Z.
2. Nickolas T L, O'Rourke M J, Yang J, et al. Sensitivity and Specificity of a Single Emergency Department Measurement of Urinary Neutrophil Gelatinase—Associated Lipocalin for Diagnosing Acute Kidney Injury. Annals of internal medicine. 2008; 148(11):810-819.
3. Nickolas T L, Schmidt-Ott K M, Canetta P, et al. Diagnostic and Prognostic Stratification in the Emergency Department Using Urinary Biomarkers of Nephron Damage: A Multicenter Prospective Cohort Study. Journal of the American College of Cardiology. 2012; 59(3):246-255.
4. Paragas N, Qiu A, Zhang Q, et al. The Ngal Reporter Mouse Detects the Response of the Kidney to Injury in Real Time. Nature medicine. Jan. 16, 2011; 17(2):216-222.
5. Singer E, Elger A, Elitok S, et al. Urinary neutrophil gelatinase-associated lipocalin distinguishes pre-renal from intrinsic renal failure and predicts outcomes. Kidney international. Mar. 16, 2011; 80(4):10.1038/ki.2011.1041.
6. Belcher J M, Sanyal A J, Peixoto A J, et al. Kidney biomarkers and differential diagnosis of patients with cirrhosis and acute kidney injury. Hepatology. 2014; 60(2):622-632.
7. Basu R K, Wong H R, Krawczeski C D, et al. Combining Functional and Tubular Damage Biomarkers Improves Diagnostic Precision for Acute Kidney Injury After Cardiac Surgery. Journal of the American College of Cardiology. 2014; 64(25):2753-2762.
8. Parravicini E, Nemerofsky S L, Michelson K A, et al. Urinary Neutrophil Gelatinase-Associated Lipocalin Is a Promising Biomarker for Late Onset Culture-Positive Sepsis in Very Low Birth Weight Infants. Pediatr Res. 06//print 2010; 67(6):636-640.
9. Paragas N, Kulkarni R, Werth M, et al. α-Intercalated cells defend the urinary system from bacterial infection. The Journal of Clinical Investigation. 06/17 07/01/received 04/24/accepted 2014; 124(7):2963-2976.
10. Goetz D H, Holmes M A, Borregaard N, Bluhm M E, Raymond K N, Strong R K. The Neutrophil Lipocalin NGAL Is a Bacteriostatic Agent that Interferes with Siderophore-Mediated Iron Acquisition. Molecular Cell. 11//2002; 10(5):1033-1043.
11. Haase. 2011.
12. Humphreys B D, Valerius M T, Kobayashi A, et al. Intrinsic epithelial cells repair the kidney after injury. Cell stem cell. Mar. 6, 2008; 2(3):284-291.
13. Lee S, Huen S, Nishio H, et al. Distinct macrophage phenotypes contribute to kidney injury and repair. Journal of the American Society of Nephrology: JASN. February 2011; 22(2):317-326.
14. Igarashi P. Kidney-specific gene targeting. Journal of the American Society of Nephrology:JASN. August 2004; 15(8):2237-2239.
15. Dworniczak B, Skryabin B, Tchinda J, et al. Inducible Cre/loxP recombination in the mouse proximal tubule. Nephron. Experimental nephrology. 2007; 106(1):e11-20.
16. Yuen P S, Jo S K, Holly M K, Hu X, Star R A. Ischemic and nephrotoxic acute renal failure are distinguished by their broad transcriptomic responses. Physiological genomics. May 16, 2006; 25(3):375-386.
17. Subramanian A, Tamayo P, Mootha V K, et al. Gene set enrichment analysis: a knowledge-based approach for interpreting genome-wide expression profiles. Proceedings of the National Academy of Sciences of the United States of America. Oct. 25, 2005; 102(43):15545-15550.
18. Tarca A L, Draghici S, Khatri P, et al. A novel signaling pathway impact analysis. Bioinformatics (Oxford, England). Jan. 1, 2009; 25(1):75-82.
19. Beck F X, Neuhofer W. Response of renal medullary cells to osmotic stress. Contributions to nephrology. 2005; 148:21-34.
20. Vanmassenhove J, Vanholder R, Nagler E, Van Biesen W. Urinary and serum biomarkers for the diagnosis of acute kidney injury: an in-depth review of the literature. Nephrology, dialysis, transplantation: official publication of the European Dialysis and Transplant Association—European Renal Association. February 2013; 28(2):254-273.
21. Mehta R L, Kellum J A, Shah S V, et al. Acute Kidney Injury Network: report of an initiative to improve outcomes in acute kidney injury. Critical care (London, England). 2007; 11(2):R31.
22. Kidney Disease: Improving Global Outcomes (KDIGO) Acute Kidney Injury Work Group. KDIGO Clinical Practice Guideline for Acute Kidney Injury. Kidney International. Suppl. 2012(2):1-138.
23. Trapnell C, Pachter L, Salzberg S L. TopHat: discovering splice junctions with RNA-Seq. Bioinformatics (Oxford, England). May 1, 2009; 25(9):1105-1111.
24. Trapnell C, Williams B A, Pertea G, et al. Transcript assembly and quantification by RNA-Seq reveals unannotated transcripts and isoform switching during cell differentiation. Nature biotechnology. May 2010; 28(5): 511-515.
25. Mortazavi A, Williams B A, McCue K, Schaeffer L, Wold B. Mapping and quantifying mammalian transcriptomes by RNA-Seq. Nature methods. July 2008; 5(7): 621-628.
26. Robinson T J, Dinan M A, Dewhirst M, Garcia-Blanco M A, Pearson J L. SplicerAV: a tool for mining microarray expression data for changes in RNA processing. BMC bioinformatics. 2010; 11:108.
27. Benjamini Y, Hochberg Y. Controlling the False Discovery Rate: A Practical and Powerful Approach to Multiple Testing. Journal of the Royal Statistical Society. Series B (Methodological). 1995; 57(1):289-300.
28. Kanehisa M, Goto S. KEGG: kyoto encyclopedia of genes and genomes. Nucleic acids research. Jan. 1, 2000; 28(1):27-30.
29. Croft D, Mundo A F, Haw R, et al. The Reactome pathway knowledgebase. Nucleic acids research. January 2014; 42(Database issue):D472-477.
30. Chen Y, Zhang Y, Yin Y, et al. SPD—a web-based secreted protein database. Nucleic acids research. Jan. 1, 2005; 33(Database issue):D169-173.
31. Flicek P, Amode M R, Barrell D, et al. Ensembl 2014. Nucleic acids research. January 2014; 42(Database issue): D749-755.
32. Activities at the Universal Protein Resource (UniProt). Nucleic acids research. January 2014; 42(Database issue): D191-198.
33. Van Sant M J, Oufiero C E, Muñoz-Garcia A, Hammond K A, Williams J B. A phylogenetic approach to total evaporative water loss in mammals. Physiol Biochem 34. Laverty G, Skadhauge E. Adaptive strategies for post-renal handling of urine in birds. Comp Biochem Physiol A Mol Integr Physiol. 2008 March; 149(3):246-54. doi: 10.1016/j.cbpa.2008.01.014. Epub 2008 Jan. 18. Review. PubMed PMID: 18276178.
35. Kidney Disease: Improving Global Outcomes (KDIGO) Acute Kidney Injury Work Group. KDIGO Clinical Practice Guideline for Acute Kidney Injury. Kidney inter., Suppl. 2012; 2: 1-138.
36. Labban B, Arora N, Restaino S, Markowitz G, Valeri A, Radhakrishnan J. The role of kidney biopsy in heart transplant candidates with kidney disease. Transplantation. 2010 Apr. 15; 89(7):887-93. doi: 10.1097/TP.0b013e3181cd4abb. PubMed PMID: 20220572.
37. Bergler-Klein J, Pinch C, Laufer G, Grimm M, Regele H, Mayer G, Oberbauer R. The long-term effect of simultaneous heart and kidney transplantation on native renal function. Transplantation. 2001 Jun. 15; 71(11): 1597-600. PubMed PMID:11435971.
38. Parikh C R, Coca S G. Acute kidney injury: defining prerenal azotemia in clinical practice and research. Nat Rev Nephrol. 2010 November; 6(11):641-2. doi:10.1038/nrneph.2010.128. PubMed PMID: 20981121.
39. Sise M E, Forster C, Singer E, Sola-Del Valle D, Hahn B, Schmidt-Ott K M, Barasch J, Nickolas T L. Urine neutrophil gelatinase-associated lipocalin identifies unilateral and bilateral urinary tract obstruction. Nephrol Dial Transplant. 2011 December; 26(12):4132-5. doi: 10.1093/ndt/gfr569. Epub 2011 Nov. 1. PubMed PMID: 22049182; PubMed Central PMCID: PMC3254163.
40. Ramcharan T, Matas A J. Long-term (20-37 years) follow-up of living kidney donors. Am J Transplant. 2002 November; 2(10):959-64. PubMed PMID: 12482149.
41. Hood B, Attman P O, Ahlmén J, Jagenburg R. Renal hemodynamics and limitations of creatinine clearance in determining filtration rate in glomerular disease. Scand J Urol Nephrol. 1971; 5(2):154-61. PubMed PMID: 4937335.
42. Haase M, Kellum J A, Ronco C. Subclinical AKI—an emerging syndrome with important consequences. *Nat Rev* Nephrol. 2012 December; 8(12):735-9. doi: 10.1038/nrneph.2012.197. Epub 2012 Sep. 25. PubMed PMID: 23007617.
43. Nickolas T L, Schmidt-Ott K M, Canetta P, Forster C, Singer E, Sise M, Elger A, Maarouf O, Sola-Del Valle D A, O'Rourke M, Sherman E, Lee P, Geara A, Imus P, Guddati A, Polland A, Rahman W, Elitok S, Malik N, Giglio J, El-Sayegh S, Devarajan P, Hebbar S, Saggi S J, Hahn B, Kettritz R, Luft F C, Barasch J. Diagnostic and prognostic stratification in the emergency department using urinary biomarkers of nephron damage: a multi-center prospective cohort study. J Am Coll Cardiol. 2012 Jan. 17; 59(3):246-55. doi: 10.1016/j.jacc.2011.10.854. PubMed PMID: 22240130; PubMed Central PMCID: PMC3487165.

What is claimed is:

1. A method for treating volume-dependent acute kidney injury (vAKI) in a subject in need thereof, the method comprising:
   a) determining the level of full-length Pappalysin-2 (PAPPA2) protein in a urine sample from the subject;
   b) determining the level of proteolytically cleaved PAPPA2 protein in a urine sample from the subject;
   c) determining the level of Neutrophil Gelatinase Associated Lipocalin (NGAL), Cytokeratin 20 (KRT20), or Tumor-associated calcium signal transducer 2 (TACSTD2) protein, or a combination thereof, in the urine sample from the subject;
   d) determining the ratio of full-length PAPPA2/proteolytically cleaved PAPPA2, full-length PAPPA2/NGAL, full-length PAPPA2/KRT20, or full-length PAPPA2/TACSTD2 in the urine sample from the subject;
   e) determining the level of full-length PAPPA2 protein in a urine sample from a subject that does not have AKI;
   f) determining the level of proteolytically cleaved PAPPA2 protein in a urine sample from the subject that does not have AKI;
   g) determining the level of NGAL, KRT20, or TACSTD2 protein, or a combination thereof, in a urine sample from a subject that does not have AKI;
   h) determining the ratio of full-length PAPPA2/proteolytically cleaved PAPPA2, full-length PAPPA2/NGAL, full-length PAPPA2/KRT20, or full-length PAPPA2/TACSTD2 in the urine sample from the subject that does not have AKI; and
   i) administering fluids to the subject if the ratio of full-length PAPPA2/proteolytically cleaved PAPPA2, full-length PAPPA2/NGAL, full-length PAPPA2/KRT20, or full-length PAPPA2/TACSTD2 in the urine sample from the subject is greater than the ratio of full-length PAPPA2/proteolytically cleaved PAPPA2, full-length PAPPA2/NGAL, full-length PAPPA2/KRT20, or full-length PAPPA2/TACSTD2 in the urine sample from a subject that does not have AKI, respectively.

2. The method of claim 1, wherein the size of full-length PAPPA2 is equal to or above 180 kDa.

3. The method of claim 1, wherein the size of proteolytically cleaved PAPPA2 is equal to or below 130 kDa.

4. The method of claim 1, further comprising determining the level of serum creatinine in the subject.

5. The method of claim 4, wherein fluids are administered to the subject if the subject additionally has a level of serum creatinine above 0.5 mg/dL.

6. The method of claim 1, further comprising, prior to step a), reducing a urine sample from a subject with a reducing agent to generate a reduced urine sample, filtering the reduced urine sample with a 300 KDa filter to produce a retentate and a filtrate, wherein step a) and/or e) is then performed on the retentate.

7. The method of claim 1, wherein the level of full-length PAPPA2, proteolytically cleaved PAPPA2, NGAL, KRT20, or TACSTD2 protein is determined by ELISA, immunoblot, Western blot, or lateral flow dip stick.

8. The method of claim 1, wherein the level of full-length PAPPA2, proteolytically cleaved PAPPA2, NGAL, KRT20, or TACSTD2 protein is determined using an antibody that specifically binds to full-length PAPPA2, proteolytically cleaved PAPPA2, NGAL, KRT20, or TACSTD2 protein, respectively, or a fragment thereof.

9. The method of claim 1, wherein the determining the level of full-length PAPPA2, proteolytically cleaved PAPPA2, NGAL, KRT20, or TACSTD2 protein in a urine sample from a subject comprises:
   (a) obtaining a urine sample from the subject; and
   (b) measuring full-length PAPPA2, proteolytically cleaved PAPPA2, NGAL, KRT20, or TACSTD2 protein levels by ELISA using an antibody directed to SEQ ID NO: 1, 2, 5, 7, or 9, or a fragment thereof; or by western blot using an antibody directed to SEQ ID NO: 1, 2, 5, 7, or 9, or a fragment thereof; or by mass spectroscopy; or by isoelectric focusing, or a combination thereof.

10. The method of claim 1, wherein the fluids comprise saline, blood, or an albumin infusion, or any combination thereof.

11. The method of claim 1, wherein the administering is done intravenously.

* * * * *

SEQUENCE LISTING

```
<160> NUMBER OF SEQ ID NOS: 22

<210> SEQ ID NO 1
<211> LENGTH: 1791
<212> TYPE: PRT
<213> ORGANISM: Homo sapiens

<400> SEQUENCE: 1

Met Met Cys Leu Lys Ile Leu Arg Ile Ser Leu Ala Ile Leu Ala Gly
1               5                   10                  15

Trp Ala Leu Cys Ser Ala Asn Ser Glu Leu Gly Trp Thr Arg Lys Lys
            20                  25                  30

Ser Leu Val Glu Arg Glu His Leu Asn Gln Val Leu Leu Glu Gly Glu
        35                  40                  45

Arg Cys Trp Leu Gly Ala Lys Val Arg Arg Pro Arg Ala Ser Pro Gln
    50                  55                  60

His His Leu Phe Gly Val Tyr Pro Ser Arg Ala Gly Asn Tyr Leu Arg
65                  70                  75                  80

Pro Tyr Pro Val Gly Glu Gln Glu Ile His His Thr Gly Arg Ser Lys
                85                  90                  95

Pro Asp Thr Glu Gly Asn Ala Val Ser Leu Val Pro Pro Asp Leu Thr
            100                 105                 110

Glu Asn Pro Ala Gly Leu Arg Gly Ala Val Glu Glu Pro Ala Ala Pro
        115                 120                 125

Trp Val Gly Asp Ser Pro Ile Gly Gln Ser Glu Leu Leu Gly Asp Asp
    130                 135                 140

Asp Ala Tyr Leu Gly Asn Gln Arg Ser Lys Glu Ser Leu Gly Glu Ala
145                 150                 155                 160

Gly Ile Gln Lys Gly Ser Ala Met Ala Ala Thr Thr Thr Ala Ile
                165                 170                 175
```

Phe Thr Thr Leu Asn Glu Pro Lys Pro Glu Thr Gln Arg Arg Gly Trp
            180                 185                 190

Ala Lys Ser Arg Gln Arg Arg Gln Val Trp Lys Arg Arg Ala Glu Asp
            195                 200                 205

Gly Gln Gly Asp Ser Gly Ile Ser Ser His Phe Gln Pro Trp Pro Lys
            210                 215                 220

His Ser Leu Lys His Arg Val Lys Lys Ser Pro Pro Glu Glu Ser Asn
225                 230                 235                 240

Gln Asn Gly Gly Glu Gly Ser Tyr Arg Glu Ala Glu Thr Phe Asn Ser
                245                 250                 255

Gln Val Gly Leu Pro Ile Leu Tyr Phe Ser Gly Arg Arg Glu Arg Leu
            260                 265                 270

Leu Leu Arg Pro Glu Val Leu Ala Glu Ile Pro Arg Glu Ala Phe Thr
            275                 280                 285

Val Glu Ala Trp Val Lys Pro Glu Gly Gly Gln Asn Asn Pro Ala Ile
            290                 295                 300

Ile Ala Gly Val Phe Asp Asn Cys Ser His Thr Val Ser Asp Lys Gly
305                 310                 315                 320

Trp Ala Leu Gly Ile Arg Ser Gly Lys Asp Lys Gly Lys Arg Asp Ala
            325                 330                 335

Arg Phe Phe Phe Ser Leu Cys Thr Asp Arg Val Lys Lys Ala Thr Ile
            340                 345                 350

Leu Ile Ser His Ser Arg Tyr Gln Pro Gly Thr Trp Thr His Val Ala
            355                 360                 365

Ala Thr Tyr Asp Gly Arg His Met Ala Leu Tyr Val Asp Gly Thr Gln
            370                 375                 380

Val Ala Ser Ser Leu Asp Gln Ser Gly Pro Leu Asn Ser Pro Phe Met
385                 390                 395                 400

Ala Ser Cys Arg Ser Leu Leu Gly Gly Asp Ser Ser Glu Asp Gly
            405                 410                 415

His Tyr Phe Arg Gly His Leu Gly Thr Leu Val Phe Trp Ser Thr Ala
            420                 425                 430

Leu Pro Gln Ser His Phe Gln His Ser Gln His Ser Ser Gly Glu
            435                 440                 445

Glu Glu Ala Thr Asp Leu Val Leu Thr Ala Ser Phe Glu Pro Val Asn
450                 455                 460

Thr Glu Trp Val Pro Phe Arg Asp Glu Lys Tyr Pro Arg Leu Glu Val
465                 470                 475                 480

Leu Gln Gly Phe Glu Pro Glu Pro Glu Ile Leu Ser Pro Leu Gln Pro
            485                 490                 495

Pro Leu Cys Gly Gln Thr Val Cys Asp Asn Val Glu Leu Ile Ser Gln
            500                 505                 510

Tyr Asn Gly Tyr Trp Pro Leu Arg Gly Glu Lys Val Ile Arg Tyr Gln
            515                 520                 525

Val Val Asn Ile Cys Asp Asp Glu Gly Leu Asn Pro Ile Val Ser Glu
            530                 535                 540

Glu Gln Ile Arg Leu Gln His Glu Ala Leu Asn Glu Ala Phe Ser Arg
545                 550                 555                 560

Tyr Asn Ile Ser Trp Gln Leu Ser Val His Gln Val His Asn Ser Thr
                565                 570                 575

Leu Arg His Arg Val Val Leu Val Asn Cys Glu Pro Ser Lys Ile Gly
            580                 585                 590

```
Asn Asp His Cys Asp Pro Glu Cys Glu His Pro Leu Thr Gly Tyr Asp
            595                 600                 605
Gly Gly Asp Cys Arg Leu Gln Gly Arg Cys Tyr Ser Trp Asn Arg Arg
610                 615                 620
Asp Gly Leu Cys His Val Glu Cys Asn Asn Met Leu Asn Asp Phe Asp
625                 630                 635                 640
Asp Gly Asp Cys Cys Asp Pro Gln Val Ala Asp Val Arg Lys Thr Cys
            645                 650                 655
Phe Asp Pro Asp Ser Pro Lys Arg Ala Tyr Met Ser Val Lys Glu Leu
                660                 665                 670
Lys Glu Ala Leu Gln Leu Asn Ser Thr His Phe Leu Asn Ile Tyr Phe
            675                 680                 685
Ala Ser Ser Val Arg Glu Asp Leu Ala Gly Ala Ala Thr Trp Pro Trp
690                 695                 700
Asp Lys Asp Ala Val Thr His Leu Gly Gly Ile Val Leu Ser Pro Ala
705                 710                 715                 720
Tyr Tyr Gly Met Pro Gly His Thr Asp Thr Met Ile His Glu Val Gly
                725                 730                 735
His Val Leu Gly Leu Tyr His Val Phe Lys Gly Val Ser Glu Arg Glu
            740                 745                 750
Ser Cys Asn Asp Pro Cys Lys Glu Thr Val Pro Ser Met Glu Thr Gly
            755                 760                 765
Asp Leu Cys Ala Asp Thr Ala Pro Thr Pro Lys Ser Glu Leu Cys Arg
            770                 775                 780
Glu Pro Glu Pro Thr Ser Asp Thr Cys Gly Phe Thr Arg Phe Pro Gly
785                 790                 795                 800
Ala Pro Phe Thr Asn Tyr Met Ser Tyr Thr Asp Asp Asn Cys Thr Asp
                805                 810                 815
Asn Phe Thr Pro Asn Gln Val Ala Arg Met His Cys Tyr Leu Asp Leu
                820                 825                 830
Val Tyr Gln Gln Trp Thr Glu Ser Arg Lys Pro Thr Pro Ile Pro Ile
            835                 840                 845
Pro Pro Met Val Ile Gly Gln Thr Asn Lys Ser Leu Thr Ile His Trp
850                 855                 860
Leu Pro Pro Ile Ser Gly Val Val Tyr Asp Arg Ala Ser Gly Ser Leu
865                 870                 875                 880
Cys Gly Ala Cys Thr Glu Asp Gly Thr Phe Arg Gln Tyr Val His Thr
                885                 890                 895
Ala Ser Ser Arg Arg Val Cys Asp Ser Ser Gly Tyr Trp Thr Pro Glu
            900                 905                 910
Glu Ala Val Gly Pro Pro Asp Val Asp Gln Pro Cys Glu Pro Ser Leu
            915                 920                 925
Gln Ala Trp Ser Pro Glu Val His Leu Tyr His Met Asn Met Thr Val
930                 935                 940
Pro Cys Pro Thr Glu Gly Cys Ser Leu Glu Leu Phe Gln His Pro
945                 950                 955                 960
Val Gln Ala Asp Thr Leu Thr Leu Trp Val Thr Ser Phe Phe Met Glu
                965                 970                 975
Ser Ser Gln Val Leu Phe Asp Thr Glu Ile Leu Leu Glu Asn Lys Glu
                980                 985                 990
Ser Val His Leu Gly Pro Leu Asp  Thr Phe Cys Asp Ile  Pro Leu Thr
            995                 1000                1005
Ile Lys  Leu His Val Asp Gly  Lys Val Ser Gly Val  Lys Val Tyr
```

-continued

```
            1010                1015                1020

Thr Phe Asp Glu Arg Ile Glu Ile Asp Ala Ala Leu Leu Thr Ser
            1025                1030                1035

Gln Pro His Ser Pro Leu Cys Ser Gly Cys Arg Pro Val Arg Tyr
            1040                1045                1050

Gln Val Leu Arg Asp Pro Pro Phe Ala Ser Gly Leu Pro Val Val
            1055                1060                1065

Val Thr His Ser His Arg Lys Phe Thr Asp Val Glu Val Thr Pro
            1070                1075                1080

Gly Gln Met Tyr Gln Tyr Gln Val Leu Ala Glu Ala Gly Gly Glu
            1085                1090                1095

Leu Gly Glu Ala Ser Pro Pro Leu Asn His Ile His Gly Ala Pro
            1100                1105                1110

Tyr Cys Gly Asp Gly Lys Val Ser Glu Arg Leu Gly Glu Glu Cys
            1115                1120                1125

Asp Asp Gly Asp Leu Val Ser Gly Asp Gly Cys Ser Lys Val Cys
            1130                1135                1140

Glu Leu Glu Glu Gly Phe Asn Cys Val Gly Glu Pro Ser Leu Cys
            1145                1150                1155

Tyr Met Tyr Glu Gly Asp Gly Ile Cys Glu Pro Phe Glu Arg Lys
            1160                1165                1170

Thr Ser Ile Val Asp Cys Gly Ile Tyr Thr Pro Lys Gly Tyr Leu
            1175                1180                1185

Asp Gln Trp Ala Thr Arg Ala Tyr Ser Ser His Glu Asp Lys Lys
            1190                1195                1200

Lys Cys Pro Val Ser Leu Val Thr Gly Glu Pro His Ser Leu Ile
            1205                1210                1215

Cys Thr Ser Tyr His Pro Asp Leu Pro Asn His Arg Pro Leu Thr
            1220                1225                1230

Gly Trp Phe Pro Cys Val Ala Ser Glu Asn Glu Thr Gln Asp Asp
            1235                1240                1245

Arg Ser Glu Gln Pro Glu Gly Ser Leu Lys Lys Glu Asp Glu Val
            1250                1255                1260

Trp Leu Lys Val Cys Phe Asn Arg Pro Gly Glu Ala Arg Ala Ile
            1265                1270                1275

Phe Ile Phe Leu Thr Thr Asp Gly Leu Val Pro Gly Glu His Gln
            1280                1285                1290

Gln Pro Thr Val Thr Leu Tyr Leu Thr Asp Val Arg Gly Ser Asn
            1295                1300                1305

His Ser Leu Gly Thr Tyr Gly Leu Ser Cys Gln His Asn Pro Leu
            1310                1315                1320

Ile Ile Asn Val Thr His His Gln Asn Val Leu Phe His His Thr
            1325                1330                1335

Thr Ser Val Leu Leu Asn Phe Ser Ser Pro Arg Val Gly Ile Ser
            1340                1345                1350

Ala Val Ala Leu Arg Thr Ser Ser Arg Ile Gly Leu Ser Ala Pro
            1355                1360                1365

Ser Asn Cys Ile Ser Glu Asp Glu Gly Gln Asn His Gln Gly Gln
            1370                1375                1380

Ser Cys Ile His Arg Pro Gly Lys Gln Asp Ser Cys Pro Ser
            1385                1390                1395

Leu Leu Leu Asp His Ala Asp Val Val Asn Cys Thr Ser Ile Gly
            1400                1405                1410
```

```
Pro Gly Leu Met Lys Cys Ala Ile Thr Cys Gln Arg Gly Phe Ala
1415                1420                1425

Leu Gln Ala Ser Ser Gly Gln Tyr Ile Arg Pro Met Gln Lys Glu
    1430                1435                1440

Ile Leu Leu Thr Cys Ser Ser Gly His Trp Asp Gln Asn Val Ser
1445                1450                1455

Cys Leu Pro Val Asp Cys Gly Val Pro Asp Pro Ser Leu Val Asn
    1460                1465                1470

Tyr Ala Asn Phe Ser Cys Ser Glu Gly Thr Lys Phe Leu Lys Arg
1475                1480                1485

Cys Ser Ile Ser Cys Val Pro Pro Ala Lys Leu Gln Gly Leu Ser
    1490                1495                1500

Pro Trp Leu Thr Cys Leu Glu Asp Gly Leu Trp Ser Leu Pro Glu
1505                1510                1515

Val Tyr Cys Lys Leu Glu Cys Asp Ala Pro Pro Ile Ile Leu Asn
    1520                1525                1530

Ala Asn Leu Leu Leu Pro His Cys Leu Gln Asp Asn His Asp Val
1535                1540                1545

Gly Thr Ile Cys Lys Tyr Glu Cys Lys Pro Gly Tyr Tyr Val Ala
    1550                1555                1560

Glu Ser Ala Glu Gly Lys Val Arg Asn Lys Leu Leu Lys Ile Gln
1565                1570                1575

Cys Leu Glu Gly Gly Ile Trp Glu Gln Gly Ser Cys Ile Pro Val
    1580                1585                1590

Val Cys Glu Pro Pro Pro Val Phe Glu Gly Met Tyr Glu Cys
1595                1600                1605

Thr Asn Gly Phe Ser Leu Asp Ser Gln Cys Val Leu Asn Cys Asn
    1610                1615                1620

Gln Glu Arg Glu Lys Leu Pro Ile Leu Cys Thr Lys Glu Gly Leu
1625                1630                1635

Trp Thr Gln Glu Phe Lys Leu Cys Glu Asn Leu Gln Gly Glu Cys
    1640                1645                1650

Pro Pro Pro Pro Ser Glu Leu Asn Ser Val Glu Tyr Lys Cys Glu
1655                1660                1665

Gln Gly Tyr Gly Ile Gly Ala Val Cys Ser Pro Leu Cys Val Ile
    1670                1675                1680

Pro Pro Ser Asp Pro Val Met Leu Pro Glu Asn Ile Thr Ala Asp
1685                1690                1695

Thr Leu Glu His Trp Met Glu Pro Val Lys Val Gln Ser Ile Val
    1700                1705                1710

Cys Thr Gly Arg Arg Gln Trp His Pro Asp Pro Val Leu Val His
1715                1720                1725

Cys Ile Gln Ser Cys Glu Pro Phe Gln Ala Asp Gly Trp Cys Asp
    1730                1735                1740

Thr Ile Asn Asn Arg Ala Tyr Cys His Tyr Asp Gly Gly Asp Cys
1745                1750                1755

Cys Ser Ser Thr Leu Ser Ser Lys Lys Val Ile Pro Phe Ala Ala
    1760                1765                1770

Asp Cys Asp Leu Asp Glu Cys Thr Cys Arg Asp Pro Lys Ala Glu
1775                1780                1785

Glu Asn Gln
1790
```

<210> SEQ ID NO 2
<211> LENGTH: 827
<212> TYPE: PRT
<213> ORGANISM: Homo sapiens

<400> SEQUENCE: 2

```
Met Met Cys Leu Lys Ile Leu Arg Ile Ser Leu Ala Ile Leu Ala Gly
1               5                   10                  15

Trp Ala Leu Cys Ser Ala Asn Ser Glu Leu Gly Trp Thr Arg Lys Lys
            20                  25                  30

Ser Leu Val Glu Arg Glu His Leu Asn Gln Val Leu Leu Glu Gly Glu
        35                  40                  45

Arg Cys Trp Leu Gly Ala Lys Val Arg Pro Arg Ala Ser Pro Gln
    50                  55                  60

His His Leu Phe Gly Val Tyr Pro Ser Arg Ala Gly Asn Tyr Leu Arg
65                  70                  75                  80

Pro Tyr Pro Val Gly Glu Gln Glu Ile His His Thr Gly Arg Ser Lys
            85                  90                  95

Pro Asp Thr Glu Gly Asn Ala Val Ser Leu Val Pro Pro Asp Leu Thr
        100                 105                 110

Glu Asn Pro Ala Gly Leu Arg Gly Ala Val Glu Pro Ala Ala Pro
    115                 120                 125

Trp Val Gly Asp Ser Pro Ile Gly Gln Ser Glu Leu Leu Gly Asp Asp
130                 135                 140

Asp Ala Tyr Leu Gly Asn Gln Arg Ser Lys Glu Ser Leu Gly Glu Ala
145                 150                 155                 160

Gly Ile Gln Lys Gly Ser Ala Met Ala Ala Thr Thr Thr Ala Ile
            165                 170                 175

Phe Thr Thr Leu Asn Glu Pro Lys Pro Glu Thr Gln Arg Arg Gly Trp
        180                 185                 190

Ala Lys Ser Arg Gln Arg Arg Gln Val Trp Lys Arg Ala Glu Asp
    195                 200                 205

Gly Gln Gly Asp Ser Gly Ile Ser Ser His Phe Gln Pro Trp Pro Lys
210                 215                 220

His Ser Leu Lys His Arg Val Lys Lys Ser Pro Glu Glu Ser Asn
225                 230                 235                 240

Gln Asn Gly Gly Glu Gly Ser Tyr Arg Glu Ala Glu Thr Phe Asn Ser
            245                 250                 255

Gln Val Gly Leu Pro Ile Leu Tyr Phe Ser Gly Arg Arg Glu Arg Leu
        260                 265                 270

Leu Leu Arg Pro Glu Val Leu Ala Glu Ile Pro Arg Glu Ala Phe Thr
    275                 280                 285

Val Glu Ala Trp Val Lys Pro Glu Gly Gly Gln Asn Asn Pro Ala Ile
290                 295                 300

Ile Ala Gly Val Phe Asp Asn Cys Ser His Thr Val Ser Asp Lys Gly
305                 310                 315                 320

Trp Ala Leu Gly Ile Arg Ser Gly Lys Asp Lys Gly Lys Arg Asp Ala
            325                 330                 335

Arg Phe Phe Phe Ser Leu Cys Thr Asp Arg Val Lys Lys Ala Thr Ile
        340                 345                 350

Leu Ile Ser His Ser Arg Tyr Gln Pro Gly Thr Trp Thr His Val Ala
    355                 360                 365

Ala Thr Tyr Asp Gly Arg His Met Ala Leu Tyr Val Asp Gly Thr Gln
370                 375                 380
```

```
Val Ala Ser Ser Leu Asp Gln Ser Gly Pro Leu Asn Ser Pro Phe Met
385                 390                 395                 400

Ala Ser Cys Arg Ser Leu Leu Gly Gly Asp Ser Ser Glu Asp Gly
            405                 410                 415

His Tyr Phe Arg Gly His Leu Gly Thr Leu Val Phe Trp Ser Thr Ala
                420                 425                 430

Leu Pro Gln Ser His Phe Gln His Ser Ser Gln His Ser Ser Gly Glu
            435                 440                 445

Glu Glu Ala Thr Asp Leu Val Leu Thr Ala Ser Phe Glu Pro Val Asn
            450                 455                 460

Thr Glu Trp Val Pro Phe Arg Asp Glu Lys Tyr Pro Arg Leu Glu Val
465                 470                 475                 480

Leu Gln Gly Phe Glu Pro Glu Pro Glu Ile Leu Ser Pro Leu Gln Pro
                485                 490                 495

Pro Leu Cys Gly Gln Thr Val Cys Asp Asn Val Glu Leu Ile Ser Gln
            500                 505                 510

Tyr Asn Gly Tyr Trp Pro Leu Arg Gly Glu Lys Val Ile Arg Tyr Gln
            515                 520                 525

Val Val Asn Ile Cys Asp Asp Glu Gly Leu Asn Pro Ile Val Ser Glu
            530                 535                 540

Glu Gln Ile Arg Leu Gln His Glu Ala Leu Asn Glu Ala Phe Ser Arg
545                 550                 555                 560

Tyr Asn Ile Ser Trp Gln Leu Ser Val His Gln Val His Asn Ser Thr
                565                 570                 575

Leu Arg His Arg Val Val Leu Val Asn Cys Glu Pro Ser Lys Ile Gly
            580                 585                 590

Asn Asp His Cys Asp Pro Glu Cys Glu His Pro Leu Thr Gly Tyr Asp
            595                 600                 605

Gly Gly Asp Cys Arg Leu Gln Gly Arg Cys Tyr Ser Trp Asn Arg Arg
610                 615                 620

Asp Gly Leu Cys His Val Glu Cys Asn Asn Met Leu Asn Asp Phe Asp
625                 630                 635                 640

Asp Gly Asp Cys Cys Asp Pro Gln Val Ala Asp Val Arg Lys Thr Cys
                645                 650                 655

Phe Asp Pro Asp Ser Pro Lys Arg Ala Tyr Met Ser Val Lys Glu Leu
                660                 665                 670

Lys Glu Ala Leu Gln Leu Asn Ser Thr His Phe Leu Asn Ile Tyr Phe
            675                 680                 685

Ala Ser Ser Val Arg Glu Asp Leu Ala Gly Ala Ala Thr Trp Pro Trp
            690                 695                 700

Asp Lys Asp Ala Val Thr His Leu Gly Gly Ile Val Leu Ser Pro Ala
705                 710                 715                 720

Tyr Tyr Gly Met Pro Gly His Thr Asp Thr Met Ile His Glu Val Gly
                725                 730                 735

His Val Leu Gly Leu Tyr His Val Phe Lys Gly Val Ser Glu Arg Glu
                740                 745                 750

Ser Cys Asn Asp Pro Cys Lys Glu Thr Val Pro Ser Met Glu Thr Gly
            755                 760                 765

Asp Leu Cys Ala Asp Thr Ala Pro Thr Pro Lys Ser Glu Leu Cys Arg
            770                 775                 780

Glu Pro Glu Pro Thr Ser Asp Thr Cys Gly Phe Thr Arg Phe Pro Gly
785                 790                 795                 800
```

```
Ala Pro Phe Thr Asn Tyr Met Ser Tyr Thr Gly Ile Thr Thr Val Leu
            805                 810                 815

Phe Cys Phe Leu Leu Arg Ile His Gly Gly Leu
            820                 825

<210> SEQ ID NO 3
<211> LENGTH: 6940
<212> TYPE: DNA
<213> ORGANISM: Homo sapiens

<400> SEQUENCE: 3
gggcatgact ctctctcttg agtaggcaca cactcccttt tctcgggtgt gtacttttttg     60 ctttgtgata catctctgca ctttcagtat tttccaactc atccttaaat tccttctcac    120
aacagtgtca agagcctgga cgccagccag gattgaggtc ctacgggtgt ttggggacct    180
ccccaagccc acgagtatca atggcagtat caattgtctg tgacagtgat taaggagcaa    240
aacacttgga acccacaaga ctcccagaag gtgaagttaa gagctcccag actcataagg    300
ttattagaac agcaaactgg cacccccaaag aactttacgg agacttgcaa cctatcaaca    360
agttggatga gggattaaaa gccttcaaca accaacaacc ccaagcatca aactgaagga    420
aacattctaa ccttcacaga cagactggag gctggatggg gacctggctg aagacatctg    480
gagaatgaaa gttaagtacc agcttgcatt tttgtgcccc tagattattt ttgcatttta    540
aaataagaag catcaaattg cgtgtctctg tgtaaaagtt ctagcaattt gttttaaggt    600
gaacttattt tggcttaggg actacaaaaa gagaaggtaa ttcctaggga aggaagaaga    660
gaaagaaatg aaaattagag aataagatta ttttgaatga cttcaggtag cgaggagtgt    720
gtgtttgtga gtgtgtattt gagagacttg gctcatgcct gtgggtcttc tcttctagta    780
tcagtgaggg gagggattac tgaagaagaa gggggggaaa aaaagaaag aaatctgagc    840 tttctgggag gaaattcaaa ggaaccaaga gaaattaact tcgttctgca aggactaaag    900
tacagcaaga ggagagaggt caagcgagaa gcgtgcggga agcacatgcc ctggggaggc    960
atagaagcca cactggcaga gcggccagca caggtagcca gcagaggcat tcttggggct   1020
atttgaaaaa gtttggtctg tgaacaaaac agtttccctg gtgactgcaa atccattgct   1080
agctgcctct ttctcgtctg cccatcactc tggtgtggta cccagaagtt gacttctggt   1140
tctgtagaaa gagctagggg aggtatgatg tgcttaaaga tcctaagaat aagcctggcg   1200
attttggctg ggtgggcact ctgttctgcc aactctgagc tgggctggac acgcaagaaa   1260
tccttggttg agagggaaca cctgaatcag gtgctgttgg aaggagaacg ttgttggctg   1320
ggggccaagg ttcgaagacc cagagcttct ccacagcatc acctctttgg agtctacccc   1380
agcagggctg ggaactacct aaggccctac cccgtggggg agcaagaaat ccatcataca   1440
ggacgcagca aaccagacac tgaaggaaat gctgtgagcc ttgttccccc agacctgact   1500
gaaaatccag caggactgag gggtgcagtt gaagagccgg ctgccccatg ggtaggggat   1560
agtcctattg gcaatctga gctgctggga gatgatgacg cttatctcgg caatcaaaga   1620
tccaaggagt ctctaggtga ggccgggatt cagaaaggct cagccatggc tgccactact   1680
accaccgcca ttttcacaac cctgaacgaa cccaaaccag agacccaaag gaggggctgg   1740
gccaagtcca ggcagcgtcg ccaagtgtgg aagaggcggg cggaagatgg gcagggagac   1800
tccggtatct cttcacattt ccaaccttgg cccaagcatt cccttaaaca cagggtcaaa   1860
aagagtccac cggaggaaag caaccaaaat ggtgagagg gctcctaccg agaagcagag   1920
acctttaact cccaagtagg actgcccatc ttatacttct ctgggaggcg ggagcggctg   1980
```

```
ctgctgcgtc cagaagtgct ggctgagatt ccccgggagg cgttcacagt ggaagcctgg    2040
gttaaaccgg agggaggaca gaacaaccca gccatcatcg caggtgtgtt tgataactgc    2100
tcccacactg tcagtgacaa aggctgggcc ctggggatcc gctcagggaa ggacaaggga    2160
aagcgggatg ctcgcttctt cttctccctc tgcaccgacc gcgtgaagaa agccaccatc    2220
ttgattagcc acagtcgcta ccaaccaggc acatggaccc atgtggcagc cacttacgat    2280
ggacggcaca tggccctgta tgtggatggc actcaggtgg ctagcagtct agaccagtct    2340
ggtcccctga cagccccctt catggcatct gccgctctt tgctcctggg gggagacagc     2400
tctgaggatg ggcactattt ccgtggacac ctgggcacac tggttttctg gtcgaccgcc    2460
ctgccacaaa gccattttca gcacagttct cagcattcaa gtggggagga ggaagcgact    2520
gacttggtcc tgacagcgag ctttgagcct gtgaacacag agtgggttcc ctttagagat    2580
gagaagtacc cacgacttga ggttctccag ggctttgagc cagagcctga gattctgtcg    2640
cctttgcagc ccccactctg tgggcaaaca gtctgtgaca atgtggaatt gatctcccag    2700
tacaatggat actggcccct tcggggagag aaggtgatac gctaccaggt ggtgaacatc    2760
tgtgatgatg agggcctaaa ccccattgtg agtgaggagc agattcgtct gcagcacgag    2820
gcactgaatg aggccttcag ccgctacaac atcagctggc agctgagcgt ccaccaggtc    2880
cacaattcca ccctgcgaca ccgggttgtg cttgtgaact gtgagcccag caagattggc    2940
aatgaccatt gtgaccccga gtgtgagcac ccactcacag gctatgatgg gggtgactgc    3000
cgcctgcagg gccgctgcta ctcctggaac cgcagggatg ggctctgtca cgtggagtgt    3060
aacaacatgc tgaacgactt tgacgacgga gactgctgcg accccaggt ggctgatgtg     3120
cgcaagacct gctttgaccc tgactcaccc aagagggcat acatgagtgt gaaggagctg    3180
aaggaggccc tgcagctgaa cagtactcac ttcctcaaca tctactttgc cagctcagtg    3240
cgggaagacc ttgcaggtgc tgccacctgg ccttgggaca aggacgctgt cactcacctg    3300
ggtggcattg tcctcagccc agcatattat gggatgcctg ccacaccga ccatgatc      3360
catgaagtgg gacatgttct gggactctac catgtcttta aaggagtcag tgaaagagaa    3420
tcctgcaatg acccctgcaa ggagacagtg ccatccatgg aaacgggaga cctctgtgcc    3480
gacaccgccc ccactcccaa gagtgagctg tgccgggaac cagagcccac tagtgacacc    3540
tgtggcttca ctcgcttccc aggggctccg ttccaact acatgagcta cggatgat       3600
aactgcactg acaacttcac tcctaaccaa gtggcccgaa tgcattgcta tttggaccta   3660
gtctatcagc agtggactga aagcagaaag cccaccccca tccccattcc acctatggtc   3720
atcggacaga ccaacaagtc cctcactatc cactggctgc ctcctattag tggagttgta   3780
tatgacaggg cctcaggcag cttgtgtggc gcttgcactg aagatgggac ctttcgtcag   3840
tatgtgcaca cagcttcctc ccggcgggtg tgtgactcct caggttattg gacccagag     3900
gaggctgtgg ggcctcctga tgtggatcag ccctgcgagc aagcttaca ggcctggagc     3960
cctgaggtcc acctgtacca catgaacatg acggtcccct gccccacaga aggctgtagc    4020
ttggagctgc tcttccaaca cccggtccaa gccgacaccc tcaccctgtg gtcacttcc    4080
ttcttcatgg agtcctcgca ggtcctcttt gacacagaga tcttgctgga aaacaaggag    4140
tcagtgcacc tgggccctt agacactttc tgtgacatcc cactcaccat caaactgcac     4200
gtggatggga aggtgtcggg ggtgaaagtc tacacctttg atgagaggat agagattgat    4260
gcagcactcc tgacttctca gccccacagt cccttgtgct ctggctgcag gcctgtgagg    4320
```

```
taccaggttc tccgcgatcc cccatttgcc agtggtttgc ccgtggtggt gacacattct    4380
cacaggaagt tcacggacgt ggaggtcaca cctggacaga tgtatcagta ccaagttcta    4440
gctgaagctg aggagaact gggagaagct tcgcctcctc tgaaccacat tcatggagct    4500
ccttattgtg gagatgggaa ggtgtcgaga gactgggag aagagtgtga tgatggagac    4560
cttgtgagcg gagatggctg ctccaaggtg tgtgagctgg aggaaggttt caactgtgta    4620
ggagagccaa gcctttgcta catgtatgag ggagatggca tatgtgaacc ttttgagaga    4680
aaaaccagca ttgtagactg tggcatctac actcccaaag gatacttgga tcaatgggct    4740
acccgggctt actcctctca tgaagacaag aagaagtgtc ctgtttcctt ggtaactgga    4800
gaacctcatt ccctaatttg cacatcatac catccagatt tacccaacca ccgtcccta    4860 actggctggt ttccctgtgt tgccagtgaa atgaaactc aggatgacag gagtgaacag    4920
ccagaaggta gcctgaagaa agaggatgag gtttggctca agtgtgtttt caatagacca    4980
ggagaggcca gcaattttt tattttttg acaactgatg gcctagttcc cggagagcat    5040
cagcagccga cagtgactct ctacctgacc gatgtccgtg gaagcaacca ctctcttgga    5100
acctatggac tgtcatgcca gcataatcca ctgattatca atgtgaccca tcaccagaat    5160
gtccttttcc accataccac ctcagtgctg ctgaatttct catccccacg ggtcggcatc    5220
tcagctgtgg ctctaaggac atcctcccgc attggtcttt cggctcccag taactgcatc    5280
tcagaggacg aggggcagaa tcatcaggga cagagctgta tccatcggcc ctgtgggaag    5340
caggacagct gtccgtcatt gctgcttgat catgctgatg tggtgaactg tacctctata    5400
ggcccaggtc tcatgaagtg tgctatcact tgtcaagggg gatttgccct tcaggccagc    5460
agtgggcagt acatcaggcc catgcagaag gaaattctgc tcacatgttc ttctgggcac    5520
tgggaccaga atgtgagctg ccttcccgtg gactgcggtg ttcccgaccc gtctttggtg    5580
aactatgcaa acttctcctg ctcagaggga accaaatttc tgaaacgctg ctcaatctct    5640
tgtgtcccac cagccaagct gcaaggactg agcccatggc tgacatgtct gaagatggt    5700 ctctggtctc tccctgaagt ctactgcaag ttggagtgtg atgctccccc tattattctg    5760
aatgccaact gctcctgcc tcactgcctc caggacaacc acgacgtggg caccatctgc    5820
aaatatgaat gcaaaccagg gtactatgtg gcagaaagtg cagagggtaa agtcaggaac    5880
aagctcctga agtacaatg cctggaaggt ggaatctggg agcaaggcag ctgcattcct    5940
gtggtgtgtg agccacccc tcctgtgttt gaaggcatgt atgaatgtac caatggcttc    6000
agcctggaca gccagtgtgt gctcaactgt aaccaggaac gtgaaaagct tcccatcctc    6060
tgcactaaag agggcctgtg gacccaggag tttaagttgt gtgagaatct gcaaggagaa    6120
tgcccaccac cccctcaga gctgaattct gtggagtaca atgtgaaca aggatatggg    6180 attggtgcag tgtgttcccc attgtgtgta atcccccca gtgacccgt gatgctacct    6240 gagaatatca ctgctgacac tctgagcac tggatggaac ctgtcaaagt ccagagcatt    6300
gtgtgcactg gccggcgtca atggcaccca gaccccgtct tagtccactg catccagtca    6360
tgtgagccct tccaagcaga tggttggtgt gacactatca caaccgagc ctactgccac    6420 tatgacgggg gagactgctg ctcttccaca ctctcctcca agaaggtcat tccatttgct    6480
gctgactgtg acctggatga gtgcacctgc cgggaccca aggcagaaga aaatcagtaa    6540
ctgtgggaac aagcccctcc ctccactgcc tcagaggcag taagaaagag aggccgaccc    6600
aggaggaaac aaagggtgaa tgaagaagaa caatcatgaa atggaagaag gaggaagagc    6660
atgaaggatc ttataagaaa tgcaagagga tattgatagg tgtgaactag ttcatcaagt    6720
```

| | |
|---|---|
| agcccaagta ggagagaatc ataggcaaaa gtttctttaa agtggcagtt gattaacatg | 6780 |
| gaaggggaaa tatgatagat atataaggac cctcctccct cacttatatt ctattaaatc | 6840 |
| ctatcctcaa ctcttgccct gctctccgct ccacccctg ccaactactc agtcccaccc | 6900 |
| aacttgtaaa ccaataccaa aaaaaaaaaa aaaaaaaaa | 6940 |

<210> SEQ ID NO 4
<211> LENGTH: 4370
<212> TYPE: DNA
<213> ORGANISM: Homo sapiens

<400> SEQUENCE: 4

| | |
|---|---|
| gggcatgact ctctctcttg agtaggcaca cactcccttt tctcgggtgt gtacttttg | 60 |
| ctttgtgata catctctgca ctttcagtat tttccaactc atccttaaat tccttctcac | 120 |
| aacagtgtca agagcctgga cgccagccag gattgaggtc ctacgggtgt ttggggacct | 180 |
| ccccaagccc acgagtatca atggcagtat caattgtctg tgacagtgat taaggagcaa | 240 |
| aacacttgga acccacaaga ctcccagaag gtgaagttaa gagctcccag actcataagg | 300 |
| ttattagaac agcaaactgg caccccaaag aactttacgg agacttgcaa cctatcaaca | 360 |
| agttggatga gggattaaaa gccttcaaca accaacaacc ccaagcatca aactgaagga | 420 |
| aacattctaa ccttcacaga cagactggag gctggatggg gacctggctg aagacatctg | 480 |
| gagaatgaaa gttaagtacc agcttgcatt tttgtgcccc tagattattt ttgcatttta | 540 |
| aaataagaag catcaaattg cgtgtctctg tgtaaaagtt ctagcaattt gttttaaggt | 600 |
| gaacttattt tggcttaggg actacaaaaa gagaaggtaa ttcctaggga aggaagaaga | 660 |
| gaaagaaatg aaaattagag aataagatta ttttgaatga cttcaggtag cgaggagtgt | 720 |
| gtgtttgtga gtgtgtattt gagagacttg gctcatgcct gtgggtcttc tcttctagta | 780 |
| tcagtgaggg gagggattac tgaagaagaa ggggggaaaa aaaagaaag aaatctgagc | 840 |
| tttctgggag gaaattcaaa ggaaccaaga gaaattaact tcgttctgca aggactaaag | 900 |
| tacagcaaga ggagagaggt caagcgagaa gcgtgcggga agcacatgcc ctggggaggc | 960 |
| atagaagcca cactggcaga gcggccagca caggtagcca gcagaggcat tcttggggct | 1020 |
| atttgaaaaa gtttggtctg tgaacaaaac agtttccctg gtgactgcaa atccattgct | 1080 |
| agctgcctct ttctcgtctg cccatcactc tggtgtggta cccagaagtt gacttctggt | 1140 |
| tctgtagaaa gagctagggg aggtatgatg tgcttaaaga tcctaagaat aagcctggcg | 1200 |
| attttggctg ggtgggcact ctgttctgcc aactctgagc tgggctggac acgcaagaaa | 1260 |
| tccttggttg agagggaaca cctgaatcag gtgctgttgg aaggagaacg ttgttggctg | 1320 |
| ggggccaagt tcgaagacc cagagcttct ccacagcatc acctctttgg agtctacccc | 1380 |
| agcagggctg ggaactacct aaggccctac cccgtggggg agcaagaaat ccatcataca | 1440 |
| ggacgcagca aaccagacac tgaaggaaat gctgtgagcc ttgttccccc agacctgact | 1500 |
| gaaaatccag caggactgag gggtgcagtt gaagagccgg ctgccccatg ggtaggggat | 1560 |
| agtcctattg gcaatctga gctgctggga gatgatgacg cttatctcgg caatcaaaga | 1620 |
| tccaaggagt ctctaggtga ggccgggatt cagaaaggct cagccatggc tgccactact | 1680 |
| accaccgcca ttttcacaac cctgaacgaa cccaaaccag agacccaaag gaggggctgg | 1740 |
| gccaagtcca ggcagcgtcg ccaagtgtgg aagaggcggg cggaagatgg gcagggagac | 1800 |
| tccggtatct cttcacattt ccaaccttgg cccaagcatt cccttaaaca cagggtcaaa | 1860 |

```
aagagtccac cggaggaaag caaccaaaat ggtggagagg gctcctaccg agaagcagag    1920
acctttaact cccaagtagg actgcccatc ttatacttct ctgggaggcg ggagcggctg    1980
ctgctgcgtc cagaagtgct ggctgagatt ccccgggagg cgttcacagt ggaagcctgg    2040
gttaaaccgg agggaggaca gaacaaccca gccatcatcg caggtgtgtt tgataactgc    2100
tcccacactg tcagtgacaa aggctgggcc ctggggatcc gctcagggaa ggacaaggga    2160
aagcgggatc tcgcttctt cttctcccctc tgcaccgacc gcgtgaagaa agccaccatc    2220
ttgattagcc acagtcgcta ccaaccaggc acatggaccc atgtggcagc cacttacgat    2280
ggacggcaca tggccctgta tgtggatggc actcaggtgg ctagcagtct agaccagtct    2340
ggtcccctga acagccccttt catggcatct tgccgctctt tgctcctggg gggagacagc    2400
tctgaggatg ggcactattt ccgtggacac ctgggcacac tggttttctg gtcgaccgcc    2460
ctgccacaaa gccattttca gcacagttct cagcattcaa gtggggagga ggaagcgact    2520
gacttggtcc tgacagcgag ctttgagcct gtgaacacag agtgggttcc ctttagagat    2580
gagaagtacc cacgacttga ggttctccag ggctttgagc cagagcctga gattctgtcg    2640
cctttgcagc ccccactctg tgggcaaaca gtctgtgaca atgtggaatt gatctcccag    2700
tacaatggat actggcccct tcggggagag aaggtgatac gctaccaggt ggtgaacatc    2760
tgtgatgatg agggcctaaa ccccattgtg agtgaggagc agattcgtct gcagcacgag    2820
gcactgaatg aggccttcag ccgctacaac atcagctggc agctgagcgt ccaccaggtc    2880
cacaattcca ccctgcgaca ccgggttgtg cttgtgaact gtgagcccag caagattggc    2940
aatgaccatt gtgaccccga gtgtgagcac ccactcacag gctatgatgg gggtgactgc    3000
cgcctgcagg gccgctgcta ctcctggaac cgcagggatg ggctctgtca cgtggagtgt    3060
aacaacatgc tgaacgactt tgacgacgga gactgctgcg accccaggt ggctgatgtg    3120 cgcaagacct gctttgaccc tgactcaccc aagagggcat acatgagtgt gaaggagctg    3180
aaggaggccc tgcagctgaa cagtactcac ttcctcaaca tctactttgc cagctcagtg    3240
cgggaagacc ttgcaggtgc tgccacctgg ccttgggaca aggacgctgt cactcacctg    3300
ggtggcattg tcctcagccc agcatattat gggatgcctg ccacaccgga caccatgatc    3360
catgaagtgg acatgttctc tggactctac catgtctttta aaggagtcag tgaaagagaa    3420
tcctgcaatg acccctgcaa ggagacagtg ccatccatgg aaacgggaga cctctgtgcc    3480
gacaccgccc ccactcccaa gagtgagctg tgccgggaac cagagcccac tagtgacacc    3540
tgtggcttca ctcgcttccc aggggctccg ttcaccaact acatgagcta cacgggtatc    3600
accactgtct tgttttgttt tctgttaaga atacatgggg gcctttgaga gctgggaggg    3660
tggaggtgtg ggagctgatg ggagaatgat taagtggtca tttgtgtcgg agagttgaag    3720
tgtatttatt ataaggtatt attatttttt catgtctttg aagaacttga agaaatactg    3780
acatattaag gtactttgtt cactgaattc tcctctacta gatattttaa aatatacttc    3840
tatcctcgat agtaaaaaag gcacagagcc aaaagccctc ttgtgatccc cttgacttct    3900
agaatgtggt tattcttatt tttgcccgca ttcttagaca tttactctga agaagagtcc    3960
aatggaaata aaggaaaaga gtttatgggt caaggtggcc cattgtactg tttttgaagt    4020
tggtcaacaa ggtggcttgg ttaatttagg ctcagcatgt tttactgtat gttactaaaa    4080
aaaaaaaaaa aaaaaatcag attctctttt tccagcacta gtcaagcaca aattcttagc    4140
tgcctaccac ccttttcccca ccaaaaggtg acatctaatt ttaaaaaaat ggcatcttcc    4200
tggccctcgg aaaaacttgt catctggtct ttcttgcctt aattcagctt ctgtattatt    4260
```

-continued

```
cttcgctgtc tctcacgcct tccttgtttc ttgtgaaaag taatagtgac tggtttccta    4320
taatggactc aaagttatcc ctaaaattaa agacttattt gatgacctag               4370
```

<210> SEQ ID NO 5
<211> LENGTH: 424
<212> TYPE: PRT
<213> ORGANISM: Homo sapiens

<400> SEQUENCE: 5

Met Asp Phe Ser Arg Arg Ser Phe His Arg Ser Leu Ser Ser Ser Leu
1               5                   10                  15

Gln Ala Pro Val Val Ser Thr Val Gly Met Gln Arg Leu Gly Thr Thr
            20                  25                  30

Pro Ser Val Tyr Gly Gly Ala Gly Gly Arg Gly Ile Arg Ile Ser Asn
        35                  40                  45

Ser Arg His Thr Val Asn Tyr Gly Ser Asp Leu Thr Gly Gly Gly Asp
    50                  55                  60

Leu Phe Val Gly Asn Glu Lys Met Ala Met Gln Asn Leu Asn Asp Arg
65                  70                  75                  80

Leu Ala Ser Tyr Leu Glu Lys Val Arg Thr Leu Glu Gln Ser Asn Ser
                85                  90                  95

Lys Leu Glu Val Gln Ile Lys Gln Trp Tyr Glu Thr Asn Ala Pro Arg
            100                 105                 110

Ala Gly Arg Asp Tyr Ser Ala Tyr Tyr Arg Gln Ile Glu Glu Leu Arg
        115                 120                 125

Ser Gln Ile Lys Asp Ala Gln Leu Gln Asn Ala Arg Cys Val Leu Gln
    130                 135                 140

Ile Asp Asn Ala Lys Leu Ala Ala Glu Asp Phe Arg Leu Lys Tyr Glu
145                 150                 155                 160

Thr Glu Arg Gly Ile Arg Leu Thr Val Glu Ala Asp Leu Gln Gly Leu
                165                 170                 175

Asn Lys Val Phe Asp Asp Leu Thr Leu His Lys Thr Asp Leu Glu Ile
            180                 185                 190

Gln Ile Glu Glu Leu Asn Lys Asp Leu Ala Leu Leu Lys Lys Glu His
        195                 200                 205

Gln Glu Glu Val Asp Gly Leu His Lys His Leu Gly Asn Thr Val Asn
    210                 215                 220

Val Glu Val Asp Ala Ala Pro Gly Leu Asn Leu Gly Val Ile Met Asn
225                 230                 235                 240

Glu Met Arg Gln Lys Tyr Glu Val Met Ala Gln Lys Asn Leu Gln Glu
                245                 250                 255

Ala Lys Glu Gln Phe Glu Arg Gln Thr Ala Val Leu Gln Gln Gln Val
            260                 265                 270

Thr Val Asn Thr Glu Glu Leu Lys Gly Thr Glu Val Gln Leu Thr Glu
        275                 280                 285

Leu Arg Arg Thr Ser Gln Ser Leu Glu Ile Glu Leu Gln Ser His Leu
    290                 295                 300

Ser Met Lys Glu Ser Leu Glu His Thr Leu Glu Glu Thr Lys Ala Arg
305                 310                 315                 320

Tyr Ser Ser Gln Leu Ala Asn Leu Gln Ser Leu Leu Ser Ser Leu Glu
                325                 330                 335

Ala Gln Leu Met Gln Ile Arg Ser Asn Met Glu Arg Gln Asn Asn Glu
            340                 345                 350

| | | | | | | | | | | | |
|---|---|---|---|---|---|---|---|---|---|---|---|
|Tyr|His|Ile|Leu|Leu|Asp|Ile|Lys|Thr|Arg|Leu|Glu|Gln|Glu|Ile|Ala|
| |355| | | |360| | | |365| | |

Thr Tyr Arg Arg Leu Leu Glu Gly Glu Asp Val Lys Thr Thr Glu Tyr
370 375 380

Gln Leu Ser Thr Leu Glu Glu Arg Asp Ile Lys Lys Thr Arg Lys Ile
385 390 395 400

Lys Thr Val Val Gln Glu Val Val Asp Gly Lys Val Val Ser Ser Glu
405 410 415

Val Lys Glu Val Glu Glu Asn Ile
420

<210> SEQ ID NO 6
<211> LENGTH: 1805
<212> TYPE: DNA
<213> ORGANISM: Homo sapiens
<400> SEQUENCE: 6

```
gagacacact ctgccccaac catcctgaag ctacaggtgc tccctcctgg aatctccaat      60
ggatttcagt cgcagaagct tccacagaag cctgagctcc tccttgcagg cccctgtagt     120
cagtacagtg ggcatgcagc gcctcgggac gacacccagc gtttatgggg gtgctggagg     180
ccggggcatc cgcatctcca actccagaca cacggtgaac tatgggagcg atctcacagg     240
cggcggggac ctgtttgttg gcaatgagaa aatggccatg cagaacctaa atgaccgtct     300
agcgagctac ctagaaaagg tgcggaccct ggagcagtcc aactccaaac ttgaagtgca     360
aatcaagcag tggtacgaaa ccaacgcccc gagggctggt cgcgactaca gtgcatatta     420
cagacaaatt gaagagctgc gaagtcagat taaggatgct caactgcaaa atgctcggtg     480
tgtcctgcaa attgataatg ctaaactggc tgctgaggac ttcagactga gtatgagac     540
tgagagagga atacgtctaa cagtggaagc tgatctccaa ggcctgaata aggtctttga     600
tgacctaacc ctacataaaa cagatttgga gattcaaatt gaagaactga ataaagacct     660
agctctcctc aaaaaggagc atcaggagga agtcgatggc ctacacaagc atctgggcaa     720
cactgtcaat gtggaggttg atgctgctcc aggcctgaac cttggcgtca tcatgaatga     780
aatgaggcag aagtatgaag tcatggccca gaagaacctt caagaggcca agaacagtt     840
tgagagacag actgcagttc tgcagcaaca ggtcacagtg aatactgaag aattaaaagg     900
aactgaggtt caactaacgg agctgagacg cacctcccag agccttgaga tagaactcca     960
gtcccatctc agcatgaaag agtctttgga gcacactcta gaggagacca aggcccgtta    1020
cagcagccag ttagccaacc tccagtcgct gttgagctct ctggaggccc aactgatgca    1080
gattcggagt aacatggaac gccagaacaa cgaataccat atccttcttg acataaagac    1140
tcgacttgaa caggaaattg ctacttaccg ccgccttctg gaaggagaag acgtaaaaac    1200
tacagaatat cagttaagca ccctggaaga gagagatata agaaaaccag gaagattaa    1260
gacagtcgtg caagaagtag tggatggcaa ggtcgtgtca tctgaagtca agagggtgga    1320
agaaaatatc taaatagcta ccagaaggag atgctgctga ggttttgaaa gaaatttggc    1380
tataatctta tctttgctcc ctgcaagaaa tcagccataa gaaagcacta ttaatactct    1440
gcagtgatta gaaggggtgg ggtggcggga atcctattta tcagactctg taattgaata    1500
taaatgtttt actcagagga gctgcaaatt gcctgcaaaa atgaaatcca gtgagcacta    1560
gaatatttaa aacatcatta ctgccatctt tatcatgaag cacatcaatt acaagctgta    1620
gaccacctaa tatcaatttg taggtaatgt tcctgaaaat tgcaatacat ttcaattata    1680
```
ctaaacctca caaagtagag gaatccatgt aaattgcaaa taaaccactt tctaattttt 1740
tcctgtttct gaattgtaaa accccctttg ggagtccctg gtttcttatt gagccaattt 1800
ctggg 1805

<210> SEQ ID NO 7
<211> LENGTH: 323
<212> TYPE: PRT
<213> ORGANISM: Homo sapiens

<400> SEQUENCE: 7

Met Ala Arg Gly Pro Gly Leu Ala Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60

Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu

<210> SEQ ID NO 8
<211> LENGTH: 2080

```
<212> TYPE: DNA
<213> ORGANISM: Homo sapiens

<400> SEQUENCE: 8
gcgggtcccc agaagcctac aggtgagtat cggttctccc cttccggct ttcggtccgg      60
aggaggcggg agcagcttcc ctgttctgat cctatcgcgg gcggcgcagg gccggcttgg     120
ccttccgtgg gacggggagg ggggcgggat gtgtcaccca ataccagtg gggacggtcg     180
gtggtggaac cagccgggca ggtcgggtag agtataagag ccggagggag cggccgggcg     240
gcagacgcct gcagaccatc ccagacgccg gagcccgagc cccgacgagt ccccgcgcct     300
catccgcccg cgtccggtcc gcgttcctcc gccccaccat ggctcgggc cccggcctcg     360
cgccgccacc gctgcggctg ccgctgctgc tgctggtgct ggcggcggtg accggccaca     420
cggccgcgca ggacaactgc acgtgtccca ccaacaagat gaccgtgtgc agccccgacg     480
gccccggcgg ccgctgccag tgccgcgcgc tgggctcggg catggcggtc gactgctcca     540
cgctgacctc caagtgtctg ctgctcaagg cgcgcatgag cgcccccaag aacgcccgca     600
cgctggtgcg gccgagtgag cacgcgctcg tggacaacga tggcctctac gaccccgact     660
gcgaccccga gggccgcttc aaggcgcgcc agtgcaacca gacgtcggtg tgctggtgcg     720
tgaactcggt gggcgtgcgc cgcacggaca gggcgacct gagcctacgc tgcgatgagc     780
tggtgcgcac ccaccacatc ctcattgacc tgcgccaccg ccccaccgcc ggcgccttca     840
accactcaga cctggacgcc gagctgaggc ggctcttccg cgagcgctat cggctgcacc     900
ccaagttcgt ggcggccgtg cactacgagc agcccaccat ccagatcgag ctgcggcaga     960
acacgtctca gaaggccgcc ggtgacgtgg atatcggcga tgccgcctac tacttcgaga    1020
gggacatcaa gggcgagtct ctattccagg gccgcgcgg cctggacttg cgcgtgcgcg    1080
gagaaccct gcaggtggag cgcacgctca tctattacct ggacgagatt cccccgaagt    1140
tctccatgaa gcgcctcacc gccggcctca tcgccgtcat cgtggtggtc gtggtggccc    1200
tcgtcgccgg catggccgtc ctggtgatca ccaaccggag aaagtcgggg aagtacaaga    1260
aggtggagat caaggaactg ggggagttga gaaaggaacc gagcttgtag gtacccggcg    1320
gggcagggga tggggtgggg taccggattt cggtatcgtc ccagacccaa gtgagtcacg    1380
cttcctgatt cctcggcgca aggagacgt ttatccttc aaattcctgc cttcccctc     1440
cctttgcgc acacaccagg tttaatagat cctggcctca gggtctcctt tctttctcac    1500
ttctgtcttg aaggaagcat ttctaaaatg tatccccttt cggtccaaca acaggaaacc    1560
tgactggggc agtgaaggaa gggatggcat agcgttatgt gtaaaaaaca agtatctgta    1620
tgacaacccg ggatcgtttg caagtaactg aatccattgc gacattgtga aggcttaaat    1680
gagtttagat gggaaatagc gttgttatcg ccttgggttt aaattatttg atgagttcca    1740
cttgtatcat ggcctacccg aggagaagag gagtttgtta actgggccta tgtagtagcc    1800
tcatttacca tcgtttgtat tactgaccac atatgcttgt cactgggaaa gaagcctgtt    1860
tcagctgcct gaacgcagtt tggatgtctt tgaggacaga cattgcccgg aaactcagtc    1920
tatttattct tcagcttgcc cttactgcca ctgatattgg taatgttctt ttttgtaaaa    1980
tgtttgtaca tatgttgtct tgataatgt tgctgtaatt ttttaaaata aaacacgaat    2040
ttaataaaat atgggaaagg cacaaaccag aaaaaaaaaa                          2080

<210> SEQ ID NO 9
<211> LENGTH: 198
<212> TYPE: PRT
```

<213> ORGANISM: Homo sapiens

<400> SEQUENCE: 9

```
Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195
```

<210> SEQ ID NO 10
<211> LENGTH: 863
<212> TYPE: DNA
<213> ORGANISM: Homo sapiens

<400> SEQUENCE: 10

```
agggccaccc aggtgagcct ctcactcgcc acctcctctt ccaccccctgc caggcccagc    60
agccaccaca gcgcctgctt cctcggccct gaaatcatgc ccctaggtct cctgtggctg   120
ggcctagccc tgttgggggc tctgcatgcc caggcccagg actccacctc agacctgatc   180
ccagccccac ctctgagcaa ggtccctctg cagcagaact ccaggacaa ccaattccag   240
gggaagtggt atgtggtagg cctggcaggg aatgcaattc tcagagaaga caaagacccg   300
caaaagatgt atgccaccat ctatgagctg aaagaagaca gagctacaa tgtcacctcc   360
gtcctgtttta ggaaaaagaa gtgtgactac tggatcagga cttttgttcc aggttgccag   420
cccggcgagt tcacgctggg caacattaag agttaccctg gattaacgag ttacctcgtc   480
cgagtggtga gcaccaacta caaccagcat gctatggtgt cttcaagaa agtttctcaa   540
aacagggagt acttcaagat caccctctac gggagaacca aggagctgac ttcggaacta   600
aaggagaact tcatccgctt ctccaaatct ctgggcctcc ctgaaaacca catcgtcttc   660
cctgtcccaa tcgaccagtg tatcgacggc tgagtgcaca ggtgccgcca gctgccgcac   720
cagcccgaac accattgagg gagctgggag accctcccca cagtgccacc catgcagctg   780
ctccccaggc caccccgctg atggagcccc accttgtctg ctaaataaac atgtgccctc   840
```
aggccaaaaa aaaaaaaaaa aaa                                              863

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatcagagcc aaagcagtga g                                                21

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggattaccta atacgactca ctatagggtt ctctgtgacc cagtccatc                  49

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctctcctctt cctcctcttc g                                                21

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggattaccta atacgactca ctatagggtg acctcacagc tcaagaaca                  49

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaaaacagaa ggcagcttta cg                                               22

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggattaccta atacgactca ctatagggaa agatggagtg gcagacaga                  49

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagagggagg acagagcaa                                                     19

<210> SEQ ID NO 18
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggccagtgaa ttgtaatacg actcactata gggaggcggg taaaggtgac agaatctcag        60
g                                                                        61

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgctccaaaa ctcagcagtg                                                    20

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggccagtgaa ttgtaatacg actcactata gggaggcggc gcctcctatt gaagtcagc         59

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcaatgggct cacaggtatt                                                    20

<210> SEQ ID NO 22
<211> LENGTH: 59
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 22
ggccagtgaa ttgtaatacg actcactata gggaggcggt ttgtatttgc ccgacttcc      59
```